US012605438B2

(12) United States Patent
Anderson et al.

(10) Patent No.: US 12,605,438 B2
(45) Date of Patent: Apr. 21, 2026

(54) SARS-CoV-2 VACCINES AND ANTIBODIES

(71) Applicant: Rutgers, the State University of New Jersey, New Brunswick, NJ (US)

(72) Inventors: Stephen Anderson, Princeton, NJ (US); Elliot Campbell, Somerset, NJ (US)

(73) Assignee: Rutgers, the State University of New Jersey, New Brunswick, NJ (US)

( * ) Notice: Subject to any disclaimer, the term of this patent is extended or adjusted under 35 U.S.C. 154(b) by 642 days.

(21) Appl. No.: 18/177,672

(22) Filed: Mar. 2, 2023

(65) Prior Publication Data

US 2023/0212232 A1 Jul. 6, 2023

Related U.S. Application Data

(63) Continuation of application No. PCT/US2021/048932, filed on Sep. 2, 2021.

(60) Provisional application No. 63/211,397, filed on Jun. 16, 2021, provisional application No. 63/132,943, filed on Dec. 31, 2020, provisional application No. 63/075,043, filed on Sep. 4, 2020.

(51) Int. Cl.
| | |
|---|---|
| *A61K 39/12* | (2006.01) |
| *A61K 39/215* | (2006.01) |
| *A61P 31/14* | (2006.01) |
| *C07K 14/005* | (2006.01) |
| *C07K 16/10* | (2006.01) |

(52) U.S. Cl.
CPC ............ *A61K 39/12* (2013.01); *A61K 39/215* (2013.01); *A61P 31/14* (2018.01); *C07K 14/005* (2013.01); *C07K 16/1003* (2023.08); *C07K 2317/33* (2013.01); *C07K 2317/76* (2013.01); *C12N 2770/20022* (2013.01); *C12N 2770/20034* (2013.01); *C12N 2770/20071* (2013.01)

(58) Field of Classification Search
None
See application file for complete search history.

(56) References Cited

FOREIGN PATENT DOCUMENTS

| | | |
|---|---|---|
| JP | 2018528191 A | 9/2018 |
| WO | 2017/031353 A1 | 2/2017 |
| WO | 2019147831 A1 | 8/2019 |
| WO | WO-2021207306 A1 * | 10/2021 ............. A61P 31/14 |

OTHER PUBLICATIONS

M. Guipponi et al., "An Integrated Genetic and Functional Analysis of the Role of Type II Transmembrane Serine Proteases (TMPRSSs) in Hearing Loss," Human Mutation, 29(1): 130-141 (2008).
M. Hoffmann et al., "SARS-CoV-2 Cell Entry Depends on ACE2 and TMPRSS2 and Is Blocked by a Clinically Proven Protease Inhibitor," Cell, 181: 271-280 (2020).
M. Vaarala et al., "The TMPRSS2 Gene Encoding Transmembrane Serine Protease is Overexpressed in a Majority of Prostate Cancer Patients: detection of mutated TMPRSS2 form in a case of aggressive disease," Int. J. Cancer, 94: 705-710 (2001).
W.B. Alsoussi et al., "A Potently Neutralizing Antibody Protects Mice Against SARS-CoV-2 Infection," J. Immunol., 205(4): 915-922 (2020).
A. Baum et al., "Antibody cocktail to SARS-CoV-2 spike protein prevents rapid mutational escape seen with individual antibodies," Science, eabd0831, 8 pages (2020).
T. Koyama et al., "Variant analysis of SARS-CoV-2 genomes," Bull. World Health Organ., 98(7): 495-504 (2020).
International Search Report and Written Opinion for Application No. PCT/US2021/048932, mailed Dec. 21, 2021 (14 pages).

* cited by examiner

*Primary Examiner* — Suzanne M Noakes
*Assistant Examiner* — Jae W Lee
(74) *Attorney, Agent, or Firm* — McNeill PLLC

(57) ABSTRACT

The invention describes a method of generating antibodies to a mixture of SARS-COV-2 peptidogenic proteins or polynucleotides encoding SARS-COV-2 peptidogenic proteins wherein the SARS-COV-2 peptidogenic protein has altered conformational dynamics as compared to a SARS-COV-2 starting protein and wherein the SARS-COV-2 peptidogenic protein has a similar conformation to the SARS-COV-2 starting protein. The SARS-COV-2 peptidogenic proteins can be used to induce an immune response, which can lead to the generation of antibodies and/or can be used to vaccinate a mammal.

22 Claims, 16 Drawing Sheets

Specification includes a Sequence Listing.

Figure 3

```
Spike_Fragment            -----------------SNFRVQPTESIVRFPNITNLCP-FGEVFNATRFAS
P0DTC2|SARS2              CALDPLSETKCTLKSFTVEKGIYQTSNFRVQPTESIVRFPNITNLCP-FGEVFNATRFAS
A0A6B9WHD3_SARS           CALDPLSETKCTLKSFTVEKGIYQTSNFRVQPTESIVRFPNITNLCP-FGEVFNATRFAS
A0A6G9KP06_9BETC          CSLDPLSETKCTLKSLTVEKGIYQTSNFRVQPTDSIVRFPNITNLCP-FGEVFNATTFAS
A0A2D1PX05_SARS/282-593   CAQNPLAELKCTIKNFNVSKGIYQTSNFRVSPTQEVVRFPNITNRCP-FGEVFNASKFAS
A0A2D1PX88_SARS/282-593   CAQNPLSELKCTIKNFNVSKGIYQTSNFRVSPTHEVIRFPNITNRCP-FDKVFNATRFPS
A0A2D1PX44_SARS/282-593   CAQNPLSELKCTIKNFNVSKGIYQTSNFRVSPTHEVVRFPNITNRCP-FDKVFNASRFPN
D2DJW4_SARS/282-593       CAQNPLSELKCTIKNFNVSKGIYQTSNFRVSPTHEVIRFPNITNRCP-FDKVFNASRFPN
A0A2D1PX73_SARS/282-593   CAQNPLAELKCTIKNFNVSKGIYQTSNFRVSPTQEVIRFPNITNRCP-FDKVFNASRFPN
Q3I5J5|BCRP3/282-593      CAQNPLAELKCTIKNFNVSKGIYQTSNFRVSPTQEVIRFPNITNRCP-FDKVFNATRFPN
Q0Q475|BC279/282-593      CSQNPLAELKCTIKNFNVSKGIYQTSNFRVTPTQEVVRFPNITNRCP-FDKVFNASRFPN
Q0QDX9_SARS/282-593       CSQNPLAELKCTIKNFNVSKGIYQTSNFRVSPTQEVVRFPNITNRCP-FDKVFNASRFPN
Q3LZX1|BCHK3              CSQNPLAELKCTIKNFNVDKGIYQTSNFRVSPTQEVIRFPNITNRCP-FDKVFNATRFPN
A0A096XNM6_SARS           CSQNPLAELKCTIKNFNVDKGIYQTSNFRVSPTQEVIRFPNITNRCP-FDKVFNVTRFPN
A0A2D1PX86_SARS           CAQNPLAELKCTIKNFNVSKGIYQTSNFRVSPTQEVIRFPNITNRCP-FDKVFNASRFPN
A0A0U1WHJ8_SARS           CSQNPLAELKCTIKNFNVNKGIYQTSNFRVSPTQEVVRFPNITNRCP-FDKVFNATRFPN
D5HJU5_BCHK3              CSQNPLAELKCTIKNFNVDKGIYQTSNFRVSPTQEVIRFPNITNRCP-FDRVFNASRFPS
A0A0U1WHI2_SARS           CSQDPLSELKCTLKNFNVTKGIYQTSNFRVTPTQEVVRFPNITNRCP-FDKVFNATRFPS
R9QTA0_SARS               CSQDPLSELKCTLKNFNITKGIYQTSNFRVSPTQEVVRFPNITNRCP-FDKVFNATRFPS
R9QTH3_SARS/282-593       CSQNPLAELKCTLKNFNVSKGIYQTSNFRVSPTEVIRFPNITNRCP-FDRVFNASRFPS
A0A1W5YKT9_9NIDO          CSQNPLAELKCTLKNFNVSKGIYQTSNFRVSPSTEVIRFPNITNRCP-FDRVFNASRFPS
A0A0U1WJY8_SARS           CSQDPLAELKCTIKNFNVSKGIYQTSNFRVSPTREVVRFPNITNRCP-FDSIFNASRFPS
A0A2D1PX37_SARS           CSQDPLAELKCTIKNFNVSKGIYQTSNFRVSPTREVVRFPNITNRCP-FDSIFNASRFPS
Q0QDZ0_SARS/282-593       CSQDPLAELKCTLKLSDVGKGIYQTSNFRVQPTVDVVRFPNITNLCP-FDAVFNATRFPS
A0A0U1WHH0_SARS/282-593   CSQDPLAELKCTLKQFDVGKGIYQTSNFRVQPTVDARFPNITNVCP-FDKVFNATRFPS
Q0Q484_SARS/282-593       CSQDPLAELKCTLKCTTKSFNVSKGIYQTSNFRVSPVTEVVRFPNITNLCP-FDKVFNATRFPS
A0A0K1Z074_SARS/282-593   CSQDPLAELKCTLKCTTKSFNVSKGIYQTSNFRVSPVTEVVRFPNITNLCP-FDKVFNATRFPS
A0A0U1UYX4_SARS           CSQNPLAELKCTLKCTTKSFNVSKGIYQTSNFRVAPVTEVVRFPNITNLCP-FDAVFNATRFPS
A0A4Y6GL43_9BETC          CSQDPLAELKCTLKQFDVGKGIYQTSNFRVQPTVDARFPNITNVCP-FDKVFNATRFPS
A3EXG6|BCHK9             CSQDPLSELKCTLKNFNVTKGIYQTSNFRVSPTQEVVRFPNITNRCP-FDKVFNASRFPS
P36334|CVHOC             CADSAAEELYCVTGSFDPPTGVYPLSRYRAQVAGF-VRVTQRGSYCTPPYSV--LQDPPQ
P25194|CVBV              CMSDFMSEIKCKTQSIAPPTGVYELNGYTVQPIADVYRRKPNLPNCN-IEAWLNDKSVPS
Q8JSP8|CVPIA            CKSDFMSEIKCKTLSIAPSTGVYELNGYTVQPIADVYRRIPNLPDCN-IEAWLNDKSVPS
Q9IKD1|CVRSD            CASDFMSEIMCKTSSITPPTGVYELNGYTVQPVATVYRIPDLPNCD-IEAWLNSKTVSS
Q5MQD0|CVHN1            CASSYTSEIKCKTQSMNPNTGVYDLSGYTVQPVGLVYRVRNLPDCK-IEEWLAANTVPS
                          CSSSFFSEIQCKTKSLLPNTGVYDLSGFTVKPVATVHRRIPDLPDCD-IDKWLNNFNVPS
```

Figure 3 (cont.)

```
Q0ZME7|CVHN5        CSSSFLSEIQCKTQSFAPNTGVYDLSGFTVKPVATVYRRIPNLPDCD-IDNWLNNVSVPS
P11224|CVMA5        CASSYTSEIKCKTQSMLPSTGVYELSGYTVQPVGVVYRRVANLPACN-IEEWLTARSVPS
P11225|CVMJH        CASSYISEIKCKTQSLLPSTGVYDLSGYTVQPVGVVYRRVPNLPDCK-IEEWLTAKSVPS
Q6Q1S2|CVHNL        C-DSPFEKLQCEHLQFGLQDGFYSANFLDDNVLPETYVALPIY-------------
P15423|CVH22        C-NSVINRLRCDQLSFDVPDGFYSTSPIQSVELPVSIVSLPVY--------------
A3EXD0|BCHK5        CGYDDLAQLQCSYESFEVETGVYSVSSFEASPRGEFIEQATTQ-ECD-FTP-MLTGTPPP
A3EX94|BCHK4        CGHDDLSQLHCSYTSFEVDTGVYSVSSYEASATGTFIEQPNAT-ECD-FSP-MLTGVAPQ
K9N5Q8|MERS1        CGFNDLSQIHCSYESFDVESGVYSVSSFEAKPSGSVVEQAEGV-ECD-FSP-LLSGTPPQ
A0A3Q8AKM0_SARS     CSQDPLSELKCTTKSLTVEKGIYQTSNFRVSPSTEVVRFPNITNLCP-FGQVFNASNFPS
E0XIZ3_9BETC        CSQDPLSELKCTTKSFTVEKGIYQTSNFRVTPTTEVVRFPNITQLCP-FNEVFNITSFPS
A0A2D1PXA9_SARS     CSQNPLAELKCSVKSFEIDKGIYQTSNFRVAPSKEVVRFPNITNLCP-FGEVFNATTFPS
U5WLK5_SARS         CSQNPLAELKCSVKSFEIDKGIYQTSNFRVAPSKEVVRFPNITNLCP-FGEVFNATTFPS
A0A2D1PX29_SARS     CSQNPLAELKCSVKSFEIDKGIYQTSNFRVAPSKEVVRFPNITNLCP-FGEVFNATTFPS
A0A2D1PX97_SARS     CSQNPLAELKCSVKSFEIDKGIYQTSNFRVAPSKEVVRFPNITNLCP-FGEVFNATTFPS
U5WHZ7_SARS         CSQNPLAELKCSVKSFEIDKGIYQTSNFRVAPSKEVVRFPNITNLCP-FGEVFNATTFPS
U5WI05_SARS         CSQNPLAELKCSVKSFEIDKGIYQTSNFRVAPSKEVVRFPNITNLCP-FGEVFNATTFPS
A0A023PUW9_SARS     CSQHPLAELKCSVKSFEIDKGIYQTSNFRVSPSKEVVRFPNITNLCP-FGEVFNATTFPS
A0A023PTS3_SARS     CSQHPLAELKCSVKSFDIDKGIYQTSNFRVSPSREVVRFPNITNLCP-FGEVFNATTFPS
A0A2D1PXC0_SARS     CSQNPLAELKCSVKSFEIDKGIYQTSNFRVAPSKEVVRFPNITNLCP-FGEVFNATTFPS
Q6TPE8_SARS         CSQNPLAELKCSVKSFEIDKGIYQTSNFRVVPSRDVVRFPNITNLCP-FGEVFNATKFPS
Q1T6X6_SARS         CSQNPLAELKCSVKSFEIDKGIYQTSNFRVVPSGDVVRFPNITNLCP-FGEVFNATKFPS
P59594_SARS         CSQNPLAELKCSVKSFEIDKGIYQTSNFRVVPSGDVVRFPNITNLCP-FGEVFNATKFPS
D2E1D2_SARS         CSQNPLAELKCSVKSFEIDKGIYQTSNFRVVPSGDVVRFPNITNLCP-FGEVFNATKFPS
Q6DSU4_SARS         CSQNPLAELKCSVKSFEIDKGIYQTSNFRVVPSGDVVRFPNITNLCP-FGEVFNATKFPS
Q202H8_SARS         CSQNPLAELKCSVKSFEIDKGIYQTSNFRVVPSGDVVRFPNITNLCP-FGEVFNATKFPS
Q202F2_SARS         CSQNPLAELKCSVKSFEIDKGIYQTSNFRVVPSGDVVRFPNITNLCP-FGEVFNATKFPS
D2E235_SARS         CSQNPLAELKCSVKSFEIDKGIYQTSNFRVVPSGDVVRFPNITNLCP-FGEVFNATKFPS
Q202H5_SARS         CSQNPLAELKCSVKSFEIDKGIYQTSNFRVVPSGDVVRFPNITNLCP-FGEVFNATKFPS
A4ZF30_SARS         CSQNPLAELKCSVKSFEIDKGIYQTSNFRVVPSGDVVRFPNITNLCP-FGEVFNATKFPS
A4ZF29_SARS         CSQNPLAELKCSVKSFEIDKGIYQTSNFRVVPSGDVVRFPNITNLCP-FGEVFNATKFPS
Q4JDP0_SARS         CSQNPLAELKCSVKSFEIDKGIYQTSNFRVVPSGDVVRFPNITNLCP-FGEVFNATKFPS
Q5GDJ7_SARS         CSQNPLAELKCSVKSFEIDKGIYQTSNFRVVPSGDVVRFPNITNLCP-FGEVFNATKFPS
Q3ZTC5_SARS         CSQNPLAELKCSVKSFEIDKGIYQTSNFRVVPSGDVVRFPNITNLCP-FGEVFNATKFPS
Q4JDN4_SARS         CSQNPLAELKCSVKSFEIDKGIYQTSNFRVVPSGDVVRFPNITNLCP-FGEVFNATKFPS
Q3ZTE0_SARS         CSQNPLAELKCSVKSFEIDKGIYQTSNFRVVPSGDVVRFPNITNLCP-FGEVFNATKFPS
Q4JDP2_SARS         CSQNPLAELKCSVKSFEIDKGIYQTSNFRVVPSGDVVRFPNITNLCP-FGEVFNATKFPS
```

Figure 3 (cont.)

```
Spike_Fragment             VYAWNRKRISNCVAD SVLYNS-ASFSTFKCYGVSPTKLNDLCFTNVYADSFV RGDEVR
P0DTC2|SARS2               VYAWNRKRISNCVAD SVLYNS-ASFSTFKCYGVSPTKLNDLCFTNVYADSFV RGDEVR
A0A6B9WHD3_SARS            VYAWNRKRISNCVADYSVLYNS-ASFSTFKCYGVSPTKLNDLCFTNVYADSFVITGDEVR
A0A6G9KP06_9BETC           VYAWNRKRISNCVADYSVLYNS-TSFSTFKCYGVSPTKLNDLCFTNVYADSFVVKGDEVR
A0A2D1PX05_SARS/282-593    VYAWERTKISDCVADYTVLYNS-TSFSTFKCYGVSPSKLIDLCFTSVYADTFLIRSSEVR
A0A2D1PX88_SARS/282-593    VYAWERTKISDCVADYTVLYNS-TSFSTFKCYGVSPSKLIDLCFTSVYADTFLIRSSEVR
A0A2D1PX44_SARS/282-593    VYAWERTKISDCVADYTVLYNS-TSFSTFKCYGVSPSKLIDLCFTSVYADTFLIRSSEVR
D2DJW4_SARS/282-593        VYAWERTKISDCVADYTVLYNS-TSFSTFKCYGVSPSKLIDLCFTSVYADTFLIRSSEVR
A0A2D1PX73_SARS/282-593    VYAWERTKISDCVADYTVLYNS-TSFSTFKCYGVSPSKLIDLCFTSVYADTFLIRSSEVR
Q3I5J5|BCRP3/282-593       VYAWERTKISDCVADYTVLYNS-TSFSTFKCYGVSPSKLIDLCFTSVYADTFLIRSSEVR
Q0Q475|BC279/282-593       VYAWERTKISDCVADYTVLYNS-TSFSTFKCYGVSPSKLIDLCFTSVYADTFLIRSSEVR
Q0QDX9_SARS/282-593        VYAWERTKISDCVADYTVLYNS-TSFSTFKCYGVSPSKLIDLCFTSVYADTFLIRSSEVR
Q3LZX1|BCHK3               VYAWERTKISDCVADYTVLYNS-TSFSTFKCYGVSPSKLIDLCFTSVYADTFLIRSSEVR
A0A096XNM6_SARS            VYAWERTKISDCVADYTVLYNS-TSFSTFKCYGVSPSKLIDLCFTSVYADTFLIRSSEVR
A0A2D1PX86_SARS            VYAWERTKISDCVADYTVLYNS-TSFSTFKCYGVSPSKLIDLCFTSVYADTFLIRSSEVR
A0A0U1WHJ8_SARS            VYAWERTKISDCVADYTVLYNS-TSFSTFKCYGVSPSKLIDLCFTSVYADTFLIRSSEVR
D5HJU5_BCHK3               VYAWERTKISECVADYTVLYNS-TSFSTFKCYGVSPSKLIDLCFTSVYADTFLIRSSEVR
A0A0U1WHI2_SARS            VYAWERTKISDCVADYTVLYNS-TSFSTFKCYGVSPSKLIDLCFTSVYADTFLIRSSEVR
R9QTA0_SARS                VYAWERTKISDCVADYTVLYNS-TSFSTFKCYGVSPSKLIDLCFTSVYADTFLIRSSEVR
R9QTH3_SARS/282-593        VYAWERTKISDCVADYTVLYNS-TLFSTFKCYGVSPSKLIDLCFTSVYADTFLIRFSEVR
A0A1W5YKT9_9NIDO           VYAWERTKISDCVADYTAFYNS-TSFSTFNCYGVSPSKLIDLCFTSVYADTFLIRFSEVR
A0A0U1WJY8_SARS            VYAWERVKISNCVADYTVFYNS-TSFSTFNCYGVSPSKLIDLCFTSVYADTFLIRFSEVR
A0A2D1PX37_SARS            VYAWERTKISDCVADYTVFYNS-TSFSTFNCYGVSPSKLIDLCFTSVYADTFLIRFSEVR
Q0QDZ0_SARS/282-593        VYAWERTKISDCVADYTVFYNS-TSFSTFNCYGVSPSKLIDLCFTSVYADTFLIRFSEVR
A0A0U1WHH0_SARS/282-593    VYAWERTKISDCVADYTVFYNS-TSFSTFNCYGVSPSKLIDLCFTSVYADTFLIRFSEVR
Q0Q484_SARS/282-593        VYAWERTKISDCVADYTVFYNS-TSFSTFNCYGVSPSKLIDLCFTSVYADTFLIRFSEVR
A0A0K1Z074_SARS/282-593    VYAWERTKISDCVADYTVFYNS-TSFSTFNCYGVSPSKLIDLCFTSVYADTFLIRFSEVR
A0A0U1UYX4_SARS            VYAWERTKISDCVADYTVLYNS-TSFSTFKCYGVSPSKLIDLCFTSVYADTFLIRFSEVR
A0A4Y6GL43_9BETC           VYAWERIKISDCVADYTVLYNS-TSFSTFKCYGVSPSKLIDLCFTSVYADTFLIRSSEVR
A3EXG6|BCHK9               PVVWRRYMLYDCVFDFTVVDS-LPTHQLQCYGVSPRRLASMCYGSVTLDVMRINETHLN
P36334|CVHOC               PLNWERKTFSNCNFNMSSLMSF-IQADSFTCNNIDAAKIYGMCFSSITIDKFAIPNGRKV
P25194|CVBV                PLNWERKTFSNCNFNMSSLMSF-IQADSFTCNNIEAAKIYGMCFSSITIDKFAIPNGRKV
Q8JSP8|CVPIA               PLNWERKIFSNCNFNMGRLMSF-IQADSFGCNNIDASRLYGMCFGSITIDKFAIPNSRKV
Q9IKD1|CVRSD               PLNWERKTFQNCNFNLSSLLRF-VQAESLSCSNIDASKVYGMCFGSISIDKFAIPNSRRV
Q5MQD0|CVHN1               PLNWERKIFSNCNFNLSTLLRL-VHTDSFSCNNFDESKIYGSCFKSIVLDKFAIPNSRRS
```

Figure 3 (cont.)

| | | |
|---|---|---|
| Q0ZME7\|CVHN5 | PLNWERRIFSNCNFNLSTLLRL-VHVDSFSCNNLDKSKIFGSCFNSITVDKFAIPNRRRD |
| P11224\|CVMA5 | PLNWERKTFQNCNFNLSSLLRY-VQAESLFCNNIDASKVYGRCFGSISVDKFAVPRSRQV |
| P11225\|CVMJH | PLNWERRTFQNCNFNLSSLLRY-VQAESLSCNNIDASKVYGMCFGSVSVDKFAIPRSRQI |
| Q6Q1S2\|CVHNL | ---Y-QHTDIN-----FT-----ATASFGGSCYVCKPHQVN------ISLNG--------NT |
| P15423\|CVH22 | ---H-KHTFIV----LY--VDFKPQSGGGKCFNCYPAGVN-----ITLANFNET---KG |
| A3EXD0\|BCHK5 | IYNFKRLVFTNCNYNLTKLLSL-FQVSEFSCHQVSPSSLATGCYSSLTVDYFAYSTDMSS |
| A3EX94\|BCHK4 | VYNFKRLVFSNCNYNLTKLLSL-FAVDEFSCNGISPDSIARGCYSTLTVDYFAYPLSMKS |
| K9N5Q8\|MERS1 | VYNFKRLVFTNCNYNLTKLLSL-FSVNDFTCSQISPAAIASNCYSSLILDYFSYPLSMKS |
| A0A3Q8AKM0_SARS | VYAWERLRISDCVADYAVLYNSSSFSTFKCYGVSPTKLNDLCFSSVYADYFVVKGDDVR |
| E0XIZ3_9BETC | VYAWERMRITNCVADYSVLYNSSASFSTFQCYGVSPTKLNDLCFSSVYADYFVVKGDDVR |
| A0A2D1PXA9_SARS | VYAWERKRISNCVADYSVLYNS-TSFSTFKCYGVSATKLNDLCFSNVYADSFVVKGDDVR |
| U5WLK5_SARS | VYAWERKRISNCVADYSVLYNS-TSFSTFKCYGVSATKLNDLCFSNVYADSFVVKGDDVR |
| A0A2D1PX29_SARS | VYAWERKRISNCVADYSILYNS-TSFSTFKCYGVSATKLNDLCFSNVYADSFVVKGDDVR |
| A0A2D1PX97_SARS | VYAWERKRISNCVADYSVLYNS-TSFSTFKCYGVSATKLNDLCFSNVYADSFVVKGDDVR |
| U5WHZ7_SARS | VYAWERKRISNCVADYSVLYNS-TSFSTFKCYGVSATKLNDLCFSNVYADSFVVKGDDVR |
| U5WI05_SARS | VYAWERKRISNCVADYSVLYNS-TSFSTFKCYGVSATKLNDLCFSNVYADSFVVKGDDVR |
| A0A023PUW9_SARS | VYAWERKRISNCVADYSVLYNS-TSFSTFKCYGVSAIKLNDLCFSNVYADSFVVKGDDVR |
| A0A023PTS3_SARS | VYAWERKRISNCVADYSVLYNS-TSFSTFKCYGVSATKLNDLCFSNVYADSFVVKGDDVR |
| A0A2D1PXC0_SARS | VYAWERKRISNCVADYSVLYNS-TSFSTFKCYGVSATKLNDLCFSNVYADSFVVKGDDVR |
| Q6TPE8_SARS | VYAWERKRISNCVADYSVLYNS-TFFSTFKCYGVSATKLNDLCFSNVYADSFVVKGDDVR |
| Q1T6X6_SARS | VYAWERKKISNCVADYSVLYNS-TFFSTFKCYGVSATKLNDLCFSNVYADSFVVKGDDVR |
| P59594_SARS | VYAWERKKISNCVADYSVLYNS-TFFSTFKCYGVSATKLNDLCFSNVYADSFVVKGDDVR |
| D2E1D2_SARS | VYAWERKKISNCVADYSVLYNS-TFFSTFKCYGVSATKLNDLCFSNVYADSFVVKGDDVR |
| Q6DSU4_SARS | VYAWERKKISNCVADYSVLYNS-TFFSTFKCYGVSATKLNDLCFSNVYADSFVVKGDDVR |
| Q202H8_SARS | VYAWERKKISNCVADYSVLYNS-TFFSTFKCYGVSATKLNDLCFSNVVDSFVVKGDDVR |
| Q202F2_SARS | VYAWERKKISNCVVDYSVLYNS-TFFSTFKCYGVSATKLNDLCFSNVYADSFVVKGDDVR |
| D2E235_SARS | VYAWERKKISNCVADYSVLYNS-TFFSTFKCYGVSATKLNDLCFSNVYADSFVVKGDDVR |
| Q202H5_SARS | VYAWERKKISNCVADYSVLYNS-TFFSTFKCYGVSATKLNDLCFSNVYADSFVVKGDDVR |
| A4ZF30_SARS | VYAWERKKISNCVADYSVLYNS-TFFSTFKCYGVSATKLNDLCFSNVYADSFVVKGDDVR |
| A4ZF29_SARS | VYAWERKKISNCVADYSVLYNS-TFFSTFKCYGVSATKLNDLCFSNVYADSFVVKGDDVR |
| Q4JDP0_SARS | VYAWERKRISNCVADYSVLYNS-TSFSTFKCYGVSATKLNDLCFSNVYADSFVVKGDDVR |
| Q5GDJ7_SARS | VYAWERKRISNCVADYSVLYNS-TSFSTFKCYGVSATKLNDLCFSNVYADSFVVKGDDVR |
| Q3ZTC5_SARS | VYAWERKRISNCVADYSVLYNS-TSFSTFKCYGVSATKLNDLCFSNVYADSFVVKGDDVR |
| Q4JDN4_SARS | VYAWERKRISNCVADYSVLYNS-TSFSTFKCYGVSATKLNDLCFSNVYADSFVVKGDDVR |
| Q3ZTE0_SARS | VYAWERKRISNCVADYSVLYNS-TSFSTFKCYGVSATKLNDLCFSNVYADSFVVKGDDVR |
| Q4JDP2_SARS | VYAWERKRISNCVADYSVLYNS-TSFSTFKCYGVSATKLNDLCFSNVYADSFVVKGDDVR |

Figure 3 (cont.)

```
Spike_Fragment              QIAPGQTGKIADYNYKLPDDFTGCVIAWNSNNL--DSKV--GGNYNYLYRLFRKSNLK--
P0DTC2|SARS2                QIAPGQTGKIADYNYKLPDDFTGCVIAWNSNNL--DSKV--GGNYNYLYRLFRKSNLK--
A0A6B9WHD3_SARS             QIAPGQTGKIADYNYKLPDDFTGCVIAWNSKHI--DAKE--GGNFNYLYRLFRKANLK--
A0A6G9KP06_9BETC            QIAPGQTGVIADYNYKLPDDFTGCVIAWNSVKQ--DALT--GGNYGYLYRLFRKSKLK--
A0A2D1PX05_SARS/282-593     QVAPGETGVIADYNYKLPDDFTGCVIAWNTAQQ--DKG------QYYRSSRKTKLK--
A0A2D1PX88_SARS/282-593     QVAPGETGVIADYNYKLPDDFTGCVIAWNTAKQ--DQG------QYYRSSRKTKLK--
A0A2D1PX44_SARS/282-593     QVAPGETGVIADYNYKLPDDFTGCVIAWNTAKQ--DQG------QYYRSSRKTKLK--
D2DJW4_SARS/282-593         QVAPGETGVIADYNYKLPDDFTGCVIAWNTAKQ--DQG------QYYRSSRKTKLK--
A0A2D1PX73_SARS/282-593     QVAPGETGVIADYNYKLPDDFTGCVIAWNTAKQ--DQG------QYYRSSRKTKLK--
Q3I5J5|BCRP3/282-593        QVAPGETGVIADYNYKLPDDFTGCVIAWNTAKQ--DQG------QYYRSHRKTKLK--
Q0Q475|BC279/282-593        QVAPGETGVIADYNYKLPDDFTGCVIAWNTAQQ--DQG------QYYRSYRKEKLK--
Q0QDX9_SARS/282-593         QVAPGETGVIADYNYKLPDDFTGCVIAWNTAQQ--DQG------QYYRSYRKEKLK--
Q3LZX1|BCHK3                QVAPGETGVIADYNYKLPDDFTGCVIAWNTAKH--DTG------NYYRSHRKTKLK--
A0A096XNM6_SARS             QVAPGETGVIADYNYKLPDDFTGCVIAWNTAKQ--DIG------NYYRSHRKTKLK--
A0A2D1PX86_SARS             QVAPGETGVIADYNYKLPDDFTGCVIAWNTAKQ--DTG------HYYRSHRKTKLK--
A0A0U1WHJ8_SARS             QVAPGETGVIADYNYKLPDDFTGCVIAWNTAKQ--DTG------NYYRSHRKTKLK--
D5HJU5_BCHK3                QVAPGETGVIADYNYKLPDDFTGCVIAWNTAKQ--DTG------NYYRSHRKTKLK--
A0A0U1WHI2_SARS             QVAPGETGVIADYNYKLPDDFTGCVIAWNTAKQ--DTG------YYYRSHRKTKLK--
R9QTA0_SARS                 QVAPGETGVIADYNYKLPDDFTGCVIAWNTANQ--DQG------QYYRSSRKEKLK--
R9QTH3_SARS/282-593         QIAPGETGVIADYNYKLPDEFTGCVIAWNTANQ--DRG------QYYRSSRKTKLK--
A0A1W5YKT9_9NIDO            QVAPGETGVIADYNYRLPDDFTGCVIAWNTANQ--DVG------SYFYRSHRSTKLK--
A0A0U1WJY8_SARS             QVAPGETGVIADYNYKLPDDFTGCVIAWNTANQ--DVG------SYFYRSHRSTKLK--
A0A2D1PX37_SARS             QVAPGETGVIADYNYKLPDDFTGCVIAWNTAKQ--DVG------SYFYRSHRSSKLK--
Q0QDZ0_SARS/282-593         QVAPGQTGVIADYNYKLPDDFTGCVIAWNTAKQ--DVG------SYFYRSHRSSKLK--
A0A0U1WHH0_SARS/282-593     QVAPGQTGVIADYNYKLPDDFTGCVIAWNTAKQ--DVG------SYFYRSHRSSKLK--
Q0Q484_SARS/282-593         QVAPGQTGVIADYNYKLPDDFIGCVIAWNTAKQ--DVG------SYFYRSHRSSKLK--
A0A0K1Z074_SARS/282-593     QVAPGQTGVIADYNYKLPDDFTGCVIAWNTAKY--DVG------SYFYRSHRSSKLK--
A0A0U1UYX4_SARS             QVAPGQTGVIADYNYKLPDDFTGCVIAWNTAKQ--DVG------SYFYRSHRSSKLK--
A0A4Y6GL43_9BETC            QVAPGETGVIADYNYKLPDDFTGCVIAWNTAKQ--DTG------SYYYRSHRKTKLK--
A3EXG6|BCHK9                NLFNRVPDTFSLYNYALPDNFYGCLHAFYLNST--APY--------AVANRFPIK--
P36334|CVHOC                DLQLGNLGYLQSFNYRIDTTATSCQLYYNLPAANVSVSRFNPSTWNKRFGFIEDSVFKPR
P25194|CVBV                 DLQLGNLGYLQSFNYRIDTTAASCQLYYNLPAANVSVSRFNPSTWNRRFGFTEQSVFKPQ
Q8JSP8|CVPIA                DLQVGKSGYLQSFNYKIDTAVSSCQLYYSLPAANVSVTHYNPSSWNRRYGFINQSF----
Q9IKD1|CVRSD                DLQLGKSGLLQSFNYKIDTRATSCQLYYSLAQDNVTVINHNPSSWNRRYGFNDVATFH--
Q5MQD0|CVHN1                DLQLGSSGFLQSSNYKIDTTSSSCQLYYSLPAINVTINNYNPSSWNRRYGFNNFN-----
Q0ZME7|CVHN5                DLQLGSSGFLQSSNYKIDISSSSCQLYYSLPLVNVTINNFNPSSWNRRYGFGSFN-----
```

Figure 3 (cont.)

```
P11224|CVMA5         DLQLGNSGFLQTANYKIDTAATSCQLHYTLPKNNVTINNHNPSSWNRRYGFNDAGVFG----
P11225|CVMJH         DLQIGNSGFLQTANYKIDTAATSCQLYYSLPKNNVTINNYNPSSWNRRYGFK--------
Q6Q1S2|CVHNL         SVCVRTSHFSIRYIYNR-----------------VKSGSPGDSSWHIYLKSGTCPFSF----
P15423|CVH22         PLCVDTSHFTTKYVAVY-------------A-----NVGRWSASINTGNCPFSF----
A3EXD0|BCHK5         YLQPGSAGAIVQFNYKQDFSNPTCRVLATVPQNLTTITK---PSNYAYLTE----CYKTS---
A3EX94|BCHK4         YIRPGSAGNIPLYNYKQSFANPTCRVMASVLANV-TITK--PHAYGYISK----CSRLT---
K9N5Q8|MERS1         DLSVSSAGPISQFNYKQSFSNPTCLILATVPHNLTTITK--PLKYSYINK----CSRFL---
A0A3Q8AKM0_SARS      QIAPAQTGVIADYNYKLPDDFTGCVLAWNTNSV--DSKS--GN--NFYRLFRHGKIK---
E0XIZ3_9BETC         QIAPAQTGVIADYNYKLPDDFTGCVIAWNTNSL--DS-----SN--EFFYRRFRHGKIK---
A0A2D1PXA9_SARS      QIAPGQTGVIADYNYKLPDDFLGCVLAWNTNSK--DSST--SGNYNYLYRWVRRSKLN---
U5WLK5_SARS          QIAPGQTGVIADYNYKLPDDFLGCVLAWNTNSK--DSST--SGNYNYLYRWVRRSKLN---
A0A2D1PX29_SARS      QIAPGQTGVIADYNYKLPDDFLGCVLAWNTNSK--DSST--SGNYNYLYRWVRRSKLN---
A0A2D1PX97_SARS      QIAPGQTGVIADYNYKLPDDFTGCVLAWNTRNI--DATQ--TGNYNYKYRSLRHGKLR---
U5WHZ7_SARS          QIAPGQTGVIADYNYKLPDDFTGCVLAWNTRNI--DATQ--TGNYNYKYRSLRHGKLR---
U5WI05_SARS          QIAPGQTGVIADYNYKLPDDFTGCVLAWNTRNI--DATQ--TGNYNYKYRSLRHGKLR---
A0A023PUW9_SARS      QIAPGQTGVIADYNYKLPDDFMGCVLAWNTRNI--DATS--SGNFNYKYRSLRHGKLR---
A0A023PTS3_SARS      QIAPGQTGVIADYNYKLPDDFMGCVLAWNTRNI--DATS--SGNFHYKYRSLRHGKLR---
A0A2D1PXC0_SARS      QIAPGQTGVIADYNYKLPDDFMGCVLAWNTRNI--DATS--TGNYNYKYRYLRHGKLR---
Q6TPE8_SARS          QIAPGQTGVIADYNYKLPDDFMGCVLAWNTRNI--DATS--TGNYNYKYRYLRHGKLR---
Q1T6X6_SARS          QIAPGQTGVIADYNYKLPDDFMGCVLAWNTRNI--DATS--TGNYNYKYRCLRHGKLR---
P59594_SARS          QIAPGQTGVIADYNYKLPDDFMGCVLAWNTRNI--DATS--TGNYNYKYRYLRHGKLR---
D2E1D2_SARS          QIAPGQTGVIADYNYKLPDDFMGCVLAWNTRNI--DATS--TGNYNYKYRYLRHGKLR---
Q6DSU4_SARS          QIAPGQTGVIADYNYKLPDDFMGCVLAWNTRNI--DATS--TGNYNYKYRYLKHGKLR---
Q202H8_SARS          QIAPGQTGVIADYNYKLPDDFMGCVLAWNTRNI--DATS--TGNYNYKYRYLRHGKLR---
Q202F2_SARS          QIAPGQTGVIADYNYKLPDDFMGCVLAWNTRNI--DATS--TGNYNYKYRYLRHGKLR---
D2E235_SARS          QIAPGQTGVIADYNYKLPDDFMGCVLAWNTRNI--DATS--TGNHNYKYRYLRHGKLR---
Q202H5_SARS          QIAPGQTGVIADYNYKLPDDFMGCVLAWNTRNI--DATS--TGNYNYKYRYLRHGKLR---
A4ZF30_SARS          QIAPGQTGVIADYNYKLPDDFMGCVLAWNTRNI--DATS--TGNYNYKYRYLRHGKLR---
A4ZF29_SARS          QIAPGQTGVIADYNYKLPDDFMGCVLAWNTRNI--DATS--TGNYNYKYRYLRHGKLR---
Q4JDP0_SARS          QIAPGQTGVIADYNYKLPDDFMGCVLAWNTRNI--DATS--TGNYNYKYRYLRHGKLR---
Q5GDJ7_SARS          QIAPGQTGVIADYNYKLPDDFMGCVLAWNTRNI--DATS--TGNYNYKYRYLRHGKLR---
Q3ZTC5_SARS          QIAPGQTGVIADYNYKLPDDFMGCVLAWNTRNI--DATS--TGNYNYKYRYLRHGKLR---
Q4JDN4_SARS          QIAPGQTGVIADYNYKLPDDFMGCVLAWNTRNI--DATS--TGNYNYKHRYLRHGKLR---
Q3ZTE0_SARS          QIAPGQTGVIADYNYKLPDDFMGCVLAWNTRNI--DATS--TGNYNYKYRYLRHGKLR---
Q4JDP2_SARS          QIAPGQTGVIADYNYKLPDDFMGCVLAWNTRNI--DATS--TGNYNYKXRYLRHGKLR---
```

Figure 3 (cont.)

```
Spike_Fragment               P-----FERDISTEIYQAGST--PCNGVEGF-------N----
P0DTC2|SARS2                 P-----FERDISTEIYQAGST--PCNGVEGF-------N----
A0A6B9WHD3_SARS              P-----FERDISTEIYQAGSK--PCNGQTGL-------N----
A0A6G9KP06_9BETC             P-----FERDISTEIYQAGST--PCNGQVGL-------N----
A0A2D1PX05_SARS/282-593      P-----FERDLSSD--------E-------N----
A0A2D1PX88_SARS/282-593      P-----FERDLSSD--------E-------N----
A0A2D1PX44_SARS/282-593      P-----FERDLTSD--------E-------N----
D2DJW4_SARS/282-593          P-----FERDLTSD--------E-------N----
A0A2D1PX73_SARS/282-593      P-----FERDLSSD--------E-------N----
Q3I5J5|BCRP3/282-593         P-----FERDLSSD--------E-------N----
Q0Q475|BC279/282-593         P-----FERDLSSD--------E-------N----
Q0QDX9_SARS/282-593          P-----FERDLSSD--------E-------N----
Q3LZX1|BCHK3                 P-----FERDLSSDD--------G-------N----
A0A096XNM6_SARS              P-----FERDLSSDD--------G-------N----
A0A2D1PX86_SARS              P-----FERDLSSDD--------G-------N----
A0A0U1WHJ8_SARS              P-----FERDLSSDD--------G-------N----
D5HJU5_BCHK3                 P-----FERDLSSDD--------G-------N----
A0A0U1WHI2_SARS              P-----FERDLSSDD--------G-------N----
R9QTA0_SARS                  P-----FERDLSSD--------E-------N----
R9QTH3_SARS/282-593          P-----FERDLSSD--------E-------N----
A0A1W5YKT9_9NIDO             P-----FERDLSSD--------E-------N----
A0A0U1WJY8_SARS              P-----FERDLSSD--------E-------N----
A0A2D1PX37_SARS              P-----FERDLSSD--------E-------N----
Q0QDZ0_SARS/282-593          P-----FERDLSSE--------E-------N----
A0A0U1WHH0_SARS/282-593      P-----FERDLSSE--------E-------N----
Q0Q484_SARS/282-593          P-----FERDLSSV--------E-------E----
A0A0K1Z074_SARS/282-593      P-----FERDLSSE--------E-------N----
A0A0U1UYX4_SARS              P-----FERDLSSE--------E-------N----
A0A4Y6GL43_9BETC             P-----FERDLSSDD--------G-------N----
A3EXG6|BCHK9                 P-------GGRQSNSAFIDT--------VINA--------A----
P36334|CVHOC                 PAGVLTNHDVVYAQHCFKAPKNFCPCKLNGS-CVGSGPGK-----NNGIGTCPAGTNYLT
P25194|CVBV                  PVGVFTHHDVVYAQHCFKAPTNFCPCKLDGSLCVGNGPGIDAGYKNSGIGTCPAGTNYLT
Q8JSP8|CVPIA                 ---GSRGLHDAVYSQQCFNTPNTYCPCRTSQ--CIG------GAGTGTCPVGTTVRK
Q9IKD1|CVRSD                 ----SGEHDVAYAEACFTVGASYCPCAKPSTVYSCVT-----GKPKSANCPTGTSNRE
Q5MQD0|CVHN1                 -----LSSHSVVYSRYCFSVNNTFCPCAKPSFASSCKS-------HKPPSASCPIGTNYRS
Q0ZME7|CVHN5                 -----LSSYDVVYSDHCFSVNSDFCPCADPSVVNSCAK-------SKPPSAICPAGTKYRH
```

Figure 3 (cont.)

```
P11224|CVMA5        ----KNQHDVVYAQQCFTVRSSYCPCAQPDIVSPCTT-----------QTK--------------
P11225|CVMJH        ---------------------------------------------------------------
Q6Q1S2|CVHNL        --SKLN-NFQKFKTICFSTVEVPGSCNFPLEA-----------------TWHY-----------
P15423|CVH22        --GKVN-NFVKFGSVCFSLKDIPGGCAMPIVA-----------------NWAY-----------
A3EXD0|BCHK5        A-----YG---KNYLYNAPGAYTPCLSLASR------------------GFSTKYQS-------
A3EX94|BCHK4        G-------ANQDVETPLYINPGEYSICRDFSPG----------------GFSEDGQVFKR
K9N5Q8|MERS1        S-------DDR-TEVPQLVNANQYSPCVSIVPS----------------TVWEDGDYYRK
A0A3Q8AKM0_SARS     P-----YERDISNVLYNSAGG--TCSSISQL------------------G-------------
E0XIZ3_9BETC        P-----YGRDLSNVLFNPSGG--TCSA-EGL------------------N-------------
A0A2D1PXA9_SARS     P-----YERDLSNDIYSPGGQ--SCSA-IGP------------------N-------------
U5WLK5_SARS         P-----YERDLSNDIYSPGGQ--SCSA-VGP------------------N-------------
A0A2D1PX29_SARS     P-----YERDLSNDIYSPGGQ--SCSA-VGP------------------N-------------
A0A2D1PX97_SARS     P-----FERDISNVPFSPDGK--PCTP-PAF------------------N-------------
U5WHZ7_SARS         P-----FERDISNVPFSPDGK--PCTP-PAF------------------N-------------
U5WI05_SARS         P-----FERDISNVPFSPDGK--PCTP-PAF------------------N-------------
A0A023PUW9_SARS     P-----FERDISNVPFSPDGK--PCTP-PAF------------------N-------------
A0A023PTS3_SARS     P-----FERDISNVPFSPDGK--PCTP-PAF------------------N-------------
A0A2D1PXC0_SARS     P-----FERDISNVPFSPDGK--PCTP-PAF------------------N-------------
Q6TPE8_SARS         P-----FERDISNVPFSPDGK--PCTP-PAL------------------N-------------
Q1T6X6_SARS         P-----FERDISNVPFSPDGK--PCTP-PAF------------------N-------------
P59594_SARS         P-----FERDISNVPFSPDGK--PCTP-PAL------------------N-------------
D2E1D2_SARS         P-----FERDISNVPFSPDGK--PCTP-PAL------------------N-------------
Q6DSU4_SARS         P-----FERDISNVPFSPDGK--PCTP-PAL------------------N-------------
Q202H8_SARS         P-----FERDISNVPFSPDGK--PCTP-PAL------------------N-------------
Q202F2_SARS         P-----FERDISNVPFSPDGK--PCTP-PAL------------------N-------------
D2E235_SARS         P-----FERDISNVPFSPDGK--PCTP-PAL------------------N-------------
Q202H5_SARS         P-----FERDISNVPFSPNGK--PCTP-PAL------------------N-------------
A4ZF30_SARS         P-----FERDISNVPFSPDGK--PCTP-PAP------------------N-------------
A4ZF29_SARS         P-----FERDISNVPFSPDGK--PCTP-PAP------------------N-------------
Q4JDP0_SARS         P-----FERDISNVPFSPDGK--PCTP-PAP------------------N-------------
Q5GDJ7_SARS         P-----FERDISNVPFSPDGK--PCTP-PAP------------------N-------------
Q3ZTC5_SARS         P-----FERDISNVPFSPDGK--PCTP-PAP------------------N-------------
Q4JDN4_SARS         P-----FERDISNVPFSPDGK--PCTP-PAP------------------N-------------
Q3ZTE0_SARS         P-----FERDISNVPFSSDGK--PCTP-PAP------------------N-------------
Q4JDP2_SARS         P-----FERDISNVPFSPXGK--PCTP-PAP------------------N-------------
```

Figure 3 (cont.)

```
Spike_Fragment     CYFP--------------LQSYGFQPT--------------NGVGYQPYR------
P0DTC2|SARS2       CYFP--------------LQSYGFQPT--------------NGVGYQPYR------
A0A6B9WHD3_SARS    CYYP--------------LYRYGFYPT--------------DGVGHQPYR------
A0A6G9KP06_9BETC   CYYP--------------LERYGFHPT--------------TGVNYQPFR------
A0A2D1PX05_SARS    GVRT--------------LSTYDFYPT--------------VPIEYQATR------
A0A2D1PX88_SARS    GVRT--------------LSTYDFYPT--------------VPIEYQATR------
A0A2D1PX44_SARS    GVRT--------------LSTYDFYPN--------------VPIEYQATR------
D2DJW4_SARS        GVRT--------------LSTYDFYPN--------------VPIEYQATR------
A0A2D1PX73_SARS    GVRT--------------LSTYDFYPT--------------VPIEYQATR------
Q3I5J5|BCRP3       GVRT--------------LSTYDFYPS--------------VPVAYQATR------
Q0Q475|BC279       GVYT--------------LSTYDFYPS--------------IPVEYQATR------
Q0QDX9_SARS        GVYT--------------LSTYDFYPS--------------IPVEYQATR------
Q3LZX1|BCHK3       GVYT--------------LSTYDFNPN--------------VPVAYQATR------
A0A096XNM6_SARS    GVYT--------------LSTYDFNPN--------------VPVAYQATR------
A0A2D1PX86_SARS    GVYT--------------LSTYDFNPN--------------VPVAYQATR------
A0A0U1WHJ8_SARS    GVYT--------------LSTYDFNPN--------------VPVAYQATR------
D5HJU5_BCHK3       GVYT--------------LSTYDFNPN--------------VPVAYQATR------
A0A0U1WHI2_SARS    GVYT--------------LSTYDFNPN--------------VPVAYQATR------
R9QTA0_SARS        GVYT--------------LSTYDFYPS--------------VPLDYQATR------
R9QTH3_SARS        GVYT--------------LSTYDFYPS--------------VPLEYQATR------
A0A1W5YKT9_9NIDO   GVRT--------------LSTYDFNPY--------------VPLDYQATR------
A0A0U1WJY8_SARS    GVRT--------------LSTYDFNPN--------------VPLDYQATR------
A0A2D1PX37_SARS    GVRT--------------LSTYDFNPN--------------VPLDYQATR------
Q0QDZ0_SARS        GVRT--------------LSTYDFNQN--------------VPLEYQATR------
A0A0U1WHH0_SARS    GVRT--------------LSTYDFNQY--------------VPLEYQATR------
Q0Q484_SARS        NGRT--------------LSTYDFNQN--------------VPLEYQATR------
A0A0K1Z074_SARS    GART--------------LSTYDFNQN--------------VPLEYQATR------
A0A0U1UYX4_SARS    GVLT--------------LSTYDFNQN--------------VPLEYQATR------
A0A4Y6GL43_9BETC   GVYT--------------LSTYDFNPN--------------VPVAYQATR------
A3EXG6|BCHK9       HYS--------------------------------------PFSY-VYG------
P36334|CVHOC       C-----------DNLCTPDPITF--TGTYKCPQTKSLVGIGEHCSGLAVKSDYCGGN--
P25194|CVBV        C------HNAAQCDCLCTPDPITSKSTGPYKCPQTKYLVGIGEHCSGLAIKSDYCGGN--
Q8JSP8|CVPIA       CFAAV--TNATKCTCWCQPDPSTYKGVNAWTCPQSKVSIQPGQHCPGLGVEDDCSGN--
Q9IKD1|CVRSD       CNVQAS-GFKSKCDCTCNPSPLTTY----DPRCLQARSMLGVGDHCEGLGILEDKCGGSN-
Q5MQD0|CVHN1       CESTTVLDHTDWCRCSCLPDPITAYD---PRSCSQKKSLVGVGEHCAGFGVDEEKCGVLDG
Q0ZME7|CVHN5       CDLDTTLYVKNWCRCSCLPDPISTYS---PNTCPQKKVVVGIGEHCPGLGINEEKCGTQL-
```

Figure 3 (cont.)

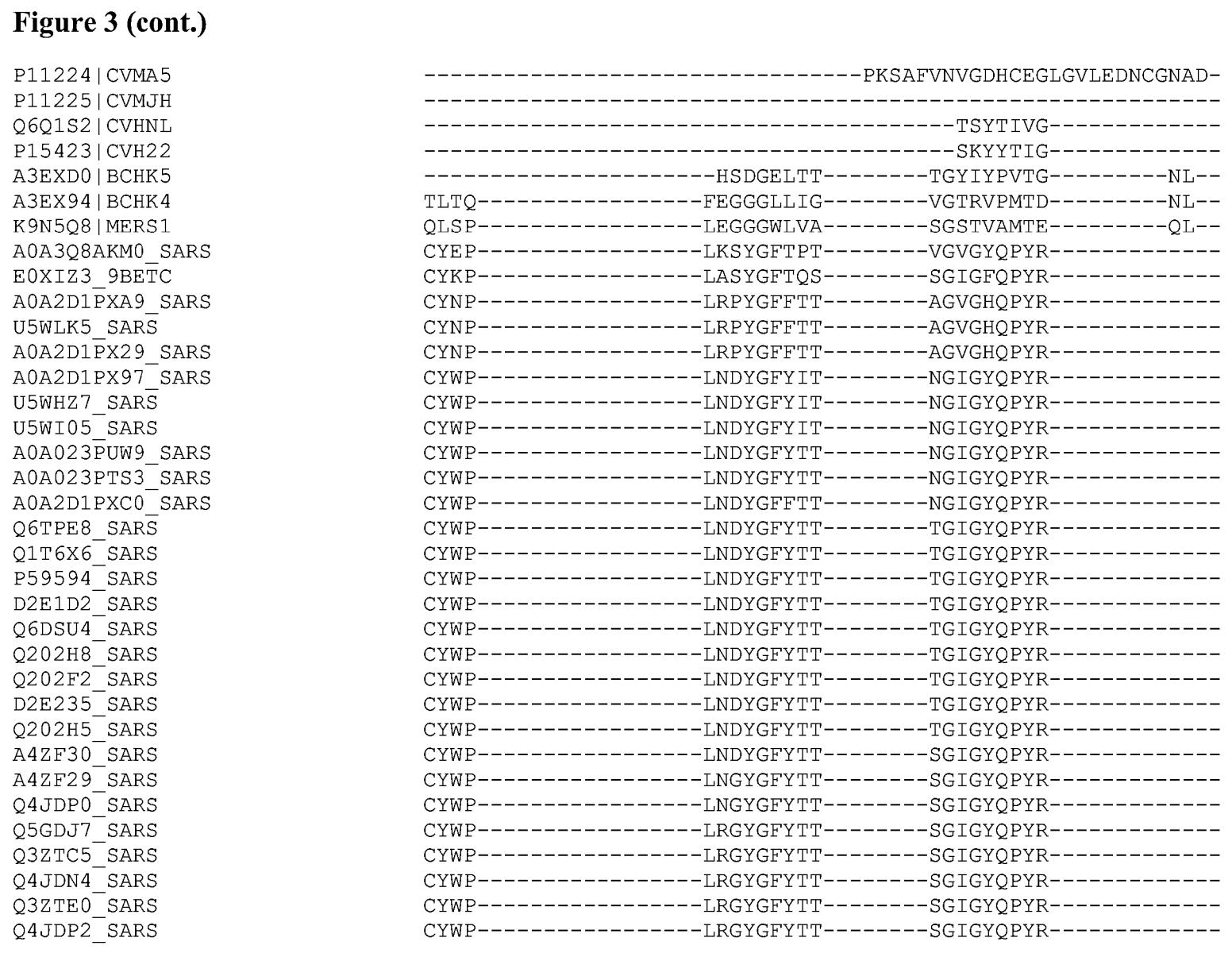

```
P11224|CVMA5       ----------------------------------PKSAFVNVGDHCEGLGVLEDNCGNAD-
P11225|CVMJH       -----------------------------------------------------------
Q6Q1S2|CVHNL       -----------------------------------------------------------
P15423|CVH22       --------------------------------------------------TSYTIVG---
A3EXD0|BCHK5       --------------------------------------------------SKYYTIG---
A3EX94|BCHK4       ----HSDGELTT---------------------------TGYIYPVTG---------NL--
K9N5Q8|MERS1       TLTQ---FEGGGLLIG------------------------VGTRVPMTD--------NL--
A0A3Q8AKM0_SARS    QLSP---LEGGGWLVA------------------------SGSTVAMTE--------QL-
E0XIZ3_9BETC       CYEP------LKSYGFTPT---------------------VGVGYQPYR----
A0A2D1PXA9_SARS    CYKP------LASYGFTQS---------------------SGIGFQPYR----
U5WLK5_SARS        CYNP------LRPYGFFTT---------------------AGVGHQPYR----
A0A2D1PX29_SARS    CYNP------LRPYGFFTT---------------------AGVGHQPYR----
A0A2D1PX97_SARS    CYNP------LRPYGFFTT---------------------AGVGHQPYR----
U5WHZ7_SARS        CYWP------LNDYGFYIT---------------------NGIGYQPYR----
U5WI05_SARS        CYWP------LNDYGFYIT---------------------NGIGYQPYR----
A0A023PUW9_SARS    CYWP------LNDYGFYTT---------------------NGIGYQPYR----
A0A023PTS3_SARS    CYWP------LNDYGFYTT---------------------NGIGYQPYR----
A0A2D1PXC0_SARS    CYWP------LNDYGFFTT---------------------NGIGYQPYR----
Q6TPE8_SARS        CYWP------LNDYGFYTT---------------------TGIGYQPYR----
Q1T6X6_SARS        CYWP------LNDYGFYTT---------------------TGIGYQPYR----
P59594_SARS        CYWP------LNDYGFYTT---------------------TGIGYQPYR----
D2E1D2_SARS        CYWP------LNDYGFYTT---------------------TGIGYQPYR----
Q6DSU4_SARS        CYWP------LNDYGFYTT---------------------TGIGYQPYR----
Q202H8_SARS        CYWP------LNDYGFYTT---------------------TGIGYQPYR----
Q202F2_SARS        CYWP------LNDYGFYTT---------------------TGIGYQPYR----
D2E235_SARS        CYWP------LNDYGFYTT---------------------TGIGYQPYR----
Q202H5_SARS        CYWP------LNDYGFYTT---------------------TGIGYQPYR----
A4ZF30_SARS        CYWP------LNDYGFYTT---------------------SGIGYQPYR----
A4ZF29_SARS        CYWP------LNGYGFYTT---------------------SGIGYQPYR----
Q4JDP0_SARS        CYWP------LNGYGFYTT---------------------SGIGYQPYR----
Q5GDJ7_SARS        CYWP------LRGYGFYTT---------------------SGIGYQPYR----
Q3ZTC5_SARS        CYWP------LRGYGFYTT---------------------SGIGYQPYR----
Q4JDN4_SARS        CYWP------LRGYGFYTT---------------------SGIGYQPYR----
Q3ZTE0_SARS        CYWP------LRGYGFYTT---------------------SGIGYQPYR----
Q4JDP2_SARS        CYWP------LRGYGFYTT---------------------SGIGYQPYR----
```

Figure 3 (cont.)

```
Spike_Fragment        ------VVLSFELLH--APATVCGPK-----KSTNLVKN
P0DTC2|SARS2          ------VVLSFELLH--APATVCGPK-----KSTNLVKN
A0A6B9WHD3_SARS       ------VVVLSFELLN--APATVCGPK-----KSTNLVKN
A0A6G9KP06_9BETC      ------VVVLSXELLN--GPATVCGPK-----LSTTLVKD
A0A2D1PX05_SARS       ------VVVLSFELLN--APATVCGPK-----LSTGLVKN
A0A2D1PX88_SARS       ------VVVLSFELLN--APATVCGPK-----LSTGLVKN
A0A2D1PX44_SARS       ------VVVLSFELLN--APATVCGPK-----LSTALVKN
D2DJW4_SARS           ------VVVLSFELLN--APATVCGPK-----LSTGLVKN
A0A2D1PX73_SARS       ------VVVLSFELLN--APATVCGPK-----LSTGLVKN
Q3I5J5|BCRP3          ------VVVLSFELLN--APATVCGPK-----LSTQLVKN
Q0Q475|BC279          ------VVVLSFELLN--APATVCGPK-----LSTQLVKN
Q0QDX9_SARS           ------VVVLSFELLN--APATVCGPK-----LSTQLVKN
Q3LZX1|BCHK3          ------VVVLSFELLN--APATVCGPK-----LSTELVKN
A0A096XNM6_SARS       ------VVVLSFELLN--APATVCGPK-----LSTQLVKN
A0A2D1PX86_SARS       ------VVVLSFELLN--APATVCGPK-----LSTQLVKN
A0A0U1WHJ8_SARS       ------VVVLSFELLN--APATVCGPK-----LSTQLVKN
D5HJU5_BCHK3          ------VVVLSFELLN--APATVCGPK-----LSTQLVKN
A0A0U1WHI2_SARS       ------VVVLSFELLN--APATVCGPK-----LSTELVKN
R9QTA0_SARS           ------VVVLSFELLN--APATVCGPK-----LSTTLVKN
R9QTH3_SARS           ------VVVLSFELLN--APATVCGPK-----LSTSLIKN
A0A1W5YKT9_9NIDO      ------VVVLSFELLN--APATVCGPK-----LSTELVKN
A0A0U1WJY8_SARS       ------VVVLSFELLN--APATVCGPK-----LSTELVKN
A0A2D1PX37_SARS       ------VVVLSFELLN--APATVCGPK-----LSTELVKN
Q0QDZ0_SARS           ------VVVLSFELLN--APATVCGPK-----LSTQLVKN
A0A0U1WHH0_SARS       ------VVVLSFELLN--APATVCGPK-----LSTSLVKN
Q0Q484_SARS           ------VVVLSFELLN--APATVCGPK-----LSTSLVKN
A0A0K1Z074_SARS       ------VVVLSFELLN--APATVCGPK-----LSTSLVKN
A0A0U1UYX4_SARS       ------VVVLSFELLN--APATVCGPK-----LSTPLVKN
A0A4Y6GL43_9BETC      ------VVVLSFELLN--APATVCGPK-----LSTQLVKN
A3EXG6|BCHK9          ------LAVITLKPAA--GSKLVCPVA-----NDTVVITD
P36334|CVHOC          ----SCTCRPQAFLGWSADSCLQGDKCNIFANFILHDVNSGLTCSTD--LQKANTDIILG
P25194|CVBV           -----PCTCQPQAFLGWSVDSCLQGDRCNIFANFILHDVNSGTTCSTD--LQKSNTDIILG
Q8JSP8|CVPIA          -----PCTCKPQAFIGWSSETCLQNGRCNIFANFILNDVNSGTTCSTD--LQQGNTNITTD
Q9IKD1|CVRSD          -----ICNCSADAFVGWAMDSCLSNARCHIFSNLMLNGINSGTTCSTD--FQLPNTEVVTG
Q5MQD0|CVHN1          SYNVSCLCSTDAFLGWSYDTCVSNNRCNIFSNFILNGINSGTTCSND--LLQPNTEVFTD
Q0ZME7|CVHN5          -NHSSCFCSPDAFLGWSFDSCISNNRCNIFSNFIFNGINSGTTCSND--LLYSNTEISTG
```

Figure 3 (cont.)

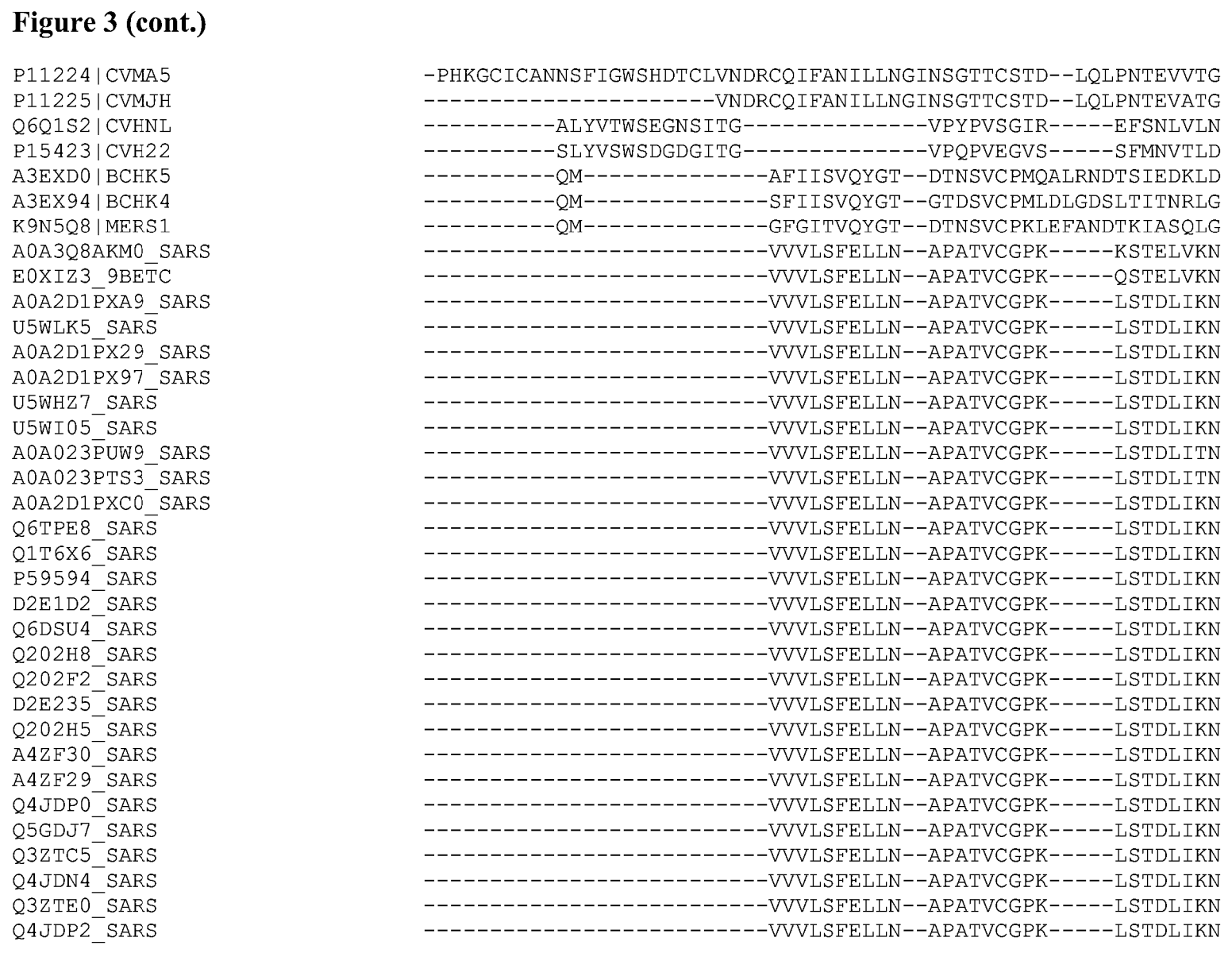

```
P11224|CVMA5        -PHKGCICANNSFIGWSHDTCLVNDRCQIFANILLNGINSGTTCSTD--LQLPNTEVVTG
P11225|CVMJH        ----------------VNDRCQIFANILLNGINSGTTCSTD--LQLPNTEVATG
Q6Q1S2|CVHNL        ------------ALYVTWSEGNSITG------------VPYPVSGIR-----EFSNLVLN
P15423|CVH22        ------------SLYVSWSDGDGITG------------VPQPVEGVS-----SFMNVTLD
A3EXD0|BCHK5        ------------QM-----------AFIISVQYGT--DTNSVCPMQALRNDTSIEDKLD
A3EX94|BCHK4        ------------QM-----------SFIISVQYGT--GTDSVCPMLDLGDSLTITNRLG
K9N5Q8|MERS1        ------------QM-----------GFGITVQYGT--DTNSVCPKLEFANDTKIASQIG
A0A3Q8AKM0_SARS     ------------VVVLSFELLN--APATVCGPK-----KSTELVKN
E0XIZ3_9BETC        ------------VVVLSFELLN--APATVCGPK-----QSTELVKN
A0A2D1PXA9_SARS     ------------VVVLSFELLN--APATVCGPK-----LSTDLIKN
U5WLK5_SARS         ------------VVVLSFELLN--APATVCGPK-----LSTDLIKN
A0A2D1PX29_SARS     ------------VVVLSFELLN--APATVCGPK-----LSTDLIKN
A0A2D1PX97_SARS     ------------VVVLSFELLN--APATVCGPK-----LSTDLIKN
U5WHZ7_SARS         ------------VVVLSFELLN--APATVCGPK-----LSTDLIKN
U5WI05_SARS         ------------VVVLSFELLN--APATVCGPK-----LSTDLIKN
A0A023PUW9_SARS     ------------VVVLSFELLN--APATVCGPK-----LSTDLITN
A0A023PTS3_SARS     ------------VVVLSFELLN--APATVCGPK-----LSTDLITN
A0A2D1PXC0_SARS     ------------VVVLSFELLN--APATVCGPK-----LSTDLIKN
Q6TPE8_SARS         ------------VVVLSFELLN--APATVCGPK-----LSTDLIKN
Q1T6X6_SARS         ------------VVVLSFELLN--APATVCGPK-----LSTDLIKN
P59594_SARS         ------------VVVLSFELLN--APATVCGPK-----LSTDLIKN
D2E1D2_SARS         ------------VVVLSFELLN--APATVCGPK-----LSTDLIKN
Q6DSU4_SARS         ------------VVVLSFELLN--APATVCGPK-----LSTDLIKN
Q202H8_SARS         ------------VVVLSFELLN--APATVCGPK-----LSTDLIKN
Q202F2_SARS         ------------VVVLSFELLN--APATVCGPK-----LSTDLIKN
D2E235_SARS         ------------VVVLSFELLN--APATVCGPK-----LSTDLIKN
Q202H5_SARS         ------------VVVLSFELLN--APATVCGPK-----LSTDLIKN
A4ZF30_SARS         ------------VVVLSFELLN--APATVCGPK-----LSTDLIKN
A4ZF29_SARS         ------------VVVLSFELLN--APATVCGPK-----LSTDLIKN
Q4JDP0_SARS         ------------VVVLSFELLN--APATVCGPK-----LSTDLIKN
Q5GDJ7_SARS         ------------VVVLSFELLN--APATVCGPK-----LSTDLIKN
Q3ZTC5_SARS         ------------VVVLSFELLN--APATVCGPK-----LSTDLIKN
Q4JDN4_SARS         ------------VVVLSFELLN--APATVCGPK-----LSTDLIKN
Q3ZTE0_SARS         ------------VVVLSFELLN--APATVCGPK-----LSTDLIKN
Q4JDP2_SARS         ------------VVVLSFELLN--APATVCGPK-----LSTDLIKN
```

Figure 3 (cont.)

```
Spike_Fragment    KCVNFNFNGLTGTGVLTESNKKF-LPFQQFGRDIADTTDAVR-DPQTLEILDITPCSFGG
P0DTC2|SARS2      KCVNFNFNGLTGTGVLTESNKKF-LPFQQFGRDIADTTDAVR-DPQTLEILDITPCSFGG
A0A6B9WHD3_SARS   KCVNFNFNGLTGTGVLTESNKKF-LPFQQFGRDIADTTDAVR-DPQTLEILDITPCSFGG
A0A6G9KP06_9BETC  KCVNFNFNGLTGTGVLTTSKKQF-LPFQQFGRDISDTTDAVR-DPQTLEILDITPCSFGG
A0A2D1PX05_SARS   QCVNFNFNGLKGTGVLTDSSKRF-QSFQQFGRDTSDFTDSVR-DPQTLQVLDITPCSFGG
A0A2D1PX88_SARS   QCVNFNFNGLKGTGVLTDSSKRF-QSFQQFGRDTSDFTDSVR-DPQTLQILDITPCSFGG
A0A2D1PX44_SARS   QCVNFNFNGLKGIGVLTDSSKRF-QSFQQFGRDTSDFTDSVR-DPQTLQILDITPCSFGG
D2DJW4_SARS       QCVNFNFNGLKGTGVLTDSSKRF-QSFQQFGRDTSDFTDSVR-DPQTLQILDITPCSFGG
A0A2D1PX73_SARS   QCVNFNFNGLKGTGVLTDSSKRF-QSFQQFGRDTSDFTDSVR-DPQTLQILDITPCSFGG
Q3I5J5|BCRP3      QCVNFNFNGLKGTGVLTESSKRF-QSFQQFGRDMSDFTDSVR-DPQTLQILDITPCSFGG
Q0Q475|BC279      QCVNFNFNGLKGTGVLTDSSKRF-QSFQQFGRDTSDFTDSVR-DPQTLEILDISPCSFGG
Q0QDX9_SARS       QCVNFNFNGLRGTGVLTTSSKRF-QSFQQFGRDTSDFTDSVR-DPQTLEILDISPCSFGG
Q3LZX1|BCHK3      QCVNFNFNGLKGTGVLTTSSKRF-QSFQQFGRDTSDFTDSVR-DPQTLEILDISPCSFGG
A0A96XNM6_SARS    QCVNFNFNGLKGTGVLTDSSKRF-QSFQQFGRDTSDFTDSVR-DPQTLEILDISPCSFGG
A0A2D1PX86_SARS   QCVNFNFNGLKGTGVLTDSSKRF-QSFQQFGRDTSDFTDSVR-DPQTLEILDITPCSFGG
A0A0U1WHJ8_SARS   QCVNFNFNGLKGTGVLTDSSKRF-QSFQQFGRDTSDFTDSVR-DPQTLEILDISPCSFGG
D5HJU5_BCHK3      QCVNFNFNGLKGTGVLTPSLKRF-QSFQQFGRDTSDFTDSVR-DPQTLEILDISPCSFGG
A0A0U1WHI2_SARS   QCVNFNFNGLKGTGVLTPSSKRF-QSFQQFGRDTSDFTDSVR-DPQTLEILDISPCSFGG
R9QTA0_SARS       QCVNFNFNGLKGTGVLTKSSKRF-QSFQQFGRDTSDFTDSVR-DPQTLEILDISPCSFGG
R9QTH3_SARS       QCVNFNFNGLKGTGVLTASSKKF-QSFQQFGRDASDFTDSVR-DPQTLEILDISPCSFGG
A0A1W5YKT9_9NIDO  QCVNFNFNGLKGTGVLTDSSKKF-QSFQQFGRDASDFTDSVR-DPQTLQILDISPCSFGG
A0A0U1WJY8_SARS   QCVNFNFNGLKGTGVLSSSSKRF-QSFQQFGRDASDFTDSVR-DPQTLEILDITPCSFGG
A0A2D1PX37_SARS   QCVNFNFNGLKGTGVLTSSSKRF-QSFQQFGRDASDFTDSVR-DPQTLEILDITPCSFGG
Q0QDZ0_SARS       QCVNFNFNGLKGTGVLTDSSKRF-QSFQQFGRDTSDFTDSVR-DPQTLDILDITPCSFGG
A0A0U1WHH0_SARS   QCVNFNFNGFKGTGVLTDSSKTF-QSFQQFGRDASDFTDSVR-DPQTLRILDISPCSFGG
Q0Q484_SARS       QCVNFNFNGFKGTGVLTDSSKTF-QSFQQFGRDASDFTDSVR-DPQTLRILDISPCSFGG
A0A0K1Z074_SARS   QCVNFNFNGFKGTGVLTDSSKTF-QSFQQFGRDASDFTDSVR-DPKTLQILDISPCSFGG
A0A0U1UYX4_SARS   QCVNFNFNGLKGTGVLTDSSKTF-QSFQQFGRDASDFTDSVR-DPQTLQILDISPCSFGG
A0A4Y6GL43_9BETC  QCVNFNFNGLTGTGVLTPSSKRF-QPFQQFGRDVSDFTDSVR-DPKTSEILDISPCSFGG
A3EXG6|BCHK9      RCVQYNLYGYTGTGVLSKNTSLV-IPDGKVFTASS-TGTIIG-VSINSTTYSIMPCVTVP
P36334|CVHOC      VCVNYDLYGILGQGIFVEVNATYYNSWQNLLYDSNGNLYGFR-DYIINRTFMIRSCYSGR
P25194|CVBV       VCVNYDLYGITGQGIFVEVNATYYNSWQNLLYDSNGNLYGFR-DYLTNRTFMIRSCYSGR
Q8JSP8|CVPIA      VCVNYDLYGITGQGILIEVNATYYNSWQNLLYDSSGNLYGFR-DYLSNRTFLIRSCYSGR
Q9IKD1|CVRSD      VCVKYDLYGSTGQGVFKEVKADYYNSWQNLLYDVNGNLNGFR-DIVTNKTYLLRSCYSGR
Q5MQD0|CVHN1      VCVDYDLYGITGQGIFKEVSAVYYNSWQNLLYDSNGNIIGFK-DFVTNKTYNIFPCYAGR
Q0ZME7|CVHN5      VCVNYDLYGITGQGIFKEVSAAYYNNWQNLLYDSNGNIIGFK-DFLTNKTYTILPCYSGR
```

Figure 3 (cont.)

```
P11224|CVMA5        ICVKYDLYGITGQGVFKEVKADYYNSWQTLLYDVNGNLNGFR-DLTTNKTYTIRSCYSGR
P11225|CVMJH        VCVRYDLYGITGQGVFKEVKADYYNSWQALLYDVNGNLNGFR-DLTTNKTYTIRSCYSGR
Q6Q1S2|CVHNL        NCTKYNIYDYVGTGIIRSSNQSLAGG--ITYVSNSGNLLGFK-NVSTGNIFIVTPCNQPD
P15423|CVH22        KCTKYNIYDVSGVGVIRVSNDTFLNG--ITYTSTSGNLLGFK-DVTKGTIYSITPCNPPD
A3EXD0|BCHK5        VCVEYSLHGITGRGVFHNCTSVG-LRNQRFVYDTFD--NLVGYHSDNGNYYCVRPCVSVP
A3EX94|BCHK4        KCVDYSLYGVTGRGVFQNCTAVG-VKQQRFVYDSFD--NLVGYYSDDGNYYCVRPCVSVP
K9N5Q8|MERS1        NCVEYSLYGVSGRGVFQNCTAVG-VRQQRFVYDAYQ--NLVGYYSDDGNYYCLRACVSVP
A0A3Q8AKM0_SARS     KCVNFNFNGLTGTGVLTSSTKKF-QPFQQFGRDVSDFTDSVR-DPKTFEILLDISPCSYGG
E0XIZ3_9BETC        KCVNFNFNGLTGTGVLTNSTKKF-QPFQQFGRDVSDFTDSVR-DPKTLEILDIAPCSYGG
A0A2D1PXA9_SARS     QCVNFNFNGLTGTGVLTPSSKRF-QPFQQFGRDVSDFTDSVR-DPKTSEILDISPCSFGG
U5WLK5_SARS         QCVNFNFNGLTGTGVLTPSSKRF-QPFQQFGRDVSDFTDSVR-DPKTSEILDISPCSFGG
A0A2D1PX29_SARS     QCVNFNFNGLTGTGVLTPSSKRF-QPFQQFGRDVSDFTDSVR-DPKTSEILDISPCSFGG
A0A2D1PX97_SARS     QCVNFNFNGLTGTGVLTPSSKRF-QPFQQFGRDVSDFTDSVR-DPKTSEILDISPCSFGG
U5WHZ7_SARS         QCVNFNFNGLTGTGVLTPSSKRF-QPFQQFGRDVSDFTDSVR-DPKTSEILDISPCSFGG
U5WI05_SARS         QCVNFNFNGLTGTGVLTPSSKRF-QPFQQFGRDVSDFTDSVR-DPKTSEILDISPCSFGG
A0A023PUW9_SARS     QCVNFNFNGLTGTGVLTPSLKRF-QPFQQFGRDVSDFTDSVR-DPKTLEVLDISPCSFGG
A0A023PTS3_SARS     QCVNFNFNGLTGTGVLTPSSKRF-QPFQQFGRDVSDFTDSVR-DPKTLEVLDISPCSFGG
A0A2D1PXC0_SARS     QCVNFNFNGLTGTGVLTSSSKRF-QPFQQFGRDVSDFTDSVR-DPKTSEILDISPCSFGG
Q6TPE8_SARS         QCVNFNFNGLTGTGVLTPSSKRF-QPFQQFGRDVSDFTDSVR-DPKTSEILDISPCSFGG
Q1T6X6_SARS         QCVNFNFNGLTGTGVLTPSSKRF-QPFQQFGRDVSDFTDSVR-DPKTSEILDISPCSFGG
P59594_SARS         QCVNFNFNGLTGTGVLTPSSKRF-QPFQQFGRDVSDFTDSVR-DPKTSEILDISPCSFGG
D2E1D2_SARS         QCVNFNFNGLTGTGVLTPSSKRF-QPFQQFGRDVSDFTDSVR-DPKTSEILDISPCSFGG
Q6DSU4_SARS         QCVNFNFNGLTGTGVLTPSSKRF-QPFQQFGRDVSDFTDSVR-DPKTSEILDISPCSFGG
Q202H8_SARS         QCVNFNFNGLTGTGVLTPSSKRF-QPFQQFGRDVSDFTDSVR-DPKTSEILDISPCSFGG
Q202F2_SARS         QCVNFNFNGLTGTGVLTPSSKRF-QPFQQFGRDVSDFTDSVR-DPKTSEILDISPCSFGG
D2E235_SARS         QCVNFNFNGLTGTGVLTPSSKRF-QPFQQFGRDVSDFTDSVR-DPKTSEILDISPCSFGG
Q202H5_SARS         QCVNFNFNGLTGTGVLTPSSKRF-QPFQQFGRDVSDFTDSVR-DPKTSEILDISPCSFGG
A4ZF30_SARS         QCVNFNFNGLTGTGVLTPSSKRF-QPFQQFGRDVSDFTDSVR-DPKTSEILDISPCAFGG
A4ZF29_SARS         QCVNFNFNGLTGTGVLTPSSKRF-QPFQQFGRDVSDFTDSVR-DPKTSEILDISPCSFGG
Q4JDP0_SARS         QCVNFNFNGLTGTGVLTPSSKRF-QPFQQFGRDVSDFTDSVR-DPKTSEILDISPCSFGG
Q5GDJ7_SARS         QCVNFNFNGLTGTGVLTPSSKRF-QPFQQFGRDVSDFTDSVR-DPKTSEILDISPCSFGG
Q3ZTC5_SARS         QCVNFNFNGLTGTGVLTPSSKRF-QPFQQFGRDVSDFTDSVR-DPKTSEILDISPCSFGG
Q4JDN4_SARS         QCVNFNFNGLTGTGVLTPSSKRF-QPFQQFGRDVSDFTDSVR-DPKTSEILDISPCSFGG
Q3ZTE0_SARS         QCVNFNFNGLTGTGVLTPSSKRF-QPFQQFGRDVSDFTDSVR-DPKTSEILDISPCSFGG
Q4JDP2_SARS         QCVNFNFNGLTGTGVLTPSSKRF-QPFQQFGRDVSDFTDSVR-DPKTSEILDISPCSFGG
```

SARS-CoV-2 VACCINES AND ANTIBODIES

CROSS-REFERENCE TO RELATED APPLICATIONS

This application is a continuation of international application PCT/US2021/048932, filed Sep. 2, 2021, which claims the benefit of priority of U.S. Provisional Application No. 63/075,043, filed Sep. 4, 2020, Application No. 63/132,943, filed Dec. 31, 2020, and Application No. 63/211,397, filed Jun. 16, 2021, all of which are incorporated by reference herein in their entirety for any purpose.

SEQUENCE LISTING

The present application is filed with a Sequence Listing in XML format. The Sequence Listing is provided as a file entitled "01308-0003-00US_Revised.xml" created on Oct. 12, 2023, which is 163,213 bytes in size. The information in the electronic format of the sequence listing is incorporated herein by reference in its entirety.

INTRODUCTION

Methods for making antibodies have been around for over 100 years and are routinely used by the skilled artisan. See, for example, Morrison et al., Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985). Improved methods for generating antibodies have extended these initial methods and have been used to generate many of the therapeutic antibodies now being sold commercially. For example, technologies such as phage display and transgenic mice, that is, mice containing the human immunoglobulin genes, have been used to generate fully human antibodies. However, certain antigens continue to challenge a researcher's ability to raise antibodies even when using the most current techniques.

To induce a cell-mediated immune response within the human body, foreign proteins are broken down into smaller peptides, usually between 8-24 amino acids in length, and are bound to MHC molecules, for display on the surface of antigen presenting cells. The MHC-bound peptides are presented to T-cells to trigger a cell mediated immune response.

The three-dimensional (3D) structure of proteins has been implicated as a factor in proteolytic processing and presentation of epitopes (see, Carmicle et al., Molecular Immunology (2007) vol. 44:1159-1168). Moreover, Ohkuri et al. (see, Okhuri et al., J. Immunol., (2010), vol. 185:4199-4205) agreed that conformational stability of a protein is an immunologically dominant factor. However, there is no consensus regarding exactly how the 3D structure affects the immune response.

Delamarre et al. (see, Delamarre et al., JEM, (2006), vol 203:2049-2055) found that less digestible forms of proteins that were less susceptible to digestion via lysosomal proteolysis were more immunogenic, and therefore, concluded that increasing protein stability improved the immune response. For example, Delamarre et al. showed that the immunogenicity of protein antigens can be improved by reducing susceptibility to proteolysis. Similarly, Mirano-Bascos et al. (see, Mirano-Bascos et al., J. of Virology, (2010), vol. 84:3303-3311) mutated cysteine residues to prevent each of three disulfide bonds from forming, and determined that the CD4+ T-cell response was broadly reduced for all three variants. Mirano-Bascos et al. similarly concluded that global destabilization of the 3-D structure of a protein reduced antigenic presentation and led to a suppressed immune response. In other studies, such as for example, Nguyen et al., Vaccine, (2015), vol. 33:2887-2896, outer domain disulfide bonds were deleted with the expectation that such deletions would improve antigenic presentation. Instead, a typical pattern of epitope dominance was observed and the authors concluded that it may not be possible to generate a substantially stronger immune response.

Other groups similarly conclude that protein stabilization is needed for an immune response. For example, Deressa et al., (see, Deressa et al., PLOS, (2014), vol. 9:1-12) concluded that even minor modifications in the amino acid sequence of an antigen caused fundamental quantitative and qualitative changes in the immune response. Likewise, Porta et al. (see, Porta et al., PLOS, (2013), vol. 9:1-8) reported that stability is needed for inducing an immune response. Other groups such as Thomas (see, Thomas et al., Human Vaccines & Immunotherapeutics, (2013), vol. 9:744-752) similarly concluded that increasing thermal stability for peptides elicited a better immune response.

In contrast, other groups such as So (see, So et al., Immunology, (2001), vol. 104:259-268) report conflicting results. So et al. investigated the effect of crosslinking (e.g., removing cross-links and adding crosslinks) on the magnitude of in vivo T-cell responses and found that removing such crosslinks led to better antigen processing and an improved immune response. Similarly, Thai et al., J. Biol. Chem. (2004) vol. 279:50257-50266) reported mutating surface accessible residues to decrease stability and increase conformational dynamics to increase the immunogenicity of the protein antigen. Thai et al. is also directed towards administration of single antigens.

There is no consensus on whether removing or adding crosslinks improves or inhibits antigen processing. Accordingly, it is unclear in the art as to whether increasing or decreasing protein stability would lead to an improved immune response comprising a broad, diverse array of antibodies.

Thus, there continues to be a need to develop new and improved methods of generating antibodies which can provide a different and broader repertoire of antibodies than previously obtained.

SUMMARY OF THE INVENTION

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject. As described herein, the invention is directed towards a composition comprising: (a) a SARS-COV-2 peptidogenic protein, wherein said peptidogenic protein has altered conformational dynamics as compared to a SARS-COV-2 starting protein and wherein the SARS-COV-2 peptidogenic protein is similar in conformation to the SARS-COV-2 starting protein, and wherein said SARS-COV-2 starting protein is selected from at least one of the proteins listed on Table 2; or (b) a Spike fragment; or (c) a polynucleotide encoding (a) or (b); or (d) any combination of (a), (b) and/or (c). This composition can be used in a method of triggering an immune response. For example, such method comprises designing a mixture of SARS-COV-2 peptidogenic proteins derived from a SARS-COV-2 starting protein, wherein the SARS-COV-2 peptidogenic proteins have altered conformational dynamics as compared to the SARS-COV-2 starting protein and wherein the SARS-COV-2 peptidogenic proteins are similar in conformation to the SARS-COV-2 starting protein, introducing the SARS-COV-2 peptidogenic proteins to an animal and generating an immune response. The SARS-COV-2 peptidogenic proteins, the Spike fragment, and/or the polynucleotides can be introduced into the animals directly (by, for instance, inoculation or immunization) or can be expressed in vivo by polynucleotides that have been introduced into the animal and which encode the SARS-COV-2 peptidogenic proteins. Upon expression of these SARS-CoV-2 peptidogenic proteins and/or the Spike fragment, the immune response is triggered to generate antibodies both to the SARS-COV-2 peptidogenic proteins and to the original SARS-COV-2 starting protein.

In preferred embodiments a non-surface amino acid residue is replaced with a smaller amino acid residue in the SARS-COV-2 starting protein. In further preferred embodiments, the smaller amino acid is an alanine or glycine. In other preferred embodiments, at least 2, 3, 4, 5, 6, 7, 8, 9 or 10 amino acids are replaced in the SARS-COV-2 starting protein. In still other preferred embodiments, at least 10 amino acids, at least 20 amino acids, at least 30 amino acids, at least 40 amino acids, or at least 50 amino acids are replaced in the SARS-COV-2 starting protein. In still other preferred embodiments, multiple amino acid replacements are distributed across a mixture of proteins. For example, in one embodiment, to mutate 10 different residues, the SARS-COV-2 starting protein is mutated 10 different times to generate 10 different SARS-COV-2 peptidogenic proteins, each with a single amino acid replacement. Each of the ten proteins (or polynucleotides encoding the ten proteins) are mixed together to inoculate the animal. In some cases, wild type SARS-COV-2 starting protein or protein fragment, i.e. the protein or protein fragment with no mutations, is part of the mixture. In further preferred embodiments, at least one disulfide bond is eliminated in the SARS-CoV-2 starting protein, such as, for example, replacing the cysteines with alanines, serines, and/or glycines, etc. In further preferred embodiments, both cysteines involved in the formation of the at least one disulfide bond in the SARS-COV-2 starting protein are replaced with alanines, serines, and/or glycines, or preferably with alanines or glycines, etc. In further preferred embodiments, the conformational dynamics of the SARS-COV-2 starting protein is altered by replacing (a) at least one threonine with a valine, alanine, glycine or serine; or (b) at least one cysteine with alanine, valine, glycine, serine or threonine; or (c) at least one valine with alanine, glycine, leucine or isoleucine; or (d) at least one leucine with alanine, valine, glycine, or isoleucine; or (e) at least one isoleucine with alanine, valine, leucine, or glycine; or (f) at least one proline, methionine, phenylalanine, tyrosine, or tryptophan with alanine, valine, leucine, isoleucine, or glycine; or (g) at least one aspartic acid or asparagine with glycine, serine, threonine, alanine, valine, leucine, or isoleucine; or (h) at least one glutamic acid or glutamine with aspartic acid, asparagine, glycine, serine, threonine, alanine, valine, leucine, or isoleucine; or (i) at least one lysine with arginine, histidine, glycine, serine, threonine, alanine, valine, methionine, leucine, or isoleucine; or (j) at least one arginine with lysine, histidine, glycine, serine, threonine, alanine, valine, methionine, leucine, or isoleucine; or (k) at least one histidine with lysine, arginine, glycine, serine, threonine, alanine, valine, glutamine, asparagine, leucine, or isoleucine; or (1) at least one alanine with a glycine; or (m) at least one residue with a non-natural amino acid; and/or (n) any of the above combinations.

In still further preferred embodiments, the conformational dynamics of the SARS-COV-2 starting protein is altered by replacing: (a) at least one tryptophan with tyrosine, phenylalanine, methionine, histidine, isoleucine, leucine, valine, alanine or glycine; or (b) at least one tyrosine with phenylalanine, methionine, histidine, isoleucine, leucine, valine, alanine or glycine; or (c) at least one phenylalanine with tyrosine, methionine, histidine, isoleucine, leucine, valine, alanine or glycine; or (d) at least one proline with methionine, leucine, isoleucine, valine, alanine, or glycine; or (e) at least one histidine with phenylalanine, tyrosine, methionine, isoleucine, leucine, valine, alanine, glycine, lysine, arginine, serine, threonine, asparagine, or glutamine; or (f) at least one methionine with isoleucine, leucine, valine, alanine or glycine; or (g) at least one isoleucine with leucine, valine, alanine or glycine; or (h) at least one leucine with isoleucine, valine, alanine or glycine; or (i) at least one valine with alanine, glycine, leucine, or isoleucine; or (j) at least one cysteine with alanine, valine, glycine, serine or threonine; or (k) at least one aspartic acid with glutamic acid, glutamine, asparagine, glycine, serine, threonine, alanine, valine, leucine, or isoleucine; or (l) at least one glutamic acid with aspartic acid, glutamine, asparagine, glycine, serine, threonine, alanine, valine, leucine, or isoleucine; or (m) at least one alanine with a glycine or proline; or (n) at least one serine with alanine or glycine; or (o) at least one glycine with alanine or proline; or (p) at least one lysine with arginine, histidine, glycine, serine, threonine, alanine, valine, methionine, leucine or isoleucine; or (q) at least one asparagine with glycine, alanine, serine, threonine, valine, leucine, isoleucine, glutamine, aspartic acid or glutamic acid; or (r) at least one glutamine with glycine, alanine, serine, threonine, valine, leucine, isoleucine, glutamine, aspartic acid, glutamic acid, or histidine; or(s) at least one arginine with lysine, histidine, glycine, serine, threonine, alanine valine, methionine, leucine, or isoleucine; or (t) at least one threonine with valine, alanine, glycine or serine; or (u) a hydrophobic residue with a smaller, similar hydrophobic residue; or (v) at least one residue with a non-natural amino acid; or (w) any of the above combinations. A combinatorial approach may be used to determine optimal substitutions to increase peptidogenicity.

In preferred embodiments, the SARS-COV-2 peptidogenic protein is selected from the Spike glycoproteins SPIKE_SARS2 (PODTC2) (SEQ ID NO:15) or SPIKE_SARS (P59594) (SEQ ID NO: 16). In further preferred embodiments, the Spike protein is mutated at any of the following positions: (A) Trp 353, Tyr 365, Phe 392, Phe 400, Tyr 423, Phe 497, and/or Phe 543 of SEQ ID NO: 15; (B) Val308, Ile326, Val350, Ile358, Ala363, Leu387, Val395, Ala397, Val401, Ile402, Ile410, Ile418, Ala419, Leu425, Val433, Ile434, Ala435, Leu492, Val510, Val511, Val512, Leu513, Val524, Val539, Leu552, Ala575, Val576, and/or Leu585 of SEQ ID NO: 15; (C) Ala 363, Ala 397, and/or Ala 575 of SEQ ID NO:15; (D) Cys 336 Ala/Cys 361 Ala, and/or Cys 379 Ala/Cys 432 Ala of SEQ ID NO: 15; and/or (E) Ala 419, Ile 980, Ala 903, Leu 916, Ala 575, Phe 1095, Cys 1032, Val 576, Tyr 365, Ile 1115, Ile 418, Leu 387, Cys 649, Leu 650, Leu 585, Ala 1080, Ile 410, Tyr 423, Ala 1087, Tyr 695, Ala 653, Phe 201, Ile 1081, Phe 497, Ala 989, Leu 552, Val 1104, and/or Cys 671 of SEQ ID NO: 15; and/or (F) or the equivalent positions in SEQ ID NO:15-16 or SEQ ID NO:43-110.

Additionally, and In further preferred embodiments, the composition comprises, or consists of, any one of the following: (1) amino acids 316-594 of SEQ ID NO: 15 or amino acids 303-580 of SEQ ID NO: 16; (2) amino acids 316-594 of SEQ ID NO: 15 along with at least one mutation at any one of the following sites: (A) Trp 353, Tyr 365, Phe 392, Phe 400, Tyr 423, Phe 497, and/or Phe 543; (B) Ile326, Val350, Ile358, Ala363, Leu387, Val395, Ala397, Val401, Ile402, Ile410, Ile418, Ala419, Leu425, Val433, Ile434, Ala435, Leu492, Val510, Val511, Val512, Leu513, Val524, Val539, Leu552, Ala575, Val576, and/or Leu585; (C) Ala 363, Ala 397, and/or Ala 575; (D) Cys 336 Ala/Cys 361 Ala, and/or Cys 379 Ala/Cys 432 Ala; (E) Ala 419, Ala 575, Val 576, Tyr 365, Ile 418, Leu 387, Leu 585, Ile 410, Tyr 423, Phe 497, and/or Leu 552; (3) amino acids 319-591 of SEQ ID NO: 15 along with at least one mutation at any one of the following sites: (A) Trp 353, Tyr 365, Phe 392, Phe 400, Tyr 423, Phe 497, and/or Phe 543; (B) Ile326, Val350, Ile358, Ala363, Leu387, Val395, Ala397, Val401, Ile402, Ile410, Ile418, Ala419, Leu425, Val433, Ile434, Ala435, Leu492, Val510, Val511, Val512, Leu513, Val524, Val539, Leu552, Ala575, Val576, and/or Leu585; (C) Ala 363, Ala 397, and/or Ala 575; (D) Cys 336 Ala/Cys 361 Ala, and/or Cys 379 Ala/Cys 432 Ala; and/or (E) Ala 419, Ala 575, Val 576, Tyr 365, Ile 418, Leu 387, Leu 585, Ile 410, Tyr 423, Phe 497, and/or Leu 552; (3) amino acids 319-541 of SEQ ID NO:15 along with at least one mutation at any one of the following sites: (A) Trp 353, Tyr 365, Phe 392, Phe 400, Tyr 423, and/or Phe 497; (B) Ile326, Val350, Ile358, Ala363, Leu387, Val395, Ala397, Val401, Ile402, Ile410, Ile418, Ala419, Leu425, Val433, Ile434, Ala435, Leu492, Val510, Val511, Val512, Leu513, Val524, and/or Val539; (C) Ala 363, and/or Ala 397; (D) Cys 336 Ala/Cys 361 Ala, and/or Cys 379 Ala/Cys 432 Ala; and/or (E) Ala 419, Tyr 365, Ile 418, Leu 387, Ile 410, Tyr 423, an/or Phe 497; (4) amino acids 319-541, 319-591, or 316-594 of SEQ ID NO:15 along with at least one mutation selected from Y365, I402, and/or V511; (5) amino acids 319-541, 319-591, or 316-594 of SEQ ID NO:15 along with at least one mutation selected from at Y365L, I402V, and/or V511A; or (6) the equivalent fragments and/or mutations in SEQ ID NO:15-16 or SEQ ID NO:43-110.

In preferred embodiments, the change in conformational dynamics of the SARS-COV-2 peptidogenic protein is measured by a change in melting temperature as compared to the SARS-COV-2 starting protein and/or by measuring a change in Gibbs free energy of stabilization. Preferred methods of measuring Gibbs free energy include, but are not limited to, denaturant modulated equilibrium unfolding. Preferred denaturants are urea and/or guanidinium hydrochloride. Alternatively, changes in conformational dynamics can be assayed by detecting a change in a proteolytic sensitivity assay, such as, for example, by measuring digestion with cathepsins and/or other proteases and then analyzing the mixture by mass spectrometry (MS) or sodium dodecylsulfate polyacrylamide gel electrophoresis (SDS-PAGE).

In preferred embodiments, determining whether SARS-COV-2 peptidogenic proteins have a similar conformation to the SARS-COV-2 starting protein can be measured by a cross-reacting antibody that binds to a 3D conformational epitope (often a discontinuous epitope) on both the SARS-CoV-2 peptidogenic proteins and the SARS-COV-2 starting protein. Methods for measuring antibody binding include, but are not limited to an immunoprecipitation assay, surface plasma resonance, isothermal titration calorimetry, oblique-incidence reflective difference (OI-RD), western blots, radioimmunoassays, ELISA (enzyme linked immunosorbent assay), "sandwich" immunoassays, gel diffusion precipitin reactions, immunodiffusion assays, agglutination assays, complement-fixation assays, immunoradiometric assays, fluorescent immunoassays, and/or protein A immunoassays.

In further preferred embodiments, a test for measuring cross-reactivity is by a binding assay. In further preferred embodiment, the antibody binding (including a cross-reacting antibody) to a SARS-COV-2 peptidogenic protein has a dissociation constant (KD) of less than or equal to $10^{-9}$M, of less than or equal to $10^{-8}$M, less than or equal to $10^{-7}$M, and/or less than or equal to $10^{-6}$M.

In preferred embodiments, the SARS-COV-2 starting protein is selected from the following SARS-COV-2 proteins listed in Table 2, with preferred mutations at one or more of the following positions:

TABLE 2

| SEQ ID NO. | Protein Name | UniProt ID No. | Exemplified Sites of Mutations to Generate Peptidogenic Protein (Each position can be substituted alone or in any combination with any of the other listed amino acid positions.) |
|---|---|---|---|
| 1 | Trans-membrane protease serine 2 | O15393 TMPS2_ HUMAN | Y37, Y45, V49, A53, C77, A84, L85, C86, I87, L89, L91, F94, L95, V96, A98, A99, L100, A101, A102, L104, L105, W106, F108, M109, C113, I118, C120, C126, W132, C133, C139, C148, V149, L151, F156, I157, L158, V160, W168, V171, C172, W176, Y180, A184, C185, M188, Y190, F194, F209, M210, L212, V219, I221, Y222, C231, V236, L239, C244, I256, V257, A262, W267, W269, V271, L273, H279, V280, C281, I285, I286, W290, I291, V292, A294, A295, H296, C297, V298, W308, A310, F311, A312, I314, L315, Y326, V328, V331, I332, H334, Y337, I346, A347, L348, M349, L351, L355, F357, V361, V364, C365, L366, L373, C379, W380, I381, W384, V396, L397, A400, V402, L404, I405, C410, V415, Y416, I420, M424, I425, C426, A427, F429, C437, L445, V446, W453, W454, L455, I456, W461, C465, A466, V473, Y474, V477, F480, W483, I484, M488 |
| 2 | Furin | P09958 FURIN_ HUMAN | Y123, L124, L132, V134, A137, I147, V148, V149, I151, L152, I156, H160, L163, A171, C198, A199, V202, A203, V213, V215, A216, A219, I221, V224, M226, L240, I247, I249, Y250, A252, A270, A273, F274, I288, F289, V290, W291, C303, C305, I312, L315, I317, A320, Y329, C333, L337, A338, I351, L356, A369, A371, L373, A374, A375, I377, I378, A379, L380, L382, L388, M393, L396, V397, V398, V420, Y424, Y426, L429, A431, M434, V435, A438, C450, I461, A473, I481, L484, H486, A487, A489, L491, L501, I503, L505, L515, |

TABLE 2-continued

| SEQ ID NO. | Protein Name | UniProt ID No. | Exemplified Sites of Mutations to Generate Peptidogenic Protein (Each position can be substituted alone or in any combination with any of the other listed amino acid positions.) |
|---|---|---|---|
| | | | L516, F528, F533, M534, H537, W539, L549, I551, L563, L568, L570 |
| 3 | ATP-dependent RNA helicase DDX1 | Q92499 DDX1_ HUMAN | M93, C111, C122, A124, L128, Y134, Y135, V137, W149, L158, F165, F167, I192, C194, L196, V203, F205, M222, L227, F228, A230, C231, V232, L233, A236, L238, L258 |
| 4 | Angiotensin-converting enzyme 2 | Q9BYF1 ACE2_ HUMAN | A25, F32, A36, A80, L97, I119, M123, V132, L148, M152, A164, W165, W168, V172, L176, Y180, Y183, A191, Y207, Y217, L222, V226, F230, I233, L240, H241, A242, V244, L248, C261, L262, A264, H265, L266, L267, M270, W275, V293, M297, I307, F308, A311, F315, V318, F327, L351, I358, L359, M360, F369, A372, H373, M376, I379, Y381, A384, F400, A403, V404, I407, M408, A412, L418, L439, L440, A443, L444, V447, L450, F452, M455, L456, W459, W461, F464, M474, W478, V485, V487, V488, C498, A501, V506, F512, Y516, L520, Y521, F523, F525, L529, C530, C542, A550, M557, L558, A569, L570, V573, V581, L584, Y587, F588, L591, L595, I618, V620, I622, F643, V647, A650, M651, F681, F683, V685, A703, F715, L722 |
| 5 | Small glutamine-rich tetra-tricopeptide repeat-containing protein alpha | O43765 SGTA_ HUMAN | A8, I12, A91, A110, Y114, A117, Y127, F128, C129, A132, A134, A144, C148, A151, A161, M165, A168, A178, Y182, A185, A202 |
| 6 | Prohibitin | P35232 PHB_ HUMAN | V22, V23, A26, L27, Y28, V30, A36, V37, I38, F39, F42, V45, V50, H55, F56, L57, I58, W60, V61, F67, C69, V76, V78, V88, I90, L92, I94, L95, F96, L103, I106, F107, I110, Y114, V118, L119, I126, L127, V130, V131, A132, F134, A136, L139, I140, V150, L154, A158, L163, I164, L165, V168, L170, L173, F175, F179, V183, A193, A196, V200, I211, I212, A214, A220, L223, I224, L228, L235, I236, L238, L241, A244, I247, A248, L251, Y259, L260, V266, L267, L268, L270 |
| 7 | Importin subunit alpha-1 | P52292 IMA1_ HUMAN | I81, I85, A96, A99, A100, L104, I115, L120, F124, F127, L128, I136, A141, A143, L144, I147, A148, V158, A163, I164, F167, L171, I178, A182, V183, A185, L186, I189, A190, V200, A205, L209, L213, L226, L229, |

TABLE 2-continued

| SEQ ID NO. | Protein Name | UniProt ID No. | Exemplified Sites of Mutations to Generate Peptidogenic Protein (Each position can be substituted alone or in any combination with any of the other listed amino acid positions.) |
|---|---|---|---|
| | | | L233, L236, C237, A248, V249, I252, L253, L256, L259, L260, V267, C272, A274, I275, L278, I286, V289, V294, V295, L298, L302, I309, A313, L314, A316, I317, I320, V331, A336, L337, F340, L343, L344, I351, A355, M359, I362, I370, V373, L378, V379, L382, V385, L386, A397, V398, A400, V401, Y404, I413, L416, I421, L425, M426, I436, I437, V439, I440, L441, A443, I444, I447, F448, A450, I464, I473, V484 |
| 8 | Bone marrow stromal antigen 2 | Q10589 BST2_ HUMAN | L23, L24, I26, I28, L29, V30, L31, I42, F44, I46, A52, C53, L57, A59, V60, M61, C63, V66, L70, L74, A77, F81, V84, C91, V95, M96, L98, M99, L102, V113, L116, I120, L123, L127, A130, V134, L137, L144, A165, L168, L169, I170, V171, L172, L173, L175 |
| 9 | MAGUK p55 subfamily member 5 | Q8N3R9 MPP5_ HUMAN | L131, I134, I147, L150, A162, F163, H166, I169, A186, V193, L208, L220, A223, H224, V278, A289, I309, L328, L332 |
| 10 | Prohibitin-2 | Q99623 PHB2_ HUMAN | A22, L23, L25, L26, L27, A29, A31, V32, A33, Y34, V36, V40, F41, V43, A49, I50, F51, F52, I55, I63, L64, L68, H69, F70, I72, W74, F75, Y81, I83, A85, I90, L99, V102, I104, L106, V108, L109, L117, M120, Y121, L124, Y128, V132, L133, I136, V137, V140, L141, V144, V145, A146, F148, A150, L153, I154, I164, L168, A172, L177, L179, V182, L183, I184, L187, F189, Y193, V197, A207, A210, V214, V226, A228, A234, M237, L238, A241, L242, Y248, I249, L251, I254, A257, I260, I264, I271, Y272, L273, L278, V279, L280, L282, L294 |
| 11 | Replicase polyprotein 1a | P0C6U8 R1A_ CVHSA | V20, L21, V26, A38, A42, C51, L53, V54, V69, F70, V86, V106, L107, V108, V1547, V1551, V1561, Y1567, F1595, Y1612, F1619, M1624, A1626, I1644, Y1652, V1656, L1657, L1658, A1659, L1660, A1669, A1671, L1672, Y1676, A1679, A1684, F1687, C1688, A1689, L1690, I1691, A1693, V1705, M1709, L1712, L1713, A1721, A1744, V1745, L1756, A1770, L1774, F1781, V1782, M1783, M1784, L1793, C1800, A1801, H1815, I1816, L1822, V1840, V1843, F1844, L1907, F1914, L1918, V1934, V1944, V1945, A1946, I1947, I1967, C1986, L1987, V3253, C3256, V3258, V3260, L3267, L3270, L3272, V3276, C3278, V3282, C3284, V3308, |

TABLE 2-continued

| SEQ ID NO. | Protein Name | UniProt ID No. | Exemplified Sites of Mutations to Generate Peptidogenic Protein (Each position can be substituted alone or in any combination with any of the other listed amino acid positions.) |
|---|---|---|---|
| | | | L3326, L3327, L3329, V3331, F3352, V3354, C3357, C3368, A3369, M3370, I3376, V3388, F3390, V3397, F3399, C3400, Y3401, M3402, H3412, A3413, L3417, V3444, L3445, A3446, L3448, Y3449, A3450, A3451, F3470, A3474, L3490, L3493, M3504, C3505, A3506, A3507, L3508, I3521, V3536, V3537, V4051, C4061, L4103, V4105, A4107, A4133, A4147, L4159, A4160, L4161, A4171, L4205, Y4206, V4219, C4307 |
| 12 | Replicase polyprotein 1ab | P0C6X7 R1AB_ CVHSA | V840, I842, V863, V876, V880, L884, L908, M921, C923, L1364, M1365, I1367, M1375, I1378, F1398, F1400, Y1401, I1410, L1414, L1421, V1422, A1438, A1439, V1450, V1451, Y1462, V1481, F1503, L1504, V1511, F1521, L1533, L1537, I1545, V1547, V1551, V1561, Y1567, F1595, V1597, Y1612, L1620, M1624, A1626, V1638, I1644, Y1652, L1653, V1656, L1657, L1658, A1659, L1660, F1667, A1669, A1671, L1672, A1675, A1679, A1681, A1684, F1687, C1688, A1689, L1690, I1691, L1692, A1693, V1705, M1709, L1712, L1713, L1725, V1742, A1744, V1745, L1756, A1770, L1774, F1781, V1782, M1783, M1784, L1793, C1800, A1801, H1812, H1815, I1816, L1822, I1825, V1840, V1843, F1844, V3253, C3256, V3258, V3260, C3262, L3267, L3270, L3272, V3276, C3278, V3282, I3283, V3308, L3315, L3326, L3327, L3329, V3331, F3352, V3354, A3356, C3357, C3368, A3369, M3370, I3376, L3381, V3388, F3390, C3396, V3397, F3399, C3400, Y3401, M3402, H3403, H3412, A3413, L3417, Y3422, V3444, L3445, A3446, W3447, L3448, Y3449, A3450, A3451, F3459, F3470, A3474, L3490, L3493, M3504, C3505, A3506, A3507, L3508, I3521, F3531, V3536, M3839, V3842, L3853, C3868, I3875, A3878, A3884, L3891, C4033, L4047, V4049, V4051, F4066, Y4068, W4073, V4078, L4103, V4105, A4107, L4116, A4132, A4147, L4159, A4160, L4161, A4171, Y4206, V4219, C4247, I4268, A4284, A4291, C4303, L4305, V4327, I4329, V4338, F4340, W4353, V4842, F4873, A5057, |

TABLE 2-continued

| SEQ ID NO. | Protein Name | UniProt ID No. | Exemplified Sites of Mutations to Generate Peptidogenic Protein (Each position can be substituted alone or in any combination with any of the other listed amino acid positions.) |
|---|---|---|---|
| | | | C5913, A5981, A5987, W5988, F5991, C5996, A6002, L6009, L6011, A6021, L6051, V6063, V6064, V6069, L6072, L6076, V6083, V6084, F6085, V6086, L6087, F6100, A6116, C6118, A6127, C6128, W6129, V6138, M6143, V6146, H6159, C6163, A6169, A6172, A6176, M6178, L6182, A6183, V6184, V6207, A6210, V6214, V6218, V6219, A6222, L6224, L6231, F6279, V6283, C6284, L6285, F6286, Y6294, A6298, V6300, C6301, L6321, A6337, F6346, F6347, I6376, M6402, M6403, L6421, V6453, A6483, I6500, L6501, I6508, I6528, V6550, F6552, F6563, V6570, L6571, I6572, A6587, A6589, F6605, F6642, F6650, V6665, F6669, L6677, L6679, I6681, C6721, I6724, L6726, L6728, F6731, I6734, I6735, I6751, F6758, L6760, A6820, Y6822, L6825, C6826, L6829, L6834, A6835, V6836, M6840, V6842, I6843, H6844, F6845, L6860, W6863, L6870, V6871, A6891, W6899, L6901, I6902, I6903, F6925, L6928, I6932, A6937, I6942, A6943, V6944, I6946, W6951, L6955, Y6956, L6958, M6959, A6967, F6968, V6969, V6972, A6974, A6979, F6980, L6981, I6982, H7000, A7001, Y7003, I7004, L7050, I7056 |
| 13 | Replicase polyprotein 1a | P0DTC1 R1A_ SARS2 | V1570, V1574, V1584, Y1590, F1618, Y1635, M1647, A1649, I1667, L1676, A1679, L1680, L1681, L1683, A1694, L1695, Y1699, A1702, A1707, F1710, C1711, A1712, A1716, V1728, M1732, L1735, F1736, A1767, V1768, F1779, A1793, L1797, V1805, M1806, M1807, C1823, A1824, H1838, I1839, L1845, I1863, V1866, F1867, L3873, A4307, A4314, C4326, V4350, I4352, V4361 |
| 14 | Replicase polyprotein 1ab | P0DTD1 R1AB_ SARS2 | I201, L204, I222, C231, I238, A239, W240, F255, I257, A260, I281, I284, F296, I300, M315, L317, M321, V337, A339, C341, C357, L360, A364, V365, I368, C370, L384, A385, Y387, L397, A405, F406, C409, V410, F411, V414, A421, Y422, W423, V424, A427, I431, V438, V439, L450, I461, I463, F467, I473, A474, I475, I476, L477, A478, F487, F499, I502, V511, I529, L533, Y534, A535, F536, A537, A540, A541, V544, F548, |

TABLE 2-continued

TABLE 2-continued

| SEQ ID NO. | Protein Name | UniProt ID No. | Exemplified Sites of Mutations to Generate Peptidogenic Protein (Each position can be substituted alone or in any combination with any of the other listed amino acid positions.) |
|---|---|---|---|
| | | | A555, V559, L562, A565, A566, I569, L570, I573, L580, A583, M584, F586, A591, L595, V596, V597, M598, A599, I601, V605, L613, I616, V620, L624, V627, L628, L631, F635, F641, L642, W646, I648, V649, F651, I652, I664, C667, I671, V675, F678, L681, V682, F685, L686, C689, I693, A698, L700, A702, L703, F709, V710, C720, F741, V756, L763, L778, V783, C784, I785, M789, L790, L791, V808, F813, V839, I841, L853, V862, V868, F871, V875, A876, V879, L883, L890, L897, W900, L907, F908, M920, C922, V1038, I1040, A1049, V1052, V1057, V1058, A1061, L1065, L1075, M1083, L1110, C1114, L1115, H1116, V1117, L1131, A1134, Y1135, F1138, L1144, L1145, A1146, L1149, C1165, V1173, L1175, L1186, Y2809, I2812, C2826, F2827, F2834, C2851, L2853, I2854, A2855, A2856, V2857, I2858, V2866, L2869, I2873, L2874, F2881, L2882, H2883, F2884, L2885, V2888, F2889, I2895, C2896, I2903, C2913, V2914, L2915, A2916, A2917, C2919, F2922, C2933, L2948, I2962, F2964, Y2968, V2975, V2976, C2984, V2996, C2997, V2998, W3004, V3005, L3006, V3017, F3018, C3019, A3023, L3026, L3027, M3030, F3031, L3041, F3067, V3078, F3153, F3156, F3157, F3175, A3178, A3179, C3181, F3183, L3184, L3185, Y3190, L3193, Y3204, Y3207, L3208, Y3226, A3229, A3230, L3234, A3235, A3237, L3238, L3249, V3276, C3279, V3281, V3283, L3293, L3295, V3299, C3301, V3305, V3331, V3349, L3350, L3352, V3354, F3375, V3377, C3380, C3391, A3392, M3393, I3399, V3411, F3413, V3420, F3422, C3423, Y3424, M3425, A3436, L3440, Y3445, V3467, L3468, A3469, L3471, Y3472, A3473, A3474, F3493, A3497, L3513, M3527, C3528, A3529, L3531, I3544, V3559, L3876, C3891, I3898, A3907, L3914, I4074, C4084, I4098, L4126, V4128, A4130, A4307, A4314, C4326, V4350, I4352, V4361, A4435, A4438, I4478, L4482, A4487, L4511, A4517, V4520, L4523, F4526, L4534, I4537, L4538, C4543, I4563, V4566, Y4567, A4577, L4578, F4584, C4585, M4588, I4593, L4597, L4599, Y4629, |
| | | | Y4630, L4632, L4633, M4634, I4636, A4642, A4645, L4674, Y4678, F4679, C4690, H4701, C4702, A4703, F4705, L4708, F4709, I4725, H4739, L4743, V4745, V4746, A4767, A4768, A4791, F4811, A4815, V4827, Y4845, M4855, C4856, I4858, L4861, V4864, V4867, V4868, A4894, L4919, I4931, V4952, C4955, M4958, F4963, H4964, I4971, V4979, L4994, L5006, A5017, M5018, M5021, L5022, I5024, M5025, A5026, A5048, C5051, A5052, V5059, L5065, A5082, V5085, F5086, I5088, C5089, A5091, V5092, A5094, V5096, A5098, L5099, V5112, L5115, L5119, F5137, L5141, F5145, M5147, I5149, A5154, V5155, V5156, C5157, V5168, A5169, F5174, V5177, L5178, V5184, M5186, I5229, L5230, C5234, F5251, A5258, L5261, V5272, Y5276, I6663, A6802, A6843, L6848, C6849, L6852, L6857, V6859, M6863, V6865, H6867, F6868, L6883, W6886, L6893, W6922, L6924, I6925, I6926, F6948, I6951, I6955, L6959, A6960, V6965, A6966, I6967, I6969, W6974, L6978, Y6979, M6982, F6985, A6990, F6991, V6992, V6995, A6997, A7002, F7003, L7004, I7005, H7023, A7024, Y7026, I7027, I7035, F7048, L7073, L7078, I7079 |
| 15 | Spike glycoprotein | P0DTC2 SPIKE_ SARS2 | V36, Y37, F55, L56, V62, F86, V90, Y91, F92, A93, I105, F106, L117, I119, V130, C131, L189, V193, F194, F201, L223, L229, F238, L241, A264, Y265, Y266, V267, F275, L276, L277, V308, I326, V350, W353, I358, C361, A363, Y365, L387, F392, V395, A397, F400, V401, I402, I410, I418, A419, Y423, L425, C432, V433, I434, A435, L492, F497, V510, V511, V512, L513, V524, V539, F543, L552, A575, V576, L585, V597, I598, A609, C649, L650, A653, C671, A672, I692, A694, Y695, I714, F718, V729, C738, I742, C749, L767, V781, I805, L806, I818, L822, A871, A876, L877, L878, A879, I882, M902, A903, F906, V911, V915, L916, I923, F927, I931, L945, L948, L962, I980, A989, I993, L996, I997, A1015, A1022, A1025, M1029, C1032, V1033, C1043, L1049, M1050, F1052, A1056, V1060, V1061, F1062, L1063, H1064, V1065, Y1067, A1080, I1081, |

13

TABLE 2-continued

| SEQ ID NO. | Protein Name | UniProt ID No. | Exemplified Sites of Mutations to Generate Peptidogenic Protein (Each position can be substituted alone or in any combination with any of the other listed amino acid positions.) |
|---|---|---|---|
| 16 | Spike glycoprotein | P59594 SPIKE_CVHSA | A1087, F1095, V1096, V1104, I1115 V40, Y41, F59, L60, V66, F69, F76, F83, I87, Y88, F89, A90, A91, V97, V98, V102, F103, V114, I115, I125, A127, C128, F130, C133, F137, F138, A139, V140, I152, L182, V186, F187, L194, V196, L209, L216, F231, A233, I234, L235, A237, F238, A250, Y252, F253, V254, L257, F262, M263, L264, Y266, L286, I295, F305, V313, F316, F325, V328, V337, W340, I345, C348, A350, Y352, L374, C378, V382, A384, F387, V388, V389, I397, A398, I405, A406, Y410, L412, M417, C419, V420, L421, A422, F483, V496, V497, V498, L499, F501, V510, C524, V525, F527, F529, L538, V562, I570, L571, V581, V583, I584, A595, V596, L597, Y598, V606, A609, C635, L636, I637, A639, I650, C657, A658, I674, V675, A676, Y677, I696, V711, M713, V718, C720, Y723, I724, C731, L745, L749, V763, F764, F782, F784, I787, L788, I800, L804, A853, A858, L859, V860, A864, M884, A885, F888, V893, V897, L898, Y899, I905, F909, A912, I913, L930, L944, I962, A971, I975, L978, I979, L986, A997, A1004, A1007, M1011, C1014, V1015, C1025, H1030, L1031, M1032, F1034, A1037, V1042, V1043, F1044, L1045, H1046, V1047, Y1049, F1057, A1060, A1062, I1063, A1069, F1077, V1078, I1097 |
| 17 | Nucleoprotein | P59595 NCAP_CVHSA | A56, L57, L65, V73, I85, Y87, Y88, W109, F111, Y113, L114, V134, A135, A139, L160, H357 |
| 18 | Protein 3a | P59632 AP3A_CVHSA | V29, A31, I35, F43, W45, L46, V47, I48, V50, A51, F52, L53, A54, V55, F56, A59, I62, I63, L65, W69, A72, F77, F79, I80, C81, L83, F87, V88, L95, L96, V97, A103, F105, L106, L108, A110, F114, C117, A120, C121, M125, C127, L129, C130, W131, C133, A143, Y145, F146, V147, C148, W149, H150, Y154, Y156, C157, I158, Y160, V163, I167, V168, V169, L180, Y184, I186, V197, Y200, V201, V202, V203, H204, Y206, F207, V210, Y212, L214, I219, I225, A228, F230, F231, I232, F233, I236, A243, I245, H246, I248, V254, A255, I262 |
| 19 | Protein 7a | P59635 NS7A_CVHSA | F63 |

14

TABLE 2-continued

| SEQ ID NO. | Protein Name | UniProt ID No. | Exemplified Sites of Mutations to Generate Peptidogenic Protein (Each position can be substituted alone or in any combination with any of the other listed amino acid positions.) |
|---|---|---|---|
| 20 | Envelope small membrane protein | P59637 VEMP_CVHSA | A36, L37, L39, C40, A41, Y42, C43, C44, I46, V47, V49, V56, V58, Y59, V62, L65 |
| 21 | Membrane protein | P59596 VME1_CVHSA | L21, V22, I23, F25, L33, L34, F44, L45, Y46, I47, I48, L50, F52, L61, A62, C63, F64, V65, L66, A68, L92, Y94, F95, V96, F99, L101, F102, M108, W109, F111, I117, L118, L119, V121, L123, I127, V128, L132, L137, V138, I139, A141, V142, I143, L148, M150, H153, L155, C158, I160, L163, I167, V169, A170, L175, Y177, Y178, F192, A193, A194, Y195, I200, Y203, L205, I216, A217, L218, L219, V220 |
| 22 | Non-structural protein 3b | P59633 NS3B_CVHSA | V22, I25, L30, V32, A34, F35, L46, V47, V48, I49, L50, I52, V56, L57, M60, L62, Y63, M64, A65, I66, F70, L74, L76, L79, L80, L83, V84, L85, M87, L88, L93, L96, L97, C103, L111, L115, I116, W119, I120, F122, M123, L129, L130, C132, L133, C134, C144 |
| 23 | Non-structural protein 6 | P59634 NS6_CVHSA | F22, I24, A25, I26, L29, V31, I32, I33, I36, V37, L40, F41, Y49, L52 |
| 24 | Protein 3a | P0DTC3 AP3A_SARS2 | V29, A31, I35, I37, F43, W45, L46, I47, V48, V50, A51, L52, L53, V55, F56, A59, I62, I63, L65, W69, A72, L73, V77, F79, V80, C81, L83, F87, V88, L95, L96, V97, A103, F105, L106, Y107, L108, A110, L111, F114, F120, V121, L127, L129, C130, W131, C133, A143, Y145, F146, L147, C148, W149, H150, C153, Y154, Y156, C157, I158, Y160, V163, I167, V168, I169, Y184, I186, Y189, V197, C200, V201, V202, L203, H204, Y206, F207, Y212, L214, L219, V225, V228, F230, F231, I232, Y233, I236, V244, I246, H247, I249, V255, V256, V259, M260, I263 |
| 25 | Membrane protein | P0DTC5 VME1_SARS2 | L22, V23, I24, F26, L34, L35, F45, L46, Y47, I48, I49, L51, F53, A63, A69, I97, F100, W110, F112, I118, L119, L120, L133, L138, V139, I140, A142, V143, I144, L149, I151, L156, L164, I168, V170, A171, L176, Y178, Y179, F193, A194, A195, Y196, Y199, I201, Y204, L206, L219, V221 |
| 26 | Protein 7a | P0DTC7 NS7A_SARS2 | C23, V29, L31, C35, Y40, F54, A55, L56, C58, F63, A64, F65, C67, V71, H73, V74, Y75, L77, A79, C113 |

TABLE 2-continued

| SEQ ID NO. | Protein Name | UniProt ID No. | Exemplified Sites of Mutations to Generate Peptidogenic Protein (Each position can be substituted alone or in any combination with any of the other listed amino acid positions.) |
|---|---|---|---|
| 27 | Nucleo-protein | P0DTC9 NCAP_ SARS2 | F53, A55, L56, L64, F66, V72, I84, Y86, Y87, W108, F110, Y112, LH3, I130, I131, W132, V133, A134, A138, I146, L159, L161, F171, A218, L219, A220, L221, L222, L223, A264, V270, A273, F274, F286, L291, Y298, W301, I304, F307, A308, A313, F314, F315, I320, L331, Y333, I337, L339, L352, L353, A359, F403, L407 |
| 28 | Protein 9b | P59636 ORF9B_ CVHSA | L22, I24, M27, Y43, I45, I46, L47, L55, M57, A58, F70, L82, L88, F92, V93, V94, V95, A97 |
| 29 | Envelope small membrane protein | P0DTC4 VEMP_ SARS2 | A36, L37, L39, C40, A41, Y42, C43, C44, I46, V47, V49, F56, V58, Y59, V62 |
| 30 | Non-structural protein 6 | P0DTC6 NS6_ SARS2 | F22, V24, I26, L29, Y31, I32, I33, I36, I37, L40, Y49, L52 |
| 31 | Non-structural protein 8 | P0DTC8 NS8_ SARS2 | C25, V33, C37, I39, F41, Y42, W45, Y46, I47, V49, L57, I58, L60, C61, I71, Y73, I76, Y79, V81, C83, F86, I88, |

TABLE 2-continued

| SEQ ID NO. | Protein Name | UniProt ID No. | Exemplified Sites of Mutations to Generate Peptidogenic Protein (Each position can be substituted alone or in any combination with any of the other listed amino acid positions.) |
|---|---|---|---|
| 32 | Protein 9b | P0DTD2 ORF9B_ SARS2 | C90, L98, V99, V100, C102, F104, F108, L109, V114, V116, V117, L118 L21, A22, V23, Y42, I44, I45, L46, L54, A57, F69, L81, L87, F91, V92, V93, V94 |
| 33 | Protein non-structural 7b | Q7TFA1 NS7B_ CVHSA | I34, C41 |
| 34 | Non-structural protein 8b | Q80H93 NS8B_ CVHSA | L21, C22, L24, L28, F30, W33, M36, V37, C40, V44, I46, C48, A55, L56, I57, A58, C60, W61, Y62, L63, F72 V75, V77, L79 |
| 35 | Uncharacterized protein 14 | P0DTD3 Y14_SARS2 | A23, V27, L31, V32, V36, V37, A38, V40, I43, V49, L52, L53, L55, W57, L58, A61, V62 |
| 36 | Protein non-structural 7b | P0DTD8 NS7B_SARS2 | I26, I27, F28, W29, F30, L32, L34, C41 |
| 37 | Protein non-structural 8a | Q7TFA0 NS8A_ CVHSA | C23, C35 |
| 38 | Uncharacterized protein 14 | Q7TLC7 Y14_ CVHSA | A23, V27, L31, V36, V37, V39, I40, I43, L45, L46, V49, I52, L53, L55, W57, L58, V61 |

SEQ ID NO: 1

MALNSGSPPAIGPYYENHGYQPENPYPAQPTVVPTVYEVHPAQYYPSPVPQYAPRVLTQASNPVVCTQPKSPSGTVCTSKTKKALCITLTLGTFLVGAAL
AAGLLWKFMGSKCSNSGIECDSSGTCINPSNWCDGVSHCPGGEDENRCVRLYGPNFILQVYSSQRKSWHPVCQDDWNENYGRAACRDMGYKNNFYSSQGI
VDDSGSTSFMKLNTSAGNVDIYKKLYHSDACSSKAVVSLRCIACGVNLNSSRQSRIVGGESALPGAWPWQVSLHVQNVHVCGGSIITPEWIVTAAHCVEK
PLNNPWHWTAFAGILRQSFMFYGAGYQVEKVISHPNYDSKTKNNDIALMKLQKPLTFNDLVKPVCLPNPGMMLQPEQLCWISGWGATEEKGKTSEVLNAA
KVLLIETQRCNSRYVYDNLITPAMICAGFLQGNVDSCQGDSGGPLVTSKNNIWWLIGDTSWGSGCAKAYRPGVYGNVMVFTDWIYRQMRADG

SEQ ID NO: 2

MELRPWLLWVVAATGTLVLLAADAQGQKVETNTWAVRIPGGPAVANSVARKHGELNLGQIFGDYYHFWHRGVTKRSLSPHRPRHSRLQREPQVQWLEQQV
AKRRTKRDVYQEPTDPKFPQQWYLSGVTQRDLNVKAAWAQGYTGHGIVVSILDDGIEKNHPDLAGNYDPGASFDVNDQDPDPQPRYTQMNDNRHGTRCAG
EVAAVANNGVCGVGVAYNARIGGVRMLDGEVTDAVEARSLGLNPNHIHIYSASWGPEDDGKTVDGPARLAEEAFFRGVSQGRGGLGSIFVWASGNGGREH
DSCNCDGYTNSIYTLSISSATQFGNVPWYSEACSSTLATTYSSGNQNEKQIVTTDLRQKCTESHTGTSASAPLAAGIIALTLEANKNLTWRDMQHLVVQT
SKPAHLNANDWATNGVGRKVSHSYGYGLLDAGAMVALAQNWTTVAPQRKCIIDILTEPKDIGKRLEVRKTVTACLGEPNHITRLEHAQARLTLSYNRRGD
LAIHLVSPMGTRSTLLAARPHDYSADGFNDWAFMTTHSWDEDPSGEWVLEIENTSEANNYGTLTKFTLVLYGTAPEGLPVPPESSGCKTLTSSQACVVCE
EGFSLHQKSCVQHCPPGFAPQVLDTHYSTENDVETIRASVCAPCHASCATCQGPALTDCLSCPSHASLDPVEQTCSRQSQSSRESPPQQQPPRLPPEVEA
GQRLRAGLLPSHLPEVVAGLSCAFIVLVFVTVFLVLQLRSGFSFRGVKVYTMDRGLISYKGLPPEAWQEECPSDSEEDEGRGERTAFIKDQSAL

SEQ ID NO: 3

MAAFSEMGVMPEIAQAVEEMDWLLPTDIQAESIPLILGGGDVLMAAETGSGKTGAFSIPVIQIVYETLKDQQEGKKGKTTIKTGASVLNKWQMNPYDRGS
AFAIGSDGLCCQSREVKEWHGCRATKGLMKGKHYYEVSCHDQGLCRVGWSTMQASLDLGTDKFGFGFGGTGKKSHNKQFDNYGEEFTMHDTIGCYLDIDK
GHVKFSKNGKDLGLAFEIPPHMKNQALFPACVLKNAELKFNFGEEEFKFPPKDGFVALSKAPDGYIVKSQHSGNAQVTQTKFLPNAPKALIVEPSRELAE
QTLNNIKQFKKYIDNPKLRELLIIGGVAARDQLSVLENGVDIVVGTPGRLDDLVSTGKLNLSQVRFLVLDEADGLLSQGYSDFINRMHNQIPQVTSDGKR
LQVIVCSATLHSFDVKKLSEKIMHFPTWVDLKGEDSVPDTVHHVVVPVNPKTDRLWERLGKSHIRTDDVHAKDNTRPGANSPEMWSEAIKILKGEYAVRA
IKEHKMDQAIIFCRTKIDCDNLEQYFIQQGGGPDKKGHQFSCVCLHGDRKPHERKQNLERFKKGDVRFLICTDVAARGIDIHGVPYVINVTLPDEKQNYV
HRIGRVGRAERMGLAISLVATEKEKVWYHVCSSRGKGCYNTRLKEDGGCTIWYNEMQLLSEIEEHLNCTISQVEPDIKVPVDEFDGKVTYGQKRAAGGGS
YKGHVDILAPTVQELAALEKEAQTSFLHLGYLPNQLFRTF

SEQ ID NO: 4

MSSSSWLLLSLVAVTAAQSTIEEQAKTFLDKFNHEAEDLFYQSSLASWNYNTNITEENVQNMNNAGDKWSAFLKEQSTLAQMYPLQEIQNLTVKLQLQAL
QQNGSSVLSEDKSKRLNTILNTMSTIYSTGKVCNPDNPQECLLLEPGLNEIMANSLDYNERLWAWESWRSEVGKQLRPLYEEYVVLKNEMARANHYEDYG
DYWRGDYEVNGVDGYDYSRGQLIEDVEHTFEEIKPLYEHLHAYVRAKLMNAYPSYISPIGCLPAHLLGDMWGRFWTNLYSLTVPFGQKPNIDVTDAMVDQ
AWDAQRIFKEAEKFFVSVGLPNMTQGFWENSMLTDPGNVQKAVCHPTAWDLGKGDFRILMCTKVTMDDFLTAHHEMGHIQYDMAYAAQPFLLRNGANEGF
HEAVGEIMSLSAATPKHLKSIGLLSPDFQEDNETEINFLLKQALTIVGTLPFTYMLEKWRWMVFKGEIPKDQWMKKWWEMKREIVGVVEPVPHDETYCDP
ASLFHVSNDYSFIRYYTRTLYQFQFQEALCQAAKHEGPLHKCDISNSTEAGQKLFNMLRLGKSEPWTLALENVVGAKNMNVRPLLNYFEPLFTWLKDQNK
NSFVGWSTDWSPYADQSIKVRISLKSALGDKAYEWNDNEMYLFRSSVAYAMRQYFLKVKNQMILFGEEDVRVANLKPRISFNFFVTAPKNVSDIIPRTEV
EKAIRMSRSRINDAFRLNDNSLEFLGIQPTLGPPNQPPVSIWLIVFGVVMGVIVVGIVILIFTGIRDRKKKNKARSGENPYASIDISKGENNPGFQNTDD
VQTSF

SEQ ID NO: 5
MDNKKRLAYAIIQFLHDQLRHGGLSSDAQESLEVAIQCLETAFGVTVEDSDLALPQTLPEIFEAAATGKEMPQDLRSPARTPPSEEDSAEAERLKTEGNE
QMKVENFEAAVHFYGKAIELNPANAVYFCNRAAAYSKLGNYAGAVQDCERAICIDPAYSKAYGRMGLALSSLNKHVEAVAYYKKALELDPDNETYKSNLK
IAELKLREAPSPTGGVGSFDIAGLLNNPGFMSMASNLMNNPQIQQLMSGMISGGNNPLGTPGTSPSQNDLASLIQAGgQFAgQMgQQNPELIEQLRSQIR
SRTPSASNDDQQE

SEQ ID NO: 6
MAAKVFESIGKFGLALAVAGGVVNSALYNVDAGHRAVIFDRFRGVQDIVVGEGTHFLIPWVQKPIIFDCRSRPRNVPVITGSKDLQNVNITLRILFRPVA
SQLPRIFTSIGEDYDERVLPSITTEILKSVVARFDAGELITQRELVSRQVSDDLTERAATFGLILDDVSLTHLTFGKEFTEAVEAKQVAQQEAERARFVV
EKAEQQKKAAIISAEGDSKAAELIANSLATAGDGLIELRKLEAAEDIAYQLSRSRNITYLPAGQSVLLQLPQ

SEQ ID NO: 7
MSTNENANTPAARLHRFKNKGKDSTEMRRRRIEVNVELRKAKKDDQMLKRRNVSSFPDDATSPLQENRNNQGTVNWSVDDIVKGINSSNVENQLQATQAA
RKLLSREKQPPIDNIIRAGLIPKFVSFLGRTDCSPIQFESAWALTNIASGTSEQTKAVVDGGAIPAFISLLASPHAHISEQAVWALGNIAGDGSVFRDLV
IKYGAVDPLLALLAVPDMSSLACGYLRNLTWTLSNLCRNKNPAPPIDAVEQILPTLVRLLHHDDPEVLADTCWAISYLTDGPNERIGMVVKTGVVPQLVK
LLGASELPIVTPALRAIGNIVTGTDEQTQVVIDAGALAVFPSLLTNPKTNIQKEATWTMSNITAGRQDQIQQVVNHGLVPFLVSVLSKADFKTQKEAVWA
VTNYTSGGTVEQIVYLVHCGIIEPLMNLLTAKDTKIILVILDAISNIFQAAEKLGETEKLSIMIEECGGLDKIEALQNHENESVYKASLSLIEKYFSVEE
EEDQNWPETTSEGYTFQVQDGAPGTFNF

SEQ ID NO: 8
MASTSYDYCRVPMEDGDKRCKLLLGIGILVLLIIVILGVPLIIFTIKANSEACRDGLRAVMECRNVTHLLQQELTEAQKGFQDVEAQAATCNHTVMALMA
SLDAEKAQGQKKVEELEGEITTLNHKLQDASAEVERLRRENQVLSVRIADKKYYPSSQDSSSAAAPQLLIVLLGLSALLQ

SEQ ID NO: 9
MTTSHMNGHVTEESDSEVKNVDLASPEEHQKHREMAVDCPGDLGTRMMPIRRSAQLERIRQQQEDMRRRREEEGKKQELDLNSSMRLKKLAQIPPKTGID
NPMFDTEEGIVLESPHYAVKILEIEDLFSSLKHIQHTLVDSQSQEDISLLLQLVQNKDFQNAFKIHNAITVHMNKASPPFPLISNAQDLAQEVQTVLKPV
HHKEGQELTALLNTPHIQALLLAHDKVAEQEMQLEPITDERVYESIGQYGGETVKIVRIEKARDIPLGATVRNEMDSVIISRIVKGGAAEKSGLLHEGDE
VLEINGIEIRGKDVNEVFDLLSDMHGTLTFVLIPSQQIKPPPAKETVIHVKAHFDYDPSDDPYVPCRELGLSFQKGDILHVISQEDPNWWQAYREGDEDN
QPLAGLVPGKSFQQQREAMKQTIEEDKEPEKSGKLWCAKKNKKKRKKVLYNANKNDDYDNEEILTYEEMSLYHQPANRKRPIILIGPQNCGQNELRQRLM
NKEKDRFASAVPHTTRSRRDQEVAGRDYHFVSRQAFEADIAAGKFIEHGEFEKNLYGTSIDSVRQVINSGKICLLSLRTQSLKTLRNSDLKPYIIFIAPP
SQERLRALLAKEGKNPKPEELREIIEKTREMEQNNGHYFDTAIVNSDLDKAYQELLRLINKLDTEPQWVPSTWLR

SEQ ID NO: 10
MAQNLKDLAGRLPAGPRGMGTALKLLLGAGAVAYGVRESVFTVEGGHRAIFFNRIGGVQQDTILAEGLHFRIPWFQYPIIYDIRARPRKISSPTGSKDLQ
MVNISLRVLSRPNAQELPSMYQRLGLDYEERVLPSIVNEVLKSVVAKFNASQLITQRAQVSLLIRRELTERAKDFSLILDDVAITELSFSREYTAAVEAK
QVAQQEAQRAQFLVEKAKQEQRQKIVQAEGEAEAAKMLGEALSKNPGYIKLRKIRAAQNISKTIATSQNRIYLTADNLVLNLQDESFTRGSDSLIKGKK

SEQ ID NO: 11
MESLVLGVNEKTHVQLSLPVLQVRDVLVRGFGDSVEEALSEAREHLKNGTCGLVELEKGVLPQLEQPYVFIKRSDALSTNHGHKVVELVAEMDGIQYGRS
GITLGVLVPHVGETPIAYRNVLLRKNGNKGAGGHSYGIDLKSYDLGDELGTDPIEDYEQNWNTKHGSGALRELTRELNGGAVTRYVDNNFCGPDGYPLDC
IKDFLARAGKSMCTLSEQLDYIESKRGVYCCRDHEHEIAWFTERSDKSYEHQTPFEIKSAKKFDTFKGECPKFVFPLNSKVKVIQPRVEKKKTEGFMGRI
RSVYPVASPQECNNMHLSTLMKCNHCDEVSWQTCDFLKATCEHCGTENLVIEGPTTCGYLPTNAVVKMPCPACQDPEIGPEHSVADYHNHSNIETRLRKG
GRTRCFGGCVFAYVGCYNKRAYWVPRASADIGSGHTGITGDNVETLNEDLLEILSRERVNINIVGDPHLNEEVAIILASFSASTSAFIDTIKSLDYKSFK
TIVESCGNYKVTKGKPVKGAWNIGQQRSVLTPLCGFPSQAAGVIRSIFARTLDAANHSIPDLQRAAVTILDGISEQSLRLVDAMVYTSDLLTNSVIIMAY
VTGGLVQQTSQWLSNLLGTTVEKLRPIFEWIEAKLSAGVEFLKDAWEILKFLITGVFDIVKGQIQVASDNIKDCVKCFIDVVNKALEMCIDQVTIAGAKL
RSLNLGEVFIAQSKGLYRQCIRGKEQLQLLMPLKAPKEVTFLEGDSHDTVLTSEEVVLKNGELEALETPVDSFTNGAIVGTPVCVNGLMLLEIKDKEQYC
ALSPGLLATNNVFRLKGGAPIKGVTFGEDTVWEVQGYKNVRITFELDERVDKVLNEKCSVYTVESGTEVTEFACVVAEAVVKTLQPVSDLLTNMGIDLDE
WSVATFYLFDDAGEENFSSRMYCSFYPPDEEEEDDAECEEEEIDETCEHEYGTEDDYQGLPLEFGASAETVRVEEEEEEDWLDDTTEQSEIEPEPEPTPE
EPVNQFTGYLKLTDNVAIKCVDIVKEAQSANPMVIVNNAANIHLKHGGGVAGALNKATNGAMQKESDDYIKLNGPLTVGGSCLLSGHNLAKKCLHVVGPNL
NAGEDIQLLKAAYENFNSQDILLAPLLSAGIFGAKPLQSLQVCVQTVRTQVYIAVNDKALYEQVVMDYLDNLKPRVEAPKQEEPPNTEDSKTEEKSVVQK
PVDVKPKIKACIDEVTTTLEETKFLTNKLLLFADINGKLYHDSQNMLRGEDMSFLEKDAPYMVGDVITSGDITCVVIPSKKAGGTTEMLSRALKKVPVDE
YITTYPGQGCAGYTLEEAKTALKKCKSAFYVLPSEAPNAKEEILGTVSWNLREMLAHAEETRKLMPICMDVRAIMATIQRKYKGIKIQEGIVDYGVRFFF
YTSKEPVASIITKLNSLNEPLVTMPIGYVTHGFNLEEAARCMRSLKAPAVVSVSSPDAVTTYNGYLTSSSKTSEEHFVETVSLAGSYRDWSYSGQRTELG
VEFLKRGDKIVYHTLESPVEFHLDGEVLSLDKLKSLLSLREVKTIKVFTTVDNTKIKPHVNHEGKTFFVLPS
DDTLRSEAFEYYHTLDESFLGRYMSALNHTKKWKFPQVGGLTSIKWADNNCYLSSVLLALQQLEVKFNAPALQEAYYRARAGDAANFCALILAYSNKTVG
ELGDVRETMTHLLQHANLESAKRVLNVVCKHCGQKTTTLTGVEAVMYGMGTLSYDNLKTGVSIPCVCGRDATQYLVQQESSFVMMSAPPAEYKLQQGTFLC
ANEYTGNYQCGHYTHITAKETLYRIDGAHLTKMSEYKGPVTDVFYKETSYTTTIKPVSYKLDGVTYTEIEPKLDGYYKKDNAYYTEQPIDLVPTQPLPNA
SFDNFKLTCSNTKFADDLNQMTGFTKPASRELSVTFFPDLNGDVVAIDYRHYSASFKKGAKLHHITPLTDNVIAVNSATTKTTFKPNTWCLRCLWSTKPVDTSN
SFEVLAVEDTQGMDNLACESQQPTSEEVVENPTIQKEVIECDVKTTEVVGNVILKPSDEGVKVTQELGHEDLMAAYVENTSITIKKPNELSLALGLKTIA
THGIAAINSVPWSKILAYVKPFLGQAAITTSNCAKRLAQRVFNNYMPYVFTLLFQLCTFTKSTNSRIRASLPTTIAKNSVKSVAKLCLDAGINYVKSPKF
SKLFTIAMWLLLLSICLGSLICVTAAFGVLLSNFGAPSYCNGVRELYLNSSNVTTMDFCEGSFPCSICLSGLDSLDSYPALETIQVTISSYKLDLTILGL
AAEWVLAYMLFTKFFYLLGLSAIMQVFFGYFASHFISNSWLMWFIISIVQMAPVSAMVRMYIFFASFYYIWKSYVHIMDGCTSSTCMMCYKRNRATRVEC
TTIVNGMKRSFYVYANGGRGFCKTHNWNCLNCDTFCTGSTFISDEVARDLSLQFKRPINPTDQSSYIVDSVAVKNGALHLYFDKAGQKTYERHPLSHFVN
LDNLRANNTKGSLPINVIVFDGKSKCDESASKSASVYYSQLMCQPILLLDQALVSDVGDSTEVSVKMFDAYVDTFSATFSVPMEKLKALVATAHSELAKG
VALDGVLSTFVSAARQGVVDTDVDTKDVIECLKLSHHSDLEVTGDSCNNFMLTYNKVENMTPRDLGACIDCNARHINAQVAKSHNVSLIWNVKDYMSLSE
QLRKQIRSAAKKNNIPFRLTCATTRQVVNNVITTKISLKGGKIVSTCFKLMLKATLLCVLAALVCYIVMPVHTLSIHDGYTNEIIGYKAIQDGVTRDIIST
DDCFANKHAGFDAWFSQRGGSYKNDKSCPVVAAIITREIGFIVNGTPLGGFLHFLPRVFSAVGNICYTPSKLIEYSDFATSACVLAAECTIFK
DAMGKPVPYCYDTNLLEGSISYSELRPDTRYVLMDGSIIQFPNTYLEGSVRVVTTFDAEYCRHGTCERSEVGICLSTSGRWVLNNEHYRALSGVFCGVDA
MNLIANIFTPLVQPVGALDVSASVVAGGIIAILVTCAAYYFMKFRRVFGEYNHVVAANALLFLMSFTILCLVPAYSFLPGVYSVFYLYLTFYFTNDVSFL
AHLQWFAMFSPIVPFWITAIYVFCISLKHCHWFFNNYLRKRVMFNGVTFSTFEEAALCTFLLNKEMYLKLRSETLLPLTQYNRYLALYNKYKYFSGALDT
TSYREAACCHLAKALNDFSNSGADVLYQPPQTSITSAVLQSGFRKMAFPSGKVEGCMVQVTCGTTTLNGLWLDDTVYCPRHVICTAEDMLNPNYEDLLIR
KSNHSFLVQAGNVQLRVIGHSMQNCLLRLKVDTSNPKTPKYKFVRIQPGQTFSVLACYNGSPSGVYQCAMRPNHTIKGSFLNGSCGSVGFNIDYDCVSFC
YMHHMELPTGVHAGTDLEGKFYGPFVDRQTAQAAGTDTTITLNVLAWLYAAVINGDRWFLNRFTTTLNDFNLVAMKYNYEPLTQDHVDILGPLSAQTGIA
VLDMCAALKELLQNGMNGRTILGSTILEDEFTPFDVVRQCSGVTFQGKFKKIVKGTHHWMLLTFLTSLLILVQSTQWSLFFFVYENAFLPFTLGIMAIAA
CAMLLVKHKHAFLCLFLLPSLATVAYFNMVYMPASWVMRIMTWLELADTSLSGYRLKDCVMYASALVLLILMTARTVYDDAARRVWTLMNVITLVYKVYY
GNALDQAISMWALVISVTSNYSGVVTTIMFLARAIVFVCVEYYPLLFITGNTLQCIMLVYCFLGYCCCCYGFLFCLLNRYFRLTLGVYDYLVSTQEFRYM
NSQGLLPPKSSIDAFKLNIKLLGIGGKPCIKVATVQSKMSDVKCTSVVLLSVLQQLRVESSSKLWAQCVQLHNDILLAKDTTEAFEKMVSLLSVLLSMQG
AVDINRLCEEMLDNRATLQAIASEFSSLPSYAAYATAQEAYEQAVANGDSEVVLKKLKKSLNVAKSEFDRDAAMQRKLEKMADQAMTQMYKQARSEDKRA

KVTSAMQTMLFTMLRKLDNDALNNIINNARDGCVPLNIIPLTTAAKLMVVVPDYGTYKNTCDGNTFTYASALWEIQQVVDADSKIVQLSEINMDNSPNLA
WPLIVTALRANSAVKLQNNELSPVALRQMSCAAGTTQTACTDDNALAYYNNSKGGRFVLALLSDHQDLKWARFPKSDGTGTIIYTELEPPCRFVTDTPKGP
KVKYLYFIKGLNNLNRGMVLGSLAATVRLQAGNATEVPANSTVLSFCAFAVDPAKAYKDYLASGGQPITNCVKMLCTHTGTGQAITVTPEANMDQESFGG
ASCCLYCRCHIDHPNPKGFCDLKGKYVQIPTTCANDPVGFTLRNTVCTVCGMWKGYGCSCDQLREPLMQSADASTFLNGFAV

SEQ ID NO: 12
MESLVLGVNEKTHVQLSLPVLQVRDVLVRGFGDSVEEALSEAREHLKNGTCGLVELEKGVLPQLEQPYVFIKRSDALSTNHGHKVVELVAEMDGIQYGRS
GITLGVLVPHVGETPIAYRNVLLRKNGNKGAGGHSYGIDLKSYDLGDELGTDPIEDYEQNWNTKHGSGALRELTRELNGGAVTRYVDNNFCGPDGYPLDC
IKDFLARAGKSMCTLSEQLDYIESKRGVYCCRDHEHEIAWFTERSDKSYEHQTPFEIKSAKKFDTFKGECPKFVFPLNSKVKVIQPRVEKKKTEGFMGRI
RSVYPVASPQECNNMHLSTLMKCNHCDEVSWQTCDFLKATCEHCGTENLVIEGPTTCGYLPTNAVVKMPCPACQDPEIGPEHSVADYHNHSNIETRLRKG
GRTRCFGGCVFAYVGCYNKRAYWVPRASADIGSGHTGITGDNVETLNEDLLEILSRERVNINIVGDPHLNEEVAIILASFSASTSAFIDTIKSLDYKSFK
TIVESCGNYKVTKGKPVKGAWNIGQQRSVLTPLCGFPSQAAGVIRSIFARTLDAANHSIPDLQRAAVTILDGISEQSLRLVDAMVYTSDLLTNSVIIMAY
VTGGLVQQTSQWLSNLLGTTVEKLRPIFEWIEAKLSAGVEFLKDAWEILKFLITGVFDIVKGQIQVASDNIKDCVKCFIDVVNKALEMCIDQVTIAGAKL
RSLNLGEVFIAQSKGLYRQCIRGKEQLQLLMPLKAPKEVTFLEGDSHDTVLTSEEVVLKNGELEALETPVDSFTNGAIVGTPVCVNGLMLLEIKDKEQYC
ALSPGLLATNNVFRLKGGAPIKGVTFGEDTVWEVQGYKNVRITFELDERVDKVLNEKCSVYTVESGTEVTEFACVVAEAVVKTLQPVSDLLTNMGIDLDE
WSVATFYLFDDAGEENFSSRMYCSFYPPDEEEEDDAECEEEEIDETCEHEYGTEDDYQGLPLEFGASAETVRVEEEEEEDWLDDTTEQSEIEPEPEPTPE
EPVNQFTGYLKLTDNVAIKCVDIVKEAQSANPMVIVNAANIHLKHGGGVAGALNKATNGAMQKESDDYIKLNGPLTVGGSCLLSGHNLAKKCLHVVGPNL
NAGEDIQLLKAAYENFNSQDILLAPLLSAGIFGAKPLQSLQVCVQTVRTQVYIAVNDKALYEQVVMDYLDNLKPRVEAPKQEEPPNTEDSKTEEKSVVQK
PVDVKPKIKACIDEVTTTLEETKFLTNKLLLFADINGKLYHDSQNMLRGEDMSFLEKDAPYMVGDVITSGDITCVVIPSKKAGGTEMLSRALKKVPVDE
YITTYPGQGCAGYTLEEAKTALKKCKSAFYVLPSEAPNAKEEILGTVSWNLREMLAHAEETRKLMPICMDVRAIMATIQRKYKGIKIQEGIVDYGVRFFF
YTSKEPVASIITKLNSLNEPLVTMPIGYVTHGFNLEEAARCMRSLKAPAVVSVSSPDAVTTYNGYLTSSSKTSEEHFVETVSLAGSYRDWSYSGQRTELG
VEFLKRGDKIVYHTLESPVEFHLDGEVLSLDKLKSLLSLREVKTIKVFTTVDNTNLHTQLVDMSMTYGQQFGPTYLDGADVTKIKPHVNHEGKTFFVLPS
DDTLRSEAFEYYHTLDESFLGRYMSALNHTKKWKFPQVGGLTSIKWADNNCYLSSVLLALQQLEVKFNAPALQEAYYRARAGDAANFCALILAYSNKTVG
ELGDVRETMTHLLQHANLESAKRVLNVVCKHCGQKTTTLTGVEAVMYMGTLSYDNLKTGVSIPCVCGRDATQYLVQQESSFVMMSAPPAEYKLQQGTFLC
ANEYTGNYQCGHYTHITAKETLYRIDGAHLTKMSEYKGPVTDVFYKETSYTTTIKPVSYKLDGVTYTEIEPKLDGYYKKDNAYYTEQPIDLVPTQPLPNA
SFDNFKLTCSNTKFADDLNQMTGFTKPASRELSVTFPPDLNGDVAIDYRHYSASFKKGAKLLHKPIVWHINQATTKTTFKPNTWCLRCLWSTKPVDTSN
SFEVLAVEDTQGMDNLACESQQPTSEEVVENPTIQKEVIECDVKTTEVVGNVILKPSDEGVKVTQELGHEDLMAAYVENTSITIKKPNELSLALGLKTIA
THGIAAINSVPWSKILAYVKPFLGQAAITTSNCAKRLAQRVFNNYMPYVETLLFQLCTETKSTNSRIRASLPTTIAKNSVKSVAKLCLDAGINYVKSPKE
SKLFTIAMWLLLLSICLGSLICVTAAFGVLLSNFGAPSYCNGVRELYLNSSNVTTMDFCEGSFPCSICLSGLDSLDSYPALETIQVTISSYKLDLTILGL
AAEWVLAYMLFTKFFYLLGLSAIMQVVFGYFASHFISNSWLMWFIISIVQMAPVSAMVRMYIFFASFYYIWKSYVHIMDGCTSSTCMMCYKRNRATRVEC
TTIVNGMKRSFYVYANGGRGFCKTHNWNCLNCDTFCTGSTFISDEVARDLSLQFKRPINPTDQSSYIVDSVAVKNGALHLYFDKAGQKTYERHPLSHFVN
LDNLRANNTKGSLPINVIVFDGKSKCDESASKSASVYYSQLMCQPILLLDQALVSDVGDSTEVSVKMFDAYVDTFSATFSVPMEKLKALVATAHSELAKG
VALDGVLSTFVSAARQGVVDTDVDTKDVIECLKLSHHSDLEVTGDSCNNFMLTYNKVENMTPRDLGACIDCNARHINAQVAKSHNVSLIWNVKDYMSLSE
QLRKQIRSAAKKNNIPFRLTCATTRQVVNVITTKISLKGGKIVSTCFKLMLKATLLCVLAALVCYIVMPVHTLSIHDGYTNEIIGYKAIQDGVTRDIIST
DDCFANKHAGFDAWFSQRGGSYKNDKSCPVVAAIITREIGFIVPGLEGSVLRAINGDFLHFLPRVFSAVGNICYTPSKLIEYSDFATSACVLAAECTIFK
DAMGKPVPYCYDTNLLEGSISYSELRPDTRYVLMDGSIIQFPNTYLEGSVRVVTTFDAEYCRHGTCERSEVGICLSTSGRWVLNNEHYRALSGVFCGVDA
MNLIANIFTPLVQPVGALDVSASVVAGGIIAILVTCAAYYFMKFRRVFGEYNHVVAANALLFLMSFTILCLVPAYSFLPGVYSVFYLYLTFYFTNDVSFL
AHLQWFAMFSPIVPFWITAIYVFCISLKHCHWFFNNYLRKRVMFNGVTFSTFEEAALCTFLLNKEMYLKLRSETLLPLTQYNRYLALYNKYKYFSGALDT
TSYREAACCHLAKALNDFSNSGADVLYQPPQTSITSAVLQSGFRKMAFPSGKVEGCMVQVTCGTTTLNGLWLDDTVYCPRHVICTAEDMLNPNYEDLLIR
KSNHSFLVQAGNVQLRVIGHSMQNCLLRLKVDTSNPKTPKYKFVRIQPGQTFSVLACYNGSPSGVYQCAMRPNHTIKGSFLNGSCGSVGFNIDYDCVSFC
YMHHMELPTGVHAGTDLEGKFYGPFVDRQTAQAAGTDTTITLNVLAWLYAAVINGDRWFLNRFTTTLNDFNLVAMKYNYEPLTQDHVDILGPLSAQTGIA
VLDMCAALKELLQNGMNGRTILGSTILEDEFTPFDVVRQCSGVTFQGKFKKIVKGTHHWMLLTFLTSLLILVQSTQWSLFFFVYENAFLPFTLGIMAIAA
CAMLLVKHKHAFLCLFLLPSLATVAYFNMVYMPASWVMRIMTWLELADTSLSGYRLKDCVMYASALVLLILMTARTVYDDAARRVWTLMNVITLVYKVYY
GNALDQAISMWALVISVTSNYSGVVTTIMFLARAIVFVCVEYYPLLFITGNTLQCIMLVYCFLGYCCCCYFGLFCLLNRYFRLTLGVYDYLVSTQEFRYM
NSQGLLPPKSSIDAFKLNIKLLGIGGKPCIKVATVQSKMSDVKCTSVVLLSVLQGLKVAQCVQLHNDILLAKDTTEAFEKMVSLLSVLLSMQG
AVDINRLCEEMLDNRATLQAIASEFSSLPSYAAYATAQEAYEQAVANGDSEVVLKKLKKSLNVAKSEFDRDAAMQRKLEKMADQAMTQMYKQARSEDKRA
KVTSAMQTMLFTMLRKLDNDALNNIINNARDGCVPLNIIPLTTAAKLMVVVPDYGTYKNTCDGNTFTYASALWEIQQVVDADSKIVQLSEINMDNSPNLA
WPLIVTALRANSAVKLQNNELSPVALRQMSCAAGTTQTACTDDNALAYYNNSKGGRFVLALLSDHQDLKWARFPKSDGTGTIIYTELEPPCRFVTDTPKGP
KVKYLYFIKGLNNLNRGMVLGSLAATVRLQAGNATEVPANSTVLSFCAFAVDPAKAYKDYLASGGQPITNCVKMLCTHTGTGQAITVTPEANMDQESFGG
ASCCLYCRCHIDHPNPKGFCDLKGKYVQIPTTCANDPVGFTLRNTVCTVCGMWKGYGCSCDQLREPLMQSADASTFLNRVCGVSAARLTPCGTGTSTDVV
YRAFDIYNEKVAGFAKFLKTNCCRFQEKDEEGNLLDSYFVVKRHTMSNYQHEETIYNLVKDCPAVAVHDFFKFRVDGDMVPHISRQRLTKYTMADLVYAL
RHFDEGNCDTLKEILVTYNCCDDDYFNKKDWYDFVENPDILRVYANLGERVRQSLLKTVQFCDAMRDAGIVGVLTLDNQDLNGNWYDFGDFVQVAPGCGV
PIVDSYYSLLMPILTLTRALAAESHMDADLAKPLIKWDLLKYDFTEERLCLFDRYFKYWDQTYHPNCINCLDDRCILHCANFNVLFSTVFPPTSFGPLVR
KIFVDGVPFVVSTGYHFRELGVVHNQDVNLHSSRLSFKELLVYAADPAMHAASGNLLLDKRTTCFSVAALTNNVAFQTVKPGNFNKDFYDFAVSKGFFKE
GSSVELKHFFFAQDGNAAISDYDYYRYNLPTMCDIRQLLFVVEVVDKYFDCYDGGCINANQVIVNNLDKSAGFPFNKWGKARLYYDSMSYEDQDALFAYT
KRNVIPTITQMNLKYAISAKNRARTVAGVSICSTMTNRQFHQKLLKSIAATRGATVVIGTSKFYGGWHNMLKTVYSDVETPHLMGWDYPKCDRAMPNMLR
IMASLVLARKHNTCCNLSHRFYRLANECAQVLSEMVMCGGSLYVKPGGTSSGDATTAYANSVFNICQAVTANVNALLSTDGNKIADKYVRNLQHRLYECL
YRNRDVDHEFVDEFYAYLRKHFSMMILSDDAVVCYNSNYAAQGLVASIKNFKAVLYYQNNVFMSEAKCWTETDLTKGPHEFCSQHTMLVKQGDDYVYLPY
PDPSRILGAGCFVDDIVKTDGTLMIERFVSLAIDAYPLTKHPNQEYADVFHLYLQYIRKLHDELTGHMLDMYSVMLTNDNTSRYWEPEFYEAMYTPHTVL
QAVGACVLCNSQTSLRCGACIRRPFLCCKCCYDHVISTSHKLVLSVNPYVCNAPGCDVTDVTQLYLGGMSYYCKSHKPPISFPLCANGQVFGLYKNTCVG
SDNVTDFNAIATCDWTNAGDYILANTCTERLKLFAAETLKATEETFKLSYGFVGLSDRELHLSWEVGKPRPPLNRRNYVFTGYRVTKNSKVQIGEYT
FEKGDYGDAVVYRGTTTYKLNVGDYFVLTSHTVMPLSAPTLVPQEHYVRITGLYPTLNISDEFSSNVANYQKVGMQKYSTLQGPPGTGKSHFAIGLALYY
PSARIVYTACSHAAVDALCEKALKYLPIDKCSRIIPARARVECFDKFKVNSTLEQYVFCTVNALPETTADIVVFDEISMATNYDLSVVNARLRAKHYVYI
GDPAQLPAPRTLLTKGTLEPEYFNSVCRLMKTIGPDMFLGTCRRCPAEIVDTVSALVYDNKLKAHKDKSAQCFKMFYKGVITHDVSSAINRPQIGVVREE
LTRNPAWRKAVFISPYNSQNAVASKILGLPTQTVDSSQGSEYDYVIFTQTTETAHSCNVNRFNVAITRAKIGILCIMSDRDLYDKLQFTSLEIPRRNVAT
LQAENVTGLFKDCSKIITGLHPTQAPTHLSVDIKFKTEGLCVDIPGIPKDMTYRRLISMMGFKMNYQVNGYPNMFITREEAIRHVRAWIGFDVEGCHATR
DAVGTNLPLQLGFSTGVNLVAVPTGYVDTENNTEFTRVNAKPPPGDQFKHLIPLMYKGLPWNVVRIKIVQMLSDTLKGLSDRVVFVLWAHGFELTSMKYE
VKIGPERTCCLCDKRATCFSTSSDTYACWNHSVGFDYVYNPFMIDVQQWGFTGNLQSNHDQHCQVHGNAHVASCDAIMTRCLAVHECFVKRVDWSVEYPI
IGDELRVNSACRKVQHMVVKSALLADKFPVLHDIGNPKAIKCVPQAEVEWKFYDAQPCSDKAYKIEELFYSYATHHDKFTDGVCLFWNCNVDRYPANAIV
CRFDTRVLSNLNLPGCDGGSLYVNKHAFHTPAFDKSAFTNLKQLPFFYYSDSPCESHGKQVVSDIDYVPLKSATCITRCNLGGAVCRHHANEYRQYLDAY
NMMISAGFSLWIYKQFDTYNLWNTFTRLQSLENVAYNVVNKGHFDGHAGEAPVSIINNAVYTKVDGIDVEIFENKTTLPVNVAFELWAKRNIKPVPEIKI
LNNLGVDIAANTVIWDYKREAPAHVSTIGVCTMTDIAKKPTESACSSLTVLFDGRVEGQVDLFRNARNGVLITEGSVKGLTPSKGPAQASVNGVTLIGES
VKTQFNYFKKVDGIIQQLPETYFTQSRDLEDFKPRSQMETDFLELAMDEFIQRYKLEGYAFEHIVYGDFSHGQLGGLHLMIGLAKRSQDSPLKLEDFIPM
DSTVKNYFITDAQTGSSKCVCSVIDLLLDDFVEIIKSQDLSVISKVVKVTIDYAEISFMLWCKDGHVETFYPKLQASQAWQPGVAMPNLYKMQRMLLEKC
DLQNYGENAVIPKGIMMNVAKYTQLCQYLNTLTLAVPYNMRVIHFGAGSDKGVAPGTAVLRQWLPTGTLLVDSDLNDFVSDADSTLIGDCATVHTANKWD
LIISDMYDPRTKHVTKENDSKEGFFTYLCGFIKQKLALGGSIAVKITEHSWNADLYKLMGHFSWWTAFVTNVNASSSEAFLIGANYLGKPKEQIDGYTMH
ANYIFWRNTNPIQLSSYSLFDMSKFPLKLRGTAVMSLKENQINDMIYSLLEKGRLIIRENNRVVVSSDILVNN

SEQ ID NO: 13
MESLVPGFNEKTHVQLSLPVLQVRDVLVRGFGDSVEEVLSEARQHLKDGTCGLVEVEKGVLPQLEQPYVFIKRSDARTAPHGHVMVELVAELEGIQYGRS
GETLGVLVPHVGEIPVAYRKVLLRKNGNKGAGGHSYGADLKSFDLGDELGTDPYEDFQENWNTKHSSGVTRELMRELNGGAYTRYVDNNFCGPDGYPLEC
IKDLLARAGKASCTLSEQLDFIDTKRGVYCCREHEHEIAWYTERSEKSYELQTPFEIKLAKKFDTFNGECPNFVFPLNSIIKTIQPRVEKKKLDGFMGRI
RSVYPVASPNECNQMCLSTLMKCDHCGETSWQTGDFVKATCEFCGTENLTKEGATTCGYLPQNAVVKIYCPACHNSEVGPEHSLAEYHNESGLKTILRKG
GRTIAFGGCVFSYVGCHNKCAYWVPRASANIGCNHTGVVGEGSEGLNDNLLEILQKEKVNINIVGDFKLNEEIAIILASFSASTSAFVETVKGLDYKAFK
QIVESCGNFKVTKGKAKKGAWNIGEQKSILSPLYAFASEAARVVRSIFSRTLETAQNSVRVLQKAAITILDGISQYSLRLIDAMMFTSDLATNNLVVMAY
ITGGVVQLTSQWLTNIFGTVYEKLKPVLDWLEEKFKEGVEFLRDGWEIVKFISTCACEIVGGQIVTCAKEIKESVQTFFKLVNKFLALCADSIIIGGAKL
KALNLGETFVTHSKGLYRKCVKSREETGLLMPLKAPKEIIFLEGETLPTEVLTEEVVLKTGDLQPLEQPTSEAVEAPLVGTPVCINGLMLLEIKDTEKYC
ALAPNMMVTNNTFTLKGGAPTKVTFGDDTVIEVQGYKSVNITFELDERIDKVLNEKCSAYTVELGTEVNEFACVVADAVIKTLQPVSELLTPLGIDLDEW
SMATYYLFDESGEFKLASHMYCSFYPPDEDEEEGDCEEEEFEPSTQYEYGTEDDYQGKPLEFGATSAALQPEEEQEEDWLDDDSQQTVGQQDGSEDNQTT
TIQTIVEVQPQLEMELTPVVQTIEVNSFSGYLKLTDNVYIKNADIVEEAKKVKPTVVVNAANVYLKHGGGVAGALNKATNNAMQVESDDYIATNGPLKVG
GSCVLSGHNLAKHCLHVVGPNVNKGEDIQLLKSAYENFNQHEVLLAPLLSAGIFGADPIHSLRVCVDTVRTNVYLAVFDKNLYDKLVSSFLEMKSEKQVE
QKIAEIPKEEVKPFITESKPSVEQRKQDDKKIKACVEEVTTTLEETKFLTENLLLYIDINGNLHPDSATLVSDIDITFLKKDAPYIVGDVVQEGVLTAVV
IPTKKAGGTTEMLAKALRKVPTDNYITTYPGQGLNGYTVEEAKTVLKKCKSAFYILPSIISNEKQEILGTVSWNLREMLAHAEETRKLMPVCVETKAIVS
TIQRKYKGIKIQEGVVDYGARFYFYTSKTTVASLINTLNDLNETLVTMPLGYVTHGLNLEEAARYMRSLKVPATVSVSSPDAVTAYNGYLTSSSKTPEEH
FIETISLAGSYKDWSYSGQSTQLGIEFLKRGDKSVYYTSNPTTFHLDGEVITFDNLKTLLSLREVRTIKVFTTVDNINLHTQVVDMSMTYGQQFGPTYLD
GADVTKIKPHNSHEGKTFYVLPNDDTLRVEAFEYYHTTDPSFLGRYMSALNHTKKWKYPQVNGLTSIKWADNNCYLATALLTLQQIELKFNPPALQDAYY
RARAGEAANFCALILAYCNKTVGELGDVRETMSYLFQHANLDSCKRVLNVVCKTCGQQTTLKGVEAVMYMGTLSYEQFKKGVQIPCTCGKQATKYLVQQ
ESPFVMMSAPPAQYELKHGTFTCASEYTGNYQCGHYKHITSKETLYCIDGALLTKSSEYKGPITDVFYKENSYTTTIKPVTYKLDGVVCTEIDPKLDNYY
KKDNSYFTEQPIDLVPNQPYPNASFDNFKFVCDNIKFADDLNQLTGYKKPASRELKVTFFPDLNGDVVAIDYKHYTPSFKKGAKLLHKPIVWHVNNATNK
ATYKPNTWCIRCLWSTKPVETSNSFDVLKSEDAQGMDNLACEDLKPVSEEVVENPTIQKDVLECNVKTTEVVGDIILKPANNSLKITEEVGHTDLMAAYV
DNSSLTIKKPNELSRVLGLKTLATHGLAAVNSVPWDTIANYAKPFLNKVVSTTTNIVTRCLNRVCTNYMPYFFTLLLQLCTFTRSTNSRIKASMPTTIAK
NTVKSVGKFCLEASFNYLKSPNFSKLINIIIWFLLLSVCLGSLIYSTAALGVLMSNLGMPSYCTGYREGYLNSTNVTIATYCTGSIPCSVCLSGLDSLDT
YPSLETIQITISSFKWDLTAFGLVAEWFLAYILFTRFFYVLGLAAIMQLFFSYFAVHFIISNSWLMWLIINLVQMAPISAMVRMYIFFASFYYVWKSYVHV
VDGCNSSTCMMCYKRNRATRVECTTIVNGVRRSFYVYANGGKGFCKLHNWNCVNCDTFCAGSTFISDEVARDLSLQFKRPINPTDQSSYIVDSVTVKNGS
IHLYFDKAGQKTYERHSLSHFVNLDNLRANNTKGSLPINVIVFDGKSKCEESSAKSASVYYSQLMCQPILLLDQALVSDVGDSAEVAVKMFDAYVNTFSS
TFNVPMEKLKTLVATAEAELAKNVSLDNVLSTFISAARQGFVDSDVETKDVVECLKLSHQSDIEVTGDSCNNYMLTYNKVENMTPRDLGACIDCSARHIN
AQVAKSHNIALIWNVKDFMSLSEQLRKQIRSAAKKNNLPFKLTCATTRQVVNVVTTKIALKGGKIVNNWLKQLIKVTLVFLFVAAIFYLITPVHVMSKHT
DFSSEIIGYKAIDGGVTRDIASTDTCFANKHADFDTWFSQRGGSYTNDKACPLIAAVITREVGFVVPGLPGTILRTTNGDFLHFLPRVFSAVGNICYTPS
KLIEYTDFATSACVLAAECTIFKDASGKPVPYCYDTNVLEGSVAYESLRPDTRYVLMDGSIIQFPNTYLEGSVRVVTTFDSEYCRHGTCERSEAGVCVST
SGRWVLNNDYYRSLPGVFCGVDAVNLLTNMFTPLIQPIGALDISASIVAGGIVAIVVTCLAYYFMRFRRAFGEYSHVVAFNTLLFLMSFTVLCLTPVYSF
LPGVYSVIYLYLTFYLTNDVSFLAHIQWMVMFTSINSWLMWLIINLVQMAPISAMVRMYVFNGVSFSTFEEAALCTFLLNKEMYLKLRSDVLLP
LTQYNRYLALYNKYKYFSGAMDTTSYREAACCHLAKALNDFSNSGSDVLYQPPQTSITSAVLQSGFRKMAFPSGKVEGCMVQVTCGTTTLNGLWLDDVVY
CPRHVICTSEDMLNPNYEDLLIRKSNHNFLVQAGNVQLRVIGHSMQNCVLKLKVDTANPKTPKYKFVRIQPGQTFSVLACYNGSPSGVYQCAMRPNFTIK
GSFLNGSCGSVGFNIDYDCVSFCYMHHMELPTGVHAGTDLEGNFYGPFVDRQTAQAAGTDTTITVNVLAWLYAAVINGDRWFLNRFTTTLNDFNLVAMKY
NYEPLTQDHVDILGPLSAQTGIAVLDMCASLKELLQNGMNGRTILGSALLEDEFTPFDVVRQCSGVTFQSAVKRTIKGTHHWLLLTILTSLLVLVQSTQW
SLFFFLYENAFLPFAMGIIAMSAFAMMFVKHKHAFLCLFLLPSLATVAYFNMVYMPASWVMRIMTWLDMVDTSLSGFKLKDCVMYASAVVLLILMTARTV
YDDGARRVWTLMNVLTLVYKVYYGNALDQAISMWALIISVTSNYSGVVTTVMFLARGIVFMCVEYCPIFFITGNTLQCIMLVYCFLGYFCTCYFGLFCLL
NRYFRLTLGVYDYLVSTQEFRYMNSQGLLPPKNSIDAFKLNIKLLGVGGKPCIKVATVQSKMSDVKCTSVVLLSVLQQLRVESSSKLWAQCVQLHNDILL
AKDTTEAFEKMVSLLSVLLSMQGAVDINKLCEEMLDNRATLQAIASEFSSLPSYAAFATAQEAYEQAVANGDSEVVLKKLKKSLNVAKSEFDRDAAMQRK
LEKMADQAMTQMYKQARSEDKRAKVTSAMQTMLFTMLRKLDNDALNNIINNARDGCVPLNIIPLTTAAKLMVVIPDYNTYKNTCDGTTFTYASALWEIQQ
VVDADSKIVQLSEISMDNSPNLAWPLIVTALRANSAVKLQNNELSPVALRQMSCAAGTTQTACTDDNALAYYNTTKGGRFVLALLSDLQDLKWARFPKSD
GTGTIYTELEPPCRFVTDTPKGPKVKYLYFIKGLNNLNRGMVLGSLAATVRLQAGNATEVPANSTVLSFCAFAVDAAKAYKDYLASGGQPITNCVKMLCT
HTGTGQAITVTPEANMDQESFGGASCCLYCRCHIDHPNPKGFCDLKGKYVQIPTTCANDPVGFTLKNTVCTVCGMWKGYGCSCDQLREPMLQSADAQSFL
NGFAV

SEQ ID NO: 14
MESLVPGFNEKTHVQLSLPVLQVRDVLVRGFGDSVEEVLSEARQHLKDGTCGLVEVEKGVLPQLEQPYVFIKRSDARTAPHGHVMVELVAELEGIQYGRS
GETLGVLVPHVGEIPVAYRKVLLRKNGNKGAGGHSYGADLKSFDLGDELGTDPYEDFQENWNTKHSSGVTRELMRELNGGAYTRYVDNNFCGPDGYPLEC
IKDLLARAGKASCTLSEQLDFIDTKRGVYCCREHEHEIAWYTERSEKSYELQTPFEIKLAKKFDTFNGECPNFVFPLNSIIKTIQPRVEKKKLDGFMGRI
RSVYPVASPNECNQMCLSTLMKCDHCGETSWQTGDFVKATCEFCGTENLTKEGATTCGYLPQNAVVKIYCPACHNSEVGPEHSLAEYHNESGLKTILRKG
GRTIAFGGCVFSYVGCHNKCAYWVPRASANIGCNHTGVVGEGSEGLNDNLLEILQKEKVNINIVGDFKLNEEIAIILASFSASTSAFVETVKGLDYKAFK
QIVESCGNFKVTKGKAKKGAWNIGEQKSILSPLYAFASEAARVVRSIFSRTLETAQNSVRVLQKAAITILDGISQYSLRLIDAMMFTSDLATNNLVVMAY
ITGGVVQLTSQWLTNIFGTVYEKLKPVLDWLEEKFKEGVEFLRDGWEIVKFISTCACEIVGGQIVTCAKEIKESVQTFFKLVNKFLALCADSIIIGGAKL
KALNLGETFVTHSKGLYRKCVKSREETGLLMPLKAPKEIIFLEGETLPTEVLTEEVVLKTGDLQPLEQPTSEAVEAPLVGTPVCINGLMLLEIKDTEKYC
ALAPNMMVTNNTFTLKGGAPTKVTFGDDTVIEVQGYKSVNITFELDERIDKVLNEKCSAYTVELGTEVNEFACVVADAVIKTLQPVSELLTPLGIDLDEW
SMATYYLFDESGEFKLASHMYCSFYPPDEDEEEGDCEEEEFEPSTQYEYGTEDDYQGKPLEFGATSAALQPEEEQEEDWLDDDSQQTVGQQDGSEDNQTT
TIQTIVEVQPQLEMELTPVVQTIEVNSFSGYLKLTDNVYIKNADIVEEAKKVKPTVVVNAANVYLKHGGGVAGALNKATNNAMQVESDDYIATNGPLKVG
GSCVLSGHNLAKHCLHVVGPNVNKGEDIQLLKSAYENFNQHEVLLAPLLSAGIFGADPIHSLRVCVDTVRTNVYLAVFDKNLYDKLVSSFLEMKSEKQVE
QKIAEIPKEEVKPFITESKPSVEQRKQDDKKIKACVEEVTTTLEETKFLTENLLLYIDINGNLHPDSATLVSDIDITFLKKDAPYIVGDVVQEGVLTAVV
IPTKKAGGTTEMLAKALRKVPTDNYITTYPGQGLNGYTVEEAKTVLKKCKSAFYILPSIISNEKQEILGTVSWNLREMLAHAEETRKLMPVCVETKAIVS
TIQRKYKGIKIQEGVVDYGARFYFYTSKTTVASLINTLNDLNETLVTMPLGYVTHGLNLEEAARYMRSLKVPATVSVSSPDAVTAYNGYLTSSSKTPEEH
FIETISLAGSYKDWSYSGQSTQLGIEFLKRGDKSVYYTSNPTTFHLDGEVITFDNLKTLLSLREVRTIKVFTTVDNINLHTQVVDMSMTYGQQFGPTYLD
GADVTKIKPHNSHEGKTFYVLPNDDTLRVEAFEYYHTTDPSFLGRYMSALNHTKKWKYPQVNGLTSIKWADNNCYLATALLTLQQIELKFNPPALQDAYY
RARAGEAANFCALILAYCNKTVGELGDVRETMSYLFQHANLDSCKRVLNVVCKTCGQQTTLKGVEAVMYMGTLSYEQFKKGVQIPCTCGKQATKYLVQQ
ESPFVMMSAPPAQYELKHGTFTCASEYTGNYQCGHYKHITSKETLYCIDGALLTKSSEYKGPITDVFYKENSYTTTIKPVTYKLDGVVCTEIDPKLDNYY
KKDNSYFTEQPIDLVPNQPYPNASFDNFKFVCDNIKFADDLNQLTGYKKPASRELKVTFFPDLNGDVVAIDYKHYTPSFKKGAKLLHKPIVWHVNNATNK
ATYKPNTWCIRCLWSTKPVETSNSFDVLKSEDAQGMDNLACEDLKPVSEEVVENPTIQKDVLECNVKTTEVVGDIILKPANNSLKITEEVGHTDLMAAYV
DNSSLTIKKPNELSRVLGLKTLATHGLAAVNSVPWDTIANYAKPFLNKVVSTTTNIVTRCLNRVCTNYMPYFFTLLLQLCTFTRSTNSRIKASMPTTIAK
NTVKSVGKFCLEASFNYLKSPNFSKLINIIIWFLLLSVCLGSLIYSTAALGVLMSNLGMPSYCTGYREGYLNSTNVTIATYCTGSIPCSVCLSGLDSLDT
YPSLETIQITISSFKWDLTAFGLVAEWFLAYILFTRFFYVLGLAAIMQLFFSYFAVHFIISNSWLMWLIINLVQMAPISAMVRMYIFFASFYYVWKSYVHV
VDGCNSSTCMMCYKRNRATRVECTTIVNGVRRSFYVYANGGKGFCKLHNWNCVNCDTFCAGSTFISDEVARDLSLQFKRPINPTDQSSYIVDSVTVKNGS
IHLYFDKAGQKTYERHSLSHFVNLDNLRANNTKGSLPINVIVFDGKSKCEESSAKSASVYYSQLMCQPILLLDQALVSDVGDSAEVAVKMFDAYVNTFSS
TFNVPMEKLKTLVATAEAELAKNVSLDNVLSTFISAARQGFVDSDVETKDVVECLKLSHQSDIEVTGDSCNNYMLTYNKVENMTPRDLGACIDCSARHIN
AQVAKSHNIALIWNVKDFMSLSEQLRKQIRSAAKKNNLPFKLTCATTRQVVNVVTTKIALKGGKIVNNWLKQLIKVTLVFLFVAAIFYLITPVHVMSKHT
DFSSEIIGYKAIDGGVTRDIASTDTCFANKHADFDTWFSQRGGSYTNDKACPLIAAVITREVGFVVPGLPGTILRTTNGDFLHFLPRVFSAVGNICYTPS
KLIEYTDFATSACVLAAECTIFKDASGKPVPYCYDTNVLEGSVAYESLRPDTRYVLMDGSIIQFPNTYLEGSVRVVTTFDSEYCRHGTCERSEAGVCVST

```
SGRWVLNNDYYRSLPGVFCGVDAVNLLTNMFTPLIQPIGALDISASIVAGGIVAIVVTCLAYYFMRFRRAFGEYSHVVAFNTLLFLMSFTVLCLTPVYSF
LPGVYSVIYLYLTFYLTNDVSFLAHIQWMVMFTPLVPFWITIAYIICISTKHFYWFFSNYLKRRVVFNGVSFSTFEEAALCTFLLNKEMYLKLRSDVLLP
LTQYNRYLALYNKYKYFSGAMDTTSYREAACCHLAKALNDFSNSGSDVLYQPPQTSITSAVLQSGFRKMAFPSGKVEGCMVQVTCGTTTLNGLWLDDVVY
CPRHVICTSEDMLNPNYEDLLIRKSNHNFLVQAGNVQLRVIGHSMQNCVLKLKVDTANPKTPKYKFVRIQPGQTFSVLACYNGSPSGVYQCAMRPNFTIK
GSFLNGSCGSVGFNIDYDCVSFCYMHHMELPTGVHAGTDLGLRFPGFVDRQTAQAAGTDTTITVNVLAWLYAAVINGDRWFLNRFTTTLNDFNLVAMKY
NYEPLTQDHVDILGPLSAQTGIAVLDMCASLKELLQNGMNGRTILGSALLEDEFTPFDVVRQCSGVTFQSAVKRTIKGTHHWLLLTILTSLLVLVQSTQW
SLFFFLYENAFLPFAMGIIAMSAFAMMFVKHKHAFLCLFLLPSLATVAYFNMVYMPASWVMRIMTWLDMVDTSLSGFKLKDCVMYASAVVLLILMTARTV
YDDGARRVWTLMNVLTLVYKVYYGNALDQAISMWALIISVTSNYSGVVTTVMFLARGIVEMCVEYCPIFEITGNTLQCIMLVYCFLGYFCTCYFGLFCLL
NRYFRLTLGVYDYLVSTQEFRYMNSQGLLPPKNSIDAFKLNIKLLGVGGKPCIKVATVQSKMSDVKCTSVVLLSVLQQLRVESSSKLWAQCVQLHNDILL
AKDTTEAFEKMVSLLSVLLSMQGAVDINKLCEEMLDNRATLQAIASEFSSLPSYAAFATAQEAYEQAVANGDSEVVLKKLKKSLNVAKSEFDRDAAMQRK
LEKMADQAMTQMYKQARSEDKRAKVTSAMQTMLFTMLRKLDNDALNNIINNARDGCVPLNIIPLTTAAKLMVVIPDYNTYKNTCDGTTFTYASALWEIQQ
VVDADSKIVQLSEISMDNSPNLAWPLIVTALRANSAVKLQNNELSPVALRQMSCAAGTTQTACTDDNALAYYNTTKGGRFVLALLSDLQDLKWARFPKSD
GTGTIYTELEPPCRFVTDTPKGPKVKYLYFIKGLNNLNRGMVLGSLAATVRLQAGNATEVPANSTVLSFCAFAVDAAKAYKDYLASGGQPITNCVKMLCT
HTGTGQAITVTPEANMDQESFGGASCCLYCRCHIDHPNPKGFCDLKGKYVQIPTTCANDPVGFTLKNTVCTVCGMWKGYGCSCDQLREPMLQSADAQSFL
NRVCGVSAARLTPCGTGTSTDVVYRAFDIYNDKVAGFAKFLKTNCCRFQEKDEDDNLIDSYFVVKRHTFSNYQHEETIYNLLKDCPAVAKHDFFKFRIDG
DMVPHISRQRLTKYTMADLVYALRHFDEGNCDTLKEILVTYNCCDDDYFNKKDWYDFVENPDILRVYANLGERVRQALLKTVQFCDAMRNAGIVGVLTLD
NQDLNGNWYDFGDFIQTTPGSGVPVVDSYYSLLMPILTLTRALTAESHVDTDLTKPYIKWDLLKYDFTEERLKLFDRYFKYWDQTYHPNCVNCLDDRCIL
HCANFNVLFSTVFPPTSFGPLVRKIFVDGVPFVVSTGYHFRELGVVHNQDVNLHSSRLSFKELLVYAADPAMHAASGNLLLDKRTTCFSVAALTNNVAFQ
TVKPGNFNKDFYDFAVSKGFFKEGSSVELKHFFFAQDGNAAISDYDYYRYNLPTMCDIRQLLFVVEVVDKYFDCYDGGCINANQVIVNNLDKSAGFPFNK
WGKARLYYDSMSYEDQDALFAYTKRNVIPTITQMNLKYAISAKNRARTVAGVSICSTMTNRQFHQKLLKSIAATRGATVVIGTSKFYGGWHNMLKTVYSD
VENPHLMGWDYPKCDRAMPNMLRIMASLVLARKHTTCCSLSHRFYRLANECAQVLSEMVMCGGSLYVKPGGTSSGDATTAYANSVFNICQAVTANVNALL
STDGNKIADKYVRNLQHRLYECLYRNRDVDTDFVNEFYAYLRKHFSMMILSDDAVVCFNSTYASQGLVASIKNFKSVLYYQNNVFMSEAKCWTETDLTKG
PHEFCSQHTMLVKQGDDYVYLPYPDPSRILGAGCFVDDIVKTDGTLMIERFVSLAIDAYPLTKHPNQEYADVFHLYLQYIRKLHDELTGHMLDMYSVMLT
NDNTSRYWEPEFYEAMYTPHTVLQAVGACVLCNSQTSLRCGACIRRPFLCCKCCYDHVISTSHKLVLSVNPYVCNAPGCDVTDVTQLYLGGMSYYCKSHK
PPISFPLCANGQVFGLYKNTCVGSDNVTDFNAIATCDWTNAGDYILANTCTERLKLFAAETLKATEETFKLSYGIATVREVLSDRELHLSWEVGKPRPPL
NRNYVFTGYRVTKNSKVQIGEYTFEKGDYGDAVVYRGTTTYKLNVGDYFVLTSHTVMPLSAPTLVPQEHYVRITGLYPTLNISDEFSSNVANYQKVGMQK
YSTLQGPPGTGKSHFAIGLALYYPSARIVYTACSHAAVDALCEKALKYLPIDKCSRIIPARARVECFDKFKVNSTLEQYVFCTVNALPETTADIVVFDEI
SMATNYDLSVVNARLRAKHYVYIGDPAQLPAPRTLLTKGTLEPEYFNSVCRLMKTIGPDMFLGTCRRCPAEIVDTVSALVYDNKLKAHKDKSAQCFKMFY
KGVITHDVSSAINRPQIGVVREFLTRNPAWRKAVFISPYNSQNAVASKILGLPTQTVDSSQGSEYDYVIFTQTTETAHSCNVNRFNVAITRAKVGILCIM
SDRDLYDKLQFTSLEIPRRNVATLQAENVTGLFKDCSKVITGLHPTQAPTHLSVDTKFKTEGLCVDIPGIPKDMTYRRLISMMGFKMNYQVNGYPNMFIT
REEAIRHVRAWIGFDVEGCHATREAVGTNLPLQLGFSTGVNLVAVPTGYVDTPNNTDFSRVSAKPPPGDQFKHLIPLMYKGLPWNVVRIKIVQMLSDTLK
NLSDRVVFVLWAHGFELTSMKYFVKIGPERTCCLCDRRATCFSTASDTYACWHHSIGFDYVYNPFMIDVQQWGFTGNLQSNHDLYCQVHGNAHVASCDAI
MTRCLAVHECFVKRVDWTIEYPIIGDELKINAACRKVQHMVVKAALLADKFPVLHDIGNPKAIKCVPQADVEWKFYDAQPCSDKAYKIEELFYSYATHSD
KFTDGVCLFWNCNVDRYPANSIVCRFDTRVLSNLNLPGCDGGSLYVNKHAPHTPAFDKSAFVNLKQLPFFYYSDSPCESHGKQVVSDIDYVPLKSATCIT
RCNLGGAVCRHHANEYRLYLDAYNMMISAGFSLWVYKQFDTYNLWNTFTRLQSLENVAFNVVNKGHFDGQQGEVPVSIINNTVYTKVDGVDVELFENKTT
LPVNVAFELWAKRNIKPVPEVKILNNLGVDIAANTVIWDYKRDAPAHISTIGVCSMTDIAKKPTETICAPLTVFFDGRVDGQVDLFRNARNGVLITEGSV
KGLQPSVGPKQASLNGVTLIGEAVKTQFNYYKKVDGVVQQLPETYFTQSRNLQEFKPRSQMEIDFLELAMDEFIERYKLEGYAFEHIVYGDFSHSQLGGL
HLLIGLAKRFKESPFELEDFIPMDSTVKNYFITDAQTGSSKCVCSVIDLLLDYGSFCTQLNRALTGIAVEQDKNTQEVFAQVKQIYKTPPIKDFGGF
FVSDADSTLIGDCATVHTANKWDLIISDMYDPKTKNVTKENDSKEGFFTYICGFIQQKLALGGSVAIKITEHSWNADLYKLMGHFAWWTAFVTNVNASSS
QAWQPGVAMPNLYKMQRMLLEKCDLQNYGDSATLPKGIMMNVAKYTQLCQYLNTLTLAVPYNMRVIHFGAGSDKGVAPGTAVLRQWLPTGTLLVDSDLND
EAFLIGCNYLGKPREQIDGYVMHANYIFWRNTNPIQLSSYSLFDMSKFPLKLRGTAVMSLKEGQINDMILSLLSKGRLIIRENNRVVISSDVLVNN

SEQ ID NO: 15
MFVFLVLLPLVSSQCVNLTTRTQLPPAYTNSFTRGVYYPDKVFRSSVLHSTQDLFLPFFSNVTWFHAIHVSGTNGTKRFDNPVLPFNDGVYFASTEKSNI
IRGWIFGTTLDSKTQSLLIVNNATNVVIKVCEFQFCNDPFLGVYYHKNNKSWMESEFRVYSSANNCTFEYVSQPFLMDLEGKQGNFKNLREFVFKNIDGY
FKIYSKHTPINLVRDLPQGFSALEPLVDLPIGINITRFQTLLALHRSYLTPGDSSSGWTAGAAAYYVGYLQPRTFLLKYNENGTITDAVDCALDPLSETK
CTLKSFTVEKGIYQTSNFRVQPTESIVRFPNITNLCPFGEVFNATRFASVYAWNRKRISNCVADYSVLYNSASFSTFKCYGVSPTKLNDLCFTNVYADSF
VIRGDEVRQIAPGQTGKIADYNYKLPDDFTGCVIAWNSNNLDSKVGGNYNYLYRLFRKSNLKPFERDISTEIYQAGSTPCNGVEGFNCYFPLQSYGFQPT
NGVGYQPYRVVVLSFELLHAPATVCGPKKSTNLVKNKCVNFNFNGLTGTGVLTESNKKFLPFQQFGRDIADTTDAVRDPQTLEILDITPCSFGGVSVITP
GTNTSNQVAVLYQDVNCTEVPVAIHADQLTPTWRVYSTGSNVFQTRAGCLIGAEHVNNSYECDIPIGAGICASYQTQTNSPRRARSVASQSIIAYTMSLG
AENSVAYSNNSIAIPTNFTISVTTEILPVSMTKTSVDCTMYICGDSTECANLLLQYGSFCTQLNRALTGIAEQDKNTQEVFAQVKQIYKTPPIKDFGGF
NFSQILPDPSKPSKRSFIEDLLFNKVTLADAGFIKQYGDCLGDIAARDLICAQKFNGLTVLPPLLTDEMIAQYTSALLAGTITSGWTFGAGAALQIPFAM
QMAYRFNGIGVTQNVLYENQKLIANQFNSAIGKIQDSLSSTASALGKLQDVVNQNAQALNTLVKQLSSNFGAISSVLNDILSRLDKVEAEVQIDRLITGR
LQSLQTYVTQQLIRAAEIRASANLAATKMSECVLGQSKRVDFCGKGYHLMSFPQSAPHGVVFLHVTYVPAQEKNFTTAPAICHDGKAHFPREGVFVSNGT
HWFVTQRNFYEPQIITTDNTFVSGNCDVVIGIVNNTVYDPLQPELDSFKEELDKYFKNHTSPDVDLGDISGINASVVNIQKEIDRLNEVAKNLNESLIDL
QELGKYEQYIKWPWYIWLGFIAGLIAIVMVTIMLCCMTSCCSCLKGCCSCGSCCKFDEDDSEPVLKGVKLHYT

SEQ ID NO: 16
MFIFLLFLTLTSGSDLDRCTTFDDVQAPNYTQHTSSMRGVYYPDEIFRSDTLYLTQDLFLPFYSNVTGFHTINHTFGNPVIPFKDGIYFAATEKSNVVRG
WVFGSTMNNKSQSVIIINNSTNVVIRACNFELCDNPFFAVSKPMGTQTHTMIFDNAFNCTFEYISDAFSLDVSEKSGNFKHLREFVFKNKDGFLYVVKGY
QPIDVVRDLPSGFNTLKPIFKLPLGINITNFRAILTAFSPAQDIWGTSAAAYFVGYLKPTTFMLKYDENGTITDAVDCSQNPLAELKCSVKSFEIDKGIY
QTSNFRVVPSGDVVRFPNITNLCPFGEVFNATKFPSVYAWERKKISNCVADYSVLYNSTFFSTFKCYGVSATKLNDLCFSNVYADSFVVKGDDVRQIAPG
QTGVIADYNYKLPDDFMGCVLAWNTRNIDATSTGNYNYKYRYLRHGKLRPFERDISNVPFSPDGKPCTPPALNCYWPLNDYGFYTTTGIGYQPYRVVVLS
FELLNAPATVCGPKLSTDLIKNQCVNFNFNGLTGTGVLTPSSKRFQPFQQFGRDVSDFTDSVRDPKTSEILDISPCSFGGVSVITPGTNASSEVAVLYQD
VNCTDVSTAIHADQLTPAWRIYSTGNNVFQTQAGCLIGAEHVDTSYECDIPIGAGICASYHTVSLLRSTSQKSIVAYTMSLGADSSIAYSNNTIAIPTNF
SISITTEVMPVSMAKTSVDCNMYICGDSTECANLLLQYGSFCTQLNRALSGIAAEQDRNTREVFAQVKQMYKTPTLKYFGGFNFSQILPDPLKPTKRSFI
EDLLFNKVTLADAGFMKQYGECLGDINARDLICAQKFNGLTVLPPLLTDDMIAAYTAALVSGTATAGWTFGAGAALQIPFAMQMAYRFNGIGVTQNVLYE
NQKQIANQFNKAISQIQESLTTTSTALGKLQDVVNQNAQALNTLVKQLSSNFGAISSVLNDILSRLDKVEAEVQIDRLITGRLQSLQTYVTQQLIRAAEI
RASANLAATKMSECVLGQSKRVDFCGKGYHLMSFPQAAPHGVVFLHVTYVPSQERNFTTAPAICHEGKAYFPREGVFVFNGTSWFITQRNFFSPQIITTD
NTFVSGNCDVVIGIINNTVYDPLQPELDSFKEELDKYFKNHTSPDVDLGDISGINASVVNIQKEIDRLNEVAKNLNESLIDLQELGKYEQYIKWPWYVWL
GFIAGLIAIVMVTILLCCMTSCCSCLKGACSCGSCCKFDEDDSEPVLKGVKLHYT

SEQ ID NO: 17
MSDNGPQSNQRSAPRITFGGPTDSTDNNQNGGRNGARPKQRRPQGLPNNTASWFTALTQHGKEELRFPRGQGVPINTNSGPDDQIGYYRRATRRVRGGDG
KMKELSPRWYFYYLGTGPEASLPYGANKEGIVWVATEGALNTPKDHIGTRNPNNNAATVLQLPQGTTLPKGFYAEGSRGGSQASSRSSSRSRGNSRNSTP
GSSRGNSPARMASGGGETALALLLLDRLNQLESKVSGKGQQQQGQTVTKKSAAEASKKPRQKRTATKQYNVTQAFGRRGPEQTQGNFGDQDLIRQGTDYK
HWPQIAQFAPSASAFFGMSRIGMEVTPSGTWLTYHGAIKLDDKDPQFKDNVILLNKHIDAYKTFPPTEPKKDKKKKTDEAQPLPQRQKKQPTVTLLPAAD
MDDFSRQLQNSMSGASADSTQA
```

SEQ ID NO: 18
MDLFMRFFTLGSITAQPVKIDNASPASTVHATATIPLQASLPFGWLVIGVAFLAVFQSATKIIALNKRWQLALYKGFQFICNLLLLFVTIYSHLLLVAAG
MEAQFLYLYALIYFLQCINACRIIMRCWLCWKCKSKNPLLYDANYFVCWHTHNYDYCIPYNSVTDTIVVTEGDGISTPKLKEDYQIGGYSEDRHSGVKDY
VVVHGYFTEVYYQLESTQITTDTGIENATFFIFNKLVKDPPNVQIHTIDGSSGVANPAMDPIYDEPTTTTSVPL

SEQ ID NO: 19
MKIILFLTLIVFTSCELYHYQECVRGTTVLLKEPCPSGTYEGNSPFHPLADNKFALTCTSTHFAFACADGTRHTYQLRARSVSPKLFIRQEEVQQELYSP
LFLIVAALVFLILCFTIKRKTE

SEQ ID NO: 20
MYSFVSEETGTLIVNSVLLFLAFVVFLLVTLAILTALRLCAYCCNIVNVSLVKPTVYVYSRVKNLNSSEGVPDLLV

SEQ ID NO: 21
MADNGTITVEELKQLLEQWNLVIGFLFLAWIMLLQFAYSNRNRFLYIIKLVFLWLLWPVTLACFVLAAVYRINWVTGGIAIAMACIVGLMWLSYFVASFR
LFARTRSMWSFNPETNILLNVPLRGTIVTRPLMESELVIGAVIIRGHLRMAGHSLGRCDIKDLPKEITVATSRTLSYYKLGASQRVGTDSGFAAYNRYRI
GNYKLNTDHAGSNDNIALLVQ

SEQ ID NO: 22
MMPTTLFAGTHITMTTVYHITVSQIQLSLLKVTAFQHQNSKKTTKLVVILRIGTQVLKTMSLYMAISPKFTTSLSLHKLLQTLVLKMLHSSSLTSLLKTH
RMCKYTQSTALQELLIQQWIQFMMSRRRLLACLCKHKKVSTNLCTHSFRKKQVR

SEQ ID NO: 23
MFHLVDFQVTIAEILIIIMRTFRIAIWNLDVIISSIVRQLFKPLTKKNYSELDDEEPMELDYP

SEQ ID NO: 24
MDLFMRIFTIGTVTLKQGEIKDATPSDFVRATATIPIQASLPFGWLIVGVALLAVFQSASKIITLKKRWQLALSKGVHFVCNLLLLFVTVYSHLLLVAAG
LEAPFLYLYALVYFLQSINFVRIIMRLWLCWKCRSKNPLLYDANYFLCWHTNCYDYCIPYNSVTSSIVITSGDGTTSPISEHDYQIGGYTEKWESGVKDC
VVLHSYFTSDYYQLYSTQLSTDTGVEHVTFFIYNKIVDEPEEHVQIHTIDGSSGVVNPVMEPIYDEPTTTTSVPL

SEQ ID NO: 25
MADSNGTITVEELKKLLEQWNLVIGFLELTWICLLQFAYANRNRFLYIIKLIFLWLLWPVTLACFVLAAVYRINWITGGIAIAMACLVGLMWLSYFIASE
RLFARTRSMWSFNPETNILLNVPLHGTILTRPLLESELVIGAVILRGHLRIAGHHLGRCDIKDLPKEITVATSRTLSYYKLGASQRVAGDSGFAAYSRYR
IGNYKLNTDHSSSSDNIALLVQ

SEQ ID NO: 26
MKIILFLALITLATCELYHYQECVRGTTVLLKEPCSSGTYEGNSPFHPLADNKFALTCFSTQFAFACPDGVKHVYQLRARSVSPKLFIRQEEVQELYSPI
FLIVAAIVFITLCFTLKRKTE

SEQ ID NO: 27
MSDNGPQNQRNAPRITFGGPSDSTGSNQNGERSGARSKQRRPQGLPNNTASWFTALTQHGKEDLKFPRGQGVPINTNSSPDDQIGYYRRATRRIRGGDGK
MKDLSPRWYFYYLGTGPEAGLPYGANKDGIIWVATEGALNTPKDHIGTRNPANNAAIVLQLPQGTTLPKGFYAEGSRGGSQASSRSSSRSRNSSRNSTPG
SSRGTSPARMAGNGGDAALALLLLDRLNQLESKMSGKGQQQQGQTVTKKSAAEASKKPRQKRTATKAYNVTQAFGRRGPEQTQGNFGDQELIRQGTDYKH
WPQIAQFAPSASAFFGMSRIGMEVTPSGTWLTYTGAIKLDDKDPNFKDQVILLNKHIDAYKTFPPTEPKKDKKKKADETQALPQRQKKQQTVTLLPAADL
DDFSKQLQQSMSSADSTQA

SEQ ID NO: 28
MDPNQTNVVPPALHLVDPQIQLTITRMEDAMGQGQNSADPKVYPIILRLGSQLSLSMARRNLDSLEARAFQSTPIVVQMTKLATTEELPDEFVVVTAK

SEQ ID NO: 29
MYSFVSEETGTLIVNSVLLFLAFVVFLLVTLAILTALRLCAYCCNIVNVSLVKPSFVYVYSRVKNLNSSRVPDLLV

SEQ ID NO: 30
MFHLVDFQVTIAEILIIIMRTFKVSIWNLDYIINLIIKNLSKSLTENKYSQLDEEQPMEID

SEQ ID NO: 31
MKFLVFLGIITTVAAFHQECSLQSCTQHQPYVVDDPCPIHFYSKWYIRVGARKSAPLIELCVDEAGSKSPIQYIDIGNYTVSCLPFTINCQEPKLGSLVV
RCSFYEDFLEYHDVRVVLDFI

SEQ ID NO: 32
MDPKISEMHPALRLVDPQIQLAVTRMENAVGRDQNNVGPKVYPIILRLGSPLSLNMARKTLNSLEDKAFQLTPIAVQMTKLATTEELPDEFVVVTVK

SEQ ID NO: 33
MNELTLIDFYLCFLAFLLFLVLIMLIIFWFSLEIQDLEEPCTKV

SEQ ID NO: 34
MCLKILVRYNTRGNTYSTAWLCALGKVLPFHRWHTMVQTCTPNVTINCQDPAGGALIARCWYLHEGHQTAAFRDVLVVLNKRTN

SEQ ID NO: 35
MLQSCYNFLKEQHCQKASTQKGAEAAVKPLLVPHHVVATVQEIQLQAAVGELLLLEWLAMAVMLLLLCCCLTD

SEQ ID NO: 36
MIELSLIDFYLCFLAFLLFLVLIMLIIFWFSLELQDHNETCHA

SEQ ID NO: 37
MKLLIVLTCISLCSCICTVVQRCASNKPHVLEDPCKVQH

SEQ ID NO: 38
MLPPCYNFLKEQHCQKASTQREAEAAVKPLLAPHHWAVIQEIQLLAAVGEILLLEWLAEWKLPSRYCC

-continued

| Protein ID | Fragment | SEQ ID NO: | Spike Fragment |
|---|---|---|---|
| Spike Fragment of P0DTC2 | 1-279 | 39 | SNFRVQPTESIVRFPNITNLCPFGEVFNATRFASVYAWNRKRISNCVADYSVLYNSASFSTFKCYGVSPT KLNDLCFTNVYADSFVIRGDEVRQIAPGQTGKIADYNYKLPDDFTGCVIAWNSNNLDSKVGGNYNYLYRL FRKSNLKPFERDISTEIYQAGSTPCNGVEGFNCYFPLQSYGFQPTNGVGYQPYRVVVLSFELLHAPATVC GPKKSTNLVKNKCVNFNFNGLTGTGVLTESNKKFLPFQQFGRDIADTTDAVRDPQTLEILDITPCSFGG |
| P0DTC2 | 316-594 | 15 | SNFRVQPTESIVRFPNITNLCPFGEVFNATRFASVYAWNRKRISNCVADYSVLYNSASFSTFKCYGVSPT KLNDLCFTNVYADSFVIRGDEVRQIAPGQTGKIADYNYKLPDDFTGCVIAWNSNNLDSKVGGNYNYLYRL FRKSNLKPFERDISTEIYQAGSTPCNGVEGFNCYFPLQSYGFQPTNGVGYQPYRVVVLSFELLHAPATVC GPKKSTNLVKNKCVNFNFNGLTGTGVLTESNKKFLPFQQFGRDIADTTDAVRDPQTLEILDITPCSFGG |
| A0A6B9WHD3 | 316-594 | 43 | SNFRVQPTDSIVRFPNITNLCPFGEVFNATTFASVYAWNRKRISNCVADYSVLYNSTSFSTFKCYGVSPT KLNDLCFTNVYADSFVITGDEVRQIAPGQTGKIADYNYKLPDDFTGCVIAWNSKHIDAKEGGNFNYLYRL FRKANLKPFERDISTEIYQAGSKPCNGQTGLNCYYPLYRYGFYPTDGVGHQPYRVVVLSFELLNAPATVC GPKKSTNLVKNKCVNFNFNGLTGTGVLTESNKKFLPFQQFGRDIADTTDAVRDPQTLEILDITPCSFGG |
| A0A6G9KP06 | 316-594 | 44 | SNFRVQPTISIVRFPNITNLCPFGEVFNASKFASVYAWNRKRISNCVADYSVLYNSTSFSTFKCYGVSPT KLNDLCFTNVYADSFVVKGDEVRQIAPGQTGVIADYNYKLPDDFTGCVIAWNSVKQDALTGGNYGYLYRL FRKSKLKPFERDISTEIYQAGSTPCNGQVGLNCYYPLERYGFHPTTGVNYQPFRVVVLSXELLNGPATVC GPKLSTTLVKDKCVNFNFNGLTGTGVLTTSKKQFLPFQQFGRDISDTTDAVRDPQTLEILDITPCSFGG |
| A0A2D1PX05 | 307-566 | 45 | SNFRVSPTQEVVRFPNITNRCPFDKVFNATRFPSVYAWERTKISDCVADYTVLYNSTSFSTFKCYGVSPS KLIDLCFTSVYADTFLIRSSEVRQVAPGETGVIADYNYKLPDDFTGCVIAWNTAQQDKGQYYYRSSRKTK LKPFERDLSSDENGVRTLSTYDFYPTVPIEYQATRVVVLSFELLNAPATVCGPKLSTGLVKNQCVNFNFN GLKGTGVLTDSSKRFQSFQQFGRDTSDFTDSVRDPQTLQVLDITPCSFGG |
| A0A2D1PX88 | 307-566 | 46 | SNFRVSPTHEVVRFPNITNRCPFDKVFNASRFPNVYAWERTKISDCVADYTVLYNSTSFSTFKCYGVSPS KLIDLCFTSVYADTFLIRSSEVRQVAPGETGVIADYNYKLPDDFTGCVIAWNTAKQDQGQYYYRSSRKTK LKPFERDLSSDENGVRTLSTYDFYPTVPIEYQATRVVVLSFELLNAPATVCGPKLSTGLVKNQCVNFNFN GLKGTGVLTDSSKRFQSFQQFGRDTSDFTDSVRDPQTLQILDITPCSFGG |
| A0A2D1PX44 | 307-566 | 47 | SNFRVSPTHEVVRFPNITNRCPFDKVFNASRFPNVYAWERTKISDCVADYTVLYNSTSFSTFKCYGVSPS KLIDLCFTSVYADTFLIRSSEVRQVAPGETGVIADYNYKLPDDFTGCVIAWNTAKQDQGQYYYRSSRKTK LKPFERDLTSDENGVRTLSTYDFYPNVPIEYQATRVVVLSFELLNAPATVCGPKLSTALVKNQCVNFNFN GLKGIGVLTDSSKRFQSFQQFGRDTSDFTDSVRDPQTLQILDITPCSFGG |
| D2DJW4 | 307-566 | 48 | SNFRVSPTHEVIRFPNITNRCPFDKVFNASRFPNVYAWERTKISDCVADYTVLYNSTSFSTFKCYGVSPS KLIDLCFTSVYADTFLIRSSEVRQVAPGETGVIADYNYKLPDDFTGCVIAWNTAKQDQGQYYYRSSRKTK LKPFERDLTSDENGVRTLSTYDFYPNVPIEYQATRVVVLSFELLNAPATVCGPKLSTGLVKNQCVNFNFN GLKGTGVLTDSSKRFQSFQQFGRDTSDFTDSVRDPQTLQILDITPCSFGG |
| A0A2D1PX73 | 307-566 | 49 | SNFRVSPTQEVIRFPNITNRCPFDKVFNASRFPNVYAWERTKISDCVADYTVLYNSTSFSTFKCYGVSPS KLIDLCFTSVYADTFLIRSSEVRQVAPGETGVIADYNYKLPDDFTGCVIAWNTAKQDQGQYYYRSSRKTK LKPFERDLSSDENGVRTLSTYDFYPTVPIEYQATRVVVLSFELLNAPATVCGPKLSTGLVKNQCVNFNFN GLKGTGVLTDSSKRFQSFQQFGRDMSDFTDSVRDPQTLQILDITPCSFGG |
| Q3I5J5 | 307-566 | 50 | SNFRVSPTQEVIRFPNITNRCPFDKVFNATRFPNVYAWERTKISDCVADYTVLYNSTSFSTFKCYGVSPS KLIDLCFTSVYADTFLIRSSEVRQVAPGETGVIADYNYKLPDDFTGCVIAWNTAKQDQGQYYYRSHRKTK LKPFERDLSSDENGVRTLSTYDFYPSVPAYQATRVVVLSFELLNAPATVCGPKLSTQLVKNQCVNFNFN GLKGTGVLTESSKRFQSFQQFGRDTSDFTDSVRDPQTLEILDISPCSFGG |
| Q0Q475 | 307-566 | 51 | SNFRVTPTQEVVRFPNITNRCPFDKVFNASRFPNVYAWERTKISDCVADYTVLYNSTSFSTFKCYGVSPS KLIDLCFTSVYADTFLIRSSEVRQVAPGETGVIADYNYKLPDDFTGCVIAWNTAQQDQGQYYYRSYRKEK LKPFERDLSSDENGVYTLSTYDFYPSIPVEYQATRVVVLSFELLNAPATVCGPKLSTQLVKNQCVNFNFN GLRGTGVLTTSSKRFQSFQQFGRDTSDFTDSVRDPQTLEILDISPCSFGG |
| Q0QDX9 | 307-566 | 52 | SNFRVTPTQEVVRFPNITNRCPFDKVFNASRFPNVYAWERTKISDCVADYTVLYNSTSFSTFKCYGVSPS KLIDLCFTSVYADTFLIRSSEVRQVAPGETGVIADYNYKLPDDFTGCVIAWNTAQQDQGQYYYRSYRKEK LKPFERDLSSDENGVYTLSTYDFYPSIPVEYQATRVVVLSFELLNAPATVCGPKLSTQLVKNQCVNFNFN GLRGTGVLTTSSKRFQSFQQFGRDTSDFTDSVRDPQTLEILDISPCSFGG |
| Q3LZX1 | 307-567 | 53 | SNFRVSPTQEVIRFPNITNRCPFDKVFNATRFPNVYAWERTKISDCVADYTVLYNSTSFSTFKCYGVSPS KLIDLCFTSVYADTFLIRSSEVRQVAPGETGVIADYNYKLPDDFTGCVIAWNTAKHDTGNYYYRSHRKTK LKPFERDLSSDDGNGVYTLSTYDFNPNVPVAYQATRVVVLSFELLNAPATVCGPKLSTELVKNQCVNFNF NGLKGTGVLTSSSKRFQSFQQFGRDTSDFTDSVRDPQTLEILDISPCSFGG |
| A0A096XNM6 | 307-567 | 54 | SNFRVSPTQEVIRFPNITNRCPFDKVFNVTRFPNVYAWERTKISDCVADYTVLYNSTSFSTFKCYGVSPS KLIDLCFTSVYADTFLIRSSEVRQVAPGETGVIADYNYKLPDDFTGCVIAWNTAKQDIGNYYYRSHRKTK LKPFERDLSSDDGNGVYTLSTYDFNPNVPVAYQATRVVVLSFELLNAPATVCGPKLSTQLVKNQCVNFNF NGLKGTGVLTSSSKRFQSFQQFGRDTSDFTDSVRDPQTLEILDISPCSFGG |
| A0A2D1PX86 | 307-567 | 55 | SNFRVSPTQEVIRFPNITNRCPFDKVFNASRFPNVYAWERTKISDCVADYTVLYNSTSFSTFKCYGVSPS KLIDLCFTSVYADTFLIRSSEVRQVAPGETGVIADYNYKLPDDFTGCVIAWNTAKQDTGHYYYRSHRKTK LKPFERDLSSDDGNGVYTLSTYDFNPNVPVAYQATRVVVLSFELLNAPATVCGPKLSTQLVKNQCVNFNF NGLKGTGVLTDSSKRFQSFQQFGRDTSDFTDSVRDPQTLEILDITPCSFGG |

-continued

```
A0A0U1WHJ8   307-567   56   SNFRVSPTQEVVRFPNITNRCPFDKVFNATRFPNVYAWERTKISDCVADYTVLYNSTSFSTFKCYGVSPS
                             KLIDLCFTSVYADTFLIRSSEVRQVAPGETGVIADYNYKLPDDFTGCVIAWNTAKQDTGNYYYRSHRKTK
                             LKPFERDLSSDDGNGVYTLSTYDFNPNVPVAYQATRVVVLSFELLNAPATVCGPKLSTQLVKNQCVNFNF
                             NGLKGTGVLTPSLKRFQSFQQFGRDTSDFTDSVRDPQTLEILDISPCSFGG

D5HJU5       307-567   57   SNFRVSPTQEVIRFPNITNRCPFDRVFNASRFPSVYAWERTKISECVADYTVLYNSTSFSTFKCYGVSPS
                             KLIDLCFTSVYADTFLIRSSEVRQVAPGETGVIADYNYKLPDDFTGCVIAWNTAKQDTGNYYYRSHRKTK
                             LKPFERDLSSDDGNGVYTLSTYDFNPNVPVAYQATRVVVLSFELLNAPATVCGPKLSTQLVKNQCVNFNF
                             NGLKGTGVLTPSSKRFQSFQQFGRDTSDFTDSVRDPQTLEILDISPCSFGG

A0A0U1WHI2   306-566   58   SNFRVTPTQEVVRFPNITNRCPFDRVFNASRFPSVYAWERTKISDCVADYTVLYNSTSFSTFKCYGVSPS
                             KLIDLCFTSVYADTFLIRSSEVRQVAPGETGVIADYNYKLPDDFTGCVIAWNTAKQDTGYYYRSHRKTK
                             LKPFERDLSSDDGNGVYTLSTYDFNPNVPVAYQATRVVVLSFELLNAPATVCGPKLSTELVKNQCVNFNF
                             NGLKGTGVLTKSSKRFQSFQQFGRDTSDFTDSVRDPQTLEILDISPCSFGG

R9QTA0       306-565   59   SNFRVSPTQEVVRFPNITNRCPFDKVFNATRFPSVYAWERTKISDCVADYTVLYNSTSFSTFKCYGVSPS
                             KLIDLCFTSVYADTFLIRSSEVRQVAPGETGVIADYNYKLPDDFTGCVIAWNTANQDQGQYYYRSSRKEK
                             LKPFERDLSSDENGVYTLSTYDFYPSVPLDYQATRVVVLSFELLNAPATVCGPKLSTTLVKNQCVNFNFN
                             GLKGTGVLTASSKKFQSFQQFGRDASDFTDSVRDPQTLEILDISPCSFGG

R9QTH3       307-566   60   SNFRVSPSTEVIRFPNITNRCPFDRVFNASRFPSVYAWERTKISDCVADYTVLYNSTSFSTFKCYGVSPS
                             KLIDLCFTSVYADTFLIRFSEVRQIAPGETGVIADYNYKLPDEFTGCVIAWNTANQDRGQYYYRSSRKTK
                             LKPFERDLSSDENGVRTLSTYDFYPSVPLEYQATRVVVLSFELLNAPATVCGPKLSTSLIKNQCVNFNFN
                             GLKGTGVLTDSSKKFQSFQQFGRDASDFTDSVRDPQTLQILDISPCSFGG

A0A1W5YKT9   299-558   61   SNFRVSPTREVVRFPNITNRCPFDSIFNASRFPSVYAWERTKISDCVADYTVLYNSTSFSTFKCYGVSPS
                             KLIDLCFTSVYADTFLIRFSEVRQVAPGETGVIADYNYRLPDDFTGCVIAWNTANQDVGSYFYRSHRSTK
                             LKPFERDLSSDENGVRTLSTYDFNPYVPLDYQATRVVVLSFELLNAPATVCGPKLSTELVKNQCVNFNFN
                             GLKGTGVLSSSSKRFQSFQQFGRDASDFTDSVRDPQTLEILDITPCSFGG

A0A0U1WJY8   299-558   62   SNFRVSPTREVVRFPNITNRCPFDSIFNASRFPSVYAWERTKISDCVADYTVLYNSTLFSTFKCYGVSPS
                             KLIDLCFTSVYADTFLIRFSEVRQVAPGETGVIADYNYRLPDDFTGCVIAWNTANQDVGSYFYRSHRSTK
                             LKPFERDLSSDENGVRTLSTYDFNPNVPLDYQATRVVVLSFELLNAPATVCGPKLSTELVKNQCVNFNFN
                             GLKGTGVLTSSSKRFQSFQQFGRDASDFTDSVRDPQTLEILDITPCSFGG

A0A2D1PX37   300-559   63   SNFRVQPTVDVVRFPNITNLCPFDAVFNATRFPSVYAWERVKISNCVADYTAFYNSTSFSTFKCYGVSPS
                             KLIDLCFTSVYADTFLIRFSEVRQVAPGETGVIADYNYKLPDDFTGCVIAWNTAKQDVGSYFYRSHRSSK
                             LKPFERDLSSDENGVRTLSTYDFNPNVPLDYQATRVVVLSFELLNAPATVCGPKLSTQLVKNQCVNFNFN
                             GLKGTGVLTDSSKRFQSFQQFGRDTSDFTDSVRDPQTLDILDITPCSFGG

Q0QDZ0       307-566   64   SNFRVSPVTEVVRFPNITNLCPFDKVFNATRFPSVYAWERTKISDCVADYTVFYNSTSFSTFNCYGVSPS
                             KLIDLCFTSVYADTFLIRFSEVRQVAPGQTGVIADYNYKLPDDFTGCVIAWNTAKQDVGSYFYRSHRSSK
                             LKPFERDLSSEENGVRTLSTYDFNQNVPLEYQATRVVVLSFELLNAPATVCGPKLSTSLVKNQCVNFNFN
                             GFKGTGVLTDSSKTFQSFQQFGRDASDFTDSVRDPQTLRILDISPCSFGG

A0A0U1WHH0   307-566   65   SNFRVSPVTEVVRFPNITNLCPFDKVFNATRFPSVYAWERTKISDCVADYTVFYNSTSFSTFNCYGVSPS
                             KLIDLCFTSVYADTFLIRFSEVRQVAPGQTGVIADYNYKLPDDFTGCVIAWNTAKQDVGSYFYRSHRSSK
                             LKPFERDLSSEENGVRTLSTYDFNQYVPLEYQATRVVVLSFELLNAPATVCGPKLSTSLVKNQCVNFNFN
                             GFKGTGVLTDSSKTFQSFQQFGRDASDFTDSVRDPQTLRILDISPCSFGG

Q0Q484       307-566   66   SNFRVSPVTEVVRFPNITNLCPFDKVFNATRFPSVYAWERTKISDCVADYTVFYNSTSFSTFNCYGVSPS
                             KLIDLCFTSVYADTFLIRFSEVRQVAPGQTGVIADYNYKLPDDFTGCVIAWNTAKQDVGSYFYRSHRSSK
                             LKPFERDLSSVEENGRTLSTYDFNQNVPLEYQATRVVVLSFELLNAPATVCGPKLSTSLVKNQCVNFNFN
                             GFKGTGVLTDSSKTFQSFQQFGRDASDFTDSVRDPQTLRILDISPCSFGG

A0A0K1Z074   307-566   67   SNFRVAPVTEVVRFPNITNLCPFDKVFNATRFPSVYAWERTKISDCVADYTVFYNSTSFSTFNCYGVSPS
                             KLIDLCFTSVYADTFLIRFSEVRQVAPGQTGVIADYNYKLPDDFTGCVIAWNTAKYDVGSYFYRSHRSSK
                             LKPFERDLSSEENGARTLSTYDFNQNVPLEYQATRVVVLSFELLNAPATVCGPKLSTSLVKNQCVNFNFN
                             GFKGTGVLTDSSKTFQSFQQFGRDASDFTDSVRDPKTLQILDISPCSFGG

A0A0U1UYX4   302-561   68   SNFRVQPTVDVARFPNITNVCPFDKVFNATRFPSVYAWERTKISDCVADYTVFYNSTSFSTFNCYGVSPS
                             KLIDLCFTSVYADTFLIRFSEVRQVAPGQTGVIADYNYKLPDDFIGCVIAWNTAKQDVGSYFYRSHRSSK
                             LKPFERDLSSEENGVLTLSTYDFNQNVPLEYQATRVVVLSFELLNAPATVCGPKLSTPLVKNQCVNFNFN
                             GLKGTGVLTDSSKTFQSFQQFGRDASDFTDSVRDPQTLQILDISPCSFGG

A0A4Y6GL43   306-566   69   SNFRVSPTQEVVRFPNITNRCPFDKVFNASRFPSVYAWERIKISDCVADYTVLYNSTSFSTFKCYGVSPS
                             KLIDLCFTSVYADTFLIRSSEVRQVAPGETGVIADYNYKLPDDFTGCVIAWNTAKQDTGSYYYRSHRKTK
                             LKPFERDLSSDDGNGVYTLSTYDFNPNVPVAYQATRVVVLSFELLNAPATVCGPKLSTQLVKNQCVNFNF
                             NGLTGTGVLTPSSKRFQPFQQFGRDVSDFTDSVRDPKTSEILDISPCSFGG

A3EXG6       338-585   70   SRYRAQVAGFVRVTQRGSYCTPPYSVLQDPPQPVVWRRYMLYDCVFDFTVVVDSLPTHQLQCYGVSPRRL
                             ASMCYGSVTLDVMRINETHLNNLFNRVPDTFSLYNYALPDNFYGCLHAFYLNSTAPYAVANRFPIKPGGR
                             QSNSAFIDTVINAAHYSPFSYVYGLAVITLKPAAGSKLVCPVANDTVVITDRCVQYNLYGYTGTGVLSKN
                             TSLVIPDGKVFTASSTGTIIGVSINSTTYSIMPCVTVP
```

```
P36334      315-678    71    NGYTVQPIADVYRRKPNLPNCNIEAWLNDKSVPSPLNWERKTFSNCNFNMSSLMSFIQADSFTCNNIDAA
                             KIYGMCFSSITIDKFAIPNGRKVDLQLGNLGYLQSFNYRIDTTATSCQLYYNLPAANVSVSRFNPSTWNK
                             RFGFIEDSVFKPRPAGVLTNHDVVYAQHCFKAPKNFCPCKLNGSCVGSGPGKNNGIGTCPAGTNYLTCDN
                             LCTPDPITFTGTYKCPQTKSLVGIGEHCSGLAVKSDYCGGNSCTCRPQAFLGWSADSCLQGDKCNIFANF
                             ILHDVNSGLTCSTDLQKANTDIILGVCVNYDLYGILGQGIFVEVNATYYNSWQNLLYDSNGNLYGFRDYI
                             INRTFMIRSCYSGR

P25194      311-688    72    NGYTVQPIADVYRRIPNLPDCNIEAWLNDKSVPSPLNWERKTFSNCNFNMSSLMSFIQADSFTCNNIEAA
                             KIYGMCFSSITIDKFAIPNGRKVDLQLGNLGYLQSFNYRIDTTAASCQLYYNLPAANVSVSRFNPSTWNR
                             RFGFTEQSVFKPQPVGVFTHHDVVYAQHCFKAPTNFCPCKLDGSLCVGNGPGIDAGYKNSGIGTCPAGTN
                             YLTCHNAAQCDCLCTPDPITSKSTGPYKCPQTKYLVGIGEHCSGLAIKSDYCGGNPCTCQPQAFLGWSVD
                             SCLQGDRCNIFANFILHDVNSGTTCSTDLQKSNTDIILGVCVNYDLYGITGQGIFVEVNATYYNSWQNLL
                             YDSNGNLYGFRDYLTNRTFMIRSCYSGR

Q8JSP8      311-674    73    NGYTVQPVATVYRRIPDLPNCDIEAWLNSKTVSSPLNWERKIFSNCNFNMGRLMSFIQADSFGCNNIDAS
                             RLYGMCFGSITIDKFAIPNSRKVDLQVGKSGYLQSFNYKIDTAVSSCQLYYSLPAANVSVTHYNPSSWNR
                             RYGFINQSFGSRGLHDAVYSQQCFNTPNTYCPCRTSQCIGGAGTGTCPVGTTVRKCFAAVTNATKCTCWC
                             QPDPSTYKGVNAWTCPQSKVSIQPGQHCPGLGLVEDDCSGNPCTCKPQAFIGWSSETCLQNGRCNIFANF
                             ILNDVNSGTTCSTDLQQGNTNITTDVCVNYDLYGITGQGILIEVNATYYNSWQNLLYDSSGNLYGFRDYL
                             SNRTFLIRSCYSGR

Q9IKD1      309-676    74    SGYTVQPVGLVYRRVRNLPDCKIEEWLAANTVPSPLNWERKTFQNCNFNLSSLLRFVQAESLSCSNIDAS
                             KVYGMCFGSISIDKFAIPNSRRVDLQLGKSGLLQSFNYKIDTRATSCQLYYSLAQDNVTVINHNPSSWNR
                             RYGFNDVATFHSGEHDVAYAEACFTVGASYCPCAKPSTVYSCVTGKPKSANCPTGTSNRECNVQASGFKS
                             KCDCTCNPSPLTTYDPRCLQARSMLGVGDHCEGLGILEDKCGGSNICNCSADAFVGWAMDSCLSNARCHI
                             FSNLMLNGINSGTTCSTDFQLPNTEVVTGVCVKYDLYGSTGQGVFKEVKADYYNSWQNLLYDVNGNLNGF
                             RDIVTNKTYLLRSCYSGR

Q5MQD0      307-678    75    SGFTVKPVATVHRRIPDLPDCDIDKWLNNFNVPSPLNWERKIFSNCNFNLSTLLRLVHTDSFSCNNFDES
                             KIYGSCFKSIVLDKFAIPNSRRSDLQLGSSGFLQSSNYKIDTTSSSCQLYYSLPAINVTINNYNPSSWNR
                             RYGFNNFNLSSHSVVYSRYCFSVNNTFCPCAKPSFASSCKSHKPPSASCPIGTNYRSCESTTVLDHTDWC
                             RCSCLPDDPITAYDPRSCSQKKSLVGVGEHCAGFGVDEEKCGVLDGSYNVSCLCSTDAFLGWSYDTCVSNN
                             RCNIFSNFILNGINSGTTCSNDLLQPNTEVFTDVCVDYDLYGITGQGIFKEVSAVYYNSWQNLLYDSNGN
                             IIGFKDFVTNKTYNIFPCYAGR

Q0ZME7      307-676    76    SGFTVKPVATVYRRIPNLPDCDIDNWLNNVSVPSPLNWERRIFSNCNFNLSTLLRLVHVDSFSCNNLDKS
                             KIFGSCFNSITVDKFAIPNRRRDDLQLGSSGFLQSSNYKIDISSSSCQLYYSLPLVNVTINNFNPSSWNR
                             RYGFGSFNLSSYDVVYSDHCFSVNSDFCPCADPSVVNSCAKSKPPSAICPAGTKYRHCDLDTTLYVKNWC
                             RCSCLPDDPISTYSPNTCPQKKVVVGIGEHCPGLGINEEKCGTQLNHSSCFCSPDAFLGWSFDSCISNNRC
                             NIFSNFIFNGINSGTTCSNDLLYSNTEISTGVCVNYDLYGITGQGIFKEVSAAYYNNWQNLLYDSNGNII
                             GFKDFLTNKTYTILPCYSGR

P11224      309-637    77    SGYTVQPVGVVYRRVANLPACNIEEWLTARSVPSPLNWERKTFQNCNFNLSSLLRYVQAESLFCNNIDAS
                             KVYGRCFGSISVDKFAVPRSRQVDLQLGNSGFLQTANYKIDTAATSCQLHYTLPKNNVTINNHNPSSWNR
                             RYGFNDAGVFGKNQHDVVYAQQCFTVRSSYCPCAQPDIVSPCTTQTKPKSAFVNVGDHCEGLGVLEDNCG
                             NADPHKGCICANNSFIGWSHDTCLVNDRCQIFANILLNGINSGTTCSTDLQLPNTEVVTGICVKYDLYGI
                             TGQGVFKEVKADYYNSWQTLLYDVNGNLNGFRDLTTNKTYTIRSCYSGR

P11225      309-548    78    SGYTVQPVGVVYRRVPNLPDCKIEEWLTAKSVPSPLNWERRTFQNCNFNLSSLLRYVQAESLSCNNIDAS
                             KVYGMCFGSVSVDKFAIPRSRQIDLQIGNSGFLQTANYKIDTAATSCQLYYSLPKNNVTINNYNPSSWNR
                             RYGFKVNDRCQIFANILLNGINSGTTCSTDLQLPNTEVATGVCVRYDLYGITGQGVFKEVKADYYNSWQA
                             LLYDVNGNLNGFRDLTTNKTYTIRSCYSGR

Q6Q1S2      462-682    79    NFLDDNVLPETYVALPIYYQHTDINFTATASFGGSCYVCKPHQVNISLNGNTSVCVRTSHFSIRYIYNRV
                             KSGSPGDSSWHIYLKSGTCPFSFSKLNNFQKFKTICFSTVEVPGSCNFPLEATWHYTSYTIVGALYVTWS
                             EGNSITGVPYPVSGIREFSNLVLNNCTKYNIYDYVGTGIIRSSNQSLAGGITYVSNSGNLLGFKNVSTGN
                             IFIVTPCNQPD

P15423      279-501    80    SPIQSVELPVSIVSLPVYHKHTFIVLYVDFKPQSGGGKCFNCYPAGVNITLANFNETKGPLCVDTSHFTT
                             KYVAVYANVGRWSASINTGNCPFSFGKVNNFVKFGSVCFSLKDIPGGCAMPIVANWAYSKYYTIGSLYVS
                             WSDGDGITGVPQPVEGVSSFMNVTLDKCTKYNIYDVSGVGVIRVSNDTFLNGITYTSTSGNLLGFKDVTK
                             GTIYSITPCNPPD

A3EXD0      203-487    81    CAGETNFKSLSLWDTPASDCVSGSYNQEATLGAFKVYFDLINCTFRYNYTITEDENAEWFGITQDTQGVH
                             LYSSRKENVFRNNMFHFATLPVYQKILYYTVIPRSIRSPFNDRKAWAAFYIYKLHPLTYLLNFDVEGYIT
                             KAVDCGYDDLAQLQCSYESFEVETGVYSVSSFEASPRGEFIEQATTQECDFTPMLTGTPPPIYNFKRLVF
                             TNCNYNLTKLLSLFQVSEFSCHQVSPSSLATGCYSSLTVDYFAYSTDMSSYLQPGSAGAIVQFNYKQDFS
                             NPTCR

A3EX94      369-663    82    SSYEASATGTFIEQPNATECDFSPMLTGVAPQVYNFKRLVFSNCNYNLTKLLSLFAVDEFSCNGISPDSI
                             ARGCYSTLTVDYFAYPLSMKSYIRPGSAGNIPLYNYKQSFANPTCRVMASVLANVTITKPHAYGYISKCS
                             RLTGANQDVETPLYINPGEYSICRDFSPGGFSEDGQVFKRTLTQFEGGGLLIGVGTRVPMTDNLQMSFII
                             SVQYGTGTDSVCPMLDLGDSLTITNRLGKCVDYSLYGVTGRGVFQNCTAVGVKQQRFVYDSFDNLVGYYS
                             DDGNYYCVRPCVSVP
```

-continued

```
K9N5Q8          203-497    83    SFATYHTPATDCSDGNYRNASLNSFKEYFNLRNCTFMYTYNITEDEILEWFGITQTAQGVHLFSSRYVD
                                 LYGGNMFQFATLPVYDTIKYYSIIPHSIRSIQSDRKAWAAFVVYKLQPLTFLLDFSVDGYIRRAIDCGFN
                                 DLSQLHCSYESFDVESGVYSVSSFEAKPSGSVVEQAEGVECDFSPLLSGTPPQVYNFKRLVFTNCNYNLT
                                 KLLSLFSVNDFTCSQISPAAIASNCYSSLILDYFSYPLSMKSDLSVSSAGPISQFNYKQSFSNPTCILA
                                 TVPHNLTTITKPLKY

A0A3Q8AKM0      306-583    84    SNFRVSPSTEVVRFPNITNLCPFGQVFNASNFPSVYAWERLRISDCVADYAVLYNSSSSFSTFKCYGVSP
                                 TKLNDLCFSSVYADYFVVKGDDVRQIAPAQTGVIADYNYKLPDDFTGCVLAWNTNSVDSKSGNNFYYRLF
                                 RHGKIKPYERDISNVLYNSAGGTCSSISQLGCYEPLKSYGFTPTVGVGYQPYRVVVLSFELLNAPATVCG
                                 PKKSTELVKNKCVNFNFNGLTGTGVLTSSTKKFQPFQQFGRDVSDFTDSVRDPKTFEILDISPCSYGG

E0XIZ3          307-581    85    SNFRVTPTTEVVRFPNITQLCPFNEVFNITSFPSVYAWERMRITNCVADYSVLYNSSASFSTFQCYGVSP
                                 TKLNDLCFSSVYADYFVVKGDDVRQIAPAQTGVIADYNYKLPDDFTGCVIAWNTNSLDSSNEFFYRRFRH
                                 GKIKPYGRDLSNVLFNPSGGTCSAEGLNCYKPLASYGFTQSSGIGFQPYRVVVLSFELLNAPATVCGPKQ
                                 STELVKNKCVNFNFNGLTGTGVLTNSTKKFQPFQQFGRDVSDFTDSVRDPKTLEILDIAPCSYGG

A0A2D1PXA9      303-580    86    SNFRVAPSKEVVRFPNITNLCPFGEVFNATTFPSVYAWERKRISNCVADYSVLYNSTSFSTFKCYGVSAT
                                 KLNDLCFSNVYADSFVVKGDDVRQIAPGQTGVIADYNYKLPDDFLGCVLAWNTNSKDSSTSGNYNYLYRW
                                 VRRSKLNPYERDLSNDIYSPGGQSCSAIGPNCYNPLRPYGFFTTAGVGHQPYRVVVLSFELLNAPATVCG
                                 PKLSTDLIKNQCVNFNFNGLTGTGVLTSSSKRFQPFQQFGRDVSDFTDSVRDPKTSEILDISPCSFGG

U5WLK5          304-581    87    SNFRVAPSKEVVRFPNITNLCPFGEVFNATTFPSVYAWERKRISNCVADYSVLYNSTSFSTFKCYGVSAT
                                 KLNDLCFSNVYADSFVVKGDDVRQIAPGQTGVIADYNYKLPDDFLGCVLAWNTNSKDSSTSGNYNYLYRW
                                 VRRSKLNPYERDLSNDIYSPGGQSCSAVGPNCYNPLRPYGFFTTAGVGHQPYRVVVLSFELLNAPATVCG
                                 PKLSTDLIKNQCVNFNFNGLTGTGVLTPSSKRFQPFQQFGRDVSDFTDSVRDPKTSEILDISPCSFGG

A0A2D1PX29      304-581    88    SNFRVAPSKEVVRFPNITNLCPFGEVFNATTFPSVYAWERKRISNCVADYSILYNSTSFSTFKCYGVSAT
                                 KLNDLCFSNVYADSFVVKGDDVRQIAPGQTGVIADYNYKLPDDFLGCVLAWNTNSKDSSTSGNYNYLYRW
                                 VRRSKLNPYERDLSNDIYSPGGQSCSAVGPNCYNPLRPYGFFTTAGVGHQPYRVVVLSFELLNAPATVCG
                                 PKLSTDLIKNQCVNFNFNGLTGTGVLTPSSKRFQPFQQFGRDVSDFTDSVRDPKTSEILDISPCSFGG

A0A2D1PX97      303-580    89    SNFRVAPSKEVVRFPNITNLCPFGEVFNATTFPSVYAWERKRISNCVADYSVLYNSTSFSTFKCYGVSAT
                                 KLNDLCFSNVYADSFVVKGDDVRQIAPGQTGVIADYNYKLPDDFTGCVLAWNTRNIDATQTGNYNYKYRS
                                 LRHGKLRPFERDISNVPFSPDGKPCTPPAFNCYWPLNDYGFYITNGIGYQPYRVVVLSFELLNAPATVCG
                                 PKLSTDLIKNQCVNFNFNGLTGTGVLTPSSKRFQPFQQFGRDVSDFTDSVRDPKTSEILDISPCSFGG

U5WHZ7          304-581    90    SNFRVAPSKEVVRFPNITNLCPFGEVFNATTFPSVYAWERKRISNCVADYSVLYNSTSFSTFKCYGVSAT
                                 KLNDLCFSNVYADSFVVKGDDVRQIAPGQTGVIADYNYKLPDDFTGCVLAWNTRNIDATQTGNYNYKYRS
                                 LRHGKLRPFERDISNVPFSPDGKPCTPPAFNCYWPLNDYGFYITNGIGYQPYRVVVLSFELLNAPATVCG
                                 PKLSTDLIKNQCVNFNFNGLTGTGVLTPSSKRFQPFQQFGRDVSDFTDSVRDPKTSEILDISPCSFGG

U5WI05          304-581    91    SNFRVAPSKEVVRFPNITNLCPFGEVFNATTFPSVYAWERKRISNCVADYSVLYNSTSFSTFKCYGVSAT
                                 KLNDLCFSNVYADSFVVKGDDVRQIAPGQTGVIADYNYKLPDDFTGCVLAWNTRNIDATQTGNYNYKYRS
                                 LRHGKLRPFERDISNVPFSPDGKPCTPPAFNCYWPLNDYGFYITNGIGYQPYRVVVLSFELLNAPATVCG
                                 PKLSTDLIKNQCVNFNFNGLTGTGVLTPSSKRFQPFQQFGRDVSDFTDSVRDPKTSEILDISPCSFGG

A0A023PUW9      307-584    92    SNFRVSPSKEVVRFPNITNLCPFGEVFNATTFPSVYAWERKRISNCVADYSVLYNSTSFSTFKCYGVSAI
                                 KLNDLCFSNVYADSFVVKGDDVRQIAPGQTGVIADYNYKLPDDFMGCVLAWNTRNIDATSSGNFNYKYRS
                                 LRHGKLRPFERDISNVPFSPDGKPCTPPAFNCYWPLNDYGFYTTNGIGYQPYRVVVLSFELLNAPATVCG
                                 PKLSTDLITNQCVNFNFNGLTGTGVLTPSLKRFQPFQQFGRDFSDFTDSVRDPKTLEVLDISPCSFGG

A0A023PTS3      307-584    93    SNFRVSPSREVVRFPNITNLCPFGEVFNATTFPSVYAWERKRISNCVADYSVLYNSTSFSTFKCYGVSAI
                                 KLNDLCFSNVYADSFVVKGDDVRQIAPGQTGVIADYNYKLPDDFMGCVLAWNTRNIDATSSGNFHYKYRS
                                 LRHGKLRPFERDISNVPFSPDGKPCTPPAFNCYWPLNDYGFYTTNGIGYQPYRVVVLSFELLNAPATVCG
                                 PKLSTDLITNQCVNFNFNGLTGTGVLTPSSKRFQPFQQFGRDVSDFTDSVRDPKTLEVLDISPCSFGG

A0A2D1PXC0      304-581    94    SNFRVAPSKEVVRFPNITNLCPFGEVFNATTFPSVYAWERKRISNCVADYSVLYNSTSFSTFKCYGVSAT
                                 KLNDLCFSNVYADSFVVKGDDVRQIAPGQTGVIADYNYKLPDDFMGCVLAWNTRNIDATSTGNYNYKYRS
                                 LRHGKLRPFERDISNVPFSPDGKPCTPPAFNCYWPLNDYGFFTTNGIGYQPYRVVVLSFELLNAPATVCG
                                 PKLSTDLIKNQCVNFNFNGLTGTGVLTSSSKRFQPFQQFGRDVSDFTDSVRDPKTSEILDISPCSFGG

Q6TPE8          303-580    95    SNFRVVPSRDVVRFPNITNLCPFGEVFNATKFPSVYAWERKRISNCVADYSVLYNSTFFSTFKCYGVSAT
                                 KLNDLCFSNVYADSFVVKGDDVRQIAPGQTGVIADYNYKLPDDFMGCVLAWNTRNIDATSTGNYNYKYRY
                                 LRHGKLRPFERDISNVPFSPDGKPCTPPALNCYWPLNDYGFYTTTGIGYQPYRVVVLSFELLNAPATVCG
                                 PKLSTDLIKNQCVNFNFNGLTGTGVLTPSSKRFQPFQQFGRDVSDFTDSVRDPKTSEILDISPCSFGG

Q1T6X6          303-580    96    SNFRVVPSGDVVRFPNITNLCPFGEVFNATKFPSVYAWERKKISNCVADYSVLYNSTFFSTFKCYGVSAT
                                 KLNDLCFSNVYADSFVVKGDDVRQIAPGQTGVIADYNYKLPDDFMGCVLAWNTRNIDATSTGNYNYKYRC
                                 LRHGKLRPFERDISNVPFSPDGKPCTPPAFNCYWPLNDYGFYTTTGIGYQPYRVVVLSFELLNAPATVCG
                                 PKLSTDLIKNQCVNFNFNGLTGTGVLTPSSKRFQPFQQFGRDVSDFTDSVRDPKTSEILDISPCSFGG

P59594          303-580    16    SNFRVVPSGDVVRFPNITNLCPFGEVFNATKFPSVYAWERKKISNCVADYSVLYNSTFFSTFKCYGVSAT
                                 KLNDLCFSNVYADSFVVKGDDVRQIAPGQTGVIADYNYKLPDDFMGCVLAWNTRNIDATSTGNYNYKYRY
                                 LRHGKLRPFERDISNVPFSPDGKPCTPPALNCYWPLNDYGFYTTTGIGYQPYRVVVLSFELLNAPATVCG
                                 PKLSTDLIKNQCVNFNFNGLTGTGVLTPSSKRFQPFQQFGRDVSDFTDSVRDPKTSEILDISPCSFGG
```

-continued

```
D2E1D2        303-580       97    SNFRVVPSGDVVRFPNITNLCPFGEVFNATKFPSVYAWERKKISNCVADYSVLYNSTFFSTFKCYGVSAT
                                  KLNDLCFSNVYADSFVVKGDDVRQIAPGQTGVIADYNYKLPDDFMGCVLAWNTRNIDATSTGNYNYKYRY
                                  LRHGKLRPFERDISNVPFSPDGKPCTPPALNCYWPLNDYGFYTTTGIGYQPYRVVVLSFELLNAPATVCG
                                  PKLSTDLIKNQCVNFNFNGLTGTGVLTPSSKRFQPFQQFGRDVSDFTDSVRDPKTSEILDISPCSFGG

Q6DSU4        303-580       98    SNFRVVPSGDVVRFPNITNLCPFGEVFNATKFPSVYAWERKKISNCVADYSVLYNSTFFSTFKCYGVSAT
                                  KLNDLCFSNVYADSFVVKGDDVRQIAPGQTGVIADYNYKLPDDFMGCVLAWNTRNIDATSTGNYNYKYRY
                                  LKHGKLRPFERDISNVPFSPDGKPCTPPALNCYWPLNDYGFYTTTGIGYQPYRVVVLSFELLNAPATVCG
                                  PKLSTDLIKNQCVNFNFNGLTGTGVLTPSSKRFQPFQQFGRDVSDFTDSVRDPKTSEILDISPCSFGG

Q202H8        303-580       99    SNFRVVPSGDVVRFPNITNLCPFGEVFNATKFPSVYAWERKKISNCVADYSVLYNSTFFSTFKCYGVSAT
                                  KLNDLCFSNVYVDSFVVKGDDVRQIAPGQTGVIADYNYKLPDDFMGCVLAWNTRNIDATSTGNYNYKYRY
                                  LRHGKLRPFERDISNVPFSPDGKPCTPPALNCYWPLNDYGFYTTTGIGYQPYRVVVLSFELLNAPATVCG
                                  PKLSTDLIKNQCVNFNFNGLTGTGVLTPSSKRFQPFQQFGRDVSDFTDSVRDPKTSEILDISPCSFGG

Q202F2        303-580       100   SNFRVVPSGDVVRFPNITNLCPFGEVFNATKFPSVYAWERKKISNCVVDYSVLYNSTFFSTFKCYGVSAT
                                  KLNDLCFSNVYADSFVVKGDDVRQIAPGQTGVIADYNYKLPDDFMGCVLAWNTRNIDATSTGNYNYKYRY
                                  LRHGKLRPFERDISNVPFSPDGKPCTPPALNCYWPLNDYGFYTTTGIGYQPYRVVVLSFELLNAPATVCG
                                  PKLSTDLIKNQCVNFNFNGLTGTGVLTPSSKRFQPFQQFGRDVSDFTDSVRDPKTSEILDISPCSFGG

D2E235        303-580       101   SNFRVVPSGDVVRFPNITNLCPFGEVFNATKFPSVYAWERKKISNCVADYSVLYNSTFFSTFKCYGVSAT
                                  KLNDLCFSNVYADSFVVKGDDVRQIAPGQTGVIADYNYKLPDDFMGCVLAWNTRNIDATSTGNHNYKYRY
                                  LRHGKLRPFERDISNVPFSPDGKPCTPPALNCYWPLNDYGFYTTTGIGYQPYRVVVLSFELLNAPATVCG
                                  PKLSTDLIKNQCVNFNFNGLTGTGVLTPSSKRFQPFQQFGRDVSDFTDSVRDPKTSEILDISPCSFGG

Q202H5        303-580       102   SNFRVVPSGDVVRFPNITNLCPFGEVFNATKFPSVYAWERKKISNCVADYSVLYNSTFFSTFKCYGVSAT
                                  KLNDLCFSNVYADSFVVKGDDVRQIAPGQTGVIADYNYKLPDDFMGCVLAWNTRNIDATSTGNYNYKYRY
                                  LRHGKLRPFERDISNVPFSPNGKPCTPPALNCYWPLNDYGFYTTTGIGYQPYRVVVLSFELLNAPATVCG
                                  PKLSTDLIKNQCVNFNFNGLTGTGVLTPSSKRFQPFQQFGRDVSDFTDSVRDPKTSEILDISPCSFGG

A4ZF30        303-580       103   SNFRVVPSGDVVRFPNITNLCPFGEVFNATKFPSVYAWERKKISNCVADYSVLYNSTFFSTFKCYGVSAT
                                  KLNDLCFSNVYADSFVVKGDDVRQIAPGQTGVIADYNYKLPDDFMGCVLAWNTRNIDATSTGNYNYKYRY
                                  LRHGKLRPFERDISNVPFSPDGKPCTPPAPNCYWPLNDYGFYTTSGIGYQPYRVVVLSFELLNAPATVCG
                                  PKLSTDLIKNQCVNFNFNGLTGTGVLTPSSKRFQPFQQFGRDVSDFTDSVRDPKTSEILDISPCAFGG

A4ZF29        303-580       104   SNFRVVPSGDVVRFPNITNLCPFGEVFNATKFPSVYAWERKKISNCVADYSVLYNSTFFSTFKCYGVSAT
                                  KLNDLCFSNVYADSFVVKGDDVRQIAPGQTGVIADYNYKLPDDFMGCVLAWNTRNIDATSTGNYNYKYRY
                                  LRHGKLRPFERDISNVPFSPDGKPCTPPAPNCYWPLNGYGFYTTSGIGYQPYRVVVLSFELLNAPATVCG
                                  PKLSTDLIKNQCVNFNFNGLTGTGVLTPSSKRFQPFQQFGRDVSDFTDSVRDPKTSEILDISPCSFGG

Q4JDP0        303-580       105   SNFRVVPSGDVVRFPNITNLCPFGEVFNATKFPSVYAWERKRISNCVADYSVLYNSTSFSTFKCYGVSAT
                                  KLNDLCFSNVYADSFVVKGDDVRQIAPGQTGVIADYNYKLPDDFMGCVLAWNTRNIDATSTGNYNYKYRY
                                  LRHGKLRPFERDISNVPFSPDGKPCTPPAPNCYWPLNGYGFYTTSGIGYQPYRVVVLSFELLNAPATVCG
                                  PKLSTDLIKNQCVNFNFNGLTGTGVLTPSSKRFQPFQQFGRDVSDFTDSVRDPKTSEILDISPCSFGG

Q5GDJ7        303-580       106   SNFRVVPSGDVVRFPNITNLCPFGEVFNATKFPSVYAWERKRISNCVADYSVLYNSTSFSTFKCYGVSAT
                                  KLNDLCFSNVYADSFVVKGDDVRQIAPGQTGVIADYNYKLPDDFMGCVLAWNTRNIDATSTGNYNYKYRY
                                  LRHGKLRPFERDISNVPFSPDGKPCTPPAPNCYWPLRGYGFYTTSGIGYQPYRVVVLSFELLNAPATVCG
                                  PKLSTDLIKNQCVNFNFNGLTGTGVLTPSSKRFQPFQQFGRDVSDFTDSVRDPKTSEILDISPCSFGG

Q3ZTC5        303-580       107   SNFRVVPSGDVVRFPNITNLCPFGEVFNATKFPSVYAWERKRISNCVADYSVLYNSTSFSTFKCYGVSAT
                                  KLNDLCFSNVYADSFVVKGDDVRQIAPGQTGVIADYNYKLPDDFMGCVLAWNTRNIDATSTGNYNYKYRY
                                  LRHGKLRPFERDISNVPFSPDGKPCTPPAPNCYWPLRGYGFYTTSGIGYQPYRVVVLSFELLNAPATVCG
                                  PKLSTDLIKNQCVNFNFNGLTGTGVLTPSSKRFQPFQQFGRDVSDFTDSVRDPKTSEILDISPCSFGG

Q4JDN4        303-580       108   SNFRVVPSGDVVRFPNITNLCPFGEVFNATKFPSVYAWERKRISNCVADYSVLYNSTSFSTFKCYGVSAT
                                  KLNDLCFSNVYADSFVVKGDDVRQIAPGQTGVIADYNYKLPDDFMGCVLAWNTRNIDATSTGNYNYKHRY
                                  LRHGKLRPFERDISNVPFSPDGKPCTPPAPNCYWPLRGYGFYTTSGIGYQPYRVVVLSFELLNAPATVCG
                                  PKLSTDLIKNQCVNFNFNGLTGTGVLTPSSKRFQPFQQFGRDVSDFTDSVRDPKTSEILDISPCSFGG

Q3ZTE0        303-580       109   SNFRVVPSGDVVRFPNITNLCPFGEVFNATKFPSVYAWERKRISNCVADYSVLYNSTSFSTFKCYGVSAT
                                  KLNDLCFSNVYADSFVVKGDDVRQIAPGQTGVIADYNYKLPDDFMGCVLAWNTRNIDATSTGNYNYKYRY
                                  LRHGKLRPFERDISNVPFSSDGKPCTPPAPNCYWPLRGYGFYTTSGIGYQPYRVVVLSFELLNAPATVCG
                                  PKLSTDLIKNQCVNFNFNGLTGTGVLTPSSKRFQPFQQFGRDVSDFTDSVRDPKTSEILDISPCSFGG

Q4JDP2        303-580       110   SNFRVVPSGDVVRFPNITNLCPFGEVFNATKFPSVYAWERKRISNCVADYSVLYNSTSFSTFKCYGVSAT
                                  KLNDLCFSNVYADSFVVKGDDVRQIAPGQTGVIADYNYKLPDDFMGCVLAWNTRNIDATSTGNYNYKXRY
                                  LRHGKLRPFERDISNVPFSPXGKPCTPPAPNCYWPLRGYGFYTTSGIGYQPYRVVVLSFELLNAPATVCG
                                  PKLSTDLIKNQCVNFNFNGLTGTGVLTPSSKRFQPFQQFGRDVSDFTDSVRDPKTSEILDISPCSFGG
```

60

As used herein a "Target" is a specifically selected protein disclosed in Table 2 that can be modified to have an improved peptidogenicity as described herein. Column 1 lists the SEQ ID NO. corresponding to the sequence provided in the Sequence Listing. Column 2 lists the "Protein Name" of each Target and Column 3 provides the "UniProt Reference Number" which is a unique "cataloging" number (UniProt Reference Numbers provide a mapping of a proteome to a reference genome assembly, e.g., as produced by the Genome Reference Consortium (GRC)) used in the art that provides publicly known and established descriptions of both the function, expression and sequence information for each Target listed in Column 2. This public information (retrieved from the UniProt database (uniprot.org) on April 2020) including the sequence information corresponding to each Target, is herein incorporated by reference in its entirety. Table 2 describes the positions of the specific residues in each target protein where mutations can be made to generate the corresponding SARS-COV-2 peptidogenic proteins along with the specific amino acids that can be substituted at each position. In preferred embodiments, multiple substitutions can be made in each target protein at the recited positions in the Sequence Listing and as shown in Table 2. In further preferred embodiments, at least 1, 2, 3, 4, 5, 6, 7, 8, 9, 10, 11, 12, 13, 14, 15, 16, 17, 18, 19, 20 or more of the residues shown in Table 2 for each target protein, in any combination, can be changed in the respective starting Target proteins listed in Column 2 using the amino acid specified in Table 2 as described in the last two paragraphs of Example 1. By spreading the mutations over multiple positions and/or target proteins, and by mixing these mutated molecules together, an immunization cocktail can be created.

For example, in evaluating ways to engineer the spike protein of SARS-COV-2 (as disclosed in Table 2) for increased immunogenicity, we applied the methods as disclosed herein to develop a prioritized short list of substitutions that could be tested.

A. Aromatic residue mutations. There are a number of aromatic residues in the core. To create moderately-sized cavities (volume of ~3 carbons) with no serious steric clashes, we propose substituting Leu for Tyr and Phe, and Phe for Trp as shown in Table 2. Preferred mutations include, but are not limited to, mutations located in the SARS-COV-2 Spike protein at the following positions: Trp 353, Tyr 365, Phe 392, Phe 400, Tyr 423, Phe 497, and/or Phe 543 of SEQ ID NO:15.

B. Aliphatic residue (excluding Ala, Cys, & Pro) mutations. There are also buried Met, Leu, Ile, and Val amino acid residues in or around the core. We propose mutating these to Ala at the positions as shown on Table 2 which, like the above mutations, creates a packing defect due to removal of 3-4 carbons. Preferred mutations in the SARS-COV-2 Spike protein include, but are not limited to, mutations located at the following positions: Val308, Ile326, Val350, Ile358, Ala363, Leu387, Val395, Ala397, Val401, Ile402, Ile410, Ile418, Ala419, Leu425, Val433, Ile434, Ala435, Leu492, Val510, Val511, Val512, Leu513, Val524, Val539, Leu552, Ala575, Val576, and/or Leu585 of SEQ ID NO:15.

C. Alanine mutations. There is a comparable number of buried alanines. The preferred substitution here is a Gly, which increases the conformational entropy of the unfolded state and thereby disfavors the folded state. Generally, such mutations typically provide only about 1.5±1.0 kcal decrement in the stabilization free energy of a globular protein, but the effect can be magnified when the residue is in a secondary structure element such as an alpha helix. The prospective mutations in this class are also shown on Table 2. Preferred mutations include, but are not limited to, mutations in the SARS-COV-2 Spike protein located at the following positions: Ala 363, Ala 397, and/or Ala 575 of SEQ ID NO: 15.

D. Cysteine mutations. Because surface disulfides generally promote reductive unfolding, we would prefer to leave the solvent-accessible disulfides intact. Therefore, we propose cysteine to alanine double mutants to remove buried or partially buried disulfides. For example in the SARS-COV-2 Spike protein, we propose the following mutations: Cys 336 Ala/Cys 361 Ala, and/or Cys 379 Ala/Cys 432 Ala of SEQ ID NO: 15.

General Considerations for Further Prioritization of Candidate Mutations:

A. T cell epitope generation. The aim is to increase the fraction of antigen that will unfold in the phagosome/lysosome with appropriate kinetics to put it within a time window that will allow thorough proteolytic processing and loading of antigen peptides onto MHCII receptors in APCs.

B. Mutation of residues with relatively low specific contact order (i.e., residues that only contact in the 3D structure other residues that are nearby in the primary amino acid sequence) and avoidance of high $\phi$-value mutations that destabilize the transition state. Contact order is a global topological property of proteins that can be calculated by determining all residue-residue contacts in a protein (using appropriate constraints), tallying the linear separation in the polypeptide chain between all pairs of contacting residues (normalized to the total protein chain length), and summing up these component distances. High contact order proteins exhibit more long-range interactions between pairs of amino acids and, generally, fold more slowly (Plaxco et al, *J. Mol. Biol.* 277:985 [1998]; Shi et al, *BMC Bioinformatics* 9:255 [2008]).

As a prioritization filter for our list of proposed residues to mutate (above) one can rank the specific contact information in the 3D structure for each candidate residue and choose those residues with the lowest contribution to the contact order. In essence, this ranking identifies those residues that tend to have smaller loop sizes (in the primary amino acid sequence) between the residue being mutated and the other residues it contacts in the 3D structure. The rationale for doing this was as follows: (i) mutation of residues that stabilize the folding transition state tends to decrease the folding rate and disfavor increases in the unfolding rate (i.e., "high $\phi$-value" residues—cf. Fersht & Daggett, *Cell* 108:573 [2002]; Chiti et al, *Nature Struct. Biol.* 6:1005 [1999]); and (ii) residues involved in establishing the native fold topology in the folding transition state tend to exhibit longer range interactions. Our prioritization procedure aims to deemphasize those residues, like the high $\phi$-value residues, having predominantly non-local contacts.

Focusing our initial mutagenesis effort on residues that have mostly local contacts with other residues proximal in the polypeptide sequence should thus favor mutations that increase the unfolding rate (and hence promote lysosomal antigen processing) while avoiding undue increases in folding rate. Locally impactful mutations in the antigen could also pay additional dividends in terms immunogenicity by promoting surface malleability. We hypothesize that this might promote widening of antigenic patches during B cell maturation or even, at the primary B cell selection stage, unmask new B cell epitopes in regions of the antigen protein surface that were heretofore unreactive to naïve B cells.

Below is a short list of prioritized mutations in the SARS-COV-2 Spike protein, all of which exhibit average specific inter-residue contact loop sizes of 40 amino acids or less: Ala 419, Ile 980, Ala 903, Leu 916, Ala 575, Phe 1095, Cys 1032, Val 576, Tyr 365, Ile 1115, Ile 418, Leu 387, Cys 649, Leu 650, Leu 585, Ala 1080, Ile 410, Tyr 423, Ala 1087, Tyr 695, Ala 653, Phe 201, Ile 1081, Phe 497, Ala 989, Leu 552, Val 1104, and/or Cys 671 of SEQ ID NO:15.

Additionally, although Table 2 specifically lists buried cysteine residues, it would be understood by the skilled person that mutating solvent accessible cysteines that are in disulfide bond pairs with cysteines identified in Table 2 are also specifically contemplated. To mutate the solvent accessible cysteine normally in disulfide bond pairs with the buried cysteine avoids leaving an unpaired cysteine residue, which will then prevent aberrant disulfide bond formation, scrambling, and oligomerization.

Combination of any of the above mutations and/or those disclosed in Table 2 are specifically contemplated. For example, a core hydrophobic cavity-creating mutation could be placed in a disulfide mutant background. Once the unfolding characteristics of a collection of the mutants have been established and an appropriate subset chosen, each mutant antigen could be tested individually in animals for immunogenicity. Then cocktails containing different combinations of the most promising mutant antigens could be assembled and also tested for immunogenicity.

In even further preferred embodiments, mutations at the following sites are preferred in the SARS-COV-2 Spike protein:

A. Trp 353, Tyr 365, Phe 392, Phe 400, Tyr 423, Phe 497, and/or Phe 543 of SEQ ID NO: 15;
B. Val308, Ile326, Val350, Ile358, Ala363, Leu387, Val395, Ala397, Val401, Ile402, Ile410, Ile418, Ala419, Leu425, Val433, Ile434, Ala435, Leu492, Val510, Val511, Val512, Leu513, Val524, Val539, Leu552, Ala575, Val576, and/or Leu585 of SEQ ID NO: 15;
C. Ala 363, Ala 397, and/or Ala 575 of SEQ ID NO:15;
D. Cys 336 Ala/Cys 361 Ala, and/or Cys 379 Ala/Cys 432 Ala of SEQ ID NO: 15; and/or
E. Ala 419, Ile 980, Ala 903, Leu 916, Ala 575, Phe 1095, Cys 1032, Val 576, Tyr 365, Ile 1115, Ile 418, Leu 387, Cys 649, Leu 650, Leu 585, Ala 1080, Ile 410, Tyr 423, Ala 1087, Tyr 695, Ala 653, Phe 201, Ile 1081, Phe 497, Ala 989, Leu 552, Val 1104, and/or Cys 671 of SEQ ID NO:15.

In even further preferred embodiments, the SARS-COV-2 peptidogenic protein is a fragment of the Spike glycoprotein. Preferably, the fragment consists of amino acids 316-594 of SEQ ID NO:15, amino acids 303-580 of SEQ ID NO:16, or equivalent fragments in the other known Spike glycoproteins of Coronaviruses as shown in FIG. 3 (SEQ ID NO:15-16 and 43-110). This truncated fragment can be used as a vaccine itself as described herein, or can be combined with mutations at any of the following sites: (A) Trp 353, Tyr 365, Phe 392, Phe 400, Tyr 423, Phe 497, and/or Phe 543 of SEQ ID NO: 15; (B) Ile326, Val350, Ile358, Ala363, Leu387, Val395, Ala397, Val401, Ile402, Ile410, Ile418, Ala419, Leu425, Val433, Ile434, Ala435, Leu492, Val510, Val511, Val512, Leu513, Val524, Val539, Leu552, Ala575, Val576, and/or Leu585 of SEQ ID NO:15; (C) Ala 363, Ala 397, and/or Ala 575 of SEQ ID NO:15; (D) Cys 336 Ala/Cys 361 Ala, and/or Cys 379 Ala/Cys 432 Ala of SEQ ID NO:15; (E) Ala 419, Ala 575, Val 576, Tyr 365, Ile 418, Leu 387, Leu 585, Ile 410, Tyr 423, Phe 497, and/or Leu 552 of SEQ ID NO: 15. In the most preferred embodiments, the fragment comprises mutations, such as Y365, I402, and/or V511 of SEQ ID NO:15. In even more preferred embodiments, the fragment comprises the following mutations Y365L, I402V, and/or V511A of SEQ ID NO:15.

In further preferred embodiments, the truncated Spike protein comprising, or consisting of amino acids 319-591 of SEQ ID NO:15 which is combined with preferred mutations at the following sites: (A) Trp 353, Tyr 365, Phe 392, Phe 400, Tyr 423, Phe 497, and/or Phe 543 of SEQ ID NO:15; (B) Ile326, Val350, Ile358, Ala363, Leu387, Val395, Ala397, Val401, Ile402, Ile410, Ile418, Ala419, Leu425, Val433, Ile434, Ala435, Leu492, Val510, Val511, Val512, Leu513, Val524, Val539, Leu552, Ala575, Val576, and/or Leu585 of SEQ ID NO:15; (C) Ala 363, Ala 397, and/or Ala 575 of SEQ ID NO: 15; (D) Cys 336 Ala/Cys 361 Ala, and/or Cys 379 Ala/Cys 432 Ala of SEQ ID NO: 15; and/or (E) Ala 419, Ala 575, Val 576, Tyr 365, Ile 418, Leu 387, Leu 585, Ile 410, Tyr 423, Phe 497, and/or Leu 552 of SEQ ID NO:15. In the most preferred embodiments, the fragment comprises mutations, such as Y365, I402 and/or V511 of SEQ ID NO:15. In even more preferred embodiments, the fragment comprises the following mutations Y365L, I402V, and/or V511A of SEQ ID NO:15.

In further preferred embodiments, the truncated Spike protein comprising, or consisting of amino acids 319-541 of SEQ ID NO:15 which is combined with preferred mutations at the following sites: (A) Trp 353, Tyr 365, Phe 392, Phe 400, Tyr 423, and/or Phe 497 of SEQ ID NO:15; (B) Ile326, Val350, Ile358, Ala363, Leu387, Val395, Ala397, Val401, Ile402, Ile410, Ile418, Ala419, Leu425, Val433, Ile434, Ala435, Leu492, Val510, Val511, Val512, Leu513, Val524, and/or Val539 of SEQ ID NO:15; (C) Ala 363, and/or Ala 397 of SEQ ID NO:15; (D) Cys 336 Ala/Cys 361 Ala, and/or Cys 379 Ala/Cys 432 Ala of SEQ ID NO: 15; and/or (E) Ala 419, Tyr 365, Ile 418, Leu 387, Ile 410, Tyr 423, an/or Phe 497 of SEQ ID NO:15. In the most preferred embodiments, the fragment comprises mutations, such as Y365, I402, and/or V511 of SEQ ID NO:15. In even more preferred embodiments, the fragment comprises the following mutations Y365L, I402V, and/or V511A of SEQ ID NO:15.

In a preferred embodiment, the mixture of polynucleotides encoding the SARS-COV-2 peptidogenic proteins and/or the fragment consisting of amino acids 316-594 of SEQ ID NO: 15 or amino acids 303-580 of SEQ ID NO: 16 can be synthesized in vitro. The polynucleotides can also preferably comprise either DNA or mRNA. In preferred embodiments, the polynucleotides are in vitro transcribed (IVT) mRNA. The mRNA, including the IVT mRNA, can further comprise a poly(A) tail and/or a 5' cap. In another preferred embodiment, the mRNA can be translated in vitro to produce the SARS-COV-2 peptidogenic proteins, including by use of coupled in vitro transcription/translation (IVTT).

The mixture of polynucleotides can comprise sequences encoding different SARS-COV-2 peptidogenic proteins derived from either the same SARS-COV-2 starting protein or from multiple SARS-COV-2 starting proteins or multiple related SARS-COV-2 starting proteins and/or the fragment consisting of amino acids 316-594 of SEQ ID NO: 15 or 303-580 of SEQ ID NO:16. In further embodiments, the polynucleotides encode a mixture of SARS-COV-2 proteins wherein one of the protein components of the mixture is the SARS-COV-2 starting protein and the other components are SARS-COV-2 peptidogenic proteins and/or the fragment consisting of amino acids 316-594 of SEQ ID NO:15 or 303-580 of SEQ ID NO: 16. In further preferred embodiments, the polynucleotides can be associated with a targeting component that targets the polynucleotides to a cell or organ. Alternatively, the polynucleotides can be unassociated with a targeting component. The polynucleotides encoding the SARS-COV-2 peptidogenic proteins may also comprise a vector sequence.

Mixtures of these polynucleotides as well as animals (genetically modified or not genetically modified) expressing mixtures of polynucleotides are also contemplated. In preferred embodiments, the animal is a mammal and in further preferred embodiments, the mammal is a human, a mouse, a rabbit, a llama, or a cow.

In further preferred embodiments, the method induces an immune response. The immune response can occur in vivo, ex vivo and/or in vitro.

The polynucleotides encoding the SARS-COV-2 peptidogenic proteins and/or the Spike fragment, including, but not limited to mixtures of polynucleotides or mixtures of the encoded proteins, can be delivered to the animal by injection. In preferred embodiments, the injection occurs in the muscle of the animal. The delivery of the polynucleotides/encoded proteins to the animal can be used for vaccination purposes, in research, or antibody development.

In further preferred embodiments, the antibody produced by the described methods is recovered and isolated. In preferred embodiments, the antibody is a fully human antibody, a chimeric antibody, a single-chain antibody, a camelid antibody, a humanized antibody, a polyclonal antibody or a monoclonal antibody. In preferred embodiments, the polyclonal antibody is further fractionated into single, isolated antibody species. In other preferred embodiments, the produced antibody is affinity matured, such as, for example, by phage display, yeast display, ribosome display or by a panning technique.

Also contemplated are polynucleotides that encode the antibodies produced by the methods described herein. These antibody encoding polynucleotides can also comprise a heterologous promoter and/or a vector sequence.

As described herein, a mixture of the SARS-COV-2 peptidogenic proteins and/or the mixtures of polynucleotides encoding the SARS-COV-2 peptidogenic proteins and/or the fragment consisting of amino acids 316-594 of SEQ ID NO: 15 or 303-580 of SEQ ID NO: 16 can be used to vaccinate a mammal.

In further preferred embodiments, the invention is a method of processing a SARS-COV-2 peptidogenic protein and/or fragment wherein the method comprises introducing to an antigen presenting cell a SARS-COV-2 peptidogenic protein and/or the fragment consisting of amino acids 316-594 of SEQ ID NO: 15 or 303-580 of SEQ ID NO:16, wherein the SARS-COV-2 peptidogenic protein has altered conformational dynamics as compared to a SARS-COV-2 starting protein and wherein the SARS-COV-2 peptidogenic protein has a similar conformation to the SARS-COV-2 starting protein; and permitting the antigen presenting cell to process and display T cell epitopes derived from the SARS-COV-2 peptidogenic protein.

In preferred embodiments, the antigen presenting cell is a dendritic cell, a B cell, a monocyte or a macrophage. In further preferred embodiments, the method is carried out in vitro or ex vivo. In further preferred embodiments, the antigen presenting cell is transfected with a polynucleotide encoding the SARS-COV-2 peptidogenic protein(s) and/or placed in contact with the SARS-COV-2 peptidogenic protein(s) and/or the fragment consisting of amino acids 316-594 of SEQ ID NO:15 or 303-580 of SEQ ID NO:16. In further preferred embodiments the antigen presenting cell undergoes phagocytosis or pinocytosis of the SARS-COV-2 peptidogenic protein(s) or polynucleotide(s) encoding the SARS-COV-2 peptidogenic protein and/or the fragment consisting of amino acids 316-594 of SEQ ID NO: 15 or 303-580 of SEQ ID NO: 16.

BRIEF DESCRIPTION OF THE DRAWINGS

FIG. 3 is an alignment of the Spike Fragment of known Coronaviruses. Arrows indicate key mutations that can be made in each of the known Spike proteins.

DETAILED DESCRIPTION OF THE INVENTION

Overview

Figure 1:
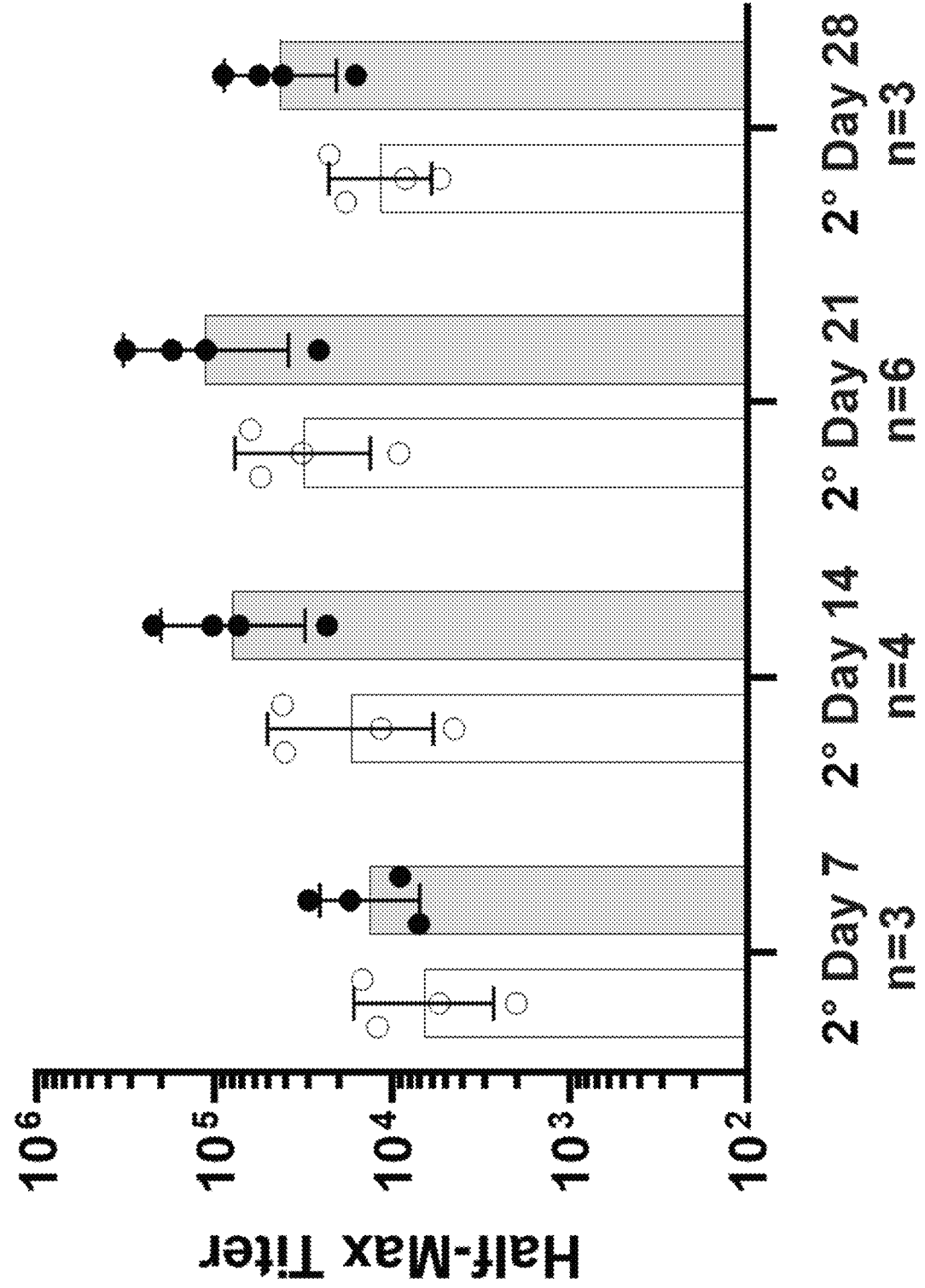
FIG. 1 shows half-max ELISA titers (geometric mean) for anti-Spike fragment IgGs from sera of BALB/C mice immunized with the Spike fragment derived from SEQ ID NO:15 (open circles) vs. a mixture of this same fragment with additional mutants Y365L and V511A (filled circles), administered with standard alum adjuvant in a prime/boost schedule.

We describe herein a novel method of generating an immune response, including enhancing the generation of antibodies by using a protein's "peptidogenic potential" via altering the conformational dynamics of a SARS-COV-2 starting protein while maintaining that protein's 3-D conformation. Alternatively, a fragment consisting of amino acids 316-594 of SEQ ID NO:15 or 303-580 of SEQ ID NO:16 (examples of the "Spike fragment") can also be used to generate antibodies, such as when used as a vaccine. These SARS-COV-2 peptidogenic proteins and/or Spike fragments can then be used to mount an immune response, used as a vaccine and/or to generate antibodies.

Thus, in one embodiment, the invention is directed to a method of triggering an immune response wherein said method comprises designing a mixture of SARS-COV-2 peptidogenic proteins derived from a SARS-COV-2 starting protein and/or Spike fragment, wherein the SARS-CoV-2 peptidogenic proteins have altered conformational dynamics as compared to the SARS-CoV-2 starting protein and wherein the SARS-COV-2 peptidogenic proteins are similar in conformation to the SARS-COV-2 starting protein, introducing the SARS-COV-2 peptidogenic proteins and/or Spike fragment to an animal and generating an immune response. The SARS-CoV-2 peptidogenic proteins and/or Spike fragment can be introduced into the animals directly (by, for instance, inoculation or immunization) or can be expressed in vivo by polynucleotides that have been introduced into the animal and which encode the SARS-COV-2 peptidogenic proteins and/or Spike fragment. Upon expression of these SARS-COV-2 peptidogenic proteins and/or Spike fragment, the immune response is triggered to generate antibodies preferably to both the SARS-COV-2 peptidogenic proteins and to the original SARS-COV-2 starting protein.

Introduction of the polynucleotides can occur, for example, by either directly or after first performing ex vivo transfection of dendritic cells. Additionally, polynucleotides encoding the SARS-COV-2 peptidogenic proteins and/or Spike fragment can be generated and introduced into an animal. The SARS-COV-2 peptidogenic proteins and/or Spike fragment can then be produced in the animal to generate antibodies to the SARS-COV-2 peptidogenic proteins. The methods described herein have the potential to profoundly impact the immunogenicity of proteins. Preferred biophysical and biochemical properties that are altered in the protein, include, but are not limited to conformational dynamics of a protein, the thermodynamic stability, MHC-II binding, and/or the protease susceptibility of the SARS-COV-2 starting protein. The methods described herein can also be used to simultaneously produce cross-reacting antibodies to different SARS-CoV-2 peptidogenic proteins (either derived from the same or different SARS-COV-2 starting proteins) which has the potential to profoundly change the way in which antibodies are currently being generated as the repertoire of antibodies that can be obtained by a single injection in an animal has the potential to streamline antibody development and vaccination efficacy.

We have recognized that the conformational dynamics of a protein are critical for the ability of the protein to mount an immune response. The propensity of an antigen to efficiently yield peptide fragments in vivo after immunization we have termed "peptidogenicity." Having the ability to alter the conformational dynamics of a SARS-COV-2 starting protein to design a mixture of SARS-COV-2 peptidogenic proteins which can be administered directly as a protein mixture or simultaneously expressed in an animal by a mixture of polynucleotides has the potential to generate a broad repertoire of antibodies with a single injection in a cost-effective manner.

Thus, as disclosed herein, immunizing an animal with a mixture of SARS-COV-2 peptidogenic proteins and/or Spike fragment can robustly stimulate the immune system, generating stronger and/or better immune responses when placed in contact with an antigen presenting cell.

The immunization with a mixture (or combinatorial cocktail) of SARS-COV-2 peptidogenic proteins and/or Spike fragment is advantageous due to the complexity of the proteolytic attack on the protein antigen(s) that produces the peptides. For example, providing multiple different SARS-COV-2 peptidogenic proteins having different amino acid sequences creates an environment where the "tuning mutation(s)" optimal for the production of a given peptide (T cell epitope) in the right time frame may be different from the mutations optimal for production of another peptide. For example, some cells, such as dendritic cells, mediate T-cell responses during an activation phase. If these cells are presented with antigens outside of this activation window (e.g., before or after activation) then a T-cell response may not be triggered. Thus, T-cells need to be presented with antigens at the appropriate time, which is governed by rates of protein degradation (e.g., proteolysis) in the antigen presenting cell, to trigger an immune response. By giving the antigens as mixtures, a multiplicity of different SARS-COV-2 peptidogenic proteins can be endocytosed by a single cell, which theoretically maximizes the diversity of the peptides produced and displayed by that cell. Additionally, the SARS-COV-2 peptidogenic proteins having increased conformational dynamics may lead to an improved MHC class II binding which is expected to maximize the immune response. For example, for proteins that are relatively non-immunogenic and/or are not good vaccine components because of being too stable, and thus protease degradation is inhibited and subsequent peptide presentation is thereby impoverished resulting in attenuation of the immune response in adaptive immunity, such proteins could be altered as described herein to generate a mixture of SARS-COV-2 peptidogenic proteins with altered conformational dynamics while maintaining a similar conformation as compared to the SARS-COV-2 starting protein.

In preferred embodiments, a SARS-COV-2 starting protein, also referred to as a test SARS-COV-2 starting protein, can be systematically mutated to alter the thermodynamic stability of the SARS-COV-2 starting protein, without significantly altering the three-dimensional structure of the corresponding folded protein, to generate SARS-COV-2 peptidogenic proteins having increased peptidogenicity while displaying essentially the same 3D (conformational) surface epitopes as the SARS-COV-2 starting protein.

Thus, increasing the immunogenicity of a SARS-COV-2 starting protein by altering its conformational dynamics to produce numerous SARS-COV-2 peptidogenic proteins which can then be simultaneously introduced into an animal will generate a robust immune response and has the potential to raise a broader repertoire of polyclonal antibodies which can be further fractionated (for example, by molecularly cloning via their respective encoding mRNAs) into single isolated species.

Definitions

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, NY; Ausubel et al., Short Protocols in Molecular Biology (1999) 4$^{th}$ ed., John Wiley & Sons, Inc.), which are incorporated herein by reference.

As used herein, "peptidogenicity" refers to the propensity of a protein to efficiently yield a robust set of diverse peptides which can be used to yield an immune response. Various assays exist for measuring peptidogenicity (see, for example, So et al., FIGS. 2c-d; Thai et al., FIG. 7c-f; and Delamarre et al., FIGS. 1b-c, 4b-c and 5a-b).

As used herein, a "SARS-COV-2 peptidogenic protein" refers to a mutated SARS-COV-2 encoded protein that has been modified in its amino acid sequence to alter its conformational dynamics as compared to the SARS-COV-2 starting protein sequence while maintaining a similar conformation to the SARS-COV-2 starting protein. Examples of such SARS-COV-2 starting proteins are shown in Table 2. Preferably, the SARS-COV-2 starting protein is the Spike protein.

As used herein, the receptor-binding domain ("RBD") includes the art recognized domain responsible for virus binding to its cell entry receptor, and which is also found within the Spike protein and is identified as amino acids 319-541 of SEQ ID NO:15 and amino acids 306-527 of SEQ ID NO:16.

As used herein, the "Spike fragment" means an amino acid fragment of the Spike protein that comprises the RBD domain contained within a Spike protein encoded by a Coronavirus and which corresponds to amino acids 316-594 of SEQ ID NO: 15 and/or amino acids 303-580 of SEQ ID NO: 16. FIG. 3 shows the amino acids beginning and ending of this equivalent fragment in the other known Coronaviruses encoded Spike Protein. It is specifically contemplated that this same Spike fragment can be readily identified by repeating the alignment in FIG. 3 when newly identified Coronaviruses are discovered. In further preferred embodiments, mixtures of Spike fragments or polynucleotides encoding such fragments, derived from different Coronaviruses, are used as described herein.

As used herein, "non-surface residues" are residues that are not surface accessible with regard to the 3D structure of a SARS-CoV-2 protein, e.g., residues that are buried within the interior of the 3D structure of the native SARS-CoV-2 protein. In preferred embodiments, "non-surface" residues are defined by the method of Lee and Richards (see, e.g., Lee B et al., J. Mol. Biol. (1971); 55(3):379-IN4. dx.doi.org/ 10.1016/0022-2836(71)90324-X.), where the relative solvent accessibility of the residue in the native protein is less than 50%, less than 40%, less than 30%, less than 25%, less than 20%, less than 10%, less than 5%, or 0%, or by the same method where the difference between the absolute solvent accessible surface area and the surface area in the fully extended Ala-X-Ala tripeptide (see, e.g., Gready J E et al., Protein Science. (1997); 6(5):983-98. doi: 10.1002/ pro.5560060504.) is greater than 40 Å², greater than 50 Å², greater than 60 Å², greater than 70 Å², greater than 80 Å², greater than 90 Å², greater than 100 Å², greater than 110 Å², or greater than 120 Å². In further preferred embodiments, "non-surface" residues are defined as residues with a solvent accessible surface area of less than 10 Å², less than 5 Å², less than 2.5 Å², or less than 1 Å², as calculated by a structural analysis software package familiar to those skilled in the art (e.g. UCSF Chimera (see, e.g., Pettersen E F et al., J. Comput. Chem. (2004); 25(13):1605-12. Epub 2004/07/ 21.), PyMol (see, e.g., Schrodinger, LLC. The PyMOL Molecular Graphics System, Version 1.8. 2015.), etc.

As used herein, a "SARS-CoV-2 starting protein" or "test SARS-CoV-2 starting protein" refers to the amino acid sequence of the "original" or "reference" SARS-CoV-2 protein that is used to derive the SARS-CoV-2 peptidogenic protein. In some examples, the "SARS-CoV-2 starting protein" can be a SARS-CoV-2 peptidogenic protein that has been further modified and can include N and/or C terminal deletions of the SARS-CoV-2 starting protein.

As used herein, an "immune response" refers to the humoral immune response and/or the cell-mediated immune response that is triggered by an antigen presenting cell after processing a protein. In the humoral immune response, B lymphocytes produce antibodies that react with native, unprocessed antigens. These antigen-antibody reactions may in some cases involve cell-surface antigens that activate the complement cascade, which causes the lysis of cells bearing those antigens. In the cell-mediated immune response, T lymphocytes mobilize macrophages in the presence of processed peptide antigens recognized as foreign. Activated T lymphocytes can also attack cells bearing foreign antigens directly.

As used herein, an "antigen presenting cell" refers to a cell that can break down ("process") a protein into peptides and present the peptides, in conjunction with the MHC allele, preferably major HLA complex class I or class II molecules, on the cell surface. Examples of antigen presenting cells include, but are not limited to dendritic cells, macrophages, B cells, and monocytes.

As used herein, "conformational dynamics" is defined as the phenomena related conformational changes and flexibility of a protein structure in the spatial arrangement of atoms or groups of atoms with respect to each other in a protein molecule. Conformational dynamics include "breathing" motions and involve the vibration, bending, twisting, rotation, and other allowed modes of movement of the atoms joined by the covalent bonds in the protein molecule, governed by intrinsic restoring forces but modulated by non-covalent interactions such as hydrogen bonds, van der Waals forces, and electrostatic interactions. These motions can subtly change the geometry of the protein on a sub-picosecond timescale and can result in a vast diversity of conformational states on a time-scale of microseconds to milliseconds. Conformational molecular dynamics of proteins is often studied using computer simulations. See, for example, Shaw et al (2010) *Science* 330, 341. Also as used herein, the conformational dynamics of a SARS-CoV-2 starting protein can be altered by chemical modifications, amino acid substitutions, and other mutations such as deletions, insertion, truncations, or any combination thereof, etc. By stating that the conformational dynamics of the SARS-CoV-2 peptidogenic protein is varied with regard to the wild type protein, it is meant that the one or more amino acid substitutions of the SARS-CoV-2 peptidogenic protein results in altered conformational dynamics as compared to the wild type protein.

As used herein, "thermodynamic stability" is defined in terms of a chemical system where no or minimal energy is either released or consumed, and thus no or minimal changes in thermal energy are present and the system is in its lowest energy state under a given set of experimental conditions. Also as used herein, a "decrease in thermodynamic stability" or "decreased thermodynamic stability" means that the parameters pertaining to thermodynamic stability of the SARS-CoV-2 peptidogenic protein are attenuated as compared to those of the SARS-CoV-2 starting protein measured under the same conditions, and this decrease can be achieved in the SARS-CoV-2 peptidogenic protein by, but not limited to, alterations to the molecular structure of the SARS-CoV-2 starting protein via chemical modifications, amino acid substitutions, and other genetic mutations. Methods of measuring a decrease in thermodynamic stability are known in the art and described herein, and include protocols incorporating the measurement of parameters such as melting temperature and urea- or guanidinium hydrochloride-induced equilibrium unfolding (denaturation). These parameters are typically arrived at by monitoring the protein unfolding reaction as a function temperature or denaturant concentration under conditions of equilibrium or quasi-equilibrium. Methods for monitoring the unfolding reaction by measuring the concentration of the unfolded state relative to that of the folded state include, but are not limited to, UV absorption, fluorescence, and circular dichroism. This approach allows the calculation of a stabilization free energy (Gibbs free energy) of the mutant protein relative to the stabilization free energy of the SARS-CoV-2 starting protein measured under the same conditions. The difference in free energy is typically denoted by $\Delta\Delta G = \Delta G_{mutant} - \Delta G_{standard(e.g., wt)}$, where $\Delta G_{mutant}$ and $\Delta G_{standard(e.g., wt)}$ are the stabilization free energies of the mutant and "standard" (e.g., wt or wild type) proteins, respectively, and $\Delta\Delta G$ is the difference. $\Delta\Delta G > 0$ indicates a mutant protein that is less stable than the standard protein, and $\Delta\Delta G < 0$ indicates a mutant protein that is more stable than the standard protein.

As used herein, a SARS-CoV-2 peptidogenic protein has a "similar conformation" to a SARS-CoV-2 starting protein if the 3-D structure is sufficiently maintained after mutating non-surface residues of the protein (and, consequently, potentially modifying its overall conformational dynamics) to allow for an antibody to cross react with both the SARS-CoV-2 peptidogenic protein and the SARS-CoV-2 starting protein. "Cross-reactivity" can be measured by a binding assay as described herein or as is well known in the art and is measured as a "binding affinity" which is based on dissociation constants ($K_D$), off rates ($k_{off}$), and/or on rates $(k_{on})$. The SARS-CoV-2 peptidogenic protein does not need to have an identical 3-D structure as the SARS-CoV-2 starting protein; just a sufficiently similar structure displaying similar 3D conformational epitopes (including discontinuous epitopes), that will allow for an antibody to recognize both proteins, even though the binding affinities may be nonidentical.

In the present invention, the term "antibody," refers to immunoglobulin molecules and immunologically active portions of immunoglobulin molecules, i.e., molecules that contain an antigen binding site that immunospecifically binds the SARS-CoV-2 peptidogenic protein, Spike fragment, and/or the SARS-CoV-2 starting protein. As such, the term antibody encompasses not only whole antibody molecules, but also antibody fragments as well as variants (including derivatives such as fusion proteins) of antibodies and antibody fragments. Examples of molecules which are described by the term "antibody" in this application include, but are not limited to: single chain Fvs (scFvs), Fab fragments, Fab' fragments, F(ab')$_2$, disulfide linked Fvs (sdFvs), Fvs, and fragments comprising or alternatively consisting of, either a VL or a VH domain. The term "single chain Fv" or "scFv" as used herein refers to a polypeptide comprising a VL domain of an antibody linked to a VH domain of an antibody. See Carter (2006) Nature Rev. Immunol. 6:243.

Additionally, antibodies of the invention include, but are not limited to, monoclonal, multi-specific, bi-specific, human, humanized, mouse, or chimeric antibodies, single chain antibodies, camelid antibodies, Fab fragments, F(ab') fragments, anti-idiotypic (anti-Id) antibodies (including, e.g., anti-Id antibodies to antibodies of the invention), domain antibodies and epitope-binding fragments of any of the above. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably, the antibodies are human antibodies. As used herein, "human" antibodies include antibodies having the amino acid sequence of a human immunoglobulin and include antibodies isolated from human immunoglobulin libraries and xenomice or other organisms that have been genetically engineered to produce human antibodies. For a detailed discussion of a few of the technologies for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598; and Lonberg and Huszar, Int. Rev. Immunol. 13:65-93 (1995).

Human antibodies or "humanized" chimeric monoclonal antibodies can be produced using techniques described herein or otherwise known in the art. For example, methods for producing chimeric antibodies are known in the art. See, for review the following references: Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).

The antibodies of the present invention may be monovalent, bivalent, trivalent or multivalent. For example, monovalent scFvs can be multimerized either chemically or by association with another protein or substance. A scFv that is fused to a hexahistidine tag or a Flag tag can be multimerized using Ni-NTA agarose (Qiagen) or using anti-Flag antibodies (Stratagene, Inc.).

The antibodies of the present invention may be monospecific, bispecific, trispecific or of greater multispecificity. Multispecific antibodies may be specific for the SARS-CoV-2 peptidogenic protein, for more than one SARS-CoV-2 peptidogenic protein, for the SARS-CoV-2 starting protein and/or for the Spike fragment, or they may be specific for both the SARS-CoV-2 peptidogenic protein and/or Spike fragment, and/or the SARS-CoV-2 starting protein and a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et. al., J. Immunol. 148:1547-1553 (1992). The term "fragment" as used herein refers to a polypeptide comprising an amino acid sequence of at least 5 amino acid residues, at least 10 amino acid residues, at least 15 amino acid residues, at least 20 amino acid residues, at least 25 amino acid residues, at least 30 amino acid residues, at least 35 amino acid residues, at least 40 amino acid residues, at least 45 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues, of the amino acid sequence of the SARS-CoV-2 peptidogenic protein and/or the SARS-CoV-2 starting protein. In some embodiments, a fragment may also refer to a polypeptide comprising an amino acid sequence of about 8 to 24 amino acid residues, or about 5 to 30 amino acid residues. In preferred embodiments, the Spike fragment consists of amino acids 316-594 of SEQ ID NO:15 or 303-580 of SEQ ID NO:16.

The term "fusion protein" as used herein refers to a polypeptide that comprises, or alternatively consists of, an amino acid sequence of the SARS-CoV-2 peptidogenic protein and/or Spike fragment, the SARS-CoV-2 starting protein, and/or the antibody raised against the SARS-CoV-2 peptidogenic protein and/or Spike fragment and an amino acid sequence of one or more heterologous peptides and/or polypeptides. For vaccine applications, the heterologous polypeptide sequence fused to the SARS-CoV-2 peptidogenic protein and/or Spike fragment is preferably from a viral protein.

The term "host cell" as used herein refers to the particular subject cell transfected with a nucleic acid molecule and the progeny or potential progeny of such a cell. Progeny may not be identical to the parent cell transfected with the nucleic acid molecule due to mutations or environmental influences or developmental steps that may occur in succeeding generations or integration of the nucleic acid molecule into the host cell genome.

A "conservative amino acid substitution" is one in which the amino acid residue is replaced with an amino acid residue having a side chain with a similar chemical nature (e.g., size, charge, steric features [e.g., beta-branched vs. non-beta-branched], polarity [hydrophilic vs. hydrophobic], aromatic vs. non-aromatic, etc.). Whether or not a particular substitution is deemed "conservative" may also depend on the structural context in the folded protein in which a substitution occurs. Amino acid side chains may be chemically similar in one respect but chemically dissimilar in another, and the context may determine which of these properties dominates in terms of how "conservative" (i.e., least disruptive) that particular substitution is. Families of amino acid residues having chemically similar side chains have been defined in the art. These families include amino acids with basic side chains (e.g., lysine, arginine), acidic side chains (e.g., aspartic acid, glutamic acid), uncharged polar side chains (e.g., asparagine, glutamine, serine, threonine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Some side chains have a hybrid character that is pH-dependent in physiologically relevant pH ranges. For example, histidine (pKa~6) becomes more positively-charged (basic) below pH 6, and polar but substantially uncharged at pH 7.5 and above. Cysteine (pKa~8.5) is substantially uncharged (and not particularly polar) below pH 8, but negatively charged (and acidic) at pH 9. The tyrosine phenolic side chain is also partially ionized and negatively charged at higher pH. Moreover, the local electrostatic environment (context) of the rest of the protein can shift these effective pH values substantially. Moreover, an acidic protein cysteine thiolate side chain can react, via thiol-disulfide exchange involving an intermediary disulfide-containing compound such as oxidized glutathione, with another protein cysteine thiol to form an intramolecular disulfide bond; such bonds are highly hydrophobic (non-polar). Additionally, both naturally occurring and/or non-naturally occurring amino acids can be used in the SARS-CoV-2 peptidogenic proteins and/or Spike fragment.

Mutations can be introduced in a site-directed fashion or randomly along all or part of the coding sequence. Libraries of mutants can be designed to introduce a single amino acid substitution, two amino acid substitutions, three amino acid substitutions, four amino acid substitutions, and so forth, up to nineteen amino acid substitutions at a given residue site. In still other embodiments, libraries of mutants can be designed to introduce more than nineteen amino acid substitutions (including natural and non-natural amino acids) at a given residue site. In addition, libraries can be combinatorially designed to simultaneously produce multiple mutations at two sites, three sites, four sites, and so on. Following mutagenesis, the encoded protein may routinely be expressed and the conformational dynamics of the encoded protein and/or peptidogenicity can be determined using techniques described herein or by routinely modifying techniques known in the art. The resultant mutant proteins can be screened and evaluated for altered thermodynamic stability or for peptidogenicity or for similar conformation to the SARS-CoV-2 starting protein and/or Spike fragment. Alternatively, the expressed protein "output" from the designed library can be used to immunize an animal without prior screening for protein properties.

As used herein, the "patient" or "subject suitable for treatment" may be a mammal, such as a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon, rhesus macaque), an ape (e.g. gorilla, chimpanzee, orangutan, gibbon), or a human. In other embodiments, non-human mammals, especially mammals that are conventionally used as models for demonstrating therapeutic efficacy in humans (e.g. murine, primate, porcine, canine, camels, llamas, or rabbits) may be employed.

Other aspects and embodiments of the invention provide the aspects and embodiments described herein with the term "comprising" replaced by the term "consisting of" and the aspects and embodiments described above with the term "comprising" replaced by the term "consisting essentially of".

As used herein, "and/or" is to be taken as specific disclosure of each of the two or more specified features or components with or without the others. For example "A, B and/or C" is to be taken as specific disclosure of each (i) A, (ii) B, (iii) C, (iv) A and B, (v) A and C, (vi) B and C and (vii) A and B and C, just as if each is set out individually.

Methods of Altering the Conformational Dynamics of a Protein

A SARS-CoV-2 peptidogenic protein and/or Spike fragment can be generated using standard molecular biology mutagenesis techniques well known in the art. For example, the SARS-CoV-2 peptidogenic protein and/or Spike fragment can be generated by random mutagenesis as is well known in the art, such as, for example, by error-prone PCR, random nucleotide insertion or deletion or other methods prior to recombination.

To generate the SARS-CoV-2 peptidogenic protein and/or Spike fragment, protein engineering may be employed. Recombinant DNA technology known to those skilled in the art can be used to create SARS-CoV-2 peptidogenic proteins and/or Spike fragment including single or multiple amino acid substitutions, deletions, insertions, or fusion proteins. Such SARS-CoV-2 peptidogenic proteins may be screened for those that have altered conformational dynamics while maintaining a similar conformation to the SARS-CoV-2 starting protein as described herein.

For example, to increase the conformational dynamics of the SARS-CoV-2 peptidogenic protein and/or Spike fragment, the following table, Table 1, shows the average change in Gibbs free energy for exemplary amino acid substitutions in a range of proteins, derived from Tables 1 and 2 of Loladze et al., J. Mol. Biol. 320, 343-357 (2002) [note: this paper uses a non-standard convention when expressing Gibbs free energies between mutant and wild type proteins, namely using negative values to indicate destabilization ($\Delta\Delta G = \Delta G(mutant) - \Delta G(WT)$); the standard convention is that positive changes indicate destabilization ($\Delta\Delta G = \Delta G(WT) - \Delta G(mutant)$, see above)]. For example, Val and Leu (and the other larger non-polar amino acid residues) can be substituted with smaller ones such as Ala, Thr, Asn, and/or Gly. In addition, the buried site of Glu in the native protein structure, can be substituted with Leu, Val, Asn, Thr, Ser, Ala, and/or Gly. The types of single site amino acid substitutions shown generally have little impact on the overall conformation of the SARS-CoV-2 starting protein.

TABLE 1

| Amino Acid Substitution (multiple positions in various proteins) | Average Gibbs Free Energy difference between mutant and wild type at core residues within a protein $\Delta\Delta G$ (kJ/mol) |
| --- | --- |
| Val –> Ala | −12.1(±3.3) |
| Val –> Thr | −11.3(±3.7) |
| Val –> Asn | −21.5(±1.0) |
| Leu –> Ala | −14.2(±4.2) |

Another illustrative paper describing destabilizing mutations in the core of a protein that increase conformational dynamics is Kim et al (1993) Protein Sci. 2:588-596. In this work, the authors show that the mutations Phe22→Ala (2.1 kcal/mol), Tyr23→Ala (7.0 kcal/mol), Tyr35→Gly (5.7 kcal/mol), Asn43→Gly (6.0 kcal/mol), and Phe45→Ala (7.2 kcal/mol) destabilize bovine pancreatic trypsin inhibitor (BPTI) at pH 3.5 by the respective amounts shown in parentheses, without seriously disrupting the overall 3D structure of BPTI.

In addition, genetic deletions, insertions, inversions, repeats, and type substitutions selected according to general rules known in the art should have little effect on activity. For example, guidance concerning how to make phenotypically silent amino acid substitutions is provided in Bowie, J. U. et at., "Deciphering the Message in Protein Sequences: Tolerance to Amino Acid Substitutions," Science 247:1306-1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality.

As the authors state, these studies have revealed that proteins are surprisingly tolerant of amino acid substitutions. The authors further indicate which amino acid changes are likely to be permissive at a certain position of the protein. For example, most buried amino acid residues require non-polar side chains, whereas few features of surface side chains are generally conserved. Other such phenotypically silent substitutions are described in Bowie, J. U. et al., supra, and the references cited therein. Typically seen as conservative substitutions are the replacements, one for another, among the aliphatic amino acids Ala, Val, Leu and Ile; interchange of the hydroxyl-bearing residues, Ser and Thr; exchange of the acidic residues, Asp and Glu; substitution between the sidechain amide-bearing residues, Asn and Gln; exchange of the basic amino acids, Lys and Arg; and replacements among the aromatic residues, Phe and Tyr.

In preferred embodiments, the conformational dynamics of the SARS-CoV-2 starting protein is altered by replacing: (a) at least one threonine with a valine, alanine, glycine or serine; or (b) at least one cysteine with alanine, valine, glycine, serine or threonine; or (c) at least one valine with alanine, glycine, leucine or isoleucine; or (d) at least one leucine with alanine, valine, glycine, or isoleucine; or (e) at least one isoleucine with alanine, valine, isoleucine, or glycine; or (f) at least one proline, methionine, phenylalanine, tyrosine, or tryptophan with alanine, valine, leucine, isoleucine, or glycine; or (g) at least one aspartic acid with glutamic acid, glutamine, asparagine, glycine, serine, threonine, alanine, valine, leucine, isoleucine; or (h) at least one glutamic acid with aspartic acid, glutamine, asparagine, glycine, serine, threonine, alanine, valine, leucine, or isoleucine; or (i) at least one lysine with arginine, histidine, glycine, serine, threonine, alanine, valine, leucine, or isoleucine; or (j) at least one arginine with lysine, histidine, glycine, serine, threonine, alanine, valine, leucine, or isoleucine; or (k) at least one histidine with lysine, arginine, glycine, serine, threonine, alanine, valine, leucine, isoleucine, or glutamine; or (l) at least one alanine with a glycine or proline; or (m) at least one asparagine with a glycine, alanine, serine, threonine, glutamine, aspartic acid, or glutamic acid; or (n) at least one glutamine with a glycine, alanine, serine, threonine, asparagine, aspartic acid, glutamic acid, or histidine; or (o) at least one glycine with an alanine or proline; or (p) at least one residue with a non-natural amino acid; or (q) any combination of (a)-(p). In still further preferred embodiments, the conformational dynamics of the SARS-CoV-2 starting protein is altered by replacing: (a) at least one tryptophan with tyrosine, phenylalanine, methionine, histidine, isoleucine, leucine, valine, alanine or glycine; or (b) at least one tyrosine with phenylalanine, methionine, histidine, isoleucine, leucine, valine, alanine or glycine; or (c) at least one phenylalanine with tyrosine, methionine, histidine, isoleucine, leucine, valine, alanine or glycine; or (d) at least one proline with methionine, leucine, isoleucine, valine, alanine, or glycine; or (e) at least one histidine with phenylalanine, tyrosine, methionine, isoleucine, leucine, valine, alanine, glycine, lysine, arginine, serine, threonine, asparagine, or glutamine; or (f) at least one methionine with isoleucine, leucine, valine, alanine or glycine; or (g) at least one isoleucine with leucine, valine, alanine or glycine; or (h) at least one leucine with isoleucine, valine, alanine or glycine; or (i) at least one valine with alanine, glycine, leucine, or isoleucine; or (j) at least one cysteine with alanine, valine, glycine, serine or threonine; or (k) at least one aspartic acid with glutamic acid, glutamine, asparagine, glycine, serine, threonine, alanine, valine, leucine, or isoleucine; or (l) at least one glutamic acid with aspartic acid, glutamine, asparagine, glycine, serine, threonine, alanine, valine, leucine, or isoleucine; or (m) at least one alanine with a glycine or proline; or (n) at least one serine with alanine or glycine; or (o) at least one glycine with alanine or proline; or (p) at least one lysine with arginine, histidine, glycine, serine, threonine, alanine, valine, methionine, leucine or isoleucine; or (q) at least one asparagine with glycine, alanine, serine, threonine, valine, leucine, isoleucine, glutamine, aspartic acid or glutamic acid; or (r) at least one glutamine with glycine, alanine, serine, threonine, valine, leucine, isoleucine, glutamine, aspartic acid, glutamic acid, or histidine; or (s) at least one arginine with lysine, histidine, glycine, serine, threonine, alanine valine, methionine, leucine, or isoleucine; or (t) at least one threonine with valine, alanine, glycine or serine; or (u) a hydrophobic residue with a smaller, similar hydrophobic residue; or (v) at least one residue with a non-natural amino acid; or (w) any of the above combinations. In some embodiments, hydrophobic resides are targeted for replacement.

Amino acids in the SARS-CoV-2 starting protein that are essential for function, conformation, and/or structure and positioned on the protein surface vs. internal can be identified by methods known in the art, such as site-directed mutagenesis or alanine-scanning mutagenesis (Cunningham and Wells, Science 244: 1081-1085 (1989)). The latter procedure introduces single alanine mutations at every residue in the molecule. The resulting mutant molecules are then tested for those having altered conformational dynamics while maintaining a similar conformation to the SARS-CoV-2 starting protein.

In an additional embodiment, the amino acid sequence of the SARS-CoV-2 starting protein has one or more amino acids (for example, 1, 2, 3, 4, 5, 6, 7, 8, 9, 10, 15, 20, 30 or 50 amino acids) replaced with the substituted amino acids as described above (either conservative or non-conservative substitutions) to produce the SARS-CoV-2 peptidogenic protein and/or Spike fragment. For example, substitutions in positions not involving a SARS-CoV-2 starting protein's activity and/or internal to the protein structure can be readily made. Sites that are critical for ligand-receptor binding can also be determined by structural analysis such as crystallization, nuclear magnetic resonance or photoaffinity labeling (Smith et al., J. Mol. Biol. 224:899-904 (1992); and de Vos et al. Science 255:306-312 (1992)).

Recombinant DNA technology that employs combinatorial mutagenesis and synthetic DNA synthesis approaches known to those skilled in the art can also be used to create a SARS-CoV-2 peptidogenic protein and/or Spike fragment including single or multiple amino acid substitutions, deletions, additions or fusion proteins. Such modified polypeptides may be then screened for altered conformational dynamics while maintaining a similar conformation as the SARS-CoV-2 starting protein.

Thus, a SARS-CoV-2 peptidogenic protein and/or Spike fragment can be made where one or more amino acid residues are deleted, added, or substituted to generate SARS-CoV-2 peptidogenic proteins having altered conformation dynamics. For example, residues in the hydrophobic "core" of the protein can be substituted with non-polar residues having smaller side chains (supra) in order to create cavities in the core and disrupt the packing, and cysteine residues can be deleted or substituted with other amino acid residues in order to eliminate disulfide bridges (which are often found in protein cores). In some embodiments, at least one disulfide bond is eliminated in the SARS-CoV-2 starting protein, such as, for example, replacing the cysteines with alanines, serines, and/or glycines, etc. In further preferred embodiments, both cysteines involved in the formation of the at least one disulfide bond are replaced with alanines, serines, and/or glycines, or preferably with alanines or glycines, etc.

The SARS-CoV-2 peptidogenic proteins are preferably provided in an isolated form, and preferably are substantially purified. Additionally, the SARS-CoV-2 peptidogenic proteins would display a stable 3D conformational epitope for B-cell activation while synthesized peptides (such as by chemical synthesis) can be co-administered, which could optimize the epitopes for MHC-II presentation. Alternatively, the SARS-CoV-2 peptidogenic proteins and peptides can be expressed by a mixture of polynucleotides. In still other embodiments, SARS-CoV-2 peptidogenic proteins and/or Spike fragment can be combined with a wild type SARS-CoV-2 starting protein and synthetic peptide(s) to elicit an immune response.

In some embodiments, the rate of polypeptide degradation may be adjusted in order to produce an optimal mix of peptides, and in the right time frame, to allow maximal diversity of the displayed peptides on the antigen presenting cells.

Immunization with mixtures (such as combinatorial cocktails) of antigens is advantageous due to the complexity of the proteolytic attack on the protein antigen(s) that produce the peptides for display. Thus, the "tuning mutation(s)" optimal for the production of a given peptide (T cell epitope) in the right time frame may be different from the mutations optimal for production of another peptide. By giving the SARS-CoV-2 peptidogenic proteins and/or Spike fragment as mixtures, a multiplicity of different mutant SARS-CoV-2 proteins may be endocytosed by a single cell or multiple cells, which maximizes the diversity of the peptides produced and displayed by that cell. Alternatively, the Spike fragment can be administered alone as a vaccine.

Combinatorial immunization, in which subjects are immunized with two or more distinct SARS-CoV-2 peptidogenic proteins that have the same overall surface features (i.e. cross-reacting B-cell epitopes) but with different conformational dynamics, enriches the diversity of T-cell epitopes. This combinatorial approach, which includes hundreds or even thousands of different SARS-CoV-2 peptidogenic proteins in a single inoculation (both protein-based and nucleotide-based) may vastly increase the B-cell epitope repertoire, since every molecule in the mix can contribute to one or more unique T-cell epitopes while maintaining a wild type-like conformation. In some aspects, because the wild-type configuration is maintained, the B-cell epitope repertoire is biased towards the most stable (and presumably wild type-like) molecules in the ensemble.

Peptidogenic Protein has a Similar Conformation as a SARS-CoV-2 Starting Protein The operational test of whether the SARS-CoV-2 peptidogenic protein has a "similar conformation to the SARS-CoV-2 starting protein" is whether or not a cross-reacting antibody, especially an antibody that recognizes a conformational (3D) epitope, specifically binds to both the SARS-CoV-2 peptidogenic protein and the SARS-CoV-2 starting protein. In the present invention "cross-reactivity" or a "cross-reacting antibody" is defined in terms of "binding affinity" which can be measured based on dissociation constant ($K_D$), off rate ($k_{off}$), and/or on rate ($k_{on}$).

For example, a cross-reacting antibody binds to both the SARS-CoV-2 peptidogenic protein and the SARS-CoV-2 starting protein at a dissociation constant or $K_D$ less than or equal to $5 \times 10^{-6}$ M, $10^{-6}$ M, $5 \times 10^{-7}$ M, $10^{-7}$M, $5 \times 10^{-8}$ M, or $10^{-8}$ M. Even more preferably, a cross-reacting antibody binds to both the SARS-CoV-2 peptidogenic protein and the SARS-CoV-2 starting protein at a dissociation constant $K_D$ less than or equal to $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, or $10 \times^{-14}$ M. The invention encompasses a dissociation constant or $K_D$ for the SARS-CoV-2 peptidogenic protein and/or the SARS-CoV-2 starting protein that is within any one of the ranges that are between each of the individual recited values. Additionally, it is specifically contemplated that the $K_D$ for the antibody that binds to a SARS-CoV-2 peptidogenic protein may not be identical to its $K_D$ with respect to the SARS-CoV-2 starting protein, and in preferred embodiments, the $K_D$ for the antibody that binds to the SARS-CoV-2 peptidogenic protein is less than the $K_D$ for its binding to the SARS-CoV-2 starting protein. It is understood that, operationally, $K_D$ in this case refers to the functional affinity of the antibody for the antigen. Functional or "apparent" affinity may be enhanced in multivalent antibodies that contain multiple interacting sites (e.g., Fab arms) that can bind to the antigen ("avidity effect").

Additionally, a cross-reacting antibody binds to both the SARS-CoV-2 peptidogenic protein and the SARS-CoV-2 starting protein with an off rate ($k_{off}$) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. More preferably, a cross-reacting antibody binds to both the SARS-CoV-2 peptidogenic protein and the SARS-CoV-2 starting protein at off rate ($k_{off}$) of less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$, $5 \times 10^{-6}$ sec$^{-1}$, $10^{-6}$ sec$^{-1}$, $5 \times 10^{-7}$ sec$^{-1}$ or $10^{-7}$ sec$^{-1}$. The invention encompasses an off rate ($k_{off}$) for the SARS-CoV-2 peptidogenic protein and/or the SARS-CoV-2 starting protein that is within any one of the ranges that are between each of the individual recited values. Additionally, it is specifically contemplated that the $k_{off}$ of the antibody for the SARS-CoV-2 peptidogenic protein may not be identical to the $k_{off}$ of the SARS-CoV-2 starting protein, and in preferred embodiments, the ($k_{off}$) for the binding of the antibody to the SARS-CoV-2 peptidogenic protein is greater than the ($k_{off}$) for the binding of the antibody to the SARS-CoV-2 starting protein.

Assays to test for the cross-reactivity are described herein or are known in the art. For example, binding assays may be performed in solution (e.g., Houghten, Bio/Techniques 13:412-421(1992)), on beads (e.g., Lam, Nature 354:82-84

(1991)), on chips (e.g., Fodor, Nature 364:555-556 (1993)), on bacteria (e.g., U.S. Pat. No. 5,223,409), on spores (e.g., U.S. Pat. Nos. 5,571,698; 5,403,484; and 5,223,409), on plasmids (e.g., Cull et al., Proc. Natl. Acad. Sci. USA 89:1865-1869 (1992)) or on phage (e.g., Scott and Smith, Science 249:386-390 (1990); Devlin, Science 249:404-406 (1990); Cwirla et al., Proc. Natl. Acad. Sci. USA 87:6378-6382 (1990); and Felici, J. Mol. Biol. 222:301-310 (1991)). Examples of such assays are described further below in the Examples.

Use as a Vaccine

A mixture of SARS-CoV-2 peptidogenic proteins and/or Spike fragment and/or polynucleotides encoding the SARS-CoV-2 peptidogenic proteins and/or the Spike fragment can be used to vaccinate an animal. This vaccination may lead to the raising of antibodies to the Spike fragment and/or SARS-CoV-2 peptidogenic proteins. A subject suitable for treatment as described above may be a mammal, such as a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon, rhesus macaque), an ape (e.g. gorilla, chimpanzee, orangutan, gibbon), or a human. In preferred embodiments, the subject is a human. In other embodiments, non-human mammals, especially mammals that are conventionally used as models for demonstrating therapeutic efficacy in humans (e.g. murine, primate, porcine, canine, or rabbit animals) may be employed.

In some embodiments, the SARS-CoV-2 peptidogenic proteins and/or Spike fragment are chimeric fusion proteins, e.g., a protein that has been fused to another protein, e.g. a viral coat protein, that are used for vaccines. Examples of viruses that could be used to deliver peptidogenic protein fused to a viral coat protein as part of a component vaccine include lentivirus vectors, adenovirus vectors (e.g. adenovirus serotype 5 (Ad5)), vaccinia viruses, alphavirus vectors, vesicular stomatitis virus (VsV) vectors, canarypox virus vectors, and measles virus vectors, among those that have been most widely used and investigated.

A vaccination strategy can be based on one or more administrations of the SARS-CoV-2 peptidogenic proteins and/or Spike fragment and/or polynucleotides encoding the SARS-CoV-2 peptidogenic proteins and/or Spike fragment to the subject as described herein to enable the development of memory B cells and memory T cells against the SARS-CoV-2 peptidogenic protein and/or Spike fragment. Vaccination can be conducted either prophylactically or therapeutically. The SARS-CoV-2 peptidogenic proteins can be derived from either the same SARS-CoV-2 starting protein or from multiple SARS-CoV-2 starting proteins. While prophylactic vaccination strategies aim to stimulate the subject's immune system in developing preventive adaptive immunity to a pathogen, the goal of therapeutic vaccination strategy is conducted after the disease has been already established or to improve a clinical situation, present in the subject.

Proteolytic processing involves antigens such as SARS-CoV-2 peptidogenic proteins and/or Spike fragment being processed in Antigen Presenting Cells after endocytosis and fusion of the endosome with a lysosome. The endosome then merges with an exocytic vesicle from the Golgi apparatus containing class II MHC molecules, to which the resultant peptides bind. The MHC-peptide complex then trafficks to the plasma membrane where the antigen is available for display to CD4$^+$ T cells. Any limitation of the proteolytic processing of the SARS-CoV-2 peptidogenic proteins and/or Spike fragment could promote a narrowing of the diversity of the peptide products, which would give the class II MHC molecules fewer options among which to select stable binding partners, and this could exacerbate the phenomenon of immunodominant determinants. Heightened immunodominance would in turn increase the proportion of non-responders in the population, because immune responsiveness is governed by the genetics of class II MHC alleles. Hence, vaccines using a mixture of SARS-CoV-2 peptidogenic proteins and/or Spike fragment and/or polynucleotides encoding the SARS-CoV-2 peptidogenic proteins and/or Spike fragment described herein should increase the variety of antigen peptides resulting from intra-endosomal proteolytic processing and therefore would be expected to increase the effectiveness of the vaccine.

For example, polynucleotides encoding the SARS-CoV-2 peptidogenic proteins and/or Spike fragment can also be directly introduced into animals. See, for example, U.S. Pat. Nos. 5,676,954; 6,875,748; 5,661,133; Sahin et al., Nat Rev Drug Discov, 2014 October; 13(10):759-80; Kariko et al., Mol Ther, 2008 November; 16(11):1833-40; Kariko et al., Nucleic Acid Res, 2011, November; 39(21):e142; U.S. Pat. No. 6,511,832. In one example, polynucleotides, such as a DNA sequences encoding a mixture of SARS-CoV-2 peptidogenic proteins and/or Spike fragment are directly injected into a host animal and the polynucleotides enter into the nucleus to be transcribed to mRNA in order to produce the SARS-CoV-2 peptidogenic proteins and/or Spike fragment. The polynucleotides may be provided as DNA vaccines comprising an expression vector (e.g. plasmid) or recombinant viral vector, wherein, for example, DNA sequences encoding a mixture of SARS-CoV-2 peptidogenic proteins and/or Spike fragment are included in a construct with appropriate transcriptional and translational control signals for their expression. Those skilled in the art will be well aware of suitable expression vectors and viral vectors for use in DNA vaccines. Such vectors are discussed in detail in, for example, Kutzler et al. Nat. Rev. Genet. 9(10):776-788 (2008). DNA vaccines may be formulated with suitable adjuvants and/or may be incorporated into various delivery vehicles such as liposomes (e.g. cationic liposomes), lipid inorganic nanoparticles (LION), and lipid-nucleic acid nanoparticle (LNP) complexes (Bruun et al., Int. J. Nanomedicine 10:5995-6008 (2015). In other cases, DNA vaccines may be "naked" DNA vaccines.

Similarly, the polynucleotides can also be mRNA sequences, such as an in vitro transcribed mRNA (IVT mRNA). Essentially, synthetic mRNAs can be engineered to express SARS-CoV-2 peptidogenic proteins and/or Spike fragment, and ideally, the mRNA is translated in the cell's cytoplasm without entering the nucleus. In the cytoplasm, the mRNA is decoded by ribosomes and is translated into the SARS-CoV-2 peptidogenic proteins and/or Spike fragment. The polynucleotides may be provided as RNA vaccines comprising an expression vector or recombinant viral vector. In some embodiments, the polynucleotides may be provided as a virus-derived replicon (repRNA) vaccine encoding an intact viral RNA polymerase complex (typically from an alphavirus), but wherein the structural protein genes would be replaced with the mRNA sequences encoding the SARS-CoV-2 peptidogenic proteins and/or Spike fragment (Xiong et al., Science 243:1188-1191 (1989)). Like DNA vaccines, vaccines comprising, for example, mRNA sequences encoding a mixture of SARS-CoV-2 peptidogenic proteins and/or Spike fragment may be formulated with suitable adjuvants and/or incorporated into various delivery vehicles such as liposomes and LNPs, or be administered in a naked form.

In either method, the SARS-CoV-2 peptidogenic proteins and/or Spike fragment are expressed from the polynucleotides and then processed and used to generate antibodies, much like immunization with a protein. The polynucleotides encoding the SARS-CoV-2 peptidogenic proteins and/or Spike fragment can be synthesized using the genetic codon degeneracy and standard DNA synthesis techniques. Mixtures of different polynucleotides encoding the same peptidogenic protein, different SARS-CoV-2 peptidogenic proteins derived from the same SARS-CoV-2 starting protein, and/or different SARS-CoV-2 peptidogenic proteins derived from different SARS-CoV-2 starting proteins can be used.

Of particular interest are vaccines that can achieve strong protective immune responses in elderly patients, a patient population especially susceptible to severe and life-threatening infection with SARS-CoV-2 (Erasmus et al., Sci. Transl. Med. 12:555 (2020); Pfizer Press release: "Pfizer and BioNTech Choose Lead mRNA Vaccine Candidate Against COVID-19 and Commence Pivotal Phase 2/3 Global Study", 27 Jul. 2020; Walsh et al, medRxiv preprint doi: doi.org/10.1101/2020.08.17.20176651 version posted Aug. 20, 2020; Koff & Williams, New Engl. J. Med. 383:805 (2020)). Dysfunction of the vacuolar ATPase and a consequent rise in lysosomal pH is common in aged individuals (Colacurcio & Nixon, Ageing Res. Rev. 32:75). Since acid pH is the primary protein denaturant in lysosomes and since the degradative lysosomal proteases (cathepsins) have acid pH activity optima, rising intralysosomal pH hinders proteolytic processing. Increased peptidogenicity of the substrate proteins counteracts this tendency and should lead to more efficient antigen processing by the antigen presenting cells (APCs) of older individuals and thus enhance the immune response. The use of certain adjuvants (e.g. liposome-based AS01B adjuvant system) and other strategies to achieve potent $CD4^+$ and $CD8^+$ T cell responses, may also be employed to achieve strong and protective immune responses in elderly patients (Weinberger, Immunity & Ageing 15:3 (2018)).

Use of the SARS-CoV-2 Peptidogenic Protein to Generate Antibodies

The SARS-CoV-2 peptidogenic protein and/or Spike fragment can also be used to generate antibodies by methods well known by the skilled artisan, such as, for example, methods described in the art. See, for instance, Sutcliffe et al., supra; Wilson et al., supra; Chow et al., Proc. Natl. Acad. Sci. USA 82:910-914 (1985); and Bittle et al., J. Gen. Virol. 66:2347-2354 (1985). If in vivo immunization is used, animals may be immunized with a SARS-CoV-2 peptidogenic protein and/or Spike fragment, and/or a SARS-CoV-2 polynucleotide encoding the SARS-CoV-2 peptidogenic protein and/or Spike fragment described herein.

Animals such as rabbits, rats, mice, llamas, camels, and/or cows can be immunized with the SARS-CoV-2 peptidogenic protein and/or Spike fragment, and/or a polynucleotide encoding the SARS-CoV-2 peptidogenic protein and/or Spike fragment. For instance, intraperitoneal and/or intradermal injection of emulsions containing about 100 micrograms of a SARS-CoV-2 peptidogenic protein and/or Spike fragment or carrier protein and Freund's adjuvant or any other adjuvant known for stimulating an immune response may be used. Several booster injections may be needed, for instance, at intervals of about two weeks, to provide a useful titer of anti-peptidogenic protein antibody which can be detected, for example, by ELISA assay using free peptidogenic protein adsorbed, directly or indirectly (e.g., via a biotinylated AviTag), to a solid surface. The titer of anti-peptidogenic protein antibodies in serum from an immunized animal may be increased by selection of anti-peptidogenic protein antibodies, for instance, by adsorption to the SARS-CoV-2 peptidogenic protein and/or Spike fragment on a solid support and elution of the selected antibodies according to methods well known in the art. Such selections could also be done using the SARS-CoV-2 starting protein.

Additionally, antibodies generated by the disclosed methods can be affinity matured using display technology, such as for example, phage display, yeast display or ribosome display. In one example, single chain antibody molecules ("scFvs") displayed on the surface of phage particles are screened to identify those scFvs that immunospecifically bind to the SARS-CoV-2 peptidogenic protein, and/or Spike fragment, and/or the SARS-CoV-2 starting protein. The present invention encompasses both scFvs and portions thereof that are identified to immunospecifically bind to the SARS-CoV-2 peptidogenic protein, and/or Spike fragment, and/or the SARS-CoV-2 starting protein. Such scFvs can routinely be "converted" to immunoglobulin molecules by inserting, for example, the nucleotide sequences encoding the VH and/or VL domains of the scFv into an expression vector containing the constant domain sequences and engineered to direct the expression of the immunoglobulin molecule.

Expression Systems

Methods which are well known to those skilled in the art can be used to construct expression vectors containing antibody coding sequences and the coding sequences for the SARS-CoV-2 peptidogenic protein and/or Spike fragment, and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding either the SARS-CoV-2 peptidogenic protein and/or Spike fragment or an antibody raised to the SARS-CoV-2 peptidogenic protein and/or Spike fragment (e.g., a whole antibody, a heavy or light chain of an antibody, a heavy or light chain variable domain of an antibody, or a portion thereof, or a heavy or light chain CDR, a single chain Fv, or fragments or variants thereof), operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy chain, the entire light chain, or both the entire heavy and light chains.

The expression vector(s) can be transferred to a host cell by conventional techniques and the transfected cells are then cultured by conventional techniques to produce either the SARS-CoV-2 peptidogenic protein and/or Spike fragment or the antibody that has been raised against a SARS-CoV-2 peptidogenic protein and/or Spike fragment. Thus, the invention includes host cells containing polynucleotide(s) encoding the SARS-CoV-2 peptidogenic protein and/or Spike fragment or an antibody raised against the SARS-CoV-2 peptidogenic protein and/or Spike fragment (e.g., whole antibody, a heavy or light chain thereof, or portion thereof, or a single chain antibody of the invention, or a fragment or variant thereof), operably linked to a heterologous promoter. In preferred embodiments, for the expression of entire antibody molecules, vectors encoding both the heavy and light chains may be co-expressed in the host cell for expression of the entire immunoglobulin molecule, as detailed below.

A variety of host-expression vector systems may be utilized to express the SARS-CoV-2 peptidogenic protein and/or Spike fragment or the antibody raised to the SARS-CoV-2 peptidogenic protein and/or Spike fragment. Such host-expression systems represent vehicles by which the coding sequences of interest may be produced and subsequently purified, but also represent cells which may, when transformed or transfected, with the appropriate nucleotide coding sequences, express the SARS-CoV-2 peptidogenic protein and/or Spike fragment or the antibody raised to the SARS-CoV-2 peptidogenic protein and/or Spike fragment. These include, but are not limited to, microorganisms such as bacteria (e.g., *E. coli, B. subtilis*) transformed with recombinant bacteriophage DNA, plasmid DNA or cosmid DNA expression vectors containing sequences; yeast (e.g., *Saccharomyces, Pichia*) transformed with recombinant yeast expression vectors containing coding sequences; insect cell systems infected with recombinant virus expression vectors (e.g., baculovirus) containing coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, are used for the expression of either the SARS-CoV-2 peptidogenic protein and/or Spike fragment or a recombinant antibody molecule. For example, mammalian cells such as Chinese hamster ovary cells (CHO), in conjunction with a vector such as the major intermediate early gene promoter element from human cytomegalovirus is an effective expression system (Foecking et al., Gene 45:101 (1986); Cockett et al., Bio/Technology 8:2 (1990)).

In bacterial systems, a number of expression vectors may be advantageously selected depending upon the intended use. For example, when a large quantity of a protein (whether a SARS-CoV-2 peptidogenic protein and/or Spike fragment or an antibody raised against the SARS-CoV-2 peptidogenic protein and/or Spike fragment) is to be produced, vectors which direct the expression of high levels of fusion protein products that are readily purified may be desirable. Such vectors include, but are not limited to, the *E. coli* expression vector pUR278 (Ruther et al., EMBO 1. 2:1791 (1983)), in which the coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with gluta-thione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or Factor Xa protease cleavage sites so that the cloned target gene product can be released from the GST moiety.

In an insect system, *Autographa californica* nuclear poly-hedrosis virus (AcNPV) may be used as a vector to express a SARS-CoV-2 peptidogenic protein and/or Spike fragment or an antibody raised against the SARS-CoV-2 peptidogenic protein and/or Spike fragment. The virus grows in *Spodop-*

*tera frugiperda* cells. Coding sequences may be cloned individually into non-essential regions (for example, the polyhedrin gene) of the virus and placed under control of an AcNPV promoter (for example, the polyhedrin promoter).

In mammalian host cells, a number of viral-based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region El or E3) will result in a recombinant virus that is viable and capable of expressing the SARS-CoV-2 peptidogenic protein and/or Spike fragment or an antibody raised against the SARS-CoV-2 peptidogenic protein and/or Spike fragment in infected hosts (e.g., see Logan & Shenk, Proc. Natl. Acad. Sci. USA 8 1:355-359 (1984)).

Specific initiation signals may also be required for efficient translation of inserted coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed, to this end, eukaryotic host cells which possess the cellular machinery for proper processing of the primary transcript, glycosylation, and phosphorylation of the gene product may be used. Such mammalian host cells include, but are not limited to, CHO, VERY, BHK, Hela, COS, NSO, MDCK, 293, 3T3, W138, and in particular, breast cancer cell lines such as, for example, BT483, Hs578T, HTB2, BT20 and T47D, and normal mammary gland cell line such as, for example, CRL7030 and HsS78Bst.

For long-term, high-yield production of recombinant proteins, stable expression is preferred. For example, cell lines which stably express the SARS-CoV-2 peptidogenic protein and/or Spike fragment or an antibody raised against the SARS-CoV-2 peptidogenic protein and/or Spike fragment may be engineered. Rather than using expression vectors which contain viral origins of replication, host cells can be transformed with a polynucleotide controlled by appropriate expression control elements (e.g., promoter, enhancer, sequences, transcription terminators, polyadenylation sites, etc.), and a selectable marker. Following the introduction of the foreign polynucleotide, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the SARS-CoV-2 peptidogenic protein and/or Spike fragment or an antibody raised against the SARS-CoV-2 peptidogenic protein and/or Spike fragment.

A number of selection systems may be used, including but not limited to, the herpes simplex virus thymidine kinase (Wigler et al., Cell 11:223 (1977)), hypoxanthineguanine phosphoribosyltransferase (Szybalska & Szybalski, Proc. Natl. Acad. Sci. USA 48:202 (1992)), and adenine phosphoribosyltransferase (Lowy et al., Cell 22:8 17 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Goldspiel et al., Clinical Pharmacy, 12: 488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62: 191-217 (1993); TIB TECH 11(5):155-2 15 (May; 1993)); and hygro, which confers resistance to hygromycin (Santerre et al., Gene 30:147 (1984)). Methods commonly known in the art of recombinant DNA technology may be routinely applied to select the desired recombinant clone, and such methods are described, for example; in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981).

The expression levels of a SARS-CoV-2 peptidogenic protein and/or Spike fragment or an antibody raised against the SARS-CoV-2 peptidogenic protein and/or Spike fragment can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing a SARS-CoV-2 peptidogenic protein and/or Spike fragment or an antibody raised against the SARS-CoV-2 peptidogenic protein and/or Spike fragment is amplifiable, an increase in the level of inhibitor present in the host cell culture will increase the number of copies of the marker gene. Since the amplified region is associated with the coding sequence, production of the SARS-CoV-2 peptidogenic protein and/or Spike fragment or an antibody raised against the SARS-CoV-2 peptidogenic protein and/or Spike fragment will also increase (Crouse et al., Mol. Cell. Biol. 3:257 (1983)).

Other elements that can be included in vector sequences include heterologous signal peptides (secretion signals), membrane anchoring sequences, introns, alternative splice sites, translation start and stop signals, inteins, biotinylation sites and other sites promoting post-translational modifications, purification tags, sequences encoding fusions to other proteins or peptides, separate coding regions separated by internal ribosome reentry sites, sequences encoding "marker" proteins that, for example, confer selectability (e.g., antibiotic resistance) or sortability (e.g., fluorescence), modified nucleotides, and other known polynucleotide cis-acting features not limited to these examples.

In the case of antibodies, the host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain is preferably placed before the heavy chain to avoid an excess of toxic free heavy chain (Proudfoot, Nature 322:52 (1986); Kohler, Proc. Natl. Acad. Sci. USA 77:2 197 (1980)). The coding sequences for the heavy and light chains may comprise cDNA or genomic DNA or synthetic DNA sequences.

For example, recombinant expression of an antibody raised using the SARS-CoV-2 peptidogenic protein and/or Spike fragment (including scFvs and other molecules comprising, or alternatively consisting of, antibody fragments or variants thereof (e.g., a heavy or light chain of an antibody of the invention or a portion thereof or a single chain antibody of the invention)), requires construction of an expression vector(s) containing a polynucleotide that encodes the antibody or fragment or variant thereof. Once a polynucleotide encoding an antibody molecule (e.g., a whole antibody, a heavy or light chain of an antibody, or variant or portion thereof (preferably, but not necessarily, containing the heavy or light chain variable domain)), of the invention has been obtained, the vector(s) for the production of the antibody molecule may be produced by recombinant DNA technology using techniques well known in the art. Thus, methods for preparing an antibody by expressing a polynucleotide containing an antibody encoding nucleotide sequence are described herein.

Once a SARS-CoV-2 peptidogenic protein and/or Spike fragment or an antibody raised against the SARS-CoV-2 peptidogenic protein and/or Spike fragment has been produced by recombinant expression, it may be purified by any method known in the art for purification of a protein, for example, by chromatography (e.g., ion exchange, affinity (particularly by Protein A affinity and immunoaffinity for the specific antigen), and sizing column chromatography), centrifugation, differential solubility, or by any other standard technique for the purification of proteins. Further, a SARS-CoV-2 peptidogenic protein and/or Spike fragment or an antibody raised against the SARS-CoV-2 peptidogenic protein and/or Spike fragment may be fused to heterologous polypeptide sequences described herein or otherwise known in the art to facilitate purification.

In one example, the SARS-CoV-2 peptidogenic protein and/or Spike fragment or the antibody raised to the SARS-CoV-2 peptidogenic protein and/or Spike fragment described herein may be fused with the constant domain of immunoglobulins (IgA, IgE, IgG, IgM), or portions thereof (CH1, CH2, CH3, or any combination thereof and portions thereof), or albumin (including but not limited to recombinant human albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998), resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394, 827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fe fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958-3964 (1995). Nucleic acids encoding the SARS-CoV-2 peptidogenic protein and/or Spike fragment or antibodies described herein can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix-binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Formulations

A pharmaceutical composition may comprise the SARS-CoV-2 peptidogenic proteins and/or Spike fragment described herein, polynucleotides encoding the SARS-CoV-2 peptidogenic proteins and/or Spike fragment, or an antibody raised to the SARS-CoV-2 peptidogenic protein and/or Spike fragment along with one or more pharmaceutically acceptable carriers, adjuvants, excipients, diluents, fillers, buffers, stabilizers, preservatives, lubricants, or other materials well known to those skilled in the art. Suitable materials will be sterile and pyrogen-free, with a suitable isotonicity and stability. Examples include sterile saline (e.g. 0.9% NaCl), water, dextrose, glycerol, ethanol or the like or combinations thereof. Such materials should be non-toxic and should not interfere with the efficacy of the active compound. The precise nature of the carrier or other material will depend on the route of administration, which may be by bolus, infusion, injection or any other suitable route, as discussed below. The composition may further contain auxiliary substances such as wetting agents, emulsifying agents, pH buffering agents or the like. Suitable carriers, excipients, etc. can be found in standard pharmaceutical texts, for example, Remington's Pharmaceutical Sciences, 18th edition, Mack Publishing Company, Easton, Pa., 1990.

The term "pharmaceutically acceptable" as used herein pertains to compounds, materials, compositions, and/or dosage forms which are, within the scope of sound medical judgment, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

In some embodiments, the SARS-CoV-2 peptidogenic proteins and/or Spike fragment, the polynucleotides encoding the SARS-CoV-2 peptidogenic proteins and/or Spike fragment, or an antibody raised to the SARS-CoV-2 peptidogenic protein and/or Spike fragment may be provided in a lyophilized form for reconstitution prior to administration.

For example, lyophilized reagents may be re-constituted in sterile water and mixed with saline prior to administration to a subject.

Additionally, "cocktails" of the SARS-CoV-2 peptidogenic proteins and/or Spike fragment, the polynucleotides encoding the SARS-CoV-2 peptidogenic proteins and/or Spike fragment, or an antibody raised to the SARS-CoV-2 peptidogenic protein and/or Spike fragment are specifically contemplated. For example, a mixture of different SARS-CoV-2 peptidogenic proteins and/or Spike fragment or polynucleotides encoding different SARS-CoV-2 peptidogenic proteins and/or Spike fragment derived from the same SARS-CoV-2 starting protein can be used to mount an immune response. Alternatively, a mixture of different SARS-CoV-2 peptidogenic proteins and/or Spike fragment or polynucleotides encoding different SARS-CoV-2 peptidogenic proteins and/or Spike fragment derived from different starting materials may also be used to mount an immune response. And finally, a single peptidogenic protein and/or Spike fragment and/or the polynucleotides encoding the SARS-CoV-2 peptidogenic proteins and/or Spike fragment, or an antibody raised to the SARS-CoV-2 peptidogenic protein and/or Spike fragment can be administered.

The formulations may conveniently be presented in unit dosage form and may be prepared by any methods known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

Optionally, other therapeutic or prophylactic agents may be included in a pharmaceutical composition or formulation.

Treatment may be any treatment and therapy, whether of a human or an animal (e.g. in veterinary applications), in which some desired therapeutic effect is achieved, for example, the inhibition or delay of the progress of the condition, and includes a reduction in the rate of progress, a halt in the rate of progress, amelioration of the condition, cure or remission (whether partial or total) of the condition, preventing, delaying, abating or arresting one or more symptoms and/or signs of the condition or prolonging survival of a subject or patient beyond that expected in the absence of treatment.

Treatment as a prophylactic measure (i.e. prophylaxis) is also included. For example, a subject susceptible to or at risk of the occurrence or re-occurrence of the disease may be treated as described herein. Such treatment may prevent or delay the occurrence or re-occurrence of the disease in the subject.

The term "therapeutically-effective amount" as used herein, pertains to that amount of the SARS-CoV-2 peptidogenic protein and/or Spike fragment or an antibody raised to the SARS-CoV-2 peptidogenic protein and/or Spike fragment, which is effective for producing some desired therapeutic effect, commensurate with a reasonable benefit/risk ratio.

It will be appreciated that appropriate dosages of the SARS-CoV-2 peptidogenic protein and/or Spike fragment or an antibody raised to the SARS-CoV-2 peptidogenic protein and/or Spike fragment can vary from patient to patient.

Determining the optimal dosage will generally involve the balancing of the level of therapeutic benefit against any risk or deleterious side effects of the administration. The selected dosage level will depend on a variety of factors including, but not limited to, the route of administration, the time of administration, the rate of excretion of the active compound, other drugs, compounds, and/or materials used in combination, and the age, sex, weight, condition, general health, and prior medical history of the patient. The amount of peptidogenic protein and/or Spike fragment, polynucleotide encoding the SARS-CoV-2 peptidogenic protein and/or Spike fragment, or an antibody raised to the SARS-CoV-2 peptidogenic protein and/or Spike fragment, and route of administration will ultimately be at the discretion of the physician, although generally the dosage will be to achieve concentrations of the active compound at a site of therapy without causing substantial harmful or deleterious side-effects.

In general, a suitable dose of the SARS-CoV-2 peptidogenic protein and/or Spike fragment is in the range of about 1 to 100 ug. In preferred embodiments, these proteins, or polynucleotides encoding these proteins, are administered on an immunization schedule of a primary inoculation, followed by a secondary dose given preferably three to four weeks later. If required, a tertiary dose can be administered after another three to four weeks. Booster schedules may also need to be implemented, with shots given on a determined yearly schedule.

Alternatively, the amount of administration of an antibody raised to the SARS-CoV-2 peptidogenic protein and/or Spike fragment should be calculated relative to a persons' weight, and is preferably ranging between 500-1500 mg per 40 kg body mass.

Administration in vivo can be effected in one dose, continuously or intermittently (e.g., in divided doses at appropriate intervals). Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the physician.

By "simultaneous" administration, it is meant that the SARS-CoV-2 peptidogenic proteins and/or Spike fragment, the polynucleotides encoding the SARS-CoV-2 peptidogenic proteins and/or Spike fragment, or an antibody raised to the SARS-CoV-2 peptidogenic protein and/or Spike fragment are administered to the subject in a single dose by the same route of administration.

By "separate" administration, it is meant that the SARS-CoV-2 peptidogenic proteins and/or Spike fragment, the polynucleotides encoding the SARS-CoV-2 peptidogenic proteins and/or Spike fragment, or an antibody raised to the SARS-CoV-2 peptidogenic protein and/or Spike fragment are administered to the subject by two different routes of administration which occur at the same time. This may occur for example where one agent is administered by infusion or parenterally and the other is given orally during the course of the infusion or parenteral administration.

By "sequential" it is meant that the SARS-CoV-2 peptidogenic proteins and/or Spike fragment, the polynucleotides encoding the SARS-CoV-2 peptidogenic proteins and/or Spike fragment, or an antibody raised to the SARS-CoV-2 peptidogenic protein and/or Spike fragment are administered at different points in time, provided that the activity of the first administered agent is present and ongoing in the subject at the time the second agent is administered. Preferably, a sequential dose will occur such that the second of the two agents is administered within 48 hours, preferably within 24 hours, such as within 12, 6, 4, 2 or 1 hour(s) of the first agent.

Multiple doses of the SARS-CoV-2 peptidogenic proteins and/or Spike fragment, the polynucleotides encoding the SARS-CoV-2 peptidogenic proteins and/or Spike fragment, and/or an antibody raised to the SARS-CoV-2 peptidogenic protein and/or Spike fragment, may be administered. For example 2, 3, 4, 5 or more than 5 doses may be administered after administration of the SARS-CoV-2 peptidogenic proteins and/or Spike fragment, the polynucleotides encoding the SARS-CoV-2 peptidogenic proteins and/or Spike fragment, and/or an antibody raised to the SARS-CoV-2 peptidogenic protein and/or Spike fragment. The administration of the SARS-CoV-2 peptidogenic proteins and/or Spike fragment, the polynucleotides encoding the SARS-CoV-2 peptidogenic proteins and/or Spike fragment, and/or an antibody raised to the SARS-CoV-2 peptidogenic protein and/or Spike fragment may continue for sustained periods of time after initial administration. For example treatment with the SARS-CoV-2 peptidogenic proteins and/or Spike fragment, the polynucleotides encoding the SARS-CoV-2 peptidogenic proteins and/or Spike fragment, or an antibody raised to the SARS-CoV-2 peptidogenic protein and/or Spike fragment may be continued for at least 1 week, at least 2 weeks, at least 3 weeks, at least 1 month or at least 2 months. Treatment with the SARS-CoV-2 peptidogenic proteins and/or Spike fragment, the polynucleotides encoding the SARS-CoV-2 peptidogenic proteins and/or Spike fragment, or an antibody raised to the SARS-CoV-2 peptidogenic protein and/or Spike fragment may be continued for as long as is necessary to achieve a therapeutic response.

The SARS-CoV-2 peptidogenic proteins and/or Spike fragment, the polynucleotides encoding the SARS-CoV-2 peptidogenic proteins and/or Spike fragment, or an antibody raised to the SARS-CoV-2 peptidogenic protein and/or Spike fragment and compositions comprising these molecules may be administered to a subject by any convenient route of administration, whether systemically/peripherally or at the site of desired action, including but not limited to, oral (e.g. by ingestion); and parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly. Usually administration will be by the intravenous route, although other routes such as intraperitoneal, subcutaneous, transdermal, oral, nasal, intramuscular or other convenient routes are not excluded.

The pharmaceutical compositions comprising the SARS-CoV-2 peptidogenic protein and/or Spike fragment, the polynucleotides encoding the SARS-CoV-2 peptidogenic proteins and/or Spike fragment, or an antibody raised to the SARS-CoV-2 peptidogenic protein and/or Spike fragment may be formulated in suitable dosage unit formulations appropriate for the intended route of administration.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or molding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilizers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 g/ml, for example from about 10 ng/ml to about 1 g/ml, from about 1 g/ml to about 10 mg/ml, from about 10 g/ml to about 1 mg/ml, from about 1 mg/ml to about 20 mg/ml, from about 10 mg/ml to about 120 mg/ml, or any other concentration suitable for administration of biological drugs (e.g., proteins, antibodies, etc.). The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Compositions comprising the SARS-CoV-2 peptidogenic proteins and/or Spike fragment, the polynucleotides encoding the SARS-CoV-2 peptidogenic proteins and/or Spike fragment, and/or an antibody raised to the SARS-CoV-2 peptidogenic protein and/or Spike fragment, may be prepared in the form of a concentrate for subsequent dilution, or may be in the form of divided doses ready for administration. Alternatively, the reagents may be provided separately within a kit, for mixing prior to administration to a human or animal subject.

The SARS-CoV-2 peptidogenic proteins and/or Spike fragment, the polynucleotides encoding the SARS-CoV-2 peptidogenic proteins and/or Spike fragment, and/or an antibody raised to the SARS-CoV-2 peptidogenic protein and/or Spike fragment may be administered alone or in combination with other treatments, either simultaneously or sequentially dependent upon the individual circumstances. For example, SARS-CoV-2 peptidogenic proteins and/or Spike fragment, the polynucleotides encoding the SARS-CoV-2 peptidogenic proteins and/or Spike fragment, or an antibody raised to the SARS-CoV-2 peptidogenic protein and/or Spike fragment as described herein may be administered in combination with one or more additional active compounds.

Various further aspects and embodiments of the present invention will be apparent to those skilled in the art in view of the present disclosure.

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such these are within the scope of the present invention. All documents and sequence database entries mentioned in this specification are incorporated herein by reference in their entirety for all purposes. The invention is further described below, with reference to the following examples.

EXAMPLES

Example 1: Generating Peptidogenic Antigens

Figure 2:
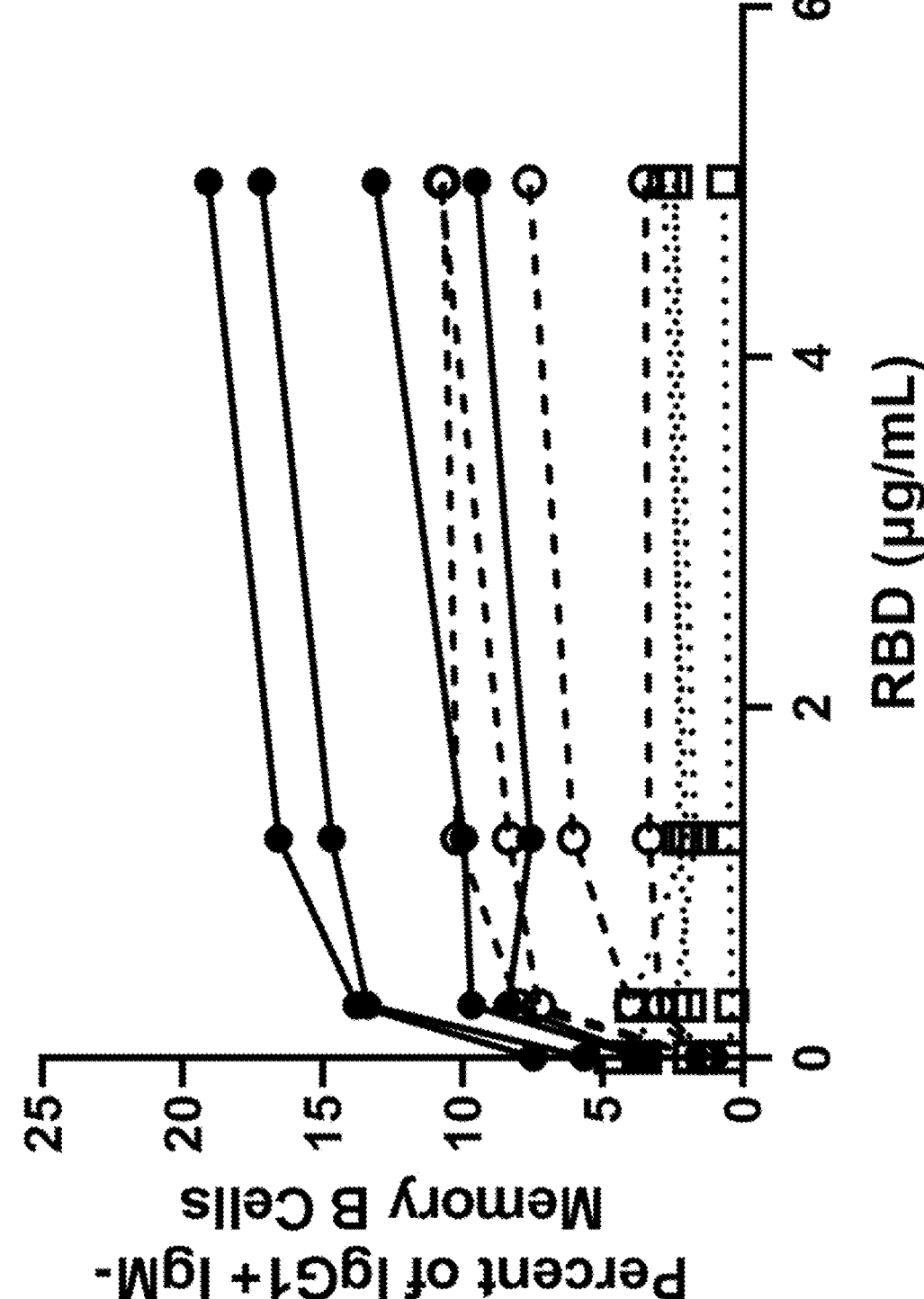
FIG. 2 shows flow cytometry of Spike fragment-specific B cells (CD3$^-$, CD19$^+$. IgM$^-$, IgG1$^+$) from immunized BALB/c mice 55 days post-boost demonstrating that a mixture of the Spike fragment plus this same fragment with additional mutants Y365L and V511A (filled circles) administered in a prime/boost immunization schedule in BALB/C mice increases anti-Spike fragment-specific IgG-secreting memory B-cells compared to anti-Spike fragment-specific IgG-secreting memory B-cells derived from immunization of mice with wild type (starting protein) alone (open circles) or naïve B-cells (open squares) from mock immunized mice.

To generate SARS-CoV-2 peptidogenic proteins, a SARS-CoV-2 starting protein can be modified at its core residues (e.g., one or more mutations) to alter its conformational dynamics. Multiple different SARS-CoV-2 peptidogenic proteins can be designed and expressed to immunize animals, such as rabbits, to generate a polyclonal antibody response. Alternatively, polynucleotides encoding the SARS-CoV-2 peptidogenic proteins can be directly administered to the animals to generate the SARS-CoV-2 peptidogenic proteins in vivo. The response will be monitored by two complementary and mutually reinforcing methods (Georgiou et al, 2014; FIG. 2): (a) purifying B cells from the blood, spleen, and bone marrow of immunized animals, isolating cDNA from mRNA encoding the variable regions of the heavy and light chains, and analyzing this repertoire via deep DNA sequencing; and (b) immunoaffinity purifying from immune sera polyclonal Fab or (Fab')2 fragments using antigen attached to a solid support, digesting the eluted Fab/(Fab')2s with proteases, and sequencing the resultant peptides using LC/MS/MS.

Specifically, challenging test animals (rabbits) with a variety of SARS-CoV-2 peptidogenic proteins (or polynucleotides encoding the SARS-CoV-2 peptidogenic proteins) where the conformation is similar to the SARS-CoV-2 starting protein, but the conformational dynamics of the SARS-CoV-2 peptidogenic protein is varied, can be performed. Using next-generation DNA sequencing technology, the humoral response in the animal can be comprehensively characterized. Immunoglobulin V-regions from B lymphocytes can be cloned and subjected to massively parallel deep sequencing (5-8). In conjunction with this, polyclonal antibodies from the same test animal can be purified by immunoaffinity chromatography, then protease-digested and subjected to LC-MS/MS to determine the peptide sequences (9, 10). Comparisons of these two datasets illuminate the repertoire of individual antibodies comprising the polyclonal response (9).

For example, small mammalian proteins that have been extremely well-characterized biophysically can be used as test antigens. Preferred examples, include, but are not limited to bovine pancreatic trypsin inhibitor and/or Alzheimer's amyloid precursor protein Kunitz domain. Alternatively, antigens relevant to unmet vaccine needs, such as for example, *P. falciparum* sporozoite antigens can also be generated and tested in this method. Additionally, optimization (or re-optimization) of synthetic vaccines with respect to conformational dynamics of the component proteins (perhaps replacing a single component with a combinatory cocktail of several versions of the same antigen with different core destabilizing mutations) can also be generated. Testing these new vaccines in clinical trials could involve monitoring of the vaccinated individuals using similar DNA sequence analyses of blood-derived B-cell V-region repertoires and proteomic characterization of immunoaffinity-purified polyclonal antibody peptides, similar to the procedures described above.

Other preferred examples of antigens that can be used according to embodiments of the invention described herein, include, but are not limited to antigens or antigens derived from, severe acute respiratory syndrome coronavirus (SARS-CoV-2), preferably those antigens described in Table 2, as well as antigens from related viruses that infect apes, monkeys, birds, pigs, camels, and other animals.

In preferred embodiments, any one of the protein antigens listed in the Table 2 can be used as a SARS-CoV-2 starting protein to derive the SARS-CoV-2 peptidogenic protein. Additionally, multiple antigens listed in Table 2 can be used as the SARS-CoV-2 starting proteins to derive multiple different SARS-CoV-2 peptidogenic proteins to be used as a vaccine, generate an immune response, including the raising of antibodies.

Moreover, combinations of different protein antigens can be used as SARS-CoV-2 starting proteins.

To alter the conformational dynamics of a SARS-CoV-2 starting protein, the following changes in Gibbs Free Energy, shown in Table 3 below, can be considered:

TABLE 3

| Amino Acid Substitution (multiple positions in various proteins) | Average Gibbs Free Energy difference between mutant and wild type at core residues within a protein ΔΔG (kJ/mol) |
| --- | --- |
| Val –> Ala | −12.1(±3.3) |
| Val –> Thr | −11.3(±3.7) |
| Val –> Asn | −21.5(±1.0) |
| Leu –> Ala | −14.2(±4.2) |

As discussed in Loladze et al (J. Mol. Biol. 320, 343-357 (2002)), the following amino acid substitutions can decrease the thermodynamic stability (e.g., reflected in the Gibbs free energy) and alter the conformational dynamics of a SARS-CoV-2 starting protein. For example, Val and Leu (and other larger non-polar amino acid residues) can be substituted with smaller ones such as Ala, Thr, Asn, and/or Gly. In addition, the buried site of Glu in the SARS-CoV-2 starting protein, can be substituted with Leu, Val, Asn, Thr, Ser, Ala, and/or Gly. These single site amino acid substitutions are expected to generate SARS-CoV-2 peptidogenic proteins with lower stability but a similar conformation to the SARS-CoV-2 starting protein.

Alternatively, the conformational dynamics of the SARS-CoV-2 starting protein is altered by replacing (a) at least one threonine with a valine, alanine, glycine or serine; or (b) at least one cysteine with alanine, valine, glycine, serine or threonine; or (c) at least one valine with alanine, glycine, leucine or isoleucine; or (d) at least one leucine with alanine, valine, glycine, or isoleucine; or (e) at least one isoleucine with alanine, valine, leucine, or glycine; or (f) at least one proline, methionine, phenylalanine, tyrosine, or tryptophan with alanine, valine, leucine, isoleucine, or glycine; or (g) at least one aspartic acid or asparagine with glycine, serine, threonine, alanine, valine, leucine, isoleucine; or (h) at least one glutamic acid or glutamine with aspartic acid, asparagine, glycine, serine, threonine, alanine, valine, leucine, or isoleucine; or (i) at least one lysine with arginine, histidine, glycine, serine, threonine, alanine, valine, methionine, leucine, or isoleucine; or (j) at least one arginine with lysine, histidine, glycine, serine, threonine, alanine, valine, methionine, leucine, or isoleucine; or (k) at least one histidine with lysine, arginine, glycine, serine, threonine, alanine, valine, glutamine, asparagine, leucine, or isoleucine; or (1) at least one alanine with a glycine; or (m) at least one residue with a non-natural amino acid; and/or (n) any of the above combinations.

In still further preferred embodiments, the conformational dynamics of the SARS-CoV-2 starting protein is altered by replacing: (a) at least one tryptophan with tyrosine, phenylalanine, methionine, histidine, isoleucine, leucine, valine, alanine or glycine; or (b) at least one tyrosine with phenylalanine, methionine, histidine, isoleucine, leucine, valine, alanine or glycine; or (c) at least one phenylalanine with tyrosine, methionine, histidine, isoleucine, leucine, valine, alanine or glycine; or (d) at least one proline with methionine, leucine, isoleucine, valine, alanine, or glycine; or (e) at least one histidine with phenylalanine, tyrosine, methionine, isoleucine, leucine, valine, alanine, glycine, lysine, arginine, serine, threonine, asparagine, or glutamine; or (f) at least one methionine with isoleucine, leucine, valine, alanine or glycine; or (g) at least one isoleucine with leucine, valine, alanine or glycine; or (h) at least one leucine with isoleucine, valine, alanine or glycine; or (i) at least one valine with alanine, glycine, leucine, or isoleucine; or (j) at least one cysteine with alanine, valine, glycine, serine or threonine; or (k) at least one aspartic acid with glutamic acid, glutamine, asparagine, glycine, serine, threonine, alanine, valine, leucine, or isoleucine; or (1) at least one glutamic acid with aspartic acid, glutamine, asparagine, glycine, serine, threonine, alanine, valine, leucine, or isoleucine; or (m) at least one alanine with a glycine or proline; or (n) at least one serine with alanine or glycine; or (o) at least one glycine with alanine or proline; or (p) at least one lysine with arginine, histidine, glycine, serine, threonine, alanine, valine, methionine, leucine or isoleucine; or (q) at least one asparagine with glycine, alanine, serine, threonine, valine, leucine, isoleucine, glutamine, aspartic acid or glutamic acid; or (r) at least one glutamine with glycine, alanine, serine, threonine, valine, leucine, isoleucine, glutamine, aspartic acid, glutamic acid, or histidine; or (s) at least one arginine with lysine, histidine, glycine, serine, threonine, alanine valine, methionine, leucine, or isoleucine; or (t) at least one threonine with valine, alanine, glycine or serine; or (u) a hydrophobic residue with a smaller, similar hydrophobic residue; or (v) at least one residue with a non-natural amino acid; or (w) any of the above combinations. A combinatorial approach may be used to determine optimal substitutions to increase immunogenicity.

Example 2: Preferred Spike Protein Vaccine

In preferred embodiments, it was identified that a specific fragment of the Spike protein provided unexpectedly improved vaccination results when compared to published efficacy results for other COVID-19 vaccines, even in those cases when the other vaccines comprise different regions of the RBD domain. Additionally, as shown in FIGS. 1 and 2, even better results were obtained when a mixture of the Spike fragment was combined with mutations as described herein. Specifically, the fragment comprising, or consisting of, amino acids 316-594 of SEQ ID NO:15 provided unexpectedly and substantially improved results. This fragment is found within the Spike Protein and includes the RBD domain (Lan et al., Nature 581:215-220 (2020); Hurlburt et al., Nat. Commun. 11:5413 (2020)) which is responsible for binding of SARS-CoV-2 to its cell entry receptor ACE2. The RBD has been found to be the most immunogenic region of the Spike protein of SARS-CoV and MERS-CoV (Du et al., Nat. Rev. MicroBiol. 7:226-236 (2009) and inclusion of the RBD in a vaccine can elicit an immune response targeting the RBD of the virus to prevent or neutralize viral entry into host cells (Du et al., Nat. Commun. 7:13473 (2016). In addition, it has been recognised that while the RBD is less conserved than non-RBD regions of the Spike protein, identical amino acids between SARS-CoV-2 and SARS are found, and offer the potential to elicit antibodies targeting conserved epitopes in the RBD that may provide cross-reactivity against different coronaviruses including SARS-CoV-2 mutants (Du et al., supra).

The specific Spike fragment as disclosed herein was identified as having unexpectedly better activity than other vaccines utilizing the RBD. The Spike fragment for SARS-CoV-2 is shown as encompassing the following fragment:

```
>sp|P0DTC2|amino acids 316-594 of SEQ ID NO: 15
                                (SEQ ID NO: 39)
SNFRVQPTESIVRFPNITNLCPFGEVFNATRFASVYAWNRKRISNCVAD

YSVLYNSASFSTFKCYGVSPTKLNDLCFTNVYADSFVIRGDEVRQIAPG

QTGKIADYNYKLPDDFTGCVIAWNSNNLDSKVGGNYNYLYRLFRKSNLK

PFERDISTEIYQAGSTPCNGVEGFNCYFPLQSYGFQPTNGVGYQPYRVV

VLSFELLHAPATVCGPKKSTNLVKNKCVNFNFNGLTGTGVLTESNKKFL

PFQQFGRDIADTTDAVRDPQTLEILDITPCSFGG
```

Additionally, this same fragment can be engineered with specific mutations. Three preferred mutations that showed even better activity include Y365L, I402V, and V511A.

```
SARS-CoV-2 Y365L Spike fragment
                                (SEQ ID NO: 40)
SNFRVQPTESIVRFPNITNLCPFGEVFNATRFASVYAWNRKRISNCVAD

LSVLYNSASFSTFKCYGVSPTKLNDLCFTNVYADSFVIRGDEVRQIAPG

QTGKIADYNYKLPDDFTGCVIAWNSNNLDSKVGGNYNYLYRLFRKSNLK

PFERDISTEIYQAGSTPCNGVEGFNCYFPLQSYGFQPTNGVGYQPYRVV

VLSFELLHAPATVCGPKKSTNLVKNKCVNFNFNGLTGTGVLTESNKKFL

PFQQFGRDIADTTDAVRDPQTLEILDITPCSFGG
```

```
SARS-CoV-2 I402V Spike fragment
                                (SEQ ID NO: 41)
SNFRVQPTESIVRFPNITNLCPFGEVFNATRFASVYAWNRKRISNCVAD

YSVLYNSASFSTFKCYGVSPTKLNDLCFTNVYADSFVVRGDEVRQIAPG

QTGKIADYNYKLPDDFTGCVIAWNSNNLDSKVGGNYNYLYRLFRKSNLK

PFERDISTEIYQAGSTPCNGVEGFNCYFPLQSYGFQPTNGVGYQPYRVV

VLSFELLHAPATVCGPKKSTNLVKNKCVNFNFNGLTGTGVLTESNKKFL

PFQQFGRDIADTTDAVRDPQTLEILDITPCSFGG

SARS-CoV-2 V511A Spike fragment
                                (SEQ ID NO: 42)
SNFRVQPTESIVRFPNITNLCPFGEVFNATRFASVYAWNRKRISNCVAD

YSVLYNSASFSTFKCYGVSPTKLNDLCFTNVYADSFVIRGDEVRQIAPG

QTGKIADYNYKLPDDFTGCVIAWNSNNLDSKVGGNYNYLYRLFRKSNLK

PFERDISTEIYQAGSTPCNGVEGFNCYFPLQSYGFQPTNGVGYQPYRVA

VLSFELLHAPATVCGPKKSTNLVKNKCVNFNFNGLTGTGVLTESNKKFL

PFQQFGRDIADTTDAVRDPQTLEILDITPCSFGG
```

This Spike fragment can be used as a vaccine directly, or can be combined with mutations (such as those shown above) to change the stability and conformational dynamics of the protein. It is believed that this specific fragment (along with mutations) may lead to increased diversity of the polyclonal antibody repertoire and unmasking of buried or partially occluded B cell epitopes.

It is expected that the truncated construct might result in a less diverse set of T cell epitopes compared to the full-length wt spike protein, due to the elimination of the N- and C-terminal extensions comprising the rest of the spike protein. However, the approach of increasing conformational flexibility of the resultant antigen fragment via micro-cavity-creating amino acid substitutions in core hydrophobics should compensate by enhancing the production and presentation of antigen fragment T cell epitope peptides by APCs, thereby boosting the immunogenicity of this domain.

Although others have suggested similar fragments of the Spike protein (e.g., Spike construct 319-591 as described in Wrapp D, Wang N, Corbett K S, Goldsmith J A, Hsieh C-L, Abiona O, Graham B S, McLellan J S. Cryo-E M structure of the 2019-nCoV spike in the prefusion conformation. Science. 2020; 367(6483):1260-3. doi: 10.1126/science-.abb2507 and Spike construct 319-541 as described in Amanat F, Stadlbauer D, Strohmeier S, Nguyen T H O, Chromikova V, McMahon M, Jiang K, Arunkumar G A, Jurczyszak D, Polanco J, Bermudez-Gonzalez M, Kleiner G, Aydillo T, Miorin L, Fierer D S, Lugo L A, Kojic E M, Stoever J, Liu S T H, Cunningham-Rundles C, Felgner P L, Moran T, Garcia-Sastre A, Caplivski D, Cheng A C, Kedzierska K, Vapalahti O, Hepojoki J M, Simon V, Krammer F. A serological assay to detect SARS-CoV-2 seroconversion in humans. Nature Medicine. 2020; 26(7):1033-6. doi: 10.1038/s41591-020-0913-5), the fragment proposed herein is expected to have improved properties.

Preferred sites for mutations that can be combined with the preferred truncated Spike protein of amino acids 316-594 are selected from: A) Trp353, Tyr 365, Phe392, Phe400, Tyr 423, Phe497, and/or Phe543; (B) Ile326, Val350, Ile358, Ala363, Leu387, Val395, Ala397, Val401, Ile402, Ile410, Ile418, Ala419, Leu425, Val433, Ile434, Ala435, Leu492, Val510, Val511, Val512, Leu513, Val524, Val539, Leu552, Ala575, Val576, and/or Leu585; (C) Ala 363, Ala 397, and/or Ala 575; (D) Cys336Ala/Cys361Ala, and/or Cys379Ala/Cys432Ala; (E) Ala 419, Ala 575, Val 576, Tyr 365, Ile 418, Leu 387, Leu 585, Ile 410, Tyr 423, Phe497, and/or Leu 552 of SEQ ID NO:15, or the corresponding mutations in SEQ ID NO:16.

In further preferred embodiments, the truncated Spike protein comprising, or consisting of amino acids 319-591 is combined with mutations at the following preferred sites: (A) Trp 353, Tyr 365, Phe 392, Phe 400, Tyr 423, Phe 497, and/or Phe 543; (B) Ile326, Val350, Ile358, Ala363, Leu387, Val395, Ala397, Val401, Ile402, Ile410, Ile418, Ala419, Leu425, Val433, Ile434, Ala435, Leu492, Val510, Val511, Val512, Leu513, Val524, Val539, Leu552, Ala575, Val576, and/or Leu585; (C) Ala 363, Ala 397, and/or Ala 575; (D) Cys 336 Ala/Cys 361 Ala, and/or Cys 379 Ala/Cys 432 Ala; and/or (E) Ala 419, Ala 575, Val 576, Tyr 365, Ile 418, Leu 387, Leu 585, Ile 410, Tyr 423, Phe 497, and/or Leu 552 of SEQ ID NO:15, or the corresponding mutations in SEQ ID NO:16.

In further preferred embodiments, the truncated Spike protein comprising, or consisting of amino acids 319-541 is combined with mutations at the following preferred sites: (A) Trp 353, Tyr 365, Phe 392, Phe 400, Tyr 423, and/or Phe 497; (B) Ile326, Val350, Ile358, Ala363, Leu387, Val395, Ala397, Val401, Ile402, Ile410, Ile418, Ala419, Leu425, Val433, Ile434, Ala435, Leu492, Val510, Val511, Val512, Leu513, Val524, and/or Val539; (C) Ala 363, and/or Ala 397; (D) Cys 336 Ala/Cys 361 Ala, and/or Cys 379 Ala/Cys 432 Ala; and/or (E) Ala 419, Tyr 365, Ile 418, Leu 387, Ile 410, Tyr 423, an/or Phe 497 of SEQ ID NO:15, or the corresponding mutations in SEQ ID NO:16.

In one such experiment, BALB/c mice were immunized twice (prime+2° boost) with either 3 µg of the wild type antigen or with a 3 µg mixture of wild type and two mutant antigens in equal proportions (i.e., 1 µg of wt antigen plus 1 µg of each mutant antigen), using alum as the adjuvant. For ELISAs, the native wild type RBD 316-594 fragment was immobilized in the wells via a C-terminal tag, allowing the elicited polyclonal antibodies to bind to wild-type RBD conformational epitopes. The geometric means of the half-max titers from replicate (n) ELISAs of the mouse antisera at various timepoints after boost were calculated. As shown in FIG. 1, immunization with a protein mixture of the Spike fragment along with the two mutants Y365L and V511 A (described above) elicited significantly increased RBD-specific anti-IgG antibody titers as compared to immunization with the Spike fragment alone.

Similarly, FIG. 2 demonstrates that immunization with the mixture of antigen fragments (Spike fragment+2 mutants [above]) also resulted in increased Spike fragment-specific memory B cell production as compared to immunization with an equimolar concentration of Spike fragment alone or to mock immunized mice.

Example 3: Assays Measuring Alterations in Conformational Dynamics

Alterations in conformational dynamics can be measured by standard methods known in the art. In preferred embodiments, alterations in conformational dynamics can be shown by measuring changes in melting temperatures, in urea-induced equilibrium unfolding studies, and/or Gibbs free energy as compared to the SARS-CoV-2 starting protein.

Changes in melting temperature can be shown by the following protocol. For example, a SARS-CoV-2 peptidogenic protein (0.20 mg/ml) and a SARS-CoV-2 starting protein (as a control) is heated from 10° C. to 72° C. in a 0.1 cm quartz cuvette with a heating rate of 1 degree×min-1 controlled by a Jasco programmable Peltier element. The dichroic activity at 209 nm and the photomultiplier tube voltage (PMTV) are continuously monitored in parallel every 0.5° C. All the thermal scans are corrected for the solvent contribution at the different temperatures. Melting temperature (Tm) values are calculated by taking the first derivative of the ellipticity at 209 nm with respect to temperature. All denaturation experiments are performed in triplicate (see Lori et al., PLoS One, 5; 8(6):e64824 (2013)).

A change in urea-induced equilibrium unfolding can be shown by the following protocol. A SARS-CoV-2 peptidogenic protein (final concentration 40 ug/ml) and a SARS-CoV-2 starting protein (as a control) is incubated at 10° C. in increasing concentrations of urea (0-8 M) in 25 mM Tris/HCl, pH 7.5, in the presence of 0.2 M NaCl and 2 mM DTT (for non-disulfide containing proteins). After 10 min, equilibrium is reached and the intrinsic fluorescence emission, absorbance at 287 nm, and/or far-UV CD spectra (0.5-cm cuvette) are recorded in parallel at 10° C. To test the reversibility of the unfolding, a SARS-CoV-2 peptidogenic protein is unfolded at 10° C. in 7.0 M urea at 0.4 mg/ml protein concentration in 25 mM Tris/HCl, pH 7.5, in the presence of 2 mM DTT and 0.2 M NaCl. After 10 min, refolding is started by 10-fold dilution of the unfolding mixture at 10° C. into solutions of the same buffer used for unfolding containing decreasing urea concentrations. The final protein concentration is 40 µg/ml. After an incubation period of 15 min to 24 h, the intrinsic fluorescence emission, absorbance at 287 nm, and/or the CD spectra are recorded as a function of urea concentration at 10° C. (see Lori et al., PLoS One, 5; 8(6):e64824 (2013)).

Alterations in Gibbs free energy can be shown by the following protocol. In order to measure Gibbs free energy, differential scanning calorimetry (DSC) experiments are performed on a VP-DSC (Microcal Inc., Northampton, MA) instrument at a scan rate of 1.5 deg/minute. Where possible, temperature-induced unfolding of a SARS-CoV-2 peptidogenic protein is checked for reversibility by comparing first and second DSC scans. It is understood that reversibility of folding and unfolding is not a requirement for the SARS-CoV-2 peptidogenic proteins described herein. The partial molar heat capacity of the protein, Cp,pr (T), is obtained from the experimentally measured apparent heat capacity difference between the sample (containing protein solution) and reference (containing corresponding buffer solution) cells, $\Delta C_p^{app}$ (T). Protein concentration is measured spectrophotometrically using a known molar extinction coefficient. Analysis of the heat capacity profiles according to a two-state model is done using non-linear regression routine NLREG and in-house written scripts. The standard thermodynamic functions under reference conditions are calculated as:

$$\Delta H_{cal}(T) = \Delta H(T_m) + \Delta C_p(T - T_m)$$

$$\Delta S(T) = \Delta S(T_m) + \Delta C_p \ln(T / T_m)$$

$$= \frac{\Delta H \mathrm{cal}(Tm)}{Tm} + \Delta C p \ln(T / Tm)$$

$$\Delta G(T) = (T_m - T)(\Delta H_{cal}(T_m)/T_m - \Delta C_p) - T\Delta C_p \ln(T / T_m)$$

Where ΔH(T), ΔS(T), and ΔG(T) are the enthalpy, entropy and Gibbs energy functions of a SARS-CoV-2 peptidogenic protein, respectively, ΔHcal is the enthalpy of unfolding at the transition temperature Tm, and ΔCp is the heat capacity of unfolding (see Loladze et al., J. Mol. Biol. 320, 343-357 (2002)).

Example 4: Assays Measuring Peptidogenicity

One of the intracellular conditions that may participate in processing of the SARS-CoV-2 peptidogenic proteins as described herein is proteolysis. The influence of the differential stability of the SARS-CoV-2 peptidogenic proteins on proteolysis can be determined using one of several in vitro or ex vivo assays.

(a) Cathepsin L Proteolysis

In one embodiment, examination of the behavior of the SARS-CoV-2 peptidogenic proteins toward proteolysis is measured by subjecting them to the action of cathepsin L, one of the enzymes known to be critical in protein antigen processing (Hsieh, C. S., deRoos, P., Honey, K., Beers, C., and Rudensky, A. Y. (2002) J. Immunol. 168, 2618-2625). Susceptibility of the SARS-CoV-2 peptidogenic proteins to proteolysis is assessed using lysosomal cathepsin L The SARS-CoV-2 peptidogenic proteins (0.5 ug/ul) are incubated with various amounts (e.g., 1.5 munits) of enzyme in 50 mM sodium acetate buffer; pH 4.5, for various lengths of time at 37° C. Digestion is stopped using 0.1% TFA, and proteolysis is monitored by reversed-phase HPLC on C18 reverse phase columns (Vydac., Hesperia, CA), Elution of the proteolytic products is carried out with a linear gradient of acetonitrile/water containing 0.1% TFA.

(b) Proteolysis Using Alpha-Chymotrypsin and Carboxypeptidase Y

In another embodiment, examination of the behavior of the SARS-CoV-2 peptidogenic proteins toward proteolysis is measured by subjecting them to the action of alphachymotrypsin and carboxypeptidase Y. Alpha-chymotrypsin is an endopeptidase which cleaves at the carboxyl terminus of aromatic amino acids; carboxypeptidase Y is an exopeptidase which removes amino acids sequentially from the carboxyl terminus. Proteolytic digestion with these enzymes is specific for unstable conformations, hence, the conformational stability of the SARS-CoV-2 peptidogenic proteins determines their resistance/susceptibility to proteolytic digestion. The SARS-CoV-2 peptidogenic proteins at 1 mg/ml in 0.5 ml of 20 mM HEPES-buffered saline, pH 7.5, are incubated at 37° C. with 100 ug of alpha-chymotrypsin from bovine pancreas and carboxypeptidase Y from yeast. Each incubation is terminated at various time-points and the digested samples are stored at −20° C. until analyzed. Samples are analyzed by sodium dodecyl sulfate-polyacrylamide gel electrophoresis (SDS-PAGE), through a 15% acrylamide gel and under reducing conditions, then stained with Coomassie Brilliant Blue for visualization.

(c) Proteolysis Using Lysosomal Extracts

In another embodiment, examination of the behavior of the SARS-CoV-2 peptidogenic proteins toward proteolysis is measured by subjecting them to the action of lysosomal extracts of bone marrow-derived dendritic cells. The SARS-CoV-2 peptidogenic proteins are incubated at various concentrations in the presence of equal amounts of proteins from crude lysosomal extracts from bone marrow-derived dendritic cells. The mixtures are incubated in 0.1 M sodium citrate buffer, 0.5% Triton X-100, and 2 mM dithiothreitol at pH 4.5. Each incubation is terminated at various time-points and the digested samples are stored at −20° C. until analyzed. Samples are analyzed by SDS-PAGE. The experiments are repeated with and without prior adsorption of SARS-CoV-2 peptidogenic proteins onto an adjuvant such as aluminum hydroxide. Bone marrow-derived dendritic cells are purified with use of anti-CD11c microbeads from bone marrow cultured in granulocyte macrophage-colony stimulating factor. See, for example, Delamarre et al., FIG. 4.

(d) Proteolysis After Internalization by Bone Marrow-Derived Dendritic Cells

In another embodiment, examination of the behavior of the SARS-CoV-2 peptidogenic proteins toward proteolysis is measured by labeling them with FITC per the manufacturer's protocol, incubating bone marrow-derived dendritic cells with the FITC-proteins, and measuring the percentage of FITC+, CD11c+ cells overtime. Bone marrow-derived dendritic cells are loaded with 0.5 mg/ml of the FITC-labeled SARS-CoV-2 peptidogenic proteins for 1 hour, are washed, and then are cultured at 37° C. for various amounts of time. FACS is then used to determine the percentage of FITC+, CD11c+ cells at each time point subtracted to the percentage of FITC+, CD11c+ cells at time 0 h. This represents the percentage of proteolysis of the SARS-CoV-2 peptidogenic proteins. The experiments are repeated with and without prior adsorption of FITC-labeled SARS-CoV-2 peptidogenic proteins onto an adjuvant such as aluminum hydroxide.

Example 5: Antibody Production and Sequencing

Ig-seq of antibody repertoires may follow previously described protocols (10, 29) with minor modifications. B cells can be isolated from the serum, spleen, or other tissues of hyperimmunized rabbits. In order to reduce the complexity of the sequencing library, this population can be sorted to enrich for $CD19^+CD3^-CD27^+CD38^{int}$ memory B cells or B cells that recognize the target antigen (5, 30, 31). These cells are then lysed and mRNA is isolated using standard methods, and reverse transcribed to cDNA using 5' RACE with 3' primers specific for the IgH or IgL constant region (9, 32). The cDNA library is then amplified with primers containing the required paired-end adapter sequences and optional barcodes to enable quantification of template and error correction by averaging multiple reads (8, 9).

Complete determination of antibody sequences requires identifying native VH-VL pairs. As each VH and VL sequence is encoded by a separate mRNA, clonal sequencing may be performed by isolating single B cells in subnanoliter volume wells (5) or microemulsion (9) prior to mRNA isolation, reverse transcription, and overlap extension or linkage PCR. As an alternative, endogenous VH-VL pairs can be identified through partial cross-linking of purified Fabs prior to LC-MS/MS. Under the appropriate conditions, this will result in a fraction of the Fab heavy and light chains forming interchain crosslinks, and the resulting peptide masses will be used to determine native pairing.

In order to identify the antibodies raised in response to a mixture of SARS-CoV-2 peptidogenic proteins and/or Spike fragment, sequence information can be combined with data from high-resolution mass spectrometry. Protein A-purified IgGs can be digested with papain to release the two Fabs from the Fc domain. These can then be immunoaffinity purified on a custom column prepared using the SARS-CoV-2 peptidogenic or Spike fragment or wild type protein immobilized on a solid support, the eluted Fabs proteolytically digested, and the peptide products subjected to mass spectrometry. The resulting peptide masses can be compared with the complete antibody sequencing data to identify the CDR sequences that recognize the antigen. Pairing of IgG VH and VL sequences can be accomplished through chemical cross-linking of the immunoaffinity purified Fabs prior to the proteolytic digest; Young et al have demonstrated the feasibility of this approach (33).

Example 6: Immunization Using a Mixture of SARS-CoV-2 Peptidogenic Proteins

Methods of raising antibodies, including as part of a vaccination protocol, in mammals are well known in the art. In one example, polyclonal antiserum against SARS-CoV-2 peptidogenic proteins is raised by immunization of pathogen free rabbits with a total of 500 µg of a mixture of SARS-CoV-2 peptidogenic proteins over a period of two months. For example, the SARS-CoV-2 peptidogenic proteins can be dissolved in PBS and emulsified with an equal volume of Freund's adjuvant. After the final booster, the serum of the rabbits can be separated to determine the titer of the polyclonal antiserum. To obtain monoclonal antibodies, 4-6 week old Balb/c mice can be immunized with a SARS-CoV-2 peptidogenic protein (for example 4 times with 2 week intervals with 10-100 µg/injection dissolved in Freunds complete adjuvant for the first injection, and Freund's incomplete adjuvant for subsequent immunizations). Splenocytes are isolated and fused with a fusion cell line such as Sp2/0 myeloma cells, followed by limiting dilution. Growing clones are screened using for example an enzyme-linked immunosorbant assay (ELISA). 96 cells plates are coated with SARS-CoV-2 peptidogenic proteins or with a control protein. The culture supernatant is added, followed by washing and addition of a labeled anti-mouse antibody for detection. After limited dilution cloning of the SARS-CoV-2 peptidogenic protein-specific antibody producing hybridomas stable hybridomas are obtained. From each cell, supernatant is collected and by affinity chromatography using protein A sepharose columns monoclonal antibodies can be purified.

For raising antibodies in humans, particularly as part of a vaccination protocol, a similar approach to that described above for the generation of polyclonal antiserum may be taken. Those skilled in the art however, would recognize the need to utilize alternative adjuvant systems instead of Freund's adjuvant. For example, suitable alternative adjuvants may include, but are not limited to, aluminium compounds such as aluminium hydroxide, aluminium phosphate, amorphous aluminium hydroxyphosphate (AAHS) and potassium aluminium sulfate (alum), monophosphoryl lipid A (MPL) based adjuvants, oil-in-water (O/W) emulsions comprising squalene, and immunostimulatory nucleic acids such as cytosine phosphoguanine (CpG) oligonucleotides. Additionally, susceptible patient populations, such as for example, the elderly and/or immunocompromised populations, the use of certain adjuvants (e.g. liposome-based AS01B adjuvant system) and other strategies to achieve even more potent CD4$^+$ and CD8$^+$ T cell responses, may also be employed to achieve strong and protective immune responses in these susceptible patients (Weinberger, Immunity & Ageing 15:3 (2018)).

Example 7: Another Example of Immunization Using a Mixture of SARS-CoV-2 Peptidogenic Proteins In an additional animal model, groups of 5 mice (C57BL/6J; Jackson Labs) can be subcutaneously immunized (primary) with 5 µg mixtures of endotoxin-free SARS-CoV-2 peptidogenic proteins and wild type starting protein emulsified in alum, which is the adjuvant most commonly used in human vaccines. Three weeks later or, optionally, three weeks after one or more subsequent boost (secondary) immunizations, mice are bled and the presence of peptidogenic and/or wild type protein antigen-specific antibodies can be determined by titering the seras by ELISA (direct binding of antibodies in sera to wild type SARS-CoV-2 protein antigen-coated, directly or indirectly (via a biotinylated tag and streptavidin), on the wells). To confirm that the SARS-CoV-2 peptidogenic proteins have a similar conformation as the SARS-CoV-2 starting protein, competitive inhibition assays are performed in which titrated amounts of SARS-CoV-2 starting protein and SARS-CoV-2 peptidogenic proteins are pre-incubated with the seras prior to adding to the SARS-CoV-2 starting protein coated plates. This provides additional evidence, with an immunological probe, that the 3D structure of the SARS-CoV-2 peptidogenic proteins has not been compromised by the engineered mutations.

To determine whether the SARS-CoV-2 peptidogenic proteins and/or Spike fragment result in better secondary antibody responses, groups of mice can be immunized as described above, and 6 weeks after the primary immunization they can be immunized a second time. One week post-secondary immunization, mice are bled and antigen-specific antibody responses are determined by ELISA as described above. Mouse dendritic cells are pulsed in vitro with the SARS-CoV-2 peptidogenic proteins and/or Spike fragment that can generate a strong antibody response, and 24 hrs later the SARS-CoV-2 peptidogenic protein-derived peptides presented by MHCII are isolated and their masses analysed by liquid chromatography and mass spectrometry (LC/MS). These studies require large numbers (>10$^7$) of dendritic cells which are purified from mice previously injected with a mouse tumor line expressing FLT-3L, a cytokine that drives dendritic cell development in vivo (the spleens of these mice fill up with dendritic cells; Segura et al, 2009). To allow for peak identification and the quantification of MHCII-peptides by mass spectrometry, the SARS-CoV-2 peptidogenic protein and/or Spike fragment can be biosynthetically labeled with stable isotopes such as 13C and 15N (during production of the recombinant protein—see above) prior to feeding to the DCs (Hoedt et al 2014).

Example 8: Immunization Using Sequences Encoding a Mixture of SARS-CoV-2 Peptidogenic Proteins Methods of directly injecting polynucleotides into animals are well described in the art. See, for example, U.S. Pat. Nos. 5,676,954; 6,875,748; 5,661,133. Briefly, using the known degeneracy of the genetic code, polynucleotides encoding a mixture of SARS-CoV-2 peptidogenic proteins described herein can be synthesized using standard DNA synthesis techniques. The polynucleotide(s) can then be directly injected into the animal, such as, for example, mice. Specifically, a mixture of polynucleotides encoding the mixture of SARS-CoV-2 peptidogenic proteins can be injected into the quadriceps muscles of restrained awake mice (female 6-12 week old BALB/c or Nude, nu/nu, from Harlan Sprague Dawley, Indianapolis, Ind.). In one embodiment, 50 µg of a polynucleotide in 50 µl solution using a disposable sterile, plastic insulin syringe and 28G ½ needle (Becton-Dickinson, Franklin Lakes, N.J., Cat. No. 329430) fitted with a plastic collar cut from a micropipette tip can be used to inject the mice, as described in Hartikka, J., et al., Hum. Gene Ther. 7:1205-1217 (1996)).

Alternatively, 6-week old Sprague Dawley female mice (body weight 20-25 grams) can be given 5000 ppm ZnOSO4 in their drinking water beginning 24 hours prior to injection. This amount of zinc has been shown to be able to activate the metallothionein promoter. Each mouse is then injected intravenously through a tail vein puncture with a 25 gauge needle with 30 μg of polynucleotides encoding the mixture of SARS-CoV-2 peptidogenic proteins complexed with 150 μg liposome (Lipofection™) in a total volume of 30 μl. In one embodiment, the polynucleotides mixture injected into the mice encodes for different SARS-CoV-2 peptidogenic proteins relating to the same SARS-CoV-2 starting protein. Alternatively, a library of SARS-CoV-2 peptidogenic proteins can be encoded by the mixture of polynucleotides, wherein the library relates to different SARS-CoV-2 starting proteins. Animal care should be maintained throughout the study and should be performed in compliance with the "Guide for the Use and Care of Laboratory Animals", Institute of Laboratory Animal Resources, Commission on Life Sciences, National Research Council, National Academy Press.

After the injected polynucleotide encoding the SARS-CoV-2 peptidogenic proteins are delivered into the cells in the animal, the SARS-CoV-2 peptidogenic proteins are then expressed in vivo. The SARS-CoV-2 peptidogenic proteins can then stimulate the production of antibodies specific to the SARS-CoV-2 peptidogenic proteins. These antibodies can be isolated and used as a polyclonal mixture or further isolated into single species or monoclonals. The process of the immune response and production of antibodies against foreign antigens in vivo are well known in the art. Unlike the traditional protocols of antibody generation, the platform invention described herein allows the simultaneously raising of a group of antibodies against multiple SARS-CoV-2 peptidogenic proteins (whether or not they rely on the same SARS-CoV-2 starting protein). This simultaneous production of antibodies to multiple proteins using a mixture of polynucleotides has the potential to change how antibody production is currently being performed.

Example 9: Immunization Using mRNA Encoding SARS-CoV-2 Peptidogenic Proteins

The methods of directly injecting in vitro transcribed (IVT) mRNA into animals are also well known in the art. See, Sahin et al., Nat Rev Drug Discov. 2014 October; 13(10):759-80; Kariko et al., Mol Ther, 2008 November; 16(11):1833-40; Kariko et al., Nucleic Acid Res, 2011, November; 39(21):e142; U.S. Pat. No. 6,511,832. For example, linearized DNA plasmid templates which encode a mixture of SARS-CoV-2 peptidogenic proteins can be used. All mRNAs can be designed to contain 5' and 3' untranslated regions, the open reading frames, and long poly(A) tails, which can help determine the translational activity and stability of the mRNA molecule after its transfer into cells. For example, mRNAs (including a poly(A) tail) encoding SARS-CoV-2 peptidogenic proteins can be synthesized using triphosphate-derivatives of pseudouridine and 5-methylcytidine (m5C) (TriLink) to generate a modified nucleoside containing RNA. A 5'-cap can be added to the mRNAs by supplementing the transcription reactions with 6 mmol/l 3'-O-Me-m7GpppG, a nonreversible cap analog (New England Biolabs, Beverly, MA) and lowering the concentration of guanosine triphosphate (3.75 mmol/l). Purification of the transcripts can be performed by Turbo DNase (Ambion, Austin, TX) digestion followed by LiCl precipitation and 75% ethanol wash. The concentrations of RNA reconstituted in water can be determined by measuring the optical density at 260 nm. Efficient incorporation of modified nucleotides to the transcripts can be determined by HPLC analyses. All RNA samples can be analyzed by denaturing agarose gel electrophoresis for quality assurance. Lipofectin (Invitrogen, Carlsbad, CA) and mRNA are then complexed in phosphate buffer in order to enhance transfection. To assemble a 50 μl complex of RNA-lipofectin, first 0.4 μl potassium phosphate buffer (0.4 mol/l, pH 6.2) containing 10 μg/μl bovine serum albumin (Sigma, St. Louis, MO) is added to 6.7 μl DMEM, then 0.8 μl lipofectin is mixed in and the sample is incubated for 10 minutes. In a separate tube, 0.25-3 μg of RNA is added to DMEM to a final volume of 3.3 μl. Diluted RNA is added to the lipofectin mix and incubated for 10 minutes. Finally, the RNA-lipofectin complex is further diluted by adding 38.8 μl DMEM.

The RNA encoding the SARS-CoV-2 peptidogenic proteins can then be injected into the mouse models described herein. In general, a composition comprising 60 μl final volume with 1 μl lipofectin and different amounts of polynucleotides encoding the SARS-CoV-2 peptidogenic proteins are injected into the lateral vein using a 1-ml syringe with a 27G½ needle (Becton Dickinson, San Diego, CA). Alternatively, the polynucleotides can be injected via intramuscular, intradermal, intranasal, subcutaneous, intravenous, intratracheal, and intrathecal deliveries. After the polynucleotides are delivered into the cells, the SARS-CoV-2 peptidogenic proteins are synthesized in vivo. The immune responses triggered by the SARS-CoV-2 peptidogenic proteins and the subsequent production of antibodies in the animals are described herein.

Example 10: Affinity Maturing Antibodies to Peptidogenic Protein Using Phage Display Once antibodies have been raised to the SARS-CoV-2 peptidogenic proteins by presenting and allowing the SARS-CoV-2 peptidogenic protein to undergo processing by an antigen presenting cell such as described in the Examples herein, the resulting antibodies can be matured using a display approach. For example, a library of phage displaying scFvs or Fabs derived from B cell mRNA encoding the target-specific antibodies can be screened in an assay to identify those phage displaying scFvs or Fabs that immunospecifically bind to a SARS-CoV-2 peptidogenic protein or to a SARS-CoV-2 starting protein. Phage displaying scFvs or Fabs that bound to immobilized peptidogenic protein or SARS-CoV-2 starting protein can be identified after panning on immobilized peptidogenic protein or SARS-CoV-2 starting protein and assessing by ELISA for binding to immobilized SARS-CoV-2 peptidogenic protein or SARS-CoV-2 starting protein. The SARS-CoV-2 peptidogenic protein or SARS-CoV-2 starting protein that is immobilized on plates for these assays can be purified from supernatants of Sf9 cells infected with a baculovirus expression construct as described in Moore et al., Science 285: 260-263 or from supernatants from HEK293 cells. Each of the identified scFvs or Fabs can then be sequenced.

To determine the specificity of each of the unique scFvs or Fabs, a phage ELISA can be performed for each scFvs or Fabs against the SARS-CoV-2 peptidogenic protein or SARS-CoV-2 starting protein and control wells. Individual E. coli colonies containing a phagemid representing one of the unique scFvs or Fabs can be inoculated into 96-well plates containing 100 μl 2TYAG medium (Tryptone+yeast broth supplemented with ampicillin and glucose) per well. Plates are incubated at 37° C. for 4 hours, shaking. M13K07 helper phage is then added to each well to a MOI of 10 and the plates are incubated for a further 1 hour at 37° C. The plates are centrifuged in a benchtop centrifuge at 2000 rpm for 10 minutes. The supernatant is removed and cell pellets are resuspended in 100 µl 2TYAK (tryptone+yeast broth supplemented with ampicillin and kanamycin) and incubated at 30° C. overnight, shaking.

The next day, plates are centrifuged at 2000 rpm for 10 min and the 100 µl phage-containing supernatant from each well are carefully transferred into a fresh 96-well plate. Twenty µl of 6×MPBS (dry milk dissolved in PBS) is added to each well, and incubated at room temperature for 1 hour to pre-block the phage prior to ELISA.

Flexible 96-well plates (Falcon) are coated overnight at 4° C. with a SARS-CoV-2 peptidogenic protein (directly or indirectly, at 1 mg/ml) in PBS, BSA (1 g/ml) in PBS, or PBS alone. After coating, the solutions are removed from the wells, and the plates are blocked for 1 hour at room temperature in MPBS. The plates are washed 3 times with PBS and then 50 µl of pre-blocked phage is added to each well. The plates are incubated at room temperature for 1 hour and then washed with 3 changes of PBST (PBS plus Tween) followed by 3 changes of PBS. To each well, 50 µl of an anti-gene VIII-HRP conjugate (Pharmacia) at a 1 to 5000 dilution in MPBS is added and the plates are incubated at room temperature for 1 hour. Each plate is washed three times with PBST followed by three times with PBS. Then 50 µl of an RP-labelled anti-mouse antibody (DAKO EnVision) diluted 1/50 in 3% MPBS is added and incubated for 1 hour at room temperature. Each plate is then washed three times with PBST followed by three times with PBS. Fifty µl of TMB substrate is then added to each well, and incubated at room temperature for 30 minutes or until color development. The reaction is stopped by the addition of 25 µl of 0.5 M H2SO4. The signal generated is measured by reading the absorbance at 450 nm (A450) using a microtiter plate reader (Bio-Rad 3550).

Conversion of scFvs or Fabs to IgG1 format can be performed as follows. The VH domain and the VL domains of scFvs or Fabs that we wish to convert into IgG molecules can be cloned into vectors containing the nucleotide sequences of the appropriate heavy (human IgG1, IgG2, etc.) or light chain (human kappa or human lambda) constant regions such that a complete heavy or light chain molecule could be expressed from these vectors when transfected into an appropriate host cell. Further, when cloned heavy and light chains are both expressed in one cell line (from either one or two vectors), they can assemble into a complete functional antibody molecule that is secreted into the cell culture medium. Methods for converting scFvs or Fabs into conventional antibody molecules are well known within the art.

The purification of the IgG from the fermentation broth is performed using a combination of conventional techniques commonly used for antibody production. Typically the culture harvest is clarified to remove cells and cellular debris prior to starting the purification scheme. This would normally be achieved by using either centrifugation or filtration of the harvest. Following clarification, the antibody would typically be captured and significantly purified using affinity chromatography on Protein A Sepharose. The antibody is bound to Protein A Sepharose at basic pH and, following washing of the matrix, is eluted by a reduction of the pH. Further purification of the antibody is then achieved by gel filtration. As well as removing components with different molecular weights from the antibody this step can also be used to buffer exchange into the desired final formulation buffer.

Example 11: Assays Used to Characterize Antibodies and Measure Cross-Reactivity

Antibodies (whether cross-reacting or antibodies raised against the SARS-CoV-2 peptidogenic protein and/or Spike fragment) (including scFvs or Fabs and other molecules comprising, or alternatively consisting of, antibody fragments or variants thereof) may be screened in a variety of assays, some of which are described below to identify those antibodies that bind to the SARS-CoV-2 peptidogenic protein and/or Spike fragment and/or SARS-CoV-2 starting protein.

In one particular assay, antibodies (whether cross-reacting or antibodies raised against the SARS-CoV-2 peptidogenic protein and/or Spike fragment) that bind to a biotinylated protein (whether the SARS-CoV-2 peptidogenic protein and/or Spike fragment and/or SARS-CoV-2 starting protein) can be captured on streptavidin coated magnetic beads. This assay may be applied to identify antibodies (whether cross-reacting or antibodies raised against the SARS-CoV-2 peptidogenic protein and/or Spike fragment) that neutralize and/or bind to the SARS-CoV-2 peptidogenic protein and/or Spike fragment and/or SARS-CoV-2 starting protein. Additionally, antibodies may be assayed in neutralization assays described herein or otherwise known in the art. For example, antibodies may be tested for their ability to inhibit the SARS-CoV-2 peptidogenic protein and/or Spike fragment and/or SARS-CoV-2 starting protein from binding to IM9 cells. In this assay, labeled peptidogenic protein and/or Spike fragment and/or SARS-CoV-2 starting protein (e.g., biotinylated) is incubated with antibodies to allow for the formation of protein-antibody complexes. Following incubation, an aliquot of the protein-antibody sample is added to IM9 cells. Binding may be determined using techniques known in the art. For example, the binding of biotinylated protein (whether the SARS-CoV-2 peptidogenic protein and/or Spike fragment and/or SARS-CoV-2 starting protein) to IM9 cells may be detected using a fluorimeter following the addition of streptavidin-delfia. Biotinylated protein, if it is not bound by antibodies that neutralize the protein, will bind to the cells and can be detected. Thus, an antibody that decreases the amount of biotinylated-protein that binds to IM9 cells (relative to a control sample in which the protein had been preincubated with an irrelevant antibody or no antibody at all) is identified as one that binds to and neutralizes the protein.

Other immunoassays which can be used to analyze cross-reactivity and/or characterize the antibodies raised against the SARS-CoV-2 peptidogenic protein and/or Spike fragment include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays, to name but a few. Such assays are routine and well known in the art (see, e.g., Ausubel et al, eds, 1994, Current Protocols in Molecular Biology, Vol. 1, John Wiley & Sons, Inc., New York.

Exemplary immunoassays are described briefly below (but are not intended by way of limitation). Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the cross-reacting antibody of interest to the cell lysate, incubating for a period of time (e.g., 1 to 4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a SARS-CoV-2 peptidogenic protein and/or Spike fragment and/or a SARS-CoV-2 starting protein can be assessed by, e.g., western blot analysis or mass spectrometry. One of skill in the art would be knowledgeable as to the parameters that can be modified to increase the binding of the antibody to a SARS-CoV-2 peptidogenic protein and/or a SARS-CoV-2 starting protein and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 1211) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

In a further example, ELISAs comprise preparing peptidogenic protein and/or Spike fragment and/or a SARS-CoV-2 starting protein, coating the well of a 96-well microtiter plate (directly or indirectly) with the SARS-CoV-2 peptidogenic protein and/or Spike fragment and/or a SARS-CoV-2 starting protein, washing away the SARS-CoV-2 peptidogenic protein and/or Spike fragment and/or a SARS-CoV-2 starting protein that did not bind the wells, adding the antibody of interest conjugated to a detectable compound such as an enzyme (e.g., horseradish peroxidase or alkaline phosphatase) to the wells and incubating for a period of time, washing away unbound antibodies or non-specifically bound antibodies, and detecting the presence of the antibodies specifically bound to the SARS-CoV-2 peptidogenic protein and/or Spike fragment and/or a SARS-CoV-2 starting protein coating the well. In ELISAs the antibody of interest does not have to be conjugated to a detectable compound; instead, a second antibody (which recognizes the antibody of interest) conjugated to a detectable compound may be added to the well.

Further, instead of coating the well with the antigen, the antibody may be coated to the well. In this case, the detectable molecule could be the SARS-CoV-2 peptidogenic protein and/or Spike fragment and/or a SARS-CoV-2 starting protein conjugated to a detectable compound such as an enzyme (e.g., horseradish peroxidase or alkaline phosphatase). One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1. The binding affinity of an antibody to a SARS-CoV-2 peptidogenic protein and/or Spike fragment and/or a SARS-CoV-2 starting protein and the off-rate of an antibody-protein interaction can be determined by competitive binding assays. One example of a competitive binding assay is a radioimmunoassay comprising the incubation of labeled SARS-CoV-2 peptidogenic protein and/or Spike fragment and/or a SARS-CoV-2 starting protein (e.g., 3H or 1251) with the antibody of interest in the presence of increasing amounts of unlabeled SARS-CoV-2 peptidogenic protein and/or Spike fragment and/or a SARS-CoV-2 starting protein, and the detection of the antibody bound to the labeled SARS-CoV-2 peptidogenic protein and/or Spike fragment and/or a SARS-CoV-2 starting protein. The affinity of the antibody of the present invention for a SARS-CoV-2 peptidogenic protein and/or Spike fragment and/or the SARS-CoV-2 starting protein and the binding off-rates can be determined from the data by Scatchard plot analysis. Competition with a second antibody can also be determined using radioimmunoassays. In this case, a SARS-CoV-2 peptidogenic protein and/or Spike fragment and/or SARS-CoV-2 starting protein is incubated with an antibody of interest conjugated to a labeled compound (e.g., 3H or 1251) in the presence of increasing amounts of an unlabeled second anti-peptidogenic protein antibody.

In a preferred embodiment, BIAcore kinetic analysis can be used to determine the binding on and off rates of antibodies to SARS-CoV-2 peptidogenic protein and/or Spike fragment and/or SARS-CoV-2 starting protein. BIAcore kinetic analysis comprises analyzing the binding and dissociation of SARS-CoV-2 peptidogenic protein and/or Spike fragment and/or SARS-CoV-2 starting protein from chips with immobilized antibodies on their surface.

Example 12: Vaccination

Further, a mixture of SARS-CoV-2 peptidogenic proteins as described herein can be used as a vaccine. For example a concentration of 320 µg/mL in phosphate-buffered saline (PBS, 155 mM NaCl, 1 mM KH2PO4, 3 mM Na2HPO3) of the SARS-CoV-2 peptidogenic proteins are aseptically emulsified with an equal volume of Montanide ISA 51 to give a final vaccine concentration of 160 µg/mL. The emulsion is achieved by homogenizing the mixture in a volume of 200 mL in a 400-mL vessel at room temperature for 6 min at 6000 rpm using an Omni Mixer-ES homogenizer (Omni International, Warren-ton, VA). Each vaccine undergoes comprehensive quality control analyses to ensure general safety, purity, identity, integrity, and uniform water-in-oil droplet size. Stability of vaccines stored at 2-8° C. is evaluated regularly using mouse immunogenicity tests and physical and biochemical assays to verify the vaccine safety, potency, uniformity, purity, and integrity until 4-10 months after the termination of the human immunizations. The 160 ug/mL peptidogenic protein vaccines are diluted with the PBS/ISA 51 (the adjuvant control vaccine) to the final dose forms of 10 ug/mL or 40 ug/mL prior to immunizations. As a result of different degrees of dilution, these vaccines contained two different ratios of vaccine-containing vs. vaccine-free compositions, namely ratios of 1:15 and 1:3 for the 10 ug/mL and 40 ug/mL formulations, respectively. The test and control vaccines may be highly viscous and require vortexing prior to and after manipulation to ensure homogeneity. The vaccine can be administered intramuscularly by needle and syringe. Vaccine-induced T-cell responses are further evaluated by means of a qualified intracellular cytokine staining assay. Peripheral-blood mononuclear cells are quantified to determine the proportion of total and memory CD4 and CD8 T cells producing interleukin-2, interferon-γ or tumor necrosis factor (TNF).

Polynucleotides encoding a mixture of SARS-CoV-2 peptidogenic proteins can also be used as a vaccine by administering to a patient the polynucleotide described herein.

LITERATURE CITED

1. Starner N, et al., The Protein Capture Reagents Program Data Portal. (Submitted). 2014.
2. Paduch M, et al., Methods. 2013; 60(1):3-14. doi: 10.1016/j.ymeth.2012.12.010.
3. Acton T B, et al., Methods in Enzymology: Academic Press; 2005. p. 210-43.
4. Xiao R, et al., Journal of structural biology. 2010; 172(1):21-33.
5. DeKosky B J, Nat Biotech. 2013; 31(2):166-9. doi: 10.1038/nbt.2492.
6. Naso and Panavas, Current drug discovery technologies. 2014; 11(1):85-95. Epub 2013/09/12. PubMed PMID: 24020911.
7. Reddy S T et al. Current Opinion in Biotechnology. 2011; 22(4):584-9.
8. Vollmers C, et al., Proceedings of the National Academy of Sciences. 2013; 110(33):13463-8. doi: 10.1073/pnas.1312146110.
9. Georgiou G, et al., Nat Biotech. 2014; 32(2):158-68. doi: 10.1038/nbt.2782.
10. Sato S, et al., Nat Biotechnol. 2012; 30(11):1039-43. Epub 2012/11/10. doi: 10.1038/nbt.2406. PubMed PMID: 23138294.
11. Dobson C M. Nature. 2003; 426(6968):884-90.
12. Bowie, and Sauer Biochemistry. 1989; 28(18):7139-43. doi: 10.1021/bi00444a001.
13. Milla M E, et al., Nat Struct Mol Biol. 1994; 1(8):518-23.
14. Waldburger C D, et al., Nat Struct Mol Biol. 1995; 2(2):122-8.
15. Ascenzi P, et al., Current Protein and Peptide Science. 2003; 4(3):231-51. doi: 10.2174/1389203033487180.
16. Marks C, et al., Science. 1987; 235(4794):1370-3. doi: 10.1126/science.2435002.
17. Nilsson B et al., Journal of Biological Chemistry. 1991; 266(5):2970-7.
18. Betz S F, Protein Science. 1993; 2(10):1551-8. doi: 10.1002/pro.5560021002.
19. Eigenbrot and Kossiakoff, Protein Engineering. 1990; 3(7):591-8. doi: 10.1093/protein/3.7.591.
20. Hurle et al., Biochemistry. 1990; 29(18):4410-9. doi: 10.1021/bi00470a021.
21. Krokoszynska I, et al., Journal of Molecular Biology. 1998; 275(3):503-13. doi: 10.1006/jmbi.1997.1460.
22. Staley J P et al., Proceedings of the National Academy of Sciences. 1992; 89(5):1519-23. doi: 10.1073/pnas.89.5.1519.
23. Castro M J M et al.,Biochemistry. 1996; 35(35):11435-46. doi: 10.1021/bi960515w.
24. Altman J D, et al., Protein Engineering. 1991; 4(5):593-600. doi: 10.1093/protein/4.5.593.
25. Cull and Schatz, Methods Enzymol. 2000; 326:430-40. Epub 2000/10/19. PubMed PMID: 11036656.
26. Fiorucci L et al., Histochem J. 1989; 21(12):721-30. doi: 10.1007/BF01002838.
27. Nori S L, et al., Peptides. 1992; 13(2):365-71. doi: dx.doi.org/10.1016/0196-9781(92)90122-J.
28. Savage M J, et al., Amyloid. 1995; 2(4):234-40. doi: doi:10.3109/13506129508999005.
29. Cheung W C et al., Nat Biotechnol. 2012; 30(5):447-52. Epub 2012/03/27. doi: 10.1038/nbt.2167. PubMed PMID: 22446692.
30. Kaminski D A et al., Frontiers in immunology. 2012; 3:302. Epub 2012/10/23. doi: 10.3389/fimmu.2012.00302. PubMed PMID: 23087687; PubMed Central PMCID: PMCPmc3467643.
31. Maecker H T et al., Nature reviews Rheumatology. 2012; 8(6):317-28. Epub 2012/06/01. doi: 10.1038/nrrheum.2012.66. PubMed PMID: 22647780; PubMed Central PMCID: PMCPmc3409841.
32. Toung J M et al., Genome research. 2011; 21(6):991-8. doi: 10.1101/gr.116335.110.
33. Young M M et al., Proceedings of the National Academy of Sciences. 2000; 97(11):5802-6. doi: 10.1073/pnas.090099097.
34. Goh C S et al., Nucleic Acids Research. 2003; 31(11): 2833-8. doi: 10.1093/nar/gkg397.
35. Glanville J, et al., Proceedings of the National Academy of Sciences. 2009; 106(48):20216-21. doi: 10.1073/pnas.0909195106.
36. Brochet X et al., Nucleic Acids Res. 2008; 36(Web Server issue):W503-8. Epub 2008/05/27. doi: 10.1093/nar/gkn316. PubMed PMID: 18503082; PubMed Central PMCID: PMCPmc2447746.
37. D'Angelo S., et al., mAbs. 2014; 6(1):160-72. Epub 2014/01/16. doi: 10.4161/mabs.27105. PubMed PMID: 24423623; PubMed Central PMCID: PMCPmc3929439.
38. Eng J K et al., Journal of the American Society for Mass Spectrometry. 1994; 5(11):976-89. a doi: dx.doi.org/10.1016/1044-0305(94)80016-2.
39. Van Regenmortel M H V. Journal of Molecular Recognition. 2011; 24(5):741-53. doi: 10.1002/jmr.1116.
40. Hurlburt et al., Nat. Commun. 11:5413 (2020).

The invention claimed is:

1. A composition comprising:
(a) at least one SARS-CoV-2 peptidogenic protein,
(b) one or more polynucleotides encoding the at least one SARS-CoV-2 peptidogenic protein of (a); or
(c) a combination of (a) and (b);
wherein the at least one SARS-CoV-2 peptidogenic protein comprises amino acids 319-541, 319-591, or 316-594 of SEQ ID NO:15 with at least one mutation selected from Y365L, I402V, and/or V511A, and wherein the SARS CoV-2 peptidogenic protein optionally further comprises 1, 2, 3, 4, 5, 6, 7, 8, 9, 10, 15, 20, 30 or 50 additional amino acid substitutions, wherein the at least one SARS CoV-2 peptidogenic protein has altered conformational dynamics as compared to a SARS-CoV-2 starting protein, and wherein the SARS-CoV-2 starting protein comprises a SARS-CoV-2 Spike fragment comprising amino acids 319-541, 319-591, or 316-594 of SEQ ID NO:15.

2. The composition of claim 1, wherein the altered conformational dynamics is obtained by:
(a) examining the 3-D structure of the SARS-CoV-2 starting protein, identifying non-surface amino acid residues of the SARS-CoV-2 starting protein and replacing at least one non-surface amino acid residue in the SARS-CoV-2 starting protein to generate the at least one SARS-CoV-2 peptidogenic protein; or
(b) examining a model of the 3-D structure of the SARS-CoV-2 starting protein, identifying non-surface amino acid residues of the SARS-CoV-2 starting protein and replacing at least one non-surface amino acid residue in the SARS-CoV-2 starting protein to generate the at least one SARS-CoV-2 peptidogenic protein; or
(c) comparing the pattern of conserved amino acid homology across proteins orthologous to the SARS-CoV-2 starting protein from different species to identify non-surface amino acid residues of the SARS-CoV-2 starting protein and replacing at least one non-surface amino acid residue in the SARS-CoV-2 starting protein to generate the at least one SARS-CoV-2 peptidogenic protein; or (d) replacing at least one non-surface amino acid residue of the SARS-CoV-2 starting protein to generate the at least one SARS-CoV-2 peptidogenic protein; or (e) replacing at least one non-surface amino acid residue with a smaller amino acid residue; or (f) replacing at least one non-surface amino acid residue with an alanine or glycine; or (g) eliminating at least one disulfide bond in the SARS-CoV-2 starting protein.

3. The composition of claim 1, wherein the at least one SARS-CoV-2 peptidogenic protein comprises at least 2, 3, 4, 5, 6, 7, 8, 9, 10, 11, 12, 13, 14, 15, 16, 17, 18, 19, or 20 amino acid substitutions compared to the SARS-CoV-2 starting protein.

4. The composition of claim 1, wherein the conformational dynamics of the SARS-CoV-2 starting protein are altered by replacing:

a. at least one non-surface threonine with a valine, alanine, glycine or serine; or b. at least one non-surface cysteine with alanine, valine, glycine, serine or threonine; or c. at least one non-surface valine with alanine, glycine, leucine or isoleucine; or d. at least one non-surface leucine with alanine, valine, glycine, or isoleucine; or e. at least one non-surface isoleucine with alanine, valine, leucine, or glycine; or f. at least one non-surface proline with methionine, alanine, valine, leucine, isoleucine, or glycine; or g. at least one non-surface methionine with alanine, valine, leucine, isoleucine, or glycine; or h. at least one non-surface phenylalanine with tyrosine, methionine, histidine, alanine, valine, leucine, isoleucine, or glycine; or i. at least one non-surface tyrosine with phenylalanine, methionine, histidine, alanine, valine, leucine, isoleucine, or glycine; or j. at least one non-surface tryptophan with tyrosine, phenylalanine, methionine, histidine, alanine, valine, leucine, isoleucine, or glycine; or k. at least one non-surface aspartic acid with glutamic acid, glutamine, asparagine, glycine, serine, threonine, alanine, valine, leucine, or isoleucine; or l. at least one non-surface asparagine with glycine, serine, threonine, alanine, valine, leucine, isoleucine, glutamine, glutamic acid, or aspartic acid; or m. at least one non-surface glutamic acid with aspartic acid, asparagine, glutamine, glycine, serine, threonine, alanine, valine, leucine, or isoleucine; or n. at least one non-surface glutamine with glutamic acid, aspartic acid, asparagine, glutamine, glycine, serine, threonine, alanine, valine, leucine, or isoleucine; or o. at least one non-surface lysine with arginine, histidine, glycine, serine, threonine, alanine, valine, methionine, leucine, or isoleucine; or p. at least one non-surface arginine with lysine, histidine, glycine, serine, threonine, alanine, valine, methionine, leucine, or isoleucine; or q. at least one non-surface histidine with phenylalanine, tyrosine, lysine, arginine, glycine, serine, threonine, alanine, valine, glutamine, asparagine, leucine, methionine or isoleucine; or r. at least one non-surface alanine with a glycine or proline; or s. at least one non-surface glycine with an alanine or proline; or t. at least one non-surface serine with an alanine or glycine; or u. at least one non-surface residue with a non-natural amino acid; or v. a combination of any of the above replacements.

5. The composition of claim 1, wherein the SARS-CoV-2 starting protein consists of the amino acid sequence of amino acids 319-541, 319-591, or 316-594 of SEQ ID NO:15.

6. The composition of claim 1, wherein the change in conformational dynamics of the at least one SARS-CoV-2 peptidogenic protein is measured by:

(a) a change in melting temperature as compared to the SARS-CoV-2 starting protein; or (b) a change in Gibbs free energy of stabilization or proteolytic sensitivity assay; or (c) a change in Gibbs free energy, wherein the change in Gibbs free energy of stabilization is measured by denaturant modulated equilibrium unfolding, wherein the denaturant is urea or guanidinium hydrochloride.

7. The composition of claim 1, wherein the composition comprises two or more SAR-CoV-2 peptidogenic proteins derived from:

(a) the same SARS-CoV-2 starting protein; or (b) multiple SARS-CoV-2 starting proteins.

8. A method of treating a SARS-CoV-2 infection in a subject in need thereof, comprising administering to the subject an effective amount of the composition of claim 1.

9. The method of claim 8, wherein the composition comprises one or more polynucleotides encoding the at least one SARS-CoV-2 peptidogenic protein.

10. The method of claim 9, wherein the composition comprises one or more polynucleotides encoding the at least one SARS-CoV-2 peptidogenic protein, wherein the one or more polynucleotides comprise DNA or in vitro transcribed mRNA, optionally wherein the mRNA comprises a poly(A) tail and/or a 5' cap.

11. A method of generating an immune response in an animal against a SARS-CoV-2 peptidogenic protein, comprising administering to the animal an effective amount of the composition of claim 1 to generate an immune response in the animal, wherein the immune response comprises the generation of antibodies.

12. The method of claim 11, wherein the method further comprises isolating antibodies from the animal.

13. A host cell comprising the one or more polynucleotides encoding the SARS-CoV-2 peptidogenic protein of claim 1.

14. The composition of claim 1, wherein the composition comprises one or more polynucleotides that encode:

(a) a mixture of SARS-CoV-2 peptidogenic proteins derived from the same SARS-CoV-2 starting protein; or (b) a mixture of SARS-CoV-2 peptidogenic proteins derived from multiple SARS-CoV-2 starting proteins.

15. A SARS-CoV-2 peptidogenic protein, wherein the SARS CoV-2 peptidogenic protein comprises amino acids 319-541, 319-591, or 316-594 of SEQ ID NO:15 with at least one mutation selected from Y365L, I402V, and/or V511A, optionally wherein the SARS CoV-2 peptidogenic protein further comprises 1, 2, 3, 4, 5, 6, 7, 8, 9, 10, 15, 20, 30 or 50 additional amino acid substitutions, and wherein the SARS-CoV-2 peptidogenic protein optionally further comprises a C-terminal tag amino acid sequence.

16. A polynucleotide encoding the SARS-CoV-2 peptidogenic protein of claim 15.

17. The composition of claim 1, wherein the composition further comprises the SARS-CoV-2 starting protein or a polynucleotide encoding the SARS-CoV-2 starting protein.

18. A method of treating a SARS-CoV-2 infection in a subject in need thereof, comprising administering to the subject an effective amount of the SARS-CoV-2 peptidogenic protein of claim 15 or a polynucleotide encoding the SARS-CoV-2 peptidogenic protein.

19. The method of claim 18, wherein the method comprises administering a DNA or an in vitro transcribed mRNA encoding the SARS-CoV-2 peptidogenic protein, optionally wherein the mRNA comprises a poly(A) tail and/or a 5' cap.

20. A method of generating an immune response in an animal against a SARS-CoV-2 peptidogenic protein, comprising administering to the animal an effective amount of the SARS-CoV-2 peptidogenic protein of claim 15 or a polynucleotide encoding the SARS-CoV-2 peptidogenic protein to generate an immune response in the animal, wherein the immune response comprises the generation of antibodies.

21. The method of claim 20 wherein the method further comprises isolating antibodies from the animal.

22. A host cell comprising a polynucleotide encoding the SARS-CoV-2 peptidogenic protein of claim 15.

\*   \*   \*   \*   \*

SEQUENCE LISTING

```
Sequence total quantity: 110
SEQ ID NO: 1          moltype = AA  length = 492
FEATURE               Location/Qualifiers
REGION                1..492
                      note = misc_feature - O15393 TMPS2_Human
source                1..492
```

```
                                 mol_type = protein
                                 organism = SARS-COV-2
SEQUENCE: 1
MALNSGSPPA IGPYYENHGY QPENPYPAQP TVVPTVYEVH PAQYYPSPVP QYAPRVLTQA     60
SNPVVCTQPK SPSGTVCTSK TKKALCITLT LGTFLVGAAL AAGLLWKFMG SKCSNSGIEC    120
DSSGTCINPS NWCDGVSHCP GGEDENRCVR LYGPNFILQV YSSQRKSWHP VCQDDWNENY    180
GRAACRDMGY KNNFYSSQGI VDDSGSTSFM KLNTSAGNVD IYKKLYHSDA CSSKAVVSLR    240
CIACGVNLNS SRQSRIVGGE SALPGAWPWQ VSLHVQNVHV CGGSIITPEW IVTAAHCVEK    300
PLNNPWHWTA FAGILRQSFM FYGAGYQVEK VISHPNYDSK TKNNDIALMK LQKPLTFNDL    360
VKPVCLPNPG MMLQPEQLCW ISGWGATEEK GKTSEVLNAA KVLLIETQRC NSRYVYDNLI    420
TPAMICAGFL QGNVDSCQGD SGGPLVTSKN NIWWLIGDTS WGSGCAKAYR PGVYGNVMVF    480
TDWIYRQMRA DG                                                       492

SEQ ID NO: 2        moltype = AA   length = 794
FEATURE             Location/Qualifiers
REGION              1..794
                    note = misc_feature - P09958 FURIN_HUMAN
source              1..794
                    mol_type = protein
                    organism = SARS-COV-2
SEQUENCE: 2
MELRPWLLWV VAATGTLVLL AADAQGQKVF TNTWAVRIPG GPAVANSVAR KHGFLNLGQI     60
FGDYYHFWHR GVTKRSLSPH RPRHSRLQRE PQVQWLEQQV AKRRTKRDVY QEPTDPKFPQ    120
QWYLSGVTQR DLNVKAAWAQ GYTGHGIVVS ILDDGIEKNH PDLAGNYDPG ASFDVNDQDP    180
DPQPRYTQMN DNRHGTRCAG EVAAVANNGV CGVGVAYNAR IGGVRMLDGE VTDAVEARSL    240
GLNPNHIHIY SASWGPEDDG KTVDGPARLA EEAFFRGVSQ GRGGLGSIFV WASGNGGREH    300
DSCNCDGYTN SIYTLSISSA TQFGNVPWYS EACSSTLATT YSSGNQNEKQ IVTTDLRQKC    360
TESHTGTSAS APLAAGIIAL TLEANKNLTW RDMQHLVVQT SKPAHLNAND WATNGVGRKV    420
SHSYGYGLLD AGAMVALAQN WTTVAPQRKC IIDILTEPKD IGKRLEVRKT VTACLGEPNH    480
ITRLEHAQAR LTLSYNRRGD LAIHLVSPMG TRSTLLAARP HDYSADGFND WAFMTTHSWD    540
EDPSGEWVLE IENTSEANNY GTLTKFTLVL YGTAPEGLPV PPESSGCKTL TSSQACVVCE    600
EGFSLHQKSC VQHCPPGFAP QVLDTHYSTE NDVETIRASV CAPCHASCAT CQGPALTDCL    660
SCPSHASLDP VEQTCSRQSQ SSRESPPQQQ PPRLPPEVEA GQRLRAGLLP SHLPEVVAGL    720
SCAFIVLVFV TVFLVLQLRS GFSFRGVKVY TMDRGLISYK GLPPEAWQEE CPSDSEEDEG    780
RGERTAFIKD QSAL                                                     794

SEQ ID NO: 3        moltype = AA   length = 740
FEATURE             Location/Qualifiers
REGION              1..740
                    note = misc_feature - Q92499 DDX1_HUMAN
source              1..740
                    mol_type = protein
                    organism = SARS-COV-2
SEQUENCE: 3
MAAFSEMGVM PEIAQAVEEM DWLLPTDIQA ESIPLILGGG DVLMAAETGS GKTGAFSIPV     60
IQIVYETLKD QQEGKKGKTT IKTGASVLNK WQMNPYDRGS AFAIGSDGLC CQSREVKEWH    120
GCRATKGLMK GKHYYEVSCH DQGLCRVGWS TMQASLDLGT DKFGFGFGGT GKKSHNKQFD    180
NYGEEFTMHD TIGCYLDIDK GHVKFSKNGK DLGLAFEIPP HMKNQALFPA CVLKNAELKF    240
NFGEEEFKFP PKDGFVALSK APDGYIVKSQ HSGNAQVTQT KFLPNAPKAL IVEPSRELAE    300
QTLNNIKQFK KYIDNPKLRE LLIIGGVAAR DQLSVLENGV DIVVGTPGRL DDLVSTGKLN    360
LSQVRFLVLD EADGLLSQGY SDFINRMHNQ IPQVTSDGKR LQVIVCSATL HSFDVKKLSE    420
KIMHFPTWVD LKGEDSVPDT VHHVVVPVNP KTDRLWERLG KSHIRTDDVH AKDNTRPGAN    480
SPEMWSEAIK ILKGEYAVRA IKEHKMDQAI IFCRTKIDCD NLEQYFIQQG GGPDKKGHQF    540
SCVCLHGDRK PHERKQNLER FKKGDVRFLI CTDVAARGID IHGVPYVINV TLPDEKQNYV    600
HRIGRVGRAE RMGLAISLVA TEKEKVWYHV CSSRGKGCYN TRLKEDGGCT IWYNEMQLLS    660
EIEEHLNCTI SQVEPDIKVP VDEFDGKVTY GQKRAAGGGS YKGHVDILAP TVQELAALEK    720
EAQTSFLHLG YLPNQLFRTF                                               740

SEQ ID NO: 4        moltype = AA   length = 805
FEATURE             Location/Qualifiers
REGION              1..805
                    note = misc_feature - Q9BYF1 ACE2_HUMAN
source              1..805
                    mol_type = protein
                    organism = SARS-COV-2
SEQUENCE: 4
MSSSSWLLLS LVAVTAAQST IEEQAKTFLD KFNHEAEDLF YQSSLASWNY NTNITEENVQ     60
NMNNAGDKWS AFLKEQSTLA QMYPLQEIQN LTVKLQLQAL QQNGSSVLSE DKSKRLNTIL    120
NTMSTIYSTG KVCNPDNPQE CLLLEPGLNE IMANSLDYNE RLWAWESWRS EVGKQLRPLY    180
EEYVVLKNEM ARANHYEDYG DYWRGDYEVN GVDGYDYSRG QLIEDVEHTF EEIKPLYEHL    240
HAYVRAKLMN AYPSYISPIG CLPAHLLGDM WGRFWTNLYS LTVPFGQKPN IDVTDAMVDQ    300
AWDAQRIFKE AEKFFVSVGL PNMTQGFWEN SMLTDPGNVQ KAVCHPTAWD LGKGDFRILM    360
CTKVTMDDFL TAHHEMGHIQ YDMAYAAQPF LLRNGANEGF HEAVGEIMSL SAATPKHLKS    420
IGLLSPDFQE DNETEINFLL KQALTIVGTL PFTYMLEKWR WMVFKGEIPK DQWMKKWWEM    480
KREIVGVVEP VPHDETYCDP ASLFHVSNDY SFIRYYTRTL YQFQFQEALC QAAKHEGPLH    540
KCDISNSTEA GQKLFNMLRL GKSEPWTLAL ENVVGAKNMN VRPLLNYFEP LFTWLKDQNK    600
NSFVGWSTDW SPYADQSIKV RISLKSALGD KAYEWNDNEM YLFRSSVAYA MRQYFLKVKN    660
QMILFGEEDV RVANLKPRIS FNFFVTAPKN VSDIIPRTEV EKAIRMSRSR INDAFRLNDN    720
SLEFLGIQPT LGPPNQPPVS IWLIVFGVVM GVIVVGIVIL IFTGIRDRKK KNKARSGENP    780
```

-continued

```
YASIDISKGE NNPGFQNTDD VQTSF                                                   805

SEQ ID NO: 5              moltype = AA  length = 313
FEATURE                   Location/Qualifiers
REGION                    1..313
                          note = misc_feature - O43765 SGTA_HUMAN
source                    1..313
                          mol_type = protein
                          organism = SARS-COV-2
SEQUENCE: 5
MDNKKRLAYA IIQFLHDQLR HGGLSSDAQE SLEVAIQCLE TAFGVTVEDS DLALPQTLPE             60
IFEAAATGKE MPQDLRSPAR TPPSEEDSAE AERLKTEGNE QMKVENFEAA VHFYGKAIEL             120
NPANAVYFCN RAAAYSKLGN YAGAVQDCER AICIDPAYSK AYGRMGLALS SLNKHVEAVA             180
YYKKALELDP DNETYKSNLK IAELKLREAP SPTGGVGSFD IAGLLNNPGF MSMASNLMNN             240
PQIQQLMSGM ISGGNNPLGT PGTSPSQNDL ASLIQAGGQF AQQMQQQNPE LIEQLRSQIR             300
SRTPSASNDD QQE                                                               313

SEQ ID NO: 6              moltype = AA  length = 272
FEATURE                   Location/Qualifiers
REGION                    1..272
                          note = misc_feature - P35232 PHB_HUMAN
source                    1..272
                          mol_type = protein
                          organism = SARS-COV-2
SEQUENCE: 6
MAAKVFESIG KFGLALAVAG GVVNSALYNV DAGHRAVIFD RFRGVQDIVV GEGTHFLIPW             60
VQKPIIFDCR SRPRNVPVIT GSKDLQNVNI TLRILFRPVA SQLPRIFTSI GEDYDERVLP             120
SITTEILKSV VARFDAGELI TQRELVSRQV SDDLTERAAT FGLILDDVSL THLTFGKEFT             180
EAVEAKQVAQ QEAERARFVV EKAEQQKKAA IISAEGDSKA AELIANSLAT AGDGLIELRK             240
LEAAEDIAYQ LSRSRNITYL PAGQSVLLQL PQ                                          272

SEQ ID NO: 7              moltype = AA  length = 529
FEATURE                   Location/Qualifiers
REGION                    1..529
                          note = misc_feature - P52292 IMA1_HUMAN
source                    1..529
                          mol_type = protein
                          organism = SARS-COV-2
SEQUENCE: 7
MSTNENANTP AARLHRFKNK GKDSTEMRRR RIEVNVELRK AKKDDQMLKR RNVSSFPDDA             60
TSPLQENRNN QGTVNWSVDD IVKGINSSNV ENQLQATQAA RKLLSREKQP PIDNIIRAGL            120
IPKFVSFLGR TDCSPIQFES AWALTNIASG TSEQTKAVVD GGAIPAFISL LASPHAHISE            180
QAVWALGNIA GDGSVFRDLV IKYGAVDPLL ALLAVPDMSS LACGYLRNLT WTLSNLCRNK            240
NPAPPIDAVE QILPTLVRLL HHDDPEVLAD TCWAISYLTD GPNERIGMVV KTGVVPQLVK            300
LLGASELPIV TPALRAIGNI VTGTDEQTQV VIDAGALAVF PSLLTNPKTN IQKEATWTMS            360
NITAGRQDQI QQVVNHGLVP FLVSVLSKAD FKTQKEAVWA VTNYTSGGTV EQIVYLVHCG            420
IIEPLMNLLT AKDTKIILVI LDAISNIFQA AEKLGETEKL SIMIEECGGL DKIEALQNHE            480
NESVYKASLS LIEKYFSVEE EEDQNVVPET TSEGYTFQVQ DGAPGTFNF                        529

SEQ ID NO: 8              moltype = AA  length = 180
FEATURE                   Location/Qualifiers
REGION                    1..180
                          note = misc_feature - Q10589 BST2_HUMAN
source                    1..180
                          mol_type = protein
                          organism = SARS-COV-2
SEQUENCE: 8
MASTSYDYCR VPMEDGDKRC KLLLGIGILV LLIIVILGVP LIIFTIKANS EACRDGLRAV            60
MECRNVTHLL QQELTEAQKG FQDVEAQAAT CNHTVMALMA SLDAEKAQGQ KKVEELEGEI            120
TTLNHKLQDA SAEVERLRRE NQVLSVRIAD KKYYPSSQDS SSAAAPQLLI VLLGLSALLQ            180

SEQ ID NO: 9              moltype = AA  length = 675
FEATURE                   Location/Qualifiers
REGION                    1..675
                          note = misc_feature - Q8N3R9 MPP5_HUMAN
source                    1..675
                          mol_type = protein
                          organism = SARS-COV-2
SEQUENCE: 9
MTTSHMNGHV TEESDSEVKN VDLASPEEHQ KHREMAVDCP GDLGTRMMPI RRSAQLERIR            60
QQQEDMRRRR EEEGKKQELD LNSSMRLKKL AQIPPKTGID NPMFDTEEGI VLESPHYAVK            120
ILEIEDLFSS LKHIQHTLVD SQSQEDISLL LQLVQNKDFQ NAFKIHNAIT VHMNKASPPF            180
PLISNAQDLA QEVQTVLKPV HHKEGQELTA LLNTPHIQAL LLAHDKVAEQ EMQLEPITDE            240
RVYESIGQYG GETVKIVRIE KARDIPLGAT VRNEMDSVII SRIVKGGAAE KSGLLHEGDE            300
VLEINGIEIR GKDVNEVFDL LSDMHGTLTF VLIPSQQIKP PPAKETVIHV KAHFDYDPSD            360
DPYVPCRELG LSFQKGDILH VISQEDPNWW QAYREGDEDN QPLAGLVPGK SFQQQREAMK            420
QTIEEDKEPE KSGKLWCAKK NKKKRKKVLY NANKNDDYDN EEILTYEEMS LYHQPANRKR            480
PIILIGPQNC GQNELRQRLM NKEKDRFASA VPHTTRSRRD QEVAGRDYHF VSRQAFEADI            540
AAGKFIEHGE FEKNLYGTSI DSVRQVINSG KICLLSLRTQ SLKTLRNSDL KPYIIFIAPP            600
```

-continued

```
SQERLRALLA KEGKNPKPEE LREIIEKTRE MEQNNGHYFD TAIVNSDLDK AYQELLRLIN   660
KLDTEPQWVP STWLR                                                       675

SEQ ID NO: 10          moltype = AA  length = 299
FEATURE                Location/Qualifiers
REGION                 1..299
                       note = misc_feature - Q99623 PHB2_HUMAN
source                 1..299
                       mol_type = protein
                       organism = SARS-COV-2
SEQUENCE: 10
MAQNLKDLAG RLPAGPRGMG TALKLLLGAG AVAYGVRESV FTVEGGHRAI FFNRIGGVQQ   60
DTILAEGLHF RIPWFQYPII YDIRARPRKI SSPTGSKDLQ MVNISLRVLS RPNAQELPSM   120
YQRLGLDYEE RVLPSIVNEV LKSVVAKFNA SQLITQRAQV SLLIRRELTE RAKDFSLILD   180
DVAITELSFS REYTAAVEAK QVAQQEAQRA QFLVEKAKQE QRQKIVQAEG EAEAAKMLGE   240
ALSKNPGYIK LRKIRAAQNI SKTIATSQNR IYLTADNLVL NLQDESFTRG SDSLIKGKK    299

SEQ ID NO: 11          moltype = AA  length = 4382
FEATURE                Location/Qualifiers
REGION                 1..4382
                       note = misc_feature - P0C6U8 R1A_CVHSA
source                 1..4382
                       mol_type = protein
                       organism = SARS-COV-2
SEQUENCE: 11
MESLVLGVNE KTHVQLSLPV LQVRDVLVRG FGDSVEEALS EAREHLKNGT CGLVELEKGV   60
LPQLEQPYVF IKRSDALSTN HGHKVVELVA EMDGIQYGRS GITLGVLVPH VGETPIAYRN   120
VLLRKNGNKG AGGHSYGIDL KSYDLGDELG TDPIEDYEQN WNTKHGSGAL RELTRELNGG   180
AVTRYVDNNF CGPDGYPLDC IKDFLARAGK SMCTLSEQLD YIESKRGVYC CRDHEHEIAW   240
FTERSDKSYE HQTPFEIKSA KKFDTFKGEC PKFVFPLNSK VKVIQPRVEK KKTEGFMGRI   300
RSVYPVASPQ ECNNMHLSTL MKCNHCDEVS WQTCDFLKAT CEHCGTENLV IEGPTTCGYL   360
PTNAVVKMPC PACQDPEIGP EHSVADYHNH SNIETRLRKG GRTRCFGGCV FAYVGCYNKR   420
AYWVPRASAD IGSGHTGITG DNVETLNEDL LEILSRERVN INIVGDFHLN EEVAIILASF   480
SASTSAFIDT IKSLDYKSFK TIVESCGNYK VTKGKPVKGA WNIGQQRSVL TPLCGFPSQA   540
AGVIRSIFAR TLDAANHSIP DLQRAAVTIL DGISEQSLRL VDAMVYTSDL LTNSVIIMAY   600
VTGGLVQQTS QWLSNLLGTT VEKLRPIFEW IEAKLSAGVE FLKDAWEILK FLITGVFDIV   660
KGQIQVASDN IKDCVKCFID VVNKALEMCI DQVTIAGAKL RSLNLGEVFI AQSKGLYRQC   720
IRGKEQLQLL MPLKAPKEVT FLEGDSHDTV LTSEEVVLKN GELEALETPV DSFTNGAIVG   780
TPVCVNGLML LEIKDKEQYC ALSPGLLATN NVFRLKGGAP IKGVTFGEDT VWEVQGYKNV   840
RITFELDERV DKVLNEKCSV YTVESGTEVT EFACVVAEAV VKTLQPVSDL LTNMGIDLDE   900
WSVATFYLFD DAGEENFSSR MYCSFYPPDE EEEDDAECEE EEIDETCEHE YGTEDDYQGL   960
PLEFGASAET VRVEEEEEED WLDDTTEQSE IEPEPEPTPE EPVNQFTGYL KLTDNVAIKC   1020
VDIVKEAQSA NPMVIVNAAN IHLKHGGGVA GALNKATNGA MQKESDDYIK LNGPLTVGGS   1080
CLLSGHNLAK KCLHVVGPNL NAGEDIQLLK AAYENFNSQD ILLAPLLSAG IFGAKPLQSL   1140
QVCVQTVRTQ VYIAVNDKAL YEQVVMDYLD NLKPRVEAPK QEEPPNTEDS KTEEKSVVQK   1200
PVDVKPKIKA CIDEVTTTLE ETKFLTNKLL LFADINGKLY HDSQNMLRGE DMSFLEKDAP   1260
YMVGDVITSG DITCVVIPSK KAGGTTEMLS RALKKVPVDE YITTYPGQGC AGYTLEEAKT   1320
ALKKCKSAFY VLPSEAPNAK EEILGTVSWN LREMLAHAEE TRKLMPICMD VRAIMATIQR   1380
KYKGIKIQEG IVDYGVRFFF YTSKEPVASI ITKLNSLNEP LVTMPIGYVT HGFNLEEAAR   1440
CMRSLKAPAV VSVSSPDAVT TYNGYLTSSS KTSEEHFVET VSLAGSYRDW SYSGQRTELG   1500
VEFLKRGDKI VYHTLESPVE FHLDGEVLSL DKLKSLLSLR EVKTIKVFTT VDNTNLHTQL   1560
VDMSMTYGQQ FGPTYLDGAD VTKIKPHVNH EGKTFFVLPS DDTLRSEAFE YYHTLDESFL   1620
GRYMSALNHT KKWKFPQVGG LTSIKWADNN CYLSSVLLAL QQLEVKFNAP ALQEAYYRAR   1680
AGDAANFCAL ILAYSNKTVG ELGDVRETMT HLLQHANLES AKRVLNVVCK HCGQKTTTLT   1740
GVEAVMYMGT LSYDNLKTGV SIPCVCGRDA TQYLVQQESS FVMMSAPPAE YKLQQGTFLC   1800
ANEYTGNYQC GHYTHITAKE TLYRIDGAHL TKMSEYKGPV TDVFYKETSY TTTIKPVSYK   1860
LDGVTYTEIE PKLDGYYKKD NAYYTEQPID LVPTQPLPNA SFDNFKLTCS NTKFADDLNQ   1920
MTGFTKPASR ELSVTFFPDL NGDVVAIDYR HYSASFKKGA KLLHKPIVWH INQATTKTTF   1980
KPNTWCLRCL WSTKPVDTSN SFEVLAVEDT QGMDNLACES QQPTSEEVVE NPTIQKEVIE   2040
CDVKTTEVVG NVILKPSDEG VKVTQELGHE DLMAAYVENT SITIKKPNEL SLALGLKTIA   2100
THGIAAINSV PWSKILAYVK PFLGQAAITT SNCAKRLAQR VFNNYMPYVF TLLFQLCTFT   2160
KSTNSRIRAS LPTTIAKNSV KSVAKLCLDA GINYVKSPKF SKLFTIAMWL LLLSICLGSL   2220
ICVTAAFGVL LSNFGAPSYC NGVRELYLNS SNVTTMDFCE GSFPCSICLS GLDSLDSYPA   2280
LETIQVTISS YKLDLTILGL AAEWVLAYML FTKFFYLLGL SAIMQVFFGY FASHFISNSW   2340
LMWFIISIVQ MAPVSAMVRM YIFFASFYYI WKSYVHIMDG CTSSTCMMCY KRNRATRVEC   2400
TTIVNGMKRS FYVYANGGRG FCKTHNWNCL NCDTFCTGST FISDEVARDL SLQFKRPINP   2460
TDQSSYIVDS VAVKNGALHL YFDKAGQKTY ERHPLSHFVN LDNLRANNTK GSLPINVIVF   2520
DGKSKCDESA SKSASVYYSQ LMCQPILLLD QALVSDVGDS TEVSVKMFDA YVDTFSATFS   2580
VPMEKLKALV ATAHSELAKG VALDGVLSTF VSAARQGVVD TDVDTKDVIE CLKLSHHSDL   2640
EVTGDSCNNF MLTYNKVENM TPRDLGACID CNARHINAQV AKSHNVSLIW NVKDYMSLSE   2700
QLRKQIRSAA KKNNIPFRLT CATTRQVVNV ITTKISLKGG KIVSTCFKLM LKATLLCVLA   2760
ALVCYIVMPV HTLSIHDGYT NEIIGYKAIQ DGVTRDIIST DDCFANKHAG FDAWFSQRGG   2820
SYKNDKSCPV VAAIITREIG FIVPGLPGTV LRAINGDFLH FLPRVFSAVG NICYTPSKLI   2880
EYSDFATSAC VLAAECTIFK DAMGKPVPYC YDTNLLEGSI SYSELRPDTR YVLMDGSIIQ   2940
FPNTYLEGSV RVVTTFDAEY CRHGTCERSE VGICLSTSGR WVLNNEHYRA LSGVFCGVDA   3000
MNLIANIFTP LVQPVGALDV SASVVAGGII AILVTCAAYY FMKFRRVFGE YNHVVAANAL   3060
LFLMSFTILC LVPAYSFLPG VYSVFYLYLT FYFTNDVSFL AHLQWFAMFS PIVPFWITAI   3120
YVFCISLKHC HWFFNNYLRK RVMFNGVTFS TFEEAALCTF LLNKEMYLKL RSETLLPLTQ   3180
YNRYLALYNK YKYFSGALDT TSYREAACCH LAKALNDFSN SGADVLYQPP QTSITSAVLQ   3240
```

```
SGFRKMAFPS GKVEGCMVQV TCGTTTLNGL WLDDTVYCPR HVICTAEDML NPNYEDLLIR   3300
KSNHSFLVQA GNVQLRVIGH SMQNCLLRLK VDTSNPKTPK YKFVRIQPGQ TFSVLACYNG   3360
SPSGVYQCAM RPNHTIKGSF LNGSCGSVGF NIDYDCVSFC YMHHMELPTG VHAGTDLEGK   3420
FYGPFVDRQT AQAAGTDTTI TLNVLAWLYA AVINGDRWFL NRFTTTLNDF NLVAMKYNYE   3480
PLTQDHVDIL GPLSAQTGIA VLDMCAALKE LLQNGMNGRT ILGSTILEDE FTPFDVVRQC   3540
SGVTFQGKFK KIVKGTHHWM LLTFLTSLLI LVQSTQWSLF FFVYENAFLP FTLGIMAIAA   3600
CAMLLVKHKH AFLCLFLLPS LATVAYFNMV YMPASWVMRI MTWLELADTS LSGYRLKDCV   3660
MYASALVLLI LMTARTVYDD AARRVWTLMN VITLVYKVYY GNALDQAISM WALVISVTSN   3720
YSGVVTTIMF LARAIVFVCV EYYPLLFITG NTLQCIMLVY CFLGYCCCCY FGLFCLLNRY   3780
FRLTLGVYDY LVSTQEFRYM NSQGLLPPKS SIDAFKLNIK LLGIGGKPCI KVATVQSKMS   3840
DVKCTSVVLL SVLQQLRVES SSKLWAQCVQ LHNDILLAKD TTEAFEKMVS LLSVLLSMQG   3900
AVDINRLCEE MLDNRATLQA IASEFSSLPS YAAYATAQEA YEQAVANGDS EVVLKKLKKS   3960
LNVAKSEFDR DAAMQRKLEK MADQAMTQMY KQARSEDKRA KVTSAMQTML FTMLRKLDND   4020
ALNNIINNAR DGCVPLNIIP LTTAAKLMVV VPDYGTYKNT CDGNTFTYAS ALWEIQQVVD   4080
ADSKIVQLSE INMDNSPNLA WPLIVTALRA NSAVKLQNNE LSPVALRQMS CAAGTTQTAC   4140
TDDNALAYYN NSKGGRFVLA LLSDHQDLKW ARFPKSDGTG TIYTELEPPC RFVTDTPKGP   4200
KVKYLYFIKG LNNLNRGMVL GSLAATVRLQ AGNATEVPAN STVLSFCAFA VDPAKAYKDY   4260
LASGGQPITN CVKMLCTHTG TGQAITVTPE ANMDQESFGG ASCCLYCRCH IDHPNPKGFC   4320
DLKGKYVQIP TTCANDPVGF TLRNTVCTVC GMWKGYGCSC DQLREPLMQS ADASTFLNGF   4380
AV                                                                 4382

SEQ ID NO: 12          moltype = AA   length = 7073
FEATURE                Location/Qualifiers
REGION                 1..7073
                       note = misc_feature - P0C6X7 R1AB_CVHSA
source                 1..7073
                       mol_type = protein
                       organism = SARS-COV-2

SEQUENCE: 12
MESLVLGVNE KTHVQLSLPV LQVRDVLVRG FGDSVEEALS EAREHLKNGT CGLVELEKGV   60
LPQLEQPYVF IKRSDALSTN HGHKVVELVA EMDGIQYGRS GITLGVLVPH VGETPIAYRN   120
VLLRKNGNKG AGGHSYGIDL KSYDLGDELG TDPIEDYEQN WNTKHGSGAL RELTRELNGG   180
AVTRYVDNNF CGPDGYPLDC IKDFLARAGK SMCTLSEQLD YIESKRGVYC CRDHEHEIAW   240
FTERSDKSYE HQTPFEIKSA KKFDTFKGEC PKFVFPLNSK VKVIQPRVEK KKTEGFMGRI   300
RSVYPVASPQ ECNNMHLSTL MKCNHCDEVS WQTCDFLKAT CEHCGTENLV IEGPTTCGYL   360
PTNAVVKMPC PACQDPEIGP EHSVADYHNH SNIETRLRKG GRTRCFGGCV FAYVGCYNKR   420
AYWVPRASAD IGSGHTGITG DNVETLNEDL LEILSRERVN INIVGDFHLN EEVAIILASF   480
SASTSAFIDT IKSLDYKSFK TIVESCGNYK VTKGKPVKGA WNIGQQRSVL TPLCGFPSQA   540
AGVIRSIFAR TLDAANHSIP DLQRAAVTIL DGISEQSLRL VDAMVYTSDL LTNSVIIMAY   600
VTGGLVQQTS QWLSNLLGTT VEKLRPIFEW IEAKLSAGVE FLKDAWEILK FLITGVFDIV   660
KGQIQVASDN IKDCVKCFID VVNKALEMCI DQVTIAGAKL RSLNLGEVFI AQSKGLYRQC   720
IRGKEQLQLL MPLKAPKEVT FLEGDSHDTV LTSEEVVLKN GELEALETPV DSFTNGAIVG   780
TPVCVNGLML LEIKDKEQYC ALSPGLLATN NVFRLKGGAP IKGVTFGEDT VWEVQGYKNV   840
RITFELDERV DKVLNEKCSV YTVESGTEVT EFACVVAEAV VKTLQPVSDL LTNMGIDLDE   900
WSVATFYLFD DAGEENFSSR MYCSFYPPDE EEEDDAECEE EIDETCEHE  YGTEDDYQGL   960
PLEFGASAET VRVEEEEED  WLDDTTEQSE IEPEPEPTPE EPVNQFTGYL KLTDNVAIKC   1020
VDIVKEAQSA NPMVIVNAAN IHLKHGGGVA GALNKATNGA MQKESDDYIK LNGPLTVGGS   1080
CLLSGHNLAK KCLHVVGPNL NAGEDIQLLK AAYENFNSQD ILLAPLLSAG IFGAKPLQSL   1140
QVCVQTVRTQ VYIAVNDKAL YEQVVMDYLD NLKPRVEAPK QEEPPNTEDS KTEEKSVVQK   1200
PVDVKPKIKA CIDEVTTTLE ETKFLTNKLL LFADINGKLY HDSQNMLRGE DMSFLEKDAP   1260
YMVGDVITSG DITCVVIPSK KAGGTTEMLS RALKKVPVDE YITTYPGQGC AGYTLEEAKT   1320
ALKKCKSAFY VLPSEAPNAK EEILGTVSWN LREMLAHAEE TRKLMPICMD VRAIMATIQR   1380
KYKGIKIQEG IVDYGVRFFF YTSKEPVASI ITKLNSLNEP LVTMPIGYVT HGFNLEEAAR   1440
CMRSLKAPAV VSVSSPDAVT TYNGYLTSSS KTSEEHFVET VSLAGSYRDW SYSGQRTELG   1500
VEFLKRGDKI VYHTLESPVE FHLDGEVLSL DKLKSLLSLR EVKTIKVFTT VDNTNLHTQL   1560
VDMSMTYGQQ FGPTYLDGAD VTKIKPHVNH EGKTFFVLPS DDTLRSEAFE YYHTLDESFL   1620
GRYMSALNHT KKWKFPQVGG LTSIKWADNN CYLSSVLLAL QQLEVKFNAP ALQEAYYRAR   1680
AGDAANFCAL ILAYSNKTVG ELGDVRETMT HLLQHANLES AKRVLNVVCK HCGQKTTTLT   1740
GVEAVMYMGT LSYDNLKTGV SIPCVCGRDA TQYLVQQESS FVMMSAPPAE YKLQQGTFLC   1800
ANEYTGNYQC GHYTHITAKE TLYRIDGAHL TKMSEYKGPV TDVFYKETSY TTTIKPVSYK   1860
LDGVTYTEIE PKLDGYYKKD NAYYTEQPID LVPTQPLPNA SFDNFKLTCS NTKFADDLNQ   1920
MTGFTKPASR ELSVTFFPDL NGDVVAIDYR HYSASFKKGA KLLHKPIVWH INQATTKTTF   1980
KPNTWCLRCL WSTKPVDTSN SFEVLAVEDT QGMDNLACES QQPTSEEVVE NPTIQKEVIE   2040
CDVKTTEVVG NVILKPSDEG VKVTQELGHE DLMAAYVENT SITIKKPNEL SLALGLKTIA   2100
THGIAAINSV PWSKILAYVK PFLGQAAITT SNCAKRLAQR VFNNYMPYVF TLLFQLCTFT   2160
KSTNSRIRAS LPTTIAKNSV KSVAKLCLDA GINYVKSPKF SKLFTIAMWL LLLSICLGSL   2220
ICVTAAFGVL LSNFGAPSYC NGVRELYLNS SNVTTMDFCE GSFPCSICLS GLDSLDSYPA   2280
LETIQVTISS YKLDLTILGL AAEWVLAYML FTKFFYLLGL SAIMQVFFGY FASHFISNSW   2340
LMWFIISIVQ MAPVSAMVRM YIFFASFYYI WKSYVHIMDG CTSSTCMMCY KRNRATRVEC   2400
TTIVNGMKRS FYVYANGGRG FCKTHNWNCL NCDTFCTGST FISDEVARDL SLQFKRPINP   2460
TDQSSYIVDS VAVKNGALHL YFDKAGQKTY ERHPLSHFVN LDNLRANNTK GSLPINVIVF   2520
DGKSKCDESA SKSASVYYSQ LMCQPILLLD QALVSDVGDS TEVSVKMFDA YVDTFSATFS   2580
VPMEKLKALV ATAHSELAKG VALDGVLSTF VSAARQGVVD TDVDTKDVIE CLKLSHHSDL   2640
EVTGDSCNNF MLTYNKVENM TPRDLGACID CNARHINAQV AKSHNVSLIW NVKDYMSLSE   2700
QLRKQIRSAA KKNNIPFRLT CATTRQVVNV ITTKISLKGG KIVSTCFKLM LKATLLCVLA   2760
ALVCYIVMPV HTLSIHDGYT NEIIGYKAIQ DGVTRDIIST DDCFANKHAG FDAWFSQRGG   2820
SYKNDKSCPV VAAIITREIG FIVPGLPGTV LRAINGDFLH FLPRVFSAVG NICYTPSKLI   2880
EYSDFATSAC VLAAECTIFK DAMGKPVPYC YDTNLLEGSI SYSELRPDTR YVLMDGSIIQ   2940
FPNTYLEGSV RVVTTFDAEY CRHGTCERSE VGICLSTSGR WVLNNEHYRA LSGVFCGVDA   3000
```

-continued

```
MNLIANIFTP LVQPVGALDV SASVVAGGII AILVTCAAYY FMKFRRVFGE YNHVVAANAL  3060
LFLMSFTILC LVPAYSFLPG VYSVFYLYLT FYFTNDVSFL AHLQWFAMFS PIVPFWITAI  3120
YVFCISLKHC HWFFNNYLRK RVMFNGVTFS TFEEAALCTF LLNKEMYLKL RSETLLPLTQ  3180
YNRYLALYNK YKYFSGALDT TSYREAACCH LAKALNDFSN SGADVLYQPP QTSITSAVLQ  3240
SGFRKMAFPS GKVEGCMVQV TCGTTTLNGL WLDDTVYCPR HVICTAEDML NPNYEDLLIR  3300
KSNHSFLVQA GNVQLRVIGH SMQNCLLRLK VDTSNPKTPK YKFVRIQPGQ TFSVLACYNG  3360
SPSGVYQCAM RPNHTIKGSF LNGSCGSVGF NIDYDCVSFC YMHHMELPTG VHAGTDLEGK  3420
FYGPFVDRQT AQAAGTDTTI TLNVLAWLYA AVINGDRWFL NRFTTTLNDF NLVAMKYNYE  3480
PLTQDHVDIL GPLSAQTGIA VLDMCAALKE LLQNGMNGRT ILGSTILEDE FTPFDVVRQC  3540
SGVTFQGKFK KIVKGTHHWM LLTFLTSLLI LVQSTQWSLF FFVYENAFLP FTLGIMAIAA  3600
CAMLLVKHKH AFLCLFLLPS LATVAYFNMV YMPASWVMRI MTWLELADTS LSGYRLKDCV  3660
MYASALVLLI LMTARTVYDD AARRVWTLMN VITLVYKVYY GNALDQAISM WALVISVTSN  3720
YSGVVTTIMF LARAIVFVCV EYYPLLFITG NTLQCIMLVY CFLGYCCCCY FGLFCLLNRY  3780
FRLTLGVYDY LVSTQEFRYM NSQGLLPPKS SIDAFKLNIK LLGIGGKPCI KVATVQSKMS  3840
DVKCTSVVLL SVLQQLRVES SSKLWAQCVQ LHNDILLAKD TTEAFEKMVS LLSVLLSMQG  3900
AVDINRLCEE MLDNRATLQA IASEFSSLPS YAAYATAQEA YEQAVANGDS EVVLKKLKKS  3960
LNVAKSEFDR DAAMQRKLEK MADQAMTQMY KQARSEDKRA KVTSAMQTML FTMLRKLDND  4020
ALNNIINNAR DGCVPLNIIP LTTAAKLMVV VPDYGTYKNT CDGNTFTYAS ALWEIQQVVD  4080
ADSKIVQLSE INMDNSPNLA WPLIVTALRA NSAVKLQNNE LSPVALRQMS CAAGTTQTAC  4140
TDDNALAYYN NSKGGRFVLA LLSDHQDLKW ARFPKSDGTG TIYTELEPPC RFVTDTPKGP  4200
KVKYLYFIKG LNNLNRGMVL GSLAATVRLQ AGNATEVPAN STVLSFCAFA VDPAKAYKDY  4260
LASGGQPITN CVKMLCTHTG TGQAITVTPE ANMDQESFGG ASCCLYCRCH IDHPNPKGFC  4320
DLKGKYVQIP TTCANDPVGF TLRNTVCTVC GMWKGYGCSC DQLREPLMQS ADASTFLNRV  4380
CGVSAARLTP CGTGTSTDVV YRAFDIYNEK VAGFAKFLKT NCCRFQEKDE EGNLLDSYFV  4440
VKRHTMSNYQ HEETIYNLVK DCPAVAVHDF FKFRVDGDMV PHISRQRLTK YTMADLVYAL  4500
RHFDEGNCDT LKEILVTYNC CDDDYFNKKD WYDFVENPDI LRVYANLGER VRQSLLKTVQ  4560
FCDAMRDAGI VGVLTLDNQD LNGNWYDFGD FVQVAPGCGV PIVDSYYSLL MPILTLTRAL  4620
AAESHMDADL AKPLIKWDLL KYDFTEERLC LFDRYFKYWD QTYHPNCINC LDDRCILHCA  4680
NFNVLFSTVF PPTSFGPLVR KIFVDGVPFV VSTGYHFREL GVVHNQDVNL HSSRLSFKEL  4740
LVYAADPAMH AASGNLLLDK RTTCFSVAAL TNNVAFQTVK PGNFNKDFYD FAVSKGFFKE  4800
GSSVELKHFF FAQDGNAAIS DYDYYRYNLP TMCDIRQLLF VVEVVDKYFD CYDGGCINAN  4860
QVIVNNLDKS AGFPFNKWGK ARLYYDSMSY EDQDALFAYT KRNVIPTITQ MNLKYAISAK  4920
NRARTVAGVS ICSTMTNRQF HQKLLKSIAA TRGATVVIGT SKFYGGWHNM LKTVYSDVET  4980
PHLMGWDYPK CDRAMPNMLR IMASLVLARK HNTCCNLSHR FYRLANECAQ VLSEMVMCGG  5040
SLYVKPGGTS SGDATTAYAN SVFNICQAVT ANVNALLSTD GNKIADKYVR NLQHRLYECL  5100
YRNRDVDHEF VDEFYAYLRK HFSMMILSDD AVVCYNSNYA AQGLVASIKN FKAVLYYQNN  5160
VFMSEAKCWT ETDLTKGPHE FCSQHTMLVK QGDDYVYLPY PDPSRILGAG CFVDDIVKTD  5220
GTLMIERFVS LAIDAYPLTK HPNQEYADVF HLYLQYIRKL HDELTGHMLD MYSVMLTNDN  5280
TSRYWEPEFY EAMYTPHTVL QAVGACVLCN SQTSLRCGAC IRRPFLCCKC CYDHVISTSH  5340
KLVLSVNPYV CNAPGCDVTD VTQLYLGGMS YYCKSHKPPI SFPLCANGQV FGLYKNTCVG  5400
SDNVTDFNAI ATCDWTNAGD YILANTCTER LKLFAAETLK ATEETFKLSY GIATVREVLS  5460
DRELHLSWEV GKPRPPLNRN YVFTGYRVTK NSKVQIGEYT FEKGDYGDAV VYRGTTTYKL  5520
NVGDYFVLTS HTVMPLSAPT LVPQEHYVRI TGLYPTLNIS DEFSSNVANY QKVGMQKYST  5580
LQGPPGTGKS HFAIGLALYY PSARIVYTAC SHAAVDALCE KALKYLPIDK CSRIIPARAR  5640
VECFDKFKVN STLEQYVFCT VNALPETTAD IVVFDEISMA TNYDLSVVNA RLRAKHYVYI  5700
GDPAQLPAPR TLLTKGTLEP EYFNSVCRLM KTIGPDMFLG TCRRCPAEIV DTVSALVYDN  5760
KLKAHKDKSA QCFKMFYKGV ITHDVSSAIN RPQIGVVREF LTRNPAWRKA VFISPYNSQN  5820
AVASKILGLP TQTVDSSQGS EYDYVIFTQT TETAHSCNVN RFNVAITRAK IGILCIMSDR  5880
DLYDKLQFTS LEIPRRNVAT LQAENVTGLF KDCSKIITGL HPTQAPTHLS VDIKFKTEGL  5940
CVDIPGIPKD MTYRRLISMM GFKMNYQVNG YPNMFITREE AIRHVRAWIG FDVEGCHATR  6000
DAVGTNLPLQ LGFSTGVNLV AVPTGYVDTE NNTEFTRVNA KPPPGDQFKH LIPLMYKGLP  6060
WNVVRIKIVQ MLSDTLKGLS DRVVFVLWAH GFELTSMKYF VKIGPERTCC LCDKRATCFS  6120
TSSDTYACWN HSVGFDYVYN PFMIDVQQWG FTGNLQSNHD QHCQVHGNAH VASCDAIMTR  6180
CLAVHECFVK RVDWSVEYPI IGDELRVNSA CRKVQHMVVK SALLADKFPV LHDIGNPKAI  6240
KCVPQAEVEW KFYDAQPCSD KAYKIEELFY SYATHHDKFT DGVCLFWNCN VDRYPANAIV  6300
CRFDTRVLSN LNLPGCDGGS LYVNKHAFHT PAFDKSAFTN LKQLPFFYYS DSPCESHGKQ  6360
VVSDIDYVPL KSATCITRCN LGGAVCRHHA NEYRQYLDAY NMMISAGFSL WIYKQFDTYN  6420
LWNTFTRLQS LENVAYNVVN KGHFDGHAGE APVSIINNAV YTKVDGIDVE IFENKTTLPV  6480
NVAFELWAKR NIKPVPEIKI LNNLGVDIAA NTVIWDYKRD CTMTDIAKKP  6540
TESACSSLTV LFDGRVEGQV DLFRNARNGV LITEGSVKGL TPSKGPAQAS VNGVTLIGES  6600
VKTQFNYFKK VDGIIQQLPE TYFTQSRDLE DFKPRSQMET DFLELAMDEF IQRYKLEGYA  6660
FEHIVYGDFS HGQLGGLHLM IGLAKRSQDS PLKLEDFIPM DSTVKNYFIT DAQTGSSKCV  6720
CSVIDLLLDD FVEIIKSQDL SVISKVVKVT IDYAEISFML WCKDGHVETF YPKLQASGAW  6780
QPGVAMPNLY KMQRMLLEKC DLQNYGENAV IPKGIMMNVA KYTQLCQYLN TLTLAVPYNM  6840
RVIHFGAGSD KGVAPGTAVL RQWLPTGTLL VDSDLNDFVS DADSTLIGDC ATVHTANKWD  6900
LIISDMYDPR TKHVTKENDS KEGFFTYLCG FIKQKLALGG SIAVKITEHS WNADLYKLMG  6960
HFSWWTAFVT NVNASSSEAF LIGANYLGKP KEQIDGYTMH ANYIFWRNTN PIQLSSYSLF  7020
DMSKFPLKLR GTAVMSLKEN QINDMIYSLL EKGRLIIREN NRVVVSSDIL VNN          7073
```

```
SEQ ID NO: 13          moltype = AA  length = 4405
FEATURE                Location/Qualifiers
REGION                 1..4405
                       note = misc_feature - P0DTC1 R1A_SARS2
source                 1..4405
                       mol_type = protein
                       organism = SARS-COV-2
SEQUENCE: 13
MESLVPGFNE KTHVQLSLPV LQVRDVLVRG FGDSVEEVLS EARQHLKDGT CGLVEVEKGV  60
LPQLEQPYVF IKRSDARTAP HGHVMVELVA ELEGIQYGRS GETLGVLVPH VGEIPVAYRK  120
```

```
VLLRKNGNKG AGGHSYGADL KSFDLGDELG TDPYEDFQEN WNTKHSSGVT RELMRELNGG    180
AYTRYVDNNF CGPDGYPLEC IKDLLARAGK ASCTLSEQLD FIDTKRGVYC CREHEHEIAW    240
YTERSEKSYE LQTPFEIKLA KKFDTFNGEC PNFVFPLNSI IKTIQPRVEK KKLDGFMGRI    300
RSVYPVASPN ECNQMCLSTL MKCDHCGETS WQTGDFVKAT CEFCGTENLT KEGATTCGYL    360
PQNAVVKIYC PACHNSEVGV EHSLAEYHNE SGLKTILRKG GRTIAFGGCV FSYVGCHNKC    420
AYWVPRASAN IGCNHTGVVG EGSEGLNDNL LEILQKEKVN INIVGDFKLN EEIAIILASF    480
SASTSAFVET VKGLDYKAFK QIVESCGNFK VTKGKAKKGA WNIGEQKSIL SPLYAFASEA    540
ARVVRSIFSR TLETAQNSVR VLQKAAITIL DGISQYSLRL IDAMMFTSDL ATNNLVVMAY    600
ITGGVVQLTS QWLTNIFGTV YEKLKPVLDW LEEKFKEGVE FLRDGWEIVK FISTCACEIV    660
GGQIVTCAKE IKESVQTFFK LVNKFLALCA DSIIIGGAKL KALNLGETFV THSKGLYRKC    720
VKSREETGLL MPLKAPKEII FLEGETLPTE VLTEEVVLKT GDLQPLEQPT SEAVEAPLVG    780
TPVCINGLML LEIKDTEKYC ALAPNMMVTN NTFTLKGGAP TKVTFGDDTV IEVQGYKSVN    840
ITFELDERID KVLNEKCSAY TVELGTEVNE FACVVADAVI KTLQPVSELL TPLGIDLDEW    900
SMATYYLFDE SGEFKLASHM YCSFYPPDED EEEGDCEEEE FEPSTQYEYG TEDDYQGKPL    960
EFGATSAALQ PEEEQEEDWL DDDSQQTVGQ QDGSEDNQTT TIQTIVEVQP QLEMELTPVV   1020
QTIEVNSFSG YLKLTDNVYI KNADIVEEAK KVKPTVVVNA ANVYLKHGGG VAGALNKATN   1080
NAMQVESDDY IATNGPLKVG GSCVLSGHNL AKHCLHVVGP NVNKGEDIQL LKSAYENFNQ   1140
HEVLLAPLLS AGIFGADPIH SLRVCVDTVR TNVYLAVFDK NLYDKLVSSF LEMKSEKQVE   1200
QKIAEIPKEE VKPFITESKP SVEQRKQDDK KIKACVEEVT TTLEETKFLT ENLLLYIDIN   1260
GNLHPDSATL VSDIDITFLK KDAPYIVGDV VQEGVLTAVV IPTKKAGGTT EMLAKALRKV   1320
PTDNYITTYP GQGLNGYTVE EAKTVLKKCK SAFYILPSII SNEKQEILGT VSWNLREMLA   1380
HAEETRKLMP VCVETKAIVS TIQRKYKGIK IQEGVVDYGA RFYFYTSKTT VASLINTLND   1440
LNETLVTMPL GYVTHGLNLE EAARYMRSLK VPATVSVSSP DAVTAYNGYL TSSSKTPEEH   1500
FIETISLAGS YKDWSYSGQS TQLGIEFLKR GDKSVYYTSN PTTFHLDGEV ITFDNLKTLL   1560
SLREVRTIKV FTTVDNINLH TQVVDMSMTY GQQFGPTYLD GADVTKIKPH NSHEGKTFYV   1620
LPNDDTLRVE AFEYYHTTDP SFLGRYMSAL NHTKKWKYPQ VNGLTSIKWA DNNCYLATAL   1680
LTLQQIELKF NPPALQDAYY RARAGEAANF CALILAYCNK TVGELGDVRE TMSYLFQHAN   1740
LDSCKRVLNV VCKTCGQQQT TLKGVEAVMY MGTLSYEQFK KGVQIPCTCG KQATKYLVQQ   1800
ESPFVMMSAP PAQYELKHGT FTCASEYTGN YQCGHYKHIT SKETLYCIDG ALLTKSSEYK   1860
GPITDVFYKE NSYTTTIKPV TYKLDGVVCT EIDPKLDNYY KKDNSYFTEQ PIDLVPNQPY   1920
PNASFDNFKF VCDNIKFADD LNQLTGYKKP ASRELKVTFF PDLNGDVVAI DYKHYTPSFK   1980
KGAKLLHKPI VWHVNNATNK ATYKPNTWCI RCLWSTKPVE TSNSFDVLKS EDAQGMDNLA   2040
CEDLKPVSEE VVENPTIQKD VLECNVKTTE VVGDIILKPA NNSLKITEEV GHTDLMAAYV   2100
DNSSLTIKKP NELSRVLGLK TLATHGLAAV NSVPWDTIAN YAKPFLNKVV STTTNIVTRC   2160
LNRVCTNYMP YFFTLLLQLC TFTRSTNSRI KASMPTTIAK NTVKSVGKFC LEASFNYLKS   2220
PNFSKLINII IWFLLLSVCL GSLIYSTAAL GVLMSNLGMP SYCTGYREGY LNSTNVTIAT   2280
YCTGSIPCSV CLSGLDSLDT YPSLETIQIT ISSFKWDLTA FGLVAEWFLA YILFTRFFYV   2340
LGLAAIMQLF FSYFAVHFIS NSWLMWLIIN LVQMAPISAM VRMYIFFASF YYVWKSYVHV   2400
VDGCNSSTCM MCYKRNRATR VECTTIVNGV RRSFYVYANG GKGFCKLHNW NCVNCDTFCA   2460
GSTFISDEVA RDLSLQFKRP INPTDQSSYI VDSVTVKNGS IHLYFDKAGQ KTYERHSLSH   2520
FVNLDNLRAN NTKGSLPINV IVFDGKSKCE ESSAKSASVY YSQLMCQPIL LLDQALVSDV   2580
GDSAEVAVKM FDAYVNTFSS TFNVPMEKLK TLVATAEAEL AKNVSLDNVL STFISAARQG   2640
FVDSDVETKD VVECLKLSHQ SDIEVTGDSC NNYMLTYNKV ENMTPRDLGA CIDCSARHIN   2700
AQVAKSHNIA LIWNVKDFMS LSEQLRKQIR SAAKKNNLPF KLTCATTRQV VNVVTTKIAL   2760
KGGKIVNNWL KQLIKVTLVF LFVAAIFYLI TPVHVMSKHT DFSSEIIGYK AIDGGVTRDI   2820
ASTDTCFANK HADFDTWFSQ RGGSYTNDKA CPLIAAVITR EVGFVVPGLP GTILRTTNGD   2880
FLHFLPRVFS AVGNICYTPS KLIEYTDFAT SACVLAAECT IKFDASGKPV PYCYDTNVLE   2940
GSVAYESLRP DTRYVLMDGS IIQFPNTYLE GSVRVVTTFD SEYCRHGTCE RSEAGVCVST   3000
SGRWVLNNDY YRSLPGVFCG VDAVNLLTNM FTPLIQPIGA LDISASIVAG GIVAIVVTCL   3060
AYYFMRFRRA FGEYSHVVAF NTLLFLMSFT VLCLTPVYSF LPGVYSVIYL YLTFYLTNDV   3120
SFLAHIQWMV MFTPLVPFWI TIAYIICIST KHFYWFFSNY LKRRVVFNGV SFSTFEEAAL   3180
CTFLLNKEMY LKLRSDVLLP LTQYNRYLAL YNKYKYFSGA MDTTSYREAA CCHLAKALND   3240
FSNSGSDVLY QPPQTSITSA VLQSGFRKMA FPSGKVEGCM VQVTCGTTTL NGLWLDDVVY   3300
CPRHVICTSE DMLNPNYEDL LIRKSNHNFL VQAGNVQLRV IGHSMQNCVL KLKVDTANPK   3360
TPKYKFVRIQ PGQTFSVLAC YNGSPSGVYQ CAMRPNFTIK GSFLNGSCGS VGFNIDYDCV   3420
SFCYMHHMEL PTGVHAGTDL EGNFYGPFVD RQTAQAAGTD TTITVNVLAW LYAAVINGDR   3480
WFLNRFTTTL NDFNLVAMKY NYEPLTQDHV DILGPLSAQT GIAVLDMCAS LKELLQNGMN   3540
GRTILGSALL EDEFTPFDVV RQCSGVTFQS AVKRTIKGTH HWLLLTILTS LLVLVQSTQW   3600
SLFFFLYENA FLPFAMGIIA MSAFAMMFVK HKHAFLCLFL LPSLATVAYF NMVYMPASWV   3660
MRIMTWLDMV DTSLSGFKLK DCVMYASAVV LLILMTARTV YDDGARRVWT LMNVLTLVYK   3720
VYYGNALDQA ISMWALIISV TSNYSGVVTT VMFLARGIVF MCVEYCPIFF ITGNTLQCIM   3780
LVYCFLGYFC TCYFGLFCLL NRYFRLTLGV YDYLVSTQEF RYMNSQGLLP PKNSIDAFKL   3840
NIKLLGVGGK PCIKVATVQS KMSDVKCTSV VLLSVLQQLR VESSSKLWAQ CVQLHNDILL   3900
AKDTTEAFEK MVSLLSVLLS MQGAVDINKL CEEMLDNRAT LQAIASEFSS LPSYAAFATA   3960
QEAYEQAVAN GDSEVVLKKL KKSLNVAKSE FDRDAAMQRK LEKMADQAMT QMYKQARSED   4020
KRAKVTSAMQ TMLFTMLRKL DNDALNNIIN NARDGCVPLN IIPLTTAAKL MVVIPDYNTY   4080
KNTCDGTTFT YASALWEIQQ VVDADSKIVQ LSEISMDNSP NLAWPLIVTA LRANSAVKLQ   4140
NNELSPVALR QMSCAAGTTQ TACTDDNALA YYNTTKGGRF VLALLSDLQD LKWARFPKSD   4200
GTGTIYTELE PPCRFVTDTP KGPKVKYLYF IKGLNNLNRG MVLGSLAATV RLQAGNATEV   4260
PANSTVLSFC AFAVDAAKAY KDYLASGGQP ITNCVKMLCT HTGTGQAITV TPEANMDQES   4320
FGGASCCLYC RCHIDHPNPK GFCDLKGKYV QIPTTCANDP VGFTLKNTVC TVCGMWKGYG   4380
CSCDQLREPM LQSADAQSFL NGFAV                                         4405
```

```
SEQ ID NO: 14        moltype = AA   length = 7096
FEATURE              Location/Qualifiers
REGION               1..7096
                     note = misc_feature - P0DTD1 R1AB_SARS2
source               1..7096
                     mol_type = protein
```

```
                              organism = SARS-COV-2
SEQUENCE: 14
MESLVPGFNE KTHVQLSLPV LQVRDVLVRG FGDSVEEVLS EARQHLKDGT CGLVEVEKGV    60
LPQLEQPYVF IKRSDARTAP HGHVMVELVA ELEGIQYGRS GETLGVLVPH VGEIPVAYRK   120
VLLRKNGNKG AGGHSYGADL KSFDLGDELG TDPYEDFQEN WNTKHSSGVT RELMRELNGG   180
AYTRYVDNNF CGPDGYPLEC IKDLLARAGK ASCTLSEQLD FIDTKRGVYC CREHEHEIAW   240
YTERSEKSYE LQTPFEIKLA KKFDTFNGEC PNFVFPLNSI IKTIQPRVEK KKLDGFMGRI   300
RSVYPVASPN ECNQMCLSTL MKCDHCGETS WQTGDFVKAT CEFCGTENLT KEGATTCGYL   360
PQNAVVKIYC PACHNSEVGP EHSLAEYHNE SGLKTILRKG GRTIAFGGCV FSYVGCHNKC   420
AYWVPRASAN IGCNHTGVVG EGSEGLNDNL LEILQKEKVN INIVGDFKLN EEIAIILASF   480
SASTSAFVET VKGLDYKAFK QIVESCGNFK VTKGKAKKGA WNIGEQKSIL SPLYAFASEA   540
ARVVRSIFSR TLETAQNSVR VLQKAAITIL DGISQYSLRL IDAMMFTSDL ATNNLVVMAY   600
ITGGVVQLTS QWLTNIFGTV YEKLKPVLDW LEEKFKEGVE FLRDGWEIVK FISTCACEIV   660
GGQIVTCAKE IKESVQTFFK LVNKFLALCA DSIIIGGAKL KALNLGETFV THSKGLYRKC   720
VKSREETGLL MPLKAPKEII FLEGETLPTE VLTEEVVLKT GDLQPLEQPT SEAVEAPLVG   780
TPVCINGLML LEIKDTEKYC ALAPNMMVTN NTFTLKGGAP TKVTFGDDTV IEVQGYKSVN   840
ITFELDERID KVLNEKCSAY TVELGTEVNE FACVVADAVI KTLQPVSELL TPLGIDLDEW   900
SMATYYLFDE SGEFKLASHM YCSFYPPDED EEEGDCEEEE FEPSTQYEYG TEDDYQGKPL   960
EFGATSAALQ PEEEQEEDWL DDDSQQTVGQ QDGSEDNQTT TIQTIVEVQP QLEMELTPVV  1020
QTIEVNSFSG YLKLTDNVYI KNADIVEEAK KVKPTVVVNA ANVYLKHGGG VAGALNKATN  1080
NAMQVESDDY IATNGPLKVG GSCVLSGHNL AKHCLHVVGP NVNKGEDIQL LKSAYENFNQ  1140
HEVLLAPLLS AGIFGADPIH SLRVCVDTVR TNVYLAVFDK NLYDKLVSSF LEMKSEKQVE  1200
QKIAEIPKEE VKPFITESKP SVEQRKQDDK KIKACVEEVT TTLEETKFLT ENLLLYIDIN  1260
GNLHPDSATL VSDIDITFLK KDAPYIVGDV VQEGVLTAVV IPTKKAGGTT EMLAKALRKV  1320
PTDNYITTYP GQGLNGYTVE EAKTVLKKCK SAFYILPSII SNEKQEILGT VSWNLREMLA  1380
HAEETRKLMP VCVETKAIVS TIQRKYKGIK IQEGVVDYGA RFYFYTSKTT VASLINTLND  1440
LNETLVTMPL GYVTHGLNLE EAARYMRSLK VPATVSVSSP DAVTAYNGYL TSSSKTPEEH  1500
FIETISLAGS YKDWSYSGQS TQLGIEFLKR GDKSVYYTSN PTTFHLDGEV ITFDNLKTLL  1560
SLREVRTIKV FTTVDNINLH TQVVDMSMTY GQQFGPTYLD GADVTKIKPH NSHEGKTFYV  1620
LPNDDTLRVE AFEYYHTTDP SFLGRYMSAL NHTKKWKYPQ VNGLTSIKWA DNNCYLATAL  1680
LTLQQIELKF NPPALQDAYY RARAGEAANF CALILAYCNK TVGELGDVRE TMSYLFQHAN  1740
LDSCKRVLNV VCKTCGQQQT TLKGVEAVMY MGTLSYEQFK KGVQIPCTCG KQATKYLVQQ  1800
ESPFVMMSAP PAQYELKHGT FTCASEYTGN YQCGHYKHIT SKETLYCIDG ALLTKSSEYK  1860
GPITDVFYKE NSYTTTIKPV TYKLDGVVCT EIDPKLDNYY KKDNSYFTEQ PIDLVPNQPY  1920
PNASFDNFKF VCDNIKFADD LNQLTGYKKP ASRELKVTFF PDLNGDVVAI DYKHYTPSFK  1980
KGAKLLHKPI VWHVNNATNK ATYKPNTWCI RCLWSTKPVE TSNSFDVLKS EDAQGMDNLA  2040
CEDLKPVSEE VVENPTIQKD VLECNVKTTE VVGDIILKPA NNSLKITEEV GHTDLMAAYV  2100
DNSSLTIKKP NELSRVLGLK TLATHGLAAV NSVPWDTIAN YAKPFLNKVV STTTNIVTRC  2160
LNRVCTNYMP YFFTLLLQLC TFTRSTNSRI KASMPTTIAK NTVKSVGKFC LEASFNYLKS  2220
PNFSKLINII IWFLLLSVCL GSLIYSTAAL GVLMSNLGMP SYCTGYREGY LNSTNVTIAT  2280
YCTGSIPCSV CLSGLDSLDT YPSLETIQIT ISSFKWDLTA FGLVAEWFLA YILFTRFFYV  2340
LGLAAIMQLF FSYFAVHFIS NSWLMWLIIN LVQMAPISAM VRMYIFFASF YYVKSYVHV   2400
VDGCNSSTCM MCYKRNRATR VECTTIVNGV RRSFYVYANG GKGFCKLHNW NCVNCDTFCA   2460
GSTFISDEVA RDLSLQFKRP INPTDQSSYI VDSVTVKNGS IHLYFDKAGQ KTYERHSLSH   2520
FVNLDNLRAN NTKGSLPINV IVFDGKSKCE ESSAKSASVY YSQLMCQPIL LLDQALVSDV   2580
GDSAEVAVKM FDAYVNTFSS TFNVPMEKLK TLVATAEAEL AKNVSLDNVL STFISAARQG   2640
FVDSDVETKD VVECLKLSHQ SDIEVTGDSC NNYMLTYNKV ENMTPRDLGA CIDCSARHIN   2700
AQVAKSHNIA LIWNVKDFMS LSEQLRKQIR SAAKKNNLPF KLTCATTRQV VNVVTTKIAL   2760
KGGKIVNNWL KQLIKVTLVF LFVAAIFYLI TPVHVMSKHT DFSSEIIGYK AIDGGVTRDI   2820
ASTDTCFANK HADFDTWFSQ RGGSYTNDKA CPLIAAVITR EVGFVVPGLP GTILRTTNGD   2880
FLHFLPRVFS AVGNICYTPS KLIEYTDFAT SACVLAAECT IKFDASGKPV PYCYDTNVLE   2940
GSVAYESLRP DTRYVLMDGS IIQFPNTYLE GSVRVVTTFD SEYCRHGTCE RSEAGVCVST   3000
SGRWVLNNDY YRSLPGVFCG VDAVNLLTNM FTPLIQPIGA LDISASIVAG GIVAIVVTCL   3060
AYYFMRFRRA FGEYSHVVAF NTLLFLMSFT VLCLTPVYSF LPGVYSVIYL YLTFYLTNDV   3120
SFLAHIQWMV MFTPLVPFWI TIAYIICIST KHFYWFFSNY LKRRVVFNGV SFSTFEEAAL   3180
CTFLLNKEMY LKLRSDVLLP LTQYNRYLAL YNKYKYFSGA MDTTSYREAA CCHLAKALND   3240
FSNSGSDVLY QPPQTSITSA VLQSGFRKMA FPSGKVEGCM VQVTCGTTTL NGLWLDDVVY   3300
CPRHVICTSE DMLNPNYEDL LIRKSNHNFL VQAGNVQLRV IGHSMQNCVL KLKVDTANPK   3360
TPKYKFVRIQ PGQTFSVLAC YNGSPSGVYQ CAMRPNFTIK GSFLNGSCGS VGFNIDYDCV   3420
SFCYMHHMEL PTGVHAGTDL EGNFYGPFVD RQTAQAAGTD TTITVNVLAW LYAAVINGDR   3480
WFLNRFTTTL NDFNLVAMKY NYEPLTQDHV DILGPLSAQT GIAVLDMCAS LKELLQNGMN   3540
GRTILGSALL EDEFTPFDVV RQCSGVTFQS AVKRTIKGTH HWLLLTILTS LLVLVQSTQW   3600
SLFFFLYENA FLPFAMGIIA MSAFAMMFVK HKHAFLCLFL LPSLATVAYF NMVYMPASWV   3660
MRIMTWLDMV DTSLSGFKLK DCVMYASAVV LLILMTARTV YDDGARRVWT LMNVLTLVYK   3720
VYYGNALDQA ISMWALIISV TSNYSGVVTT VMFLARGIVF MCVEYCPIFF ITGNTLQCIM   3780
LVYCFLGYFC TCYFGLFCLL NRYFRLTLGV YDYLVSTQEF RYMNSQGLLP PKNSIDAFKL   3840
NIKLLGVGGK PCIKVATVQS KMSDVKCTSV VLLSVLQQLR VESSSKLWAQ CVQLHNDILL   3900
AKDTTEAFEK MVSLLSVLLS MQGAVDINKL CEEMLDNRAT LQAIASEFSS LPSYAAFATA   3960
QEAYEQAVAN GDSEVVLKKL KKSLNVAKSE FDRDAAMQRK LEKMADQAMT QMYKQARSED   4020
KRAKVTSAMQ TMLFTMLRKL DNDALNNIIN NARDGCVPLN IIPLTTAAKL MVVIPDYNTY   4080
KNTCDGTTFT YASALWEIQQ VVDADSKIVQ LSEISMDNSP NLAWPLIVTA LRANSAVKLQ   4140
NNELSPVALR QMSCAAGTTQ TACTDDNALA YYNTTKGGRF VLALLSDLQD LKWARFPKSD   4200
GTGTIYTELE PPCRFVTDTP KGPKVKYLYF IKGLNNLNRG MVLGSLAATV RLQAGNATEV   4260
PANSTVLSFC AFAVDAAKAY KDYLASGGQP ITNCVKMLCT HTGTGQAITV TPEANMDQES   4320
FGGASCCLYC RCHIDHPNPK GFCDLKGKYV QIPTTCANDP VGFTLKNTVC TVCGMWKGYG   4380
CSCDQLREPM LQSADAQSFL NRVCGVSAAR LTPCGTGTST DVVYRAFDIY NDKVAGFAKF   4440
LKTNCCRFQE KDEDDNLIDS YFVVKRHTFS NYQHEETIYN LLKDCPAVAK HDFFKFRIDG   4500
DMVPHISRQR LTKYTMADLV YALRHFDEGN CDTLKEILVT YNCCDDDYFN KKDWYDFVEN   4560
PDILRVYANL GERVRQALLK TVQFCDAMRN AGIVGVLTLD NQDLNGNWYD FGDFIQTTPG   4620
```

-continued

```
SGVPVVDSYY SLLMPILTLT RALTAESHVD TDLTKPYIKW DLLKYDFTEE RLKLFDRYFK 4680
YWDQTYHPNC VNCLDDRCIL HCANFNVLFS TVFPPTSFGP LVRKIFVDGV PFVVSTGYHF 4740
RELGVVHNQD VNLHSSRLSF KELLVYAADP AMHAASGNLL LDKRTTCFSV AALTNNVAFQ 4800
TVKPGNFNKD FYDFAVSKGF FKEGSSVELK HFFFAQDGNA AISDYDYYRY NLPTMCDIRQ 4860
LLFVVEVVDK YFDCYDGGCI NANQVIVNNL DKSAGFPFNK WGKARLYYDS MSYEDQDALF 4920
AYTKRNVIPT ITQMNLKYAI SAKNRARTVA GVSICSTMTN RQFHQKLLKS IAATRGATVV 4980
IGTSKFYGGW HNMLKTVYSD VENPHLMGWD YPKCDRAMPN MLRIMASLVL ARKHTTCCSL 5040
SHRFYRLANE CAQVLSEMVM CGGSLYVKPG GTSSGDATTA YANSVFNICQ AVTANVNALL 5100
STDGNKIADK YVRNLQHRLY ECLYRNRDVD TDFVNEFYAY LRKHFSMMIL SDDAVVCFNS 5160
TYASQGLVAS IKNFKSVLYY QNNVFMSEAK CWTETDLTKG PHEFCSQHTM LVKQGDDYVY 5220
LPYPDPSRIL GAGCFVDDIV KTDGTLMIER FVSLAIDAYP LTKHPNQEYA DVFHLYLQYI 5280
RKLHDELTGH MLDMYSVMLT NDNTSRYWEP EFYEAMYTPH TVLQAVGACV LCNSQTSLRC 5340
GACIRRPFLC CKCCYDHVIS TSHKLVLSVN PYVCNAPGCD VTDVTQLYLG GMSYYCKSHK 5400
PPISFPLCAN GQVFGLYKNT CVGSDNVTDF NAIATCDWTN AGDYILANTC TERLKLFAAE 5460
TLKATEETFK LSYGIATVRE VLSDRELHLS WEVGKPRPPL NRNYVFTGYR VTKNSKVQIG 5520
EYTFEKGDYG DAVVYRGTTT YKLNVGDYFV LTSHTVMPLS APTLVPQEHY VRITGLYPTL 5580
NISDEFSSNV ANYQKVGMQK YSTLQGPPGT GKSHFAIGLA LYYPSARIVY TACSHAAVDA 5640
LCEKALKYLP IDKCSRIIPA RARVECFDKF KVNSTLEQYV FCTVNALPET TADIVVFDEI 5700
SMATNYDLSV VNARLRAKHY VYIGDPAQLP APRTLLTKGT LEPEYFNSVC RLMKTIGPDM 5760
FLGTCRRCPA EIVDTVSALV YDNKLKAHKD KSAQCFKMFY KGVITHDVSS AINRPQIGVV 5820
REFLTRNPAW RKAVFISPYN SQNAVASKIL GLPTQTVDSS QGSEYDYVIF TQTTETAHSC 5880
NVNRFNVAIT RAKVGILCIM SDRDLYDKLQ FTSLEIPRRN VATLQAENVT GLFKDCSKVI 5940
TGLHPTQAPT HLSVDTKFKT EGLCVDIPGI PKDMTYRRLI SMMGFKMNYQ VNGYPNMFIT 6000
REEAIRHVRA WIGFDVEGCH ATREAVGTNL PLQLGFSTGV NLVAVPTGYV DTPNNTDFSR 6060
VSAKPPPGDQ FKHLIPLMYK GLPWNVVRIK IVQMLSDTLK NLSDRVVFVL WAHGFELTSM 6120
KYFVKIGPER TCCLCDRRAT CFSTASDTYA CWHHSIGFDY VYNPFMIDVQ QWGFTGNLQS 6180
NHDLYCQVHG NAHVASCDAI MTRCLAVHEC FVKRVDWTIE YPIIGDELKI NAACRKVQHM 6240
VVKAALLADK FPVLHDIGNP KAIKCVPQAD VEWKFYDAQP CSDKAYKIEE LFYSYATHSD 6300
KFTDGVCLFW NCNVDRYPAN SIVCRFDTRV LSNLNLPGCD GGSLYVNKHA FHTPAFDKSA 6360
FVNLKQLPFF YYSDSPCESH GKQVVSDIDY VPLKSATCIT RCNLGGAVCR HHANEYRLYL 6420
DAYNMMISAG FSLWVYKQFD TYNLWNTFTR LQSLENVAFN VVNKGHFDGQ QGEVPVSIIN 6480
NTVYTKVDGV DVELFENKTT LPVNVAFELW AKRNIKPVPE VKILNNLGVD IAANTVIWDY 6540
KRDAPAHIST IGVCSMTDIA KKPTETICAP LTVFFDGRVD GQVDLFRNAR NGVLITEGSV 6600
KGLQPSVGPK QASLNGVTLI GEAVKTQFNY YKKVDGVVQQ LPETYFTQSR NLQEFKPRSQ 6660
MEIDFLELAM DEFIERYKLE GYAFEHIVYG DFSHSQLGGL HLLIGLAKRF KESPFELEDF 6720
IPMDSTVKNY FITDAQTGSS KCVCSVIDLL LDDFVEIIKS QDLSVVSKVV KVTIDYTEIS 6780
FMLWCKDGHV ETFYPKLQSS QAWQPGVAMP NLYKMQRMLL EKCDLQNYGD SATLPKGIMM 6840
NVAKYTQLCQ YLNTLTLAVP YNMRVIHFGA GSDKGVAPGT AVLRQWLPTG TLLVDSDLND 6900
FVSDADSTLI GDCATVHTAN KWDLIISDMY DPKTKNVTKE NDSKEGFFTY ICGFIQQKLA 6960
LGGSVAIKIT EHSWNADLYK LMGHFAWWTA FVTNVNASSS EAFLIGCNYL GKPREQIDGY 7020
VMHANYIFWR NTNPIQLSSY SLFDMSKFPL KLRGTAVMSL KEGQINDMIL SLLSKGRLII 7080
RENNRVVISS DVLVNN 7096

SEQ ID NO: 15            moltype = AA  length = 1273
FEATURE                  Location/Qualifiers
REGION                   1..1273
                         note = misc_feature - P0DTC2 SPIKE_SARS2
source                   1..1273
                         mol_type = protein
                         organism = SARS-COV-2
SEQUENCE: 15
MFVFLVLLPL VSSQCVNLTT RTQLPPAYTN SFTRGVYYPD KVFRSSVLHS TQDLFLPFFS 60
NVTWFHAIHV SGTNGTKRFD NPVLPFNDGV YFASTEKSNI IRGWIFGTTL DSKTQSLLIV 120
NNATNVVIKV CEFQFCNDPF LGVYYHKNNK SWMESEFRVY SSANNCTFEY VSQPFLMDLE 180
GKQGNFKNLR EFVFKNIDGY FKIYSKHTPI NLVRDLPQGF SALEPLVDLP IGINITRFQT 240
LLALHRSYLT PGDSSSGWTA GAAAYYVGYL QPRTFLLKYN ENGTITDAVD CALDPLSETK 300
CTLKSFTVEK GIYQTSNFRV QPTESIVRFP NITNLCPFGE VFNATRFASV YAWNRKRISN 360
CVADYSVLYN SASFSTFKCY GVSPTKLNDL CFTNVYADSF VIRGDEVRQI APGQTGKIAD 420
YNYKLPDDFT GCVIAWNSNN LDSKVGGNYN YLYRLFRKSN LKPFERDIST EIYQAGSTPC 480
NGVEGFNCYF PLQSYGFQPT NGVGYQPYRV VVLSFELLHA PATVCGPKKS TNLVKNKCVN 540
FNFNGLTGTG VLTESNKKFL PFQQFGRDIA DTTDAVRDPQ TLEILDITPC SFGGVSVITP 600
GTNTSNQVAV LYQDVNCTEV PVAIHADQLT PTWRVYSTGS NVFQTRAGCL IGAEHVNNSY 660
ECDIPIGAGI CASYQTQTNS PRRARSVASQ SIIAYTMSLG AENSVAYSNN SIAIPTNFTI 720
SVTTEILPVS MTKTSVDCTM YICGDSTECS NLLLQYGSFC TQLNRALTGI AVEQDKNTQE 780
VFAQVKQIYK TPPIKDFGGF NFSQILPDPS KPSKRSFIED LLFNKVTLAD AGFIKQYGDC 840
LGDIAARDLI CAQKFNGLTV LPPLLTDEMI AQYTSALLAG TITSGWTFGA GAALQIPFAM 900
QMAYRFNGIG VTQNVLYENQ KLIANQFNSA IGKIQDSLSS TASALGKLQD VVNQNAQALN 960
TLVKQLSSNF GAISSVLNDI LSRLDKVEAE VQIDRLITGR LQSLQTYVTQ QLIRAAEIRA 1020
SANLAATKMS ECVLGQSKRV DFCGKGYHLM SFPQSAPHGV VFLHVTYVPA QEKNFTTAPA 1080
ICHDGKAHFP REGVFVSNGT HWFVTQRNFY EPQIITTDNT FVSGNCDVVI GIVNNTVYDP 1140
LQPELDSFKE ELDKYFKNHT SPDVDLGDIS GINASVVNIQ KEIDRLNEVA KNLNESLIDL 1200
QELGKYEQYI KWPWYIWLGF IAGLIAIVMV TIMLCCMTSC CSCLKGCCSC GSCCKFDEDD 1260
SEPVLKGVKL HYT 1273

SEQ ID NO: 16            moltype = AA  length = 1255
FEATURE                  Location/Qualifiers
REGION                   1..1255
                         note = misc_feature - P59594 SPIKE_CVHSA
source                   1..1255
```

-continued

```
                        mol_type = protein
                        organism = SARS-COV-2
SEQUENCE: 16
MFIFLLFLTL TSGSDLDRCT TFDDVQAPNY TQHTSSMRGV YYPDEIFRSD TLYLTQDLFL    60
PPFYSNVTGFH TINHTFGNPV IPFKDGIYFA ATEKSNVVRG WVFGSTMNNK SQSVIIINNS   120
TNVVIRACNF ELCDNPFFAV SKPMGTQTHT MIFDNAFNCT FEYISDAFSL DVSEKSGNFK   180
HLREFVFKNK DGFLYVYKGY QPIDVVRDLP SGFNTLKPIF KLPLGINITN FRAILTAFSP   240
AQDIWGTSAA AYFVGYLKPT TFMLKYDENG TITDAVDCSQ NPLAELKCSV KSFEIDKGIY   300
QTSNFRVVPS GDVVRFPNIT NLCPFGEVFN ATKFPSVYAW ERKKISNCVA DYSVLYNSTF   360
FSTFKCYGVS ATKLNDLCFS NVYADSFVVK GDDVRQIAPG QTGVIADYNY KLPDDFMGCV   420
LAWNTRNIDA TSTGNYNYKY RYLRHGKLRP FERDISNVPF SPDGKPCTPP ALNCYWPLND   480
YGFYTTTGIG YQPYRVVVLS FELLNAPATV CGPKLSTDLI KNQCVNFNFN GLTGTGVLTP   540
SSKRFQPFQQ FGRDVSDFTD SVRDPKTSEI LDISPCSFGG VSVITPGTNA SSEVAVLYQD   600
VNCTDVSTAI HADQLTPAWR IYSTGNNVFQ TQAGCLIGAE HVDTSYECDI PIGAGICASY   660
HTVSLLRSTS QKSIVAYTMS LGADSSIAYS NNTIAIPTNF SISITTEVMP VSMAKTSVDC   720
NMYICGDSTE CANLLLQYGS FCTQLNRALS GIAAEQDRNT REVFAQVKQM YKTPTLKYFG   780
GFNFSQILPD PLKPTKRSFI EDLLFNKVTL ADAGFMKQYG ECLGDINARD LICAQKFNGL   840
TVLPPLLTDD MIAAYTAALV SGTATAGWTF GAGAALQIPF AMQMAYRFNG IGVTQNVLYE   900
NQKQIANQFN KAISQIQESL TTTSTALGKL QDVVNQNAQA LNTLVKQLSS NFGAISSVLN   960
DILSRLDKVE AEVQIDRLIT GRLQSLQTYV TQQLIRAAEI RASANLAATK MSECVLGQSK   1020
RVDFCGKGYH LMSFPQAAPH GVVFLHVTYV PSQERNFTTA PAICHEGKAY FPREGVFVFN   1080
GTSWFITQRN FFSPQIITTD NTFVSGNCDV VIGIINNTVY DPLQPELDSF KEELDKYFKN   1140
HTSPDVDLGD ISGINASVVN IQKEIDRLNE VAKNLNESLI DLQELGKYEQ YIKWPWYVWL   1200
GFIAGLIAIV MVTILLCCMT SCCSCLKGAC SCGSCCKFDE DDSEPVLKGV KLHYT        1255

SEQ ID NO: 17            moltype = AA  length = 422
FEATURE                  Location/Qualifiers
REGION                   1..422
                         note = misc_feature - P59595 NCAP_CVHSA
source                   1..422
                         mol_type = protein
                         organism = SARS-COV-2

SEQUENCE: 17
MSDNGPQSNQ RSAPRITFGG PTDSTDNNQN GGRNGARPKQ RRPQGLPNNT ASWFTALTQH    60
GKEELRFPRG QGVPINTNSG PDDQIGYYRR ATRRVRGGDG KMKELSPRWY FYYLGTGPEA   120
SLPYGANKEG IVWVATEGAL NTPKDHIGTR NPNNNAATVL QLPQGTTLPK GFYAEGSRGG   180
SQASSRSSSR SRGNSRNSTP GSSRGNSPAR MASGGGETAL ALLLLDRLNQ LESKVSGKGQ   240
QQQGQTVTKK SAAEASKKPR QKRTATKQYN VTQAFGRRGP EQTQGNFGDQ DLIRQGTDYK   300
HWPQIAQFAP SASAFFGMSR IGMEVTPSGT WLTYHGAIKL DDKDPQFKDN VILLNKHIDA   360
YKTFPPTEPK KDKKKKTDEA QPLPQRQKKQ PTVTLLPAAD MDDFSRQLQN SMSGASADST   420
QA                                                                  422

SEQ ID NO: 18            moltype = AA  length = 274
FEATURE                  Location/Qualifiers
REGION                   1..274
                         note = misc_feature - P59632 AP3A_CVHSA
source                   1..274
                         mol_type = protein
                         organism = SARS-COV-2

SEQUENCE: 18
MDLFMRFFTL GSITAQPVKI DNASPASTVH ATATIPLQAS LPFGWLVIGV AFLAVFQSAT    60
KIIALNKRWQ LALYKGFQFI CNLLLLFVTI YSHLLLVAAG MEAQFLYLYA LIYFLQCINA   120
CRIIMRCWLC WKCKSKNPLL YDANYFVCWH THNYDYCIPY NSVTDTIVVT EGDGISTPKL   180
KEDYQIGGYS EDRHSGVKDY VVVHGYFTEV YYQLESTQIT TDTGIENATF FIFNKLVKDP   240
PNVQIHTIDG SSGVANPAMD PIYDEPTTTT SVPL                               274

SEQ ID NO: 19            moltype = AA  length = 122
FEATURE                  Location/Qualifiers
REGION                   1..122
                         note = misc_feature - P59635 NS7A_CVHSA
source                   1..122
                         mol_type = protein
                         organism = SARS-COV-2
SEQUENCE: 19
MKIILFLTLI VFTSCELYHY QECVRGTTVL LKEPCPSGTY EGNSPFHPLA DNKFALTCTS    60
THFAFACADG TRHTYQLRAR SVSPKLFIRQ EEVQQELYSP LFLIVAALVF LILCFTIKRK   120
TE                                                                  122

SEQ ID NO: 20            moltype = AA  length = 76
FEATURE                  Location/Qualifiers
REGION                   1..76
                         note = misc_feature - P59637 VEMP_CVHSA
source                   1..76
                         mol_type = protein
                         organism = SARS-COV-2

SEQUENCE: 20
MYSFVSEETG TLIVNSVLLF LAFVVFLLVT LAILTALRLC AYCCNIVNVS LVKPTVYVYS    60
RVKNLNSSEG VPDLLV                                                    76
```

-continued

```
SEQ ID NO: 21           moltype = AA   length = 221
FEATURE                 Location/Qualifiers
REGION                  1..221
                        note = misc_feature - P59596 VME1_CVHSA
source                  1..221
                        mol_type = protein
                        organism = SARS-COV-2
SEQUENCE: 21
MADNGTITVE ELKQLLEQWN LVIGFLFLAW IMLLQFAYSN RNRFLYIIKL VFLWLLWPVT   60
LACFVLAAVY RINWVTGGIA IAMACIVGLM WLSYFVASFR LFARTRSMWS FNPETNILLN   120
VPLRGTIVTR PLMESELVIG AVIIRGHLRM AGHSLGRCDI KDLPKEITVA TSRTLSYYKL   180
GASQRVGTDS GFAAYNRYRI GNYKLNTDHA GSNDNIALLV Q                       221

SEQ ID NO: 22           moltype = AA   length = 154
FEATURE                 Location/Qualifiers
REGION                  1..154
                        note = misc_feature - P59633 NS3B_CVHSA
source                  1..154
                        mol_type = protein
                        organism = SARS-COV-2
SEQUENCE: 22
MMPTTLFAGT HITMTTVYHI TVSQIQLSLL KVTAFQHQNS KKTTKLVVIL RIGTQVLKTM   60
SLYMAISPKF TTSLSLHKLL QTLVLKMLHS SSLTSLLKTH RMCKYTQSTA LQELLIQQWI   120
QFMMSRRRLL ACLCKHKKVS TNLCTHSFRK KQVR                              154

SEQ ID NO: 23           moltype = AA   length = 63
FEATURE                 Location/Qualifiers
REGION                  1..63
                        note = misc_feature - P59634 NS6_CVHSA
source                  1..63
                        mol_type = protein
                        organism = SARS-COV-2
SEQUENCE: 23
MFHLVDFQVT IAEILIIIMR TFRIAIWNLD VIISSIVRQL FKPLTKKNYS ELDDEEPMEL   60
DYP                                                                63

SEQ ID NO: 24           moltype = AA   length = 275
FEATURE                 Location/Qualifiers
REGION                  1..275
                        note = misc_feature - P0DTC3 AP3A_SARS2
source                  1..275
                        mol_type = protein
                        organism = SARS-COV-2
SEQUENCE: 24
MDLFMRIFTI GTVTLKQGEI KDATPSDFVR ATATIPIQAS LPFGWLIVGV ALLAVFQSAS   60
KIITLKKRWQ LALSKGVHFV CNLLLLFVTV YSHLLLVAAG LEAPFLYLYA LVYFLQSINF   120
VRIIMRLWLC WKCRSKNPLL YDANYFLCWH TNCYDYCIPY NSVTSSIVIT SGDGTTSPIS   180
EHDYQIGGYT EKWESGVKDC VVLHSYFTSD YYQLYSTQLS TDTGVEHVTF FIYNKIVDEP   240
EEHVQIHTID GSSGVVNPVM EPIYDEPTTT TSVPL                             275

SEQ ID NO: 25           moltype = AA   length = 222
FEATURE                 Location/Qualifiers
REGION                  1..222
                        note = misc_feature - P0DTC5 VME1_SARS2
source                  1..222
                        mol_type = protein
                        organism = SARS-COV-2
SEQUENCE: 25
MADSNGTITV EELKKLLEQW NLVIGFLFLT WICLLQFAYA NRNRFLYIIK LIFLWLLWPV   60
TLACFVLAAV YRINWITGGI AIAMACLVGL MWLSYFIASF RLFARTRSMW SFNPETNILL   120
NVPLHGTILT RPLLESELVI GAVILRGHLR IAGHHLGRCD IKDLPKEITV ATSRTLSYYK   180
LGASQRVAGD SGFAAYSRYR IGNYKLNTDH SSSSDNIALL VQ                     222

SEQ ID NO: 26           moltype = AA   length = 121
FEATURE                 Location/Qualifiers
REGION                  1..121
                        note = misc_feature - P0DTC7 NS7A_SARS2
source                  1..121
                        mol_type = protein
                        organism = SARS-COV-2
SEQUENCE: 26
MKIILFLALI TLATCELYHY QECVRGTTVL LKEPCSSGTY EGNSPFHPLA DNKFALTCFS   60
TQFAFACPDG VKHVYQLRAR SVSPKLFIRQ EEVQELYSPI FLIVAAIVFI TLCFTLKRKT   120
E                                                                  121

SEQ ID NO: 27           moltype = AA   length = 419
FEATURE                 Location/Qualifiers
REGION                  1..419
                        note = misc_feature - P0DTC9 NCAP_SARS2
```

-continued

```
source                   1..419
                         mol_type = protein
                         organism = SARS-COV-2
SEQUENCE: 27
MSDNGPQNQR NAPRITFGGP SDSTGSNQNG ERSGARSKQR RPQGLPNNTA SWFTALTQHG   60
KEDLKFPRGQ GVPINTNSSP DDQIGYYRRA TRRIRGGDGK MKDLSPRWYF YYLGTGPEAG  120
LPYGANKDGI IWVATEGALN TPKDHIGTRN PANNAAIVLQ LPQGTTLPKG FYAEGSRGGS  180
QASSRSSSRS RNSSRNSTPG SSRGTSPARM AGNGGDAALA LLLLDRLNQL ESKMSGKGQQ  240
QQGQTVTKKS AAEASKKPRQ KRTATKAYNV TQAFGRRGPE QTQGNFGDQE LIRQGTDYKH  300
WPQIAQFAPS ASAFFGMSRI GMEVTPSGTW LTYTGAIKLD DKDPNFKDQV ILLNKHIDAY  360
KTFPPTEPKK DKKKKADETQ ALPQRQKKQQ TVTLLPAADL DDFSKQLQQS MSSADSTQA   419

SEQ ID NO: 28           moltype = AA  length = 98
FEATURE                 Location/Qualifiers
REGION                  1..98
                        note = misc_feature - P59636 ORF9B_CVHSA
source                  1..98
                        mol_type = protein
                        organism = SARS-COV-2
SEQUENCE: 28
MDPNQTNVVP PALHLVDPQI QLTITRMEDA MGQGQNSADP KVYPIILRLG SQLSLSMARR   60
NLDSLEARAF QSTPIVVQMT KLATTEELPD EFVVVTAK                           98

SEQ ID NO: 29           moltype = AA  length = 75
FEATURE                 Location/Qualifiers
REGION                  1..75
                        note = misc_feature - P0DTC4 VEMP_SARS2
source                  1..75
                        mol_type = protein
                        organism = SARS-COV-2
SEQUENCE: 29
MYSFVSEETG TLIVNSVLLF LAFVVFLLVT LAILTALRLC AYCCNIVNVS LVKPSFYVYS   60
RVKNLNSSRV PDLLV                                                    75

SEQ ID NO: 30           moltype = AA  length = 61
FEATURE                 Location/Qualifiers
REGION                  1..61
                        note = misc_feature - P0DTC6 NS6_SARS2
source                  1..61
                        mol_type = protein
                        organism = SARS-COV-2
SEQUENCE: 30
MFHLVDFQVT IAEILLIIMR TFKVSIWNLD YIINLIIKNL SKSLTENKYS QLDEEQPMEI   60
D                                                                  61

SEQ ID NO: 31           moltype = AA  length = 121
FEATURE                 Location/Qualifiers
REGION                  1..121
                        note = misc_feature - P0DTC8 NS8_SARS2
source                  1..121
                        mol_type = protein
                        organism = SARS-COV-2
SEQUENCE: 31
MKFLVFLGII TTVAAFHQEC SLQSCTQHQP YVVDDPCPIH FYSKWYIRVG ARKSAPLIEL   60
CVDEAGSKSP IQYIDIGNYT VSCLPFTINC QEPKLGSLVV RCSFYEDFLE YHDVRVVLDF  120
I                                                                  121

SEQ ID NO: 32           moltype = AA  length = 97
FEATURE                 Location/Qualifiers
REGION                  1..97
                        note = misc_feature - P0DTD2 ORF9B_SARS2
source                  1..97
                        mol_type = protein
                        organism = SARS-COV-2
SEQUENCE: 32
MDPKISEMHP ALRLVDPQIQ LAVTRMENAV GRDQNNVGPK VYPIILRLGS PLSLNMARKT   60
LNSLEDKAFQ LTPIAVQMTK LATTEELPDE FVVVTVK                            97

SEQ ID NO: 33           moltype = AA  length = 44
FEATURE                 Location/Qualifiers
REGION                  1..44
                        note = misc_feature - Q7TFA1 NS7B_CVHSA
source                  1..44
                        mol_type = protein
                        organism = SARS-COV-2
SEQUENCE: 33
MNELTLIDFY LCFLAFLLFL VLIMLIIFWF SLEIQDLEEP CTKV                    44

SEQ ID NO: 34           moltype = AA  length = 84
```

-continued

```
FEATURE            Location/Qualifiers
REGION             1..84
                   note = misc_feature - Q80H93 NS8B_CVHSA
source             1..84
                   mol_type = protein
                   organism = SARS-COV-2
SEQUENCE: 34
MCLKILVRYN TRGNTYSTAW LCALGKVLPF HRWHTMVQTC TPNVTINCQD PAGGALIARC   60
WYLHEGHQTA AFRDVLVVLN KRTN                                          84

SEQ ID NO: 35      moltype = AA  length = 73
FEATURE            Location/Qualifiers
REGION             1..73
                   note = misc_feature - P0DTD3 Y14_SARS2
source             1..73
                   mol_type = protein
                   organism = SARS-COV-2
SEQUENCE: 35
MLQSCYNFLK EQHCQKASTQ KGAEAAVKPL LVPHHVVATV QEIQLQAAVG ELLLLEWLAM   60
AVMLLLLCCC LTD                                                      73

SEQ ID NO: 36      moltype = AA  length = 43
FEATURE            Location/Qualifiers
REGION             1..43
                   note = misc_feature - P0DTD8 NS7B_SARS2
source             1..43
                   mol_type = protein
                   organism = SARS-COV-2
SEQUENCE: 36
MIELSLIDFY LCFLAFLLFL VLIMLIIFWF SLELQDHNET CHA                     43

SEQ ID NO: 37      moltype = AA  length = 39
FEATURE            Location/Qualifiers
REGION             1..39
                   note = misc_feature - Q7TFA0 NS8A_CVHSA
source             1..39
                   mol_type = protein
                   organism = SARS-COV-2
SEQUENCE: 37
MKLLIVLTCI SLCSCICTVV QRCASNKPHV LEDPCKVQH                          39

SEQ ID NO: 38      moltype = AA  length = 70
FEATURE            Location/Qualifiers
REGION             1..70
                   note = misc_feature - Q7TLC7 Y14_CVHSA
source             1..70
                   mol_type = protein
                   organism = SARS-COV-2
SEQUENCE: 38
MLPPCYNFLK EQHCQKASTQ REAEAAVKPL LAPHHVAVI QEIQLLAAVG EILLLEWLAE    60
VVKLPSRYCC                                                          70

SEQ ID NO: 39      moltype = AA  length = 279
FEATURE            Location/Qualifiers
source             1..279
                   mol_type = protein
                   organism = SARS-COV-2
SEQUENCE: 39
SNFRVQPTES IVRFPNITNL CPFGEVFNAT RFASVYAWNR KRISNCVADY SVLYNSASFS   60
TFKCYGVSPT KLNDLCFTNV YADSFVIRGD EVRQIAPGQT GKIADYNYKL PDDFTGCVIA  120
WNSNNLDSKV GGNYNYLYRL FRKSNLKPFE RDISTEIYQA GSTPCNGVEG FNCYFPLQSY  180
GFQPTNGVGY QPYRVVVLSF ELLHAPATVC GPKKSTNLVK NKCVNFNFNG LTGTGVLTES  240
NKKFLPFQQF GRDIADTTDA VRDPQTLEIL DITPCSFGG                         279

SEQ ID NO: 40      moltype = AA  length = 279
FEATURE            Location/Qualifiers
source             1..279
                   mol_type = protein
                   organism = SARS-COV-2
SEQUENCE: 40
SNFRVQPTES IVRFPNITNL CPFGEVFNAT RFASVYAWNR KRISNCVADL SVLYNSASFS   60
TFKCYGVSPT KLNDLCFTNV YADSFVIRGD EVRQIAPGQT GKIADYNYKL PDDFTGCVIA  120
WNSNNLDSKV GGNYNYLYRL FRKSNLKPFE RDISTEIYQA GSTPCNGVEG FNCYFPLQSY  180
GFQPTNGVGY QPYRVVVLSF ELLHAPATVC GPKKSTNLVK NKCVNFNFNG LTGTGVLTES  240
NKKFLPFQQF GRDIADTTDA VRDPQTLEIL DITPCSFGG                         279

SEQ ID NO: 41      moltype = AA  length = 279
FEATURE            Location/Qualifiers
source             1..279
```

-continued

```
                                mol_type = protein
                                organism = SARS-COV-2
SEQUENCE: 41
SNFRVQPTES IVRFPNITNL CPFGEVFNAT RFASVYAWNR KRISNCVADY SVLYNSASFS   60
TFKCYGVSPT KLNDLCFTNV YADSFVVRGD EVRQIAPGQT GKIADYNYKL PDDFTGCVIA  120
WNSNNLDSKV GGNYNYLYRL FRKSNLKPFE RDISTEIYQA GSTPCNGVEG FNCYFPLQSY  180
GFQPTNGVGY QPYRVVVLSF ELLHAPATVC GPKKSTNLVK NKCVNFNFNG LTGTGVLTES  240
NKKFLPFQQF GRDIADTTDA VRDPQTLEIL DITPCSFGG                         279

SEQ ID NO: 42          moltype = AA  length = 279
FEATURE                Location/Qualifiers
source                 1..279
                       mol_type = protein
                       organism = SARS-COV-2
SEQUENCE: 42
SNFRVQPTES IVRFPNITNL CPFGEVFNAT RFASVYAWNR KRISNCVADY SVLYNSASFS   60
TFKCYGVSPT KLNDLCFTNV YADSFVIRGD EVRQIAPGQT GKIADYNYKL PDDFTGCVIA  120
WNSNNLDSKV GGNYNYLYRL FRKSNLKPFE RDISTEIYQA GSTPCNGVEG FNCYFPLQSY  180
GFQPTNGVGY QPYRVAVLSF ELLHAPATVC GPKKSTNLVK NKCVNFNFNG LTGTGVLTES  240
NKKFLPFQQF GRDIADTTDA VRDPQTLEIL DITPCSFGG                         279

SEQ ID NO: 43          moltype = AA  length = 279
FEATURE                Location/Qualifiers
source                 1..279
                       mol_type = protein
                       organism = SARS-COV-2
SEQUENCE: 43
SNFRVQPTDS IVRFPNITNL CPFGEVFNAT TFASVYAWNR KRISNCVADY SVLYNSTSFS   60
TFKCYGVSPT KLNDLCFTNV YADSFVITGD EVRQIAPGQT GKIADYNYKL PDDFTGCVIA  120
WNSKHIDAKE GGNFNYLYRL FRKANLKPFE RDISTEIYQA GSKPCNGQTG LNCYYPLYRY  180
GFYPTDGVGH QPYRVVVLSF ELLNAPATVC GPKKSTNLVK NKCVNFNFNG LTGTGVLTES  240
NKKFLPFQQF GRDIADTTDA VRDPQTLEIL DITPCSFGG                         279

SEQ ID NO: 44          moltype = AA  length = 279
FEATURE                Location/Qualifiers
source                 1..279
                       mol_type = protein
                       organism = SARS-COV-2
SEQUENCE: 44
SNFRVQPTIS IVRFPNITNL CPFGEVFNAS KFASVYAWNR KRISNCVADY SVLYNSTSFS   60
TFKCYGVSPT KLNDLCFTNV YADSFVVKGD EVRQIAPGQT GVIADYNYKL PDDFTGCVIA  120
WNSVKQDALT GGNYGYLYRL FRKSKLKPFE RDISTEIYQA GSTPCNGQVG LNCYYPLERY  180
GFHPTTGVNY QPFRVVVLSX ELLNGPATVC GPKLSTTLVK DKCVNFNFNG LTGTGVLTTS  240
KKQFLPFQQF GRDISDTTDA VRDPQTLEIL DITPCSFGG                         279

SEQ ID NO: 45          moltype = AA  length = 260
FEATURE                Location/Qualifiers
source                 1..260
                       mol_type = protein
                       organism = SARS-COV-2
SEQUENCE: 45
SNFRVSPTQE VVRFPNITNR CPFDKVFNAT RFPSVYAWER TKISDCVADY TVLYNSTSFS   60
TFKCYGVSPS KLIDLCFTSV YADTFLIRSS EVRQVAPGET GVIADYNYKL PDDFTGCVIA  120
WNTAQQDKGQ YYYRSSRKTK LKPFERDLSS DENGVRTLST YDFYPTVPIE YQATRVVVLS  180
FELLNAPATV CGPKLSTGLV KNQCVNFNFN GLKGTGVLTD SSKRFQSFQQ FGRDTSDFTD  240
SVRDPQTLQV LDITPCSFGG                                             260

SEQ ID NO: 46          moltype = AA  length = 260
FEATURE                Location/Qualifiers
source                 1..260
                       mol_type = protein
                       organism = SARS-COV-2
SEQUENCE: 46
SNFRVSPTHE VIRFPNITNR CPFDKVFNAS RFPNVYAWER TKISDCVADY TVLYNSTSFS   60
TFKCYGVSPS KLIDLCFTSV YADTFLIRSS EVRQVAPGET GVIADYNYKL PDDFTGCVIA  120
WNTAKQDQGQ YYYRSSRKTK LKPFERDLSS DENGVRTLST YDFYPTVPIE YQATRVVVLS  180
FELLNAPATV CGPKLSTGLV KNQCVNFNFN GLKGTGVLTD SSKRFQSFQQ FGRDTSDFTD  240
SVRDPQTLQI LDITPCSFGG                                             260

SEQ ID NO: 47          moltype = AA  length = 260
FEATURE                Location/Qualifiers
source                 1..260
                       mol_type = protein
                       organism = SARS-COV-2
SEQUENCE: 47
SNFRVSPTHE VVRFPNITNR CPFDKVFNAS RFPNVYAWER TKISDCVADY TVLYNSTSFS   60
TFKCYGVSPS KLIDLCFTSV YADTFLIRSS EVRQVAPGET GVIADYNYKL PDDFTGCVIA  120
WNTAKQDQGQ YYYRSSRKTK LKPFERDLTS DENGVRTLST YDFYPNVPIE YQATRVVVLS  180
FELLNAPATV CGPKLSTALV KNQCVNFNFN GLKGIGVLTD SSKRFQSFQQ FGRDTSDFTD  240
```

-continued

```
SVRDPQTLQI LDITPCSFGG                                                         260

SEQ ID NO: 48           moltype = AA  length = 260
FEATURE                 Location/Qualifiers
source                  1..260
                        mol_type = protein
                        organism = SARS-COV-2
SEQUENCE: 48
SNFRVSPTHE VIRFPNITNR CPFDKVFNAS RFPNVYAWER TKISDCVADY TVLYNSTSFS   60
TFKCYGVSPS KLIDLCFTSV YADTFLIRSS EVRQVAPGET GVIADYNYKL PDDFTGCVIA   120
WNTAKQDQGQ YYYRSSRKTK LKPFERDLTS DENGVRTLST YDFYPNVPIE YQATRVVVLS   180
FELLNAPATV CGPKLSTGLV KNQCVNFNFN GLKGTGVLTD SSKRFQSFQQ FGRDTSDFTD   240
SVRDPQTLQI LDITPCSFGG                                                         260

SEQ ID NO: 49           moltype = AA  length = 260
FEATURE                 Location/Qualifiers
source                  1..260
                        mol_type = protein
                        organism = SARS-COV-2
SEQUENCE: 49
SNFRVSPTQE VIRFPNITNR CPFDKVFNAS RFPNVYAWER TKISDCVADY TVLYNSTSFS   60
TFKCYGVSPS KLIDLCFTSV YADTFLIRSS EVRQVAPGET GVIADYNYKL PDDFTGCVIA   120
WNTAKQDQGQ YYYRSSRKTK LKPFERDLSS DENGVRTLST YDFYPTVPIE YQATRVVVLS   180
FELLNAPATV CGPKLSTGLV KNQCVNFNFN GLKGTGVLTD SSKRFQSFQQ FGRDMSDFTD   240
SVRDPQTLQI LDITPCSFGG                                                         260

SEQ ID NO: 50           moltype = AA  length = 260
FEATURE                 Location/Qualifiers
source                  1..260
                        mol_type = protein
                        organism = SARS-COV-2
SEQUENCE: 50
SNFRVSPTQE VIRFPNITNR CPFDKVFNAS RFPNVYAWER TKISDCVADY TVLYNSTSFS   60
TFKCYGVSPS KLIDLCFTSV YADTFLIRSS EVRQVAPGET GVIADYNYKL PDDFTGCVIA   120
WNTAKQDQGQ YYYRSSRKTK LKPFERDLSS DENGVRTLST YDFYPTVPIE YQATRVVVLS   180
FELLNAPATV CGPKLSTGLV KNQCVNFNFN GLKGTGVLTD SSKRFQSFQQ FGRDMSDFTD   240
SVRDPQTLQI LDITPCSFGG                                                         260

SEQ ID NO: 51           moltype = AA  length = 260
FEATURE                 Location/Qualifiers
source                  1..260
                        mol_type = protein
                        organism = SARS-COV-2
SEQUENCE: 51
SNFRVTPTQE VVRFPNITNR CPFDKVFNAS RFPNVYAWER TKISDCVADY TVLYNSTSFS   60
TFKCYGVSPS KLIDLCFTSV YADTFLIRSS EVRQVAPGET GVIADYNYKL PDDFTGCVIA   120
WNTAQQDQGQ YYYRSYRKEK LKPFERDLSS DENGVYTLST YDFYPSIPVE YQATRVVVLS   180
FELLNAPATV CGPKLSTQLV KNQCVNFNFN GLRGTGVLTT SSKRFQSFQQ FGRDTSDFTD   240
SVRDPQTLEI LDISPCSFGG                                                         260

SEQ ID NO: 52           moltype = AA  length = 260
FEATURE                 Location/Qualifiers
source                  1..260
                        mol_type = protein
                        organism = SARS-COV-2
SEQUENCE: 52
SNFRVTPTQE VVRFPNITNR CPFDKVFNAS RFPNVYAWER TKISDCVADY TVLYNSTSFS   60
TFKCYGVSPS KLIDLCFTSV YADTFLIRSS EVRQVAPGET GVIADYNYKL PDDFTGCVIA   120
WNTAQQDQGQ YYYRSYRKEK LKPFERDLSS DENGVYTLST YDFYPSIPVE YQATRVVVLS   180
FELLNAPATV CGPKLSTQLV KNQCVNFNFN GLRGTGVLTT SSKRFQSFQQ FGRDTSDFTD   240
SVRDPQTLEI LDISPCSFGG                                                         260

SEQ ID NO: 53           moltype = AA  length = 261
FEATURE                 Location/Qualifiers
source                  1..261
                        mol_type = protein
                        organism = SARS-COV-2
SEQUENCE: 53
SNFRVSPTQE VIRFPNITNR CPFDKVFNAT RFPNVYAWER TKISDCVADY TVLYNSTSFS   60
TFKCYGVSPS KLIDLCFTSV YADTFLIRSS EVRQVAPGET GVIADYNYKL PDDFTGCVIA   120
WNTAKHDTGN YYYRSHRKTK LKPFERDLSS DDGNGVYTLS TYDFNPNVPV AYQATRVVVL   180
SFELLNAPAT VCGPKLSTEL VKNQCVNFNF NGLKGTGVLT SSSKRFQSFQ QFGRDTSDFT   240
DSVRDPQTLE ILDISPCSFG G                                                       261

SEQ ID NO: 54           moltype = AA  length = 261
FEATURE                 Location/Qualifiers
source                  1..261
                        mol_type = protein
                        organism = SARS-COV-2
```

-continued

```
SEQUENCE: 54
SNFRVSPTQE VIRFPNITNR CPFDKVFNVT RFPNVYAWER TKISDCVADY TVLYNSTSFS   60
TFKCYGVSPS KLIDLCFTSV YADTFLIRSS EVRQVAPGET GVIADYNYKL PDDFTGCVIA  120
WNTAKQDIGN YYYRSHRKTK LKPFERDLSS DDGNGVYTLS TYDFNPNVPV AYQATRVVVL  180
SFELLNAPAT VCGPKLSTQL VKNQCVNFNF NGLKGTGVLT SSSKRFQSFQ QFGRDTSDFT  240
DSVRDPQTLE ILDISPCSFG G                                           261

SEQ ID NO: 55              moltype = AA  length = 261
FEATURE                    Location/Qualifiers
source                     1..261
                           mol_type = protein
                           organism = SARS-COV-2
SEQUENCE: 55
SNFRVSPTQE VIRFPNITNR CPFDKVFNAS RFPNVYAWER TKISDCVADY TVLYNSTSFS   60
TFKCYGVSPS KLIDLCFTSV YADTFLIRSS EVRQVAPGET GVIADYNYKL PDDFTGCVIA  120
WNTAKQDTGH YYYRSHRKTK LKPFERDLSS DDGNGVYTLS TYDFNPNVPV AYQATRVVVL  180
SFELLNAPAT VCGPKLSTQL VKNQCVNFNF NGLKGTGVLT DSSKRFQSFQ QFGRDTSDFT  240
DSVRDPQTLE ILDITPCSFG G                                           261

SEQ ID NO: 56              moltype = AA  length = 261
FEATURE                    Location/Qualifiers
source                     1..261
                           mol_type = protein
                           organism = SARS-COV-2
SEQUENCE: 56
SNFRVSPTQE VVRFPNITNR CPFDKVFNAT RFPNVYAWER TKISDCVADY TVLYNSTSFS   60
TFKCYGVSPS KLIDLCFTSV YADTFLIRSS EVRQVAPGET GVIADYNYKL PDDFTGCVIA  120
WNTAKQDTGN YYYRSHRKTK LKPFERDLSS DDGNGVYTLS TYDFNPNVPV AYQATRVVVL  180
SFELLNAPAT VCGPKLSTQL VKNQCVNFNF NGLKGTGVLT PSLKRFQSFQ QFGRDTSDFT  240
DSVRDPQTLE ILDISPCSFG G                                           261

SEQ ID NO: 57              moltype = AA  length = 261
FEATURE                    Location/Qualifiers
source                     1..261
                           mol_type = protein
                           organism = SARS-COV-2
SEQUENCE: 57
SNFRVSPTQE VIRFPNITNR CPFDRVFNAS RFPSVYAWER TKISECVADY TVLYNSTSFS   60
TFKCYGVSPS KLIDLCFTSV YADTFLIRSS EVRQVAPGET GVIADYNYKL PDDFTGCVIA  120
WNTAKQDTGN YYYRSHRKTK LKPFERDLSS DDGNGVYTLS TYDFNPNVPV AYQATRVVVL  180
SFELLNAPAT VCGPKLSTQL VKNQCVNFNF NGLKGTGVLT PSSKRFQSFQ QFGRDTSDFT  240
DSVRDPQTLE ILDISPCSFG G                                           261

SEQ ID NO: 58              moltype = AA  length = 261
FEATURE                    Location/Qualifiers
source                     1..261
                           mol_type = protein
                           organism = SARS-COV-2
SEQUENCE: 58
SNFRVTPTQE VVRFPNITNR CPFDRVFNAS RFPSVYAWER TKISDCVADY TVLYNSTSFS   60
TFKCYGVSPS KLIDLCFTSV YADTFLIRSS EVRQVAPGET GVIADYNYKL PDDFTGCVIA  120
WNTAKQDTGY YYYRSHRKTK LKPFERDLSS DDGNGVYTLS TYDFNPNVPV AYQATRVVVL  180
SFELLNAPAT VCGPKLSTEL VKNQCVNFNF NGLKGTGVLT KSSKRFQSFQ QFGRDTSDFT  240
DSVRDPQTLE ILDISPCSFG G                                           261

SEQ ID NO: 59              moltype = AA  length = 260
FEATURE                    Location/Qualifiers
source                     1..260
                           mol_type = protein
                           organism = SARS-COV-2
SEQUENCE: 59
SNFRVSPTQE VVRFPNITNR CPFDKVFNAT RFPSVYAWER TKISDCVADY TVLYNSTSFS   60
TFKCYGVSPS KLIDLCFTSV YADTFLIRSS EVRQVAPGET GVIADYNYKL PDDFTGCVIA  120
WNTANQDQGQ YYYRSSRKEK LKPFERDLSS DENGVYTLS YDFYPSVPLD YQATRVVVLS  180
FELLNAPATV CGPKLSTTLV KNQCVNFNFN GLKGTGVLTA SSKKFQSFQQ FGRDASDFTD  240
SVRDPQTLEI LDISPCSFGG                                             260

SEQ ID NO: 60              moltype = AA  length = 260
FEATURE                    Location/Qualifiers
source                     1..260
                           mol_type = protein
                           organism = SARS-COV-2
SEQUENCE: 60
SNFRVSPSTE VIRFPNITNR CPFDRVFNAS RFPSVYAWER TKISDCVADY TVLYNSTSFS   60
TFKCYGVSPS KLIDLCFTSV YADTFLIRFS EVRQIAPGET GVIADYNYKL PDEFTGCVIA  120
WNTANQDRGQ YYYRSSRKTK LKPFERDLSS DENGVRTLST YDFYPSVPLE YQATRVVVLS  180
FELLNAPATV CGPKLSTSLI KNQCVNFNFN GLKGTGVLTD SSKKFQSFQQ FGRDASDFTD  240
SVRDPQTLQI LDISPCSFGG                                             260
```

```
SEQ ID NO: 61          moltype = AA  length = 260
FEATURE                Location/Qualifiers
source                 1..260
                       mol_type = protein
                       organism = SARS-COV-2
SEQUENCE: 61
SNFRVSPTRE VVRFPNITNR CPFDSIFNAS RFPSVYAWER TKISDCVADY TVLYNSTSFS    60
TFKCYGVSPS KLIDLCFTSV YADTFLIRFS EVRQVAPGET GVIADYNYRL PDDFTGCVIA   120
WNTANQDVGS YFYRSHRSTK LKPFERDLSS DENGVRTLST YDFNPYVPLD YQATRVVVLS   180
FELLNAPATV CGPKLSTELV KNQCVNFNFN GLKGTGVLSS SSKRFQSFQQ FGRDASDFTD   240
SVRDPQTLEI LDITPCSFGG                                              260

SEQ ID NO: 62          moltype = AA  length = 260
FEATURE                Location/Qualifiers
source                 1..260
                       mol_type = protein
                       organism = SARS-COV-2
SEQUENCE: 62
SNFRVSPTRE VVRFPNITNR CPFDSIFNAS RFPSVYAWER TKISDCVADY TVLYNSTLFS    60
TFKCYGVSPS KLIDLCFTSV YADTFLIRFS EVRQVAPGET GVIADYNYRL PDDFTGCVIA   120
WNTANQDVGS YFYRSHRSTK LKPFERDLSS DENGVRTLST YDFNPNVPLD YQATRVVVLS   180
FELLNAPATV CGPKLSTELV KNQCVNFNFN GLKGTGVLTS SSKRFQSFQQ FGRDASDFTD   240
SVRDPQTLEI LDITPCSFGG                                              260

SEQ ID NO: 63          moltype = AA  length = 260
FEATURE                Location/Qualifiers
source                 1..260
                       mol_type = protein
                       organism = SARS-COV-2
SEQUENCE: 63
SNFRVQPTVD VVRFPNITNL CPFDAVFNAT RFPSVYAWER VKISNCVADY TAFYNSTSFS    60
TFKCYGVSPS KLIDLCFTSV YADTFLIRFS EVRQVAPGET GVIADYNYKL PDDFTGCVIA   120
WNTAKQDVGS YFYRSHRSSK LKPFERDLSS DENGVRTLST YDFNPNVPLD YQATRVVVLS   180
FELLNAPATV CGPKLSTQLV KNQCVNFNFN GLKGTGVLTD SSKRFQSFQQ FGRDTSDFTD   240
SVRDPQTLDI LDITPCSFGG                                              260

SEQ ID NO: 64          moltype = AA  length = 260
FEATURE                Location/Qualifiers
source                 1..260
                       mol_type = protein
                       organism = SARS-COV-2
SEQUENCE: 64
SNFRVSPVTE VVRFPNITNL CPFDKVFNAT RFPSVYAWER TKISDCVADY TVFYNSTSFS    60
TFNCYGVSPS KLIDLCFTSV YADTFLIRFS EVRQVAPGQT GVIADYNYKL PDDFTGCVIA   120
WNTAKQDVGS YFYRSHRSSK LKPFERDLSS EENGVRTLST YDFNQNVPLE YQATRVVVLS   180
FELLNAPATV CGPKLSTSLV KNQCVNFNFN GFKGTGVLTD SSKTFQSFQQ FGRDASDFTD   240
SVRDPQTLRI LDISPCSFGG                                              260

SEQ ID NO: 65          moltype = AA  length = 260
FEATURE                Location/Qualifiers
source                 1..260
                       mol_type = protein
                       organism = SARS-COV-2
SEQUENCE: 65
SNFRVSPVTE VVRFPNITNL CPFDKVFNAT RFPSVYAWER TKISDCVADY TVFYNSTSFS    60
TFNCYGVSPS KLIDLCFTSV YADTFLIRFS EVRQVAPGQT GVIADYNYKL PDDFTGCVIA   120
WNTAKQDVGS YFYRSHRSSK LKPFERDLSS EENGVRTLST YDFNQYVPLE YQATRVVVLS   180
FELLNAPATV CGPKLSTSLV KNQCVNFNFN GFKGTGVLTD SSKTFQSFQQ FGRDASDFTD   240
SVRDPQTLRI LDISPCSFGG                                              260

SEQ ID NO: 66          moltype = AA  length = 260
FEATURE                Location/Qualifiers
source                 1..260
                       mol_type = protein
                       organism = SARS-COV-2
SEQUENCE: 66
SNFRVSPVTE VVRFPNITNL CPFDKVFNAT RFPSVYAWER TKISDCVADY TVFYNSTSFS    60
TFNCYGVSPS KLIDLCFTSV YADTFLIRFS EVRQVAPGQT GVIADYNYKL PDDFTGCVIA   120
WNTAKQDVGS YFYRSHRSSK LKPFERDLSS VEENGRTLST YDFNQNVPLE YQATRVVVLS   180
FELLNAPATV CGPKLSTSLV KNQCVNFNFN GFKGTGVLTD SSKTFQSFQQ FGRDASDFTD   240
SVRDPQTLRI LDISPCSFGG                                              260

SEQ ID NO: 67          moltype = AA  length = 260
FEATURE                Location/Qualifiers
source                 1..260
                       mol_type = protein
                       organism = SARS-COV-2
SEQUENCE: 67
SNFRVAPVTE VVRFPNITNL CPFDKVFNAT RFPSVYAWER TKISDCVADY TVFYNSTSFS    60
```

-continued

```
TFNCYGVSPS KLIDLCFTSV YADTFLIRFS EVRQVAPGQT GVIADYNYKL PDDFTGCVIA    120
WNTAKYDVGS YFYRSHRSSK LKPFERDLSS EENGARTLST YDFNQNVPLE YQATRVVVLS    180
FELLNAPATV CGPKLSTSLV KNQCVNFNFN GFKGTGVLTD SSKTFQSFQQ FGRDASDFTD    240
SVRDPKTLQI LDISPCSFGG                                               260

SEQ ID NO: 68              moltype = AA  length = 260
FEATURE                    Location/Qualifiers
source                     1..260
                           mol_type = protein
                           organism = SARS-COV-2
SEQUENCE: 68
SNFRVQPTVD VARFPNITNV CPFDKVFNAT RFPSVYAWER TKISDCVADY TVFYNSTSFS    60
TFNCYGVSPS KLIDLCFTSV YADTFLIRFS EVRQVAPGQT GVIADYNYKL PDDFIGCVIA    120
WNTAKQDVGS YFYRSHRSSK LKPFERDLSS EENGVLTLST YDFNQNVPLE YQATRVVVLS    180
FELLNAPATV CGPKLSTPLV KNQCVNFNFN GLKGTGVLTD SSKTFQSFQQ FGRDASDFTD    240
SVRDPQTLQI LDISPCSFGG                                               260

SEQ ID NO: 69              moltype = AA  length = 261
FEATURE                    Location/Qualifiers
source                     1..261
                           mol_type = protein
                           organism = SARS-COV-2
SEQUENCE: 69
SNFRVSPTQE VVRFPNITNR CPFDKVFNAS RFPSVYAWER IKISDCVADY TVLYNSTSFS    60
TPKCYGVSPS KLIDLCFTSV YADTFLIRSS EVRQVAPGET GVIADYNYKL PDDFTGCVIA    120
WNTAKQDTGS YYYRSHRKTK LKPFERDLSS DDGNGVYTLS TYDFNPNVPV AYQATRVVVL    180
SFELLNAPAT VCGPKLSTQL VKNQCVNFNF NGLTGTGVLT PSSKRFQPFQ QFGRDVSDFT    240
DSVRDPKTSE ILDISPCSFG G                                             261

SEQ ID NO: 70              moltype = AA  length = 248
FEATURE                    Location/Qualifiers
source                     1..248
                           mol_type = protein
                           organism = SARS-COV-2
SEQUENCE: 70
SRYRAQVAGF VRVTQRGSYC TPPYSVLQDP PQPVVWRRYM LYDCVFDFTV VVDSLPTHQL    60
QCYGVSPRRL ASMCYGSVTL DVMRINETHL NNLFNRVPDT FSLYNYALPD NFYGCLHAFY    120
LNSTAPYAVA NRFPIKPGGR QSNSAFIDTV INAAHYSPFS YVYGLAVITL KPAAGSKLVC    180
PVANDTVVIT DRCVQYNLYG YTGTGVLSKN TSLVIPDGKV FTASSTGTII GVSINSTTYS    240
IMPCVTVP                                                            248

SEQ ID NO: 71              moltype = AA  length = 364
FEATURE                    Location/Qualifiers
source                     1..364
                           mol_type = protein
                           organism = SARS-COV-2
SEQUENCE: 71
NGYTVQPIAD VYRRKPNLPN CNIEAWLNDK SVPSPLNWER KTFSNCNFNM SSLMSFIQAD    60
SFTCNNIDAA KIYGMCFSSI TIDKFAIPNG RKVDLQLGNL GYLQSFNYRI DTTATSCQLY    120
YNLPAANVSV SRFNPSTWNK RFGFIEDSVF KPRPAGVLTN HDVVYAQHCF KAPKNFCPCK    180
LNGSCVGSGP GKNNGIGTCP AGTNYLTCDN LCTPDPITFT GTYKCPQTKS LVGIGEHCSG    240
LAVKSDYCGG NSCTCRPQAF LGWSADSCLQ GDKCNIFANF ILHDVNSGLT CSTDLQKANT    300
DIILGVCVNY DLYGILGQGI FVEVNATYYN SWQNLLYDSN GNLYGFRDYI INRTFMIRSC    360
YSGR                                                               364

SEQ ID NO: 72              moltype = AA  length = 378
FEATURE                    Location/Qualifiers
source                     1..378
                           mol_type = protein
                           organism = SARS-COV-2
SEQUENCE: 72
NGYTVQPIAD VYRRIPNLPD CNIEAWLNDK SVPSPLNWER KTFSNCNFNM SSLMSFIQAD    60
SFTCNNIEAA KIYGMCFSSI TIDKFAIPNG RKVDLQLGNL GYLQSFNYRI DTTAASCQLY    120
YNLPAANVSV SRFNPSTWNR RFGFTEQSVF KPQPVGVFTH HDVVYAQHCF KAPTNFCPCK    180
LDGSLCVGNG PGIDAGYKNS GIGTCPAGTN YLTCHNAAQC DCLCTPDPIT SKSTGPYKCP    240
QTKYLVGIGE HCSGLAIKSD YCGGNPCTCQ PQAFLGWSVD SCLQGDRCNI FANFILHDVN    300
SGTTCSTDLQ KSNTDIILGV CVNYDLYGIT GQGIFVEVNA TYYNSWQNLL YDSNGNLYGF    360
RDYLTNRTFM IRSCYSGR                                                 378

SEQ ID NO: 73              moltype = AA  length = 364
FEATURE                    Location/Qualifiers
source                     1..364
                           mol_type = protein
                           organism = SARS-COV-2
SEQUENCE: 73
NGYTVQPVAT VYRRIPDLPN CDIEAWLNSK TVSSPLNWER KIFSNCNFNM GRLMSFIQAD    60
SFGCNNIDAS RLYGMCFGSI TIDKFAIPNS RKVDLQVGKS GYLQSFNYKI DTAVSSCQLY    120
YSLPAANVSV THYNPSSWNR RYGFINQSFG SRGLHDAVYS QQCFNTPNTY CPCRTSQCIG    180
GAGTGTCPVG TTVRKCFAAV TNATKCTCWC QPDPSTYKGV NAWTCPQSKV SIQPGQHCPG    240
```

-continued

```
LGLVEDDCSG NPCTCKPQAF IGWSSETCLQ NGRCNIFANF ILNDVNSGTT CSTDLQQGNT   300
NITTDVCVNY DLYGITGQGI LIEVNATYYN SWQNLLYDSS GNLYGFRDYL SNRTFLIRSC   360
YSGR                                                               364

SEQ ID NO: 74            moltype = AA  length = 368
FEATURE                  Location/Qualifiers
source                   1..368
                         mol_type = protein
                         organism = SARS-COV-2
SEQUENCE: 74
SGYTVQPVGL VYRRVRNLPD CKIEEWLAAN TVPSPLNWER KTFQNCNFNL SSLLRFVQAE   60
SLSCSNIDAS KVYGMCFGSI SIDKFAIPNS RRVDLQLGKS GLLQSFNYKI DTRATSCQLY   120
YSLAQDNVTV INHNPSSWNR RYGFNDVATF HSGEHDVAYA EACFTVGASY CPCAKPSTVY   180
SCVTGKPKSA NCPTGTSNRE CNVQASGFKS KCDCTCNPSP LTTYDPRCLQ ARSMLGVGDH   240
CEGLGILEDK CGGSNICNCS ADAFVGWAMD SCLSNARCHI FSNLMLNGIN SGTTCSTDFQ   300
LPNTEVVTGV CVKYDLYGST GQGVFKEVKA DYYNSWQNLL YDVNGNLNGF RDIVTNKTYL   360
LRSCYSGR                                                           368

SEQ ID NO: 75            moltype = AA  length = 372
FEATURE                  Location/Qualifiers
source                   1..372
                         mol_type = protein
                         organism = SARS-COV-2
SEQUENCE: 75
SGFTVKPVAT VHRRIPDLPD CDIDKWLNNF NVPSPLNWER KIFSNCNFNL STLLRLVHTD   60
SFSCNNFDES KIYGSCFKSI VLDKFAIPNS RRSDLQLGSS GFLQSSNYKI DTTSSSCQLY   120
YSLPAINVTI NNYNPSSWNR RYGFNNFNLS SHSVVYSRYC FSVNNTFCPC AKPSFASSCK   180
SHKPPSASCP IGTNYRSCES TTVLDHTDWC RCSCLPDPIT AYDPRSCSQK KSLVGVGEHC   240
AGFGVDEEKC GVLDGSYNVS CLCSTDAFLG WSYDTCVSNN RCNIFSNFIL NGINSGTTCS   300
NDLLQPNTEV FTDVCVDYDL YGITGQGIFK EVSAVYYNSW QNLLYDSNGN IIGFKDFVTN   360
KTYNIFPCYA GR                                                       372

SEQ ID NO: 76            moltype = AA  length = 370
FEATURE                  Location/Qualifiers
source                   1..370
                         mol_type = protein
                         organism = SARS-COV-2
SEQUENCE: 76
SGFTVKPVAT VYRRIPNLPD CDIDNWLNNV SVPSPLNWER RIFSNCNFNL STLLRLVHVD   60
SFSCNNLDKS KIFGSCFNSI TVDKFAIPNR RRDDLQLGSS GFLQSSNYKI DISSSSCQLY   120
YSLPLVNVTI NNFNPSSWNR RYGFGSFNLS SYDVVYSDHC FSVNSDFCPC ADPSVVNSCA   180
KSKPPSAICP AGTKYRHCDL DTTLYVKNWC RCSCLPDPIS TYSPNTCPQK KVVVGIGEHC   240
PGLGINEEKC GTQLNHSSCF CSPDAFLGWS FDSCISNNRC NIFSNFIFNG INSGTTCSND   300
LLYSNTEIST GVCVNYDLYG ITGQGIFKEV SAAYYNNWQN LLYDSNGNII GFKDFLTNKT   360
YTILPCYSGR                                                         370

SEQ ID NO: 77            moltype = AA  length = 329
FEATURE                  Location/Qualifiers
source                   1..329
                         mol_type = protein
                         organism = SARS-COV-2
SEQUENCE: 77
SGYTVQPVGV VYRRVANLPA CNIEEWLTAR SVPSPLNWER KTFQNCNFNL SSLLRYVQAE   60
SLFCNNIDAS KVYGRCFGSI SVDKFAVPRS RQVDLQLGNS GFLQTANYKI DTAATSCQLH   120
YTLPKNNVTI NNHNPSSWNR RYGFNDAGVF GKNQHDVVYA QQCFTVRSSY CPCAQPDIVS   180
PCTTQTKPKS AFVNVGDHCE GLGVLEDNCG NADPHKGCIC ANNSFIGWSH DTCLVNDRCQ   240
IFANILLNGI NSGTTCSTDL QLPNTEVVTG ICVKYDLYGI TGQGVFKEVK ADYYNSWQTL   300
LYDVNGNLNG FRDLTTNKTY TIRSCYSGR                                    329

SEQ ID NO: 78            moltype = AA  length = 240
FEATURE                  Location/Qualifiers
source                   1..240
                         mol_type = protein
                         organism = SARS-COV-2
SEQUENCE: 78
SGYTVQPVGV VYRRVPNLPD CKIEEWLTAK SVPSPLNWER RTFQNCNFNL SSLLRYVQAE   60
SLSCNNIDAS KVYGMCFGSV SVDKFAIPRS RQIDLQIGNS GFLQTANYKI DTAATSCQLY   120
YSLPKNNVTI NNYNPSSWNR RYGFKVNDRC QIFANILLNG INSGTTCSTD LQLPNTEVAT   180
GVCVRYDLYG ITGQGVFKEV KADYYNSWQA LLYDVNGNLN GFRDLTTNKT YTIRSCYSGR   240

SEQ ID NO: 79            moltype = AA  length = 221
FEATURE                  Location/Qualifiers
source                   1..221
                         mol_type = protein
                         organism = SARS-COV-2
SEQUENCE: 79
NFLDDNVLPE TYVALPIYYQ HTDINFTATA SFGGSCYVCK PHQVNISLNG NTSVCVRTSH   60
FSIRYIYNRV KSGSPGDSSW HIYLKSGTCP FSFSKLNNFQ KFKTICFSTV EVPGSCNFPL   120
EATWHYTSYT IVGALYVTWS EGNSITGVPY PVSGIREFSN LVLNNCTKYN IYDYVGTGII   180
```

-continued

```
RSSNQSLAGG ITYVSNSGNL LGFKNVSTGN IFIVTPCNQP D                         221

SEQ ID NO: 80            moltype = AA   length = 223
FEATURE                  Location/Qualifiers
source                   1..223
                         mol_type = protein
                         organism = SARS-COV-2
SEQUENCE: 80
SPIQSVELPV SIVSLPVYHK HTFIVLYVDF KPQSGGGKCF NCYPAGVNIT LANFNETKGP     60
LCVDTSHFTT KYVAVYANVG RWSASINTGN CPFSFGKVNN FVKFGSVCFS LKDIPGGCAM     120
PIVANWAYSK YYTIGSLYVS WSDGDGITGV PQPVEGVSSF MNVTLDKCTK YNIYDVSGVG     180
VIRVSNDTFL NGITYTSTSG NLLGFKDVTK GTIYSITPCN PPD                       223

SEQ ID NO: 81            moltype = AA   length = 285
FEATURE                  Location/Qualifiers
source                   1..285
                         mol_type = protein
                         organism = SARS-COV-2
SEQUENCE: 81
CAGETNFKSL SLWDTPASDC VSGSYNQEAT LGAFKVYFDL INCTFRYNYT ITEDENAEWF     60
GITQDTQGVH LYSSRKENVF RNNMFHFATL PVYQKILYYT VIPRSIRSPF NDRKAWAAFY     120
IYKLHPLTYL LNFDVEGYIT KAVDCGYDDL AQLQCSYESF EVETGVYSVS SFEASPRGEF     180
IEQATTQECD FTPMLTGTPP PIYNFKRLVF TNCNYNLTKL LSLFQVSEFS CHQVSPSSLA     240
TGCYSSLTVD YFAYSTDMSS YLQPGSAGAI VQFNYKQDFS NPTCR                     285

SEQ ID NO: 82            moltype = AA   length = 295
FEATURE                  Location/Qualifiers
source                   1..295
                         mol_type = protein
                         organism = SARS-COV-2
SEQUENCE: 82
SSYEASATGT FIEQPNATEC DFSPMLTGVA PQVYNFKRLV FSNCNYNLTK LLSLFAVDEF     60
SCNGISPDSI ARGCYSTLTV DYFAYPLSMK SYIRPGSAGN IPLYNYKQSF ANPTCRVMAS     120
VLANVTITKP HAYGYISKCS RLTGANQDVE TPLYINPGEY SICRDFSPGG FSEDGQVFKR     180
TLTQFEGGGL LIGVGTRVPM TDNLQMSFII SVQYGTGTDS VCPMLDLGDS LTITNRLGKC     240
VDYSLYGVTG RGVFQNCTAV GVKQQRFVYD SFDNLVGYYS DDGNYYCVRP CVSVP          295

SEQ ID NO: 83            moltype = AA   length = 295
FEATURE                  Location/Qualifiers
source                   1..295
                         mol_type = protein
                         organism = SARS-COV-2
SEQUENCE: 83
SFATYHTPAT DCSDGNYNRN ASLNSFKEYF NLRNCTFMYT YNITEDEILE WFGITQTAQG     60
VHLFSSRYVD LYGGNMFQFA TLPVYDTIKY YSIIPHSIRS IQSDRKAWAA FYVYKLQPLT     120
FLLDFSVDGY IRRAIDCGFN DLSQLHCSYE SFDVESGVYS VSSFEAKPSG SVVEQAEGVE     180
CDFSPLLSGT PPQVYNFKRL VFTNCNYNLT KLLSLFSVND FTCSQISPAA IASNCYSSLI     240
LDYFSYPLSM KSDLSVSSAG PISQFNYKQS FSNPTCLILA TVPHNLTTIT KPLKY          295

SEQ ID NO: 84            moltype = AA   length = 278
FEATURE                  Location/Qualifiers
source                   1..278
                         mol_type = protein
                         organism = SARS-COV-2
SEQUENCE: 84
SNFRVSPSTE VVRFPNITNL CPFGQVFNAS NFPSVYAWER LRISDCVADY AVLYNSSSSF     60
STFKCYGVSP TKLNDLCFSS VYADYFVVKG DDVRQIAPAQ TGVIADYNYK LPDDFTGCVL     120
AWNTNSVDSK SGNNFYYRLF RHGKIKPYER DISNVLYNSA GGTCSSISQL GCYEPLKSYG     180
FTPTVGVGYQ PYRVVVLSFE LLNAPATVCG PKKSTELVKN KCVNFNFNGL TGTGVLTSST     240
KKFQPFQQFG RDVSDFTDSV RDPKTFEILD ISPCSYGG                             278

SEQ ID NO: 85            moltype = AA   length = 275
FEATURE                  Location/Qualifiers
source                   1..275
                         mol_type = protein
                         organism = SARS-COV-2
SEQUENCE: 85
SNFRVTPTTE VVRFPNITQL CPFNEVFNIT SFPSVYAWER MRITNCVADY SVLYNSSASF     60
STFQCYGVSP TKLNDLCFSS VYADYFVVKG DDVRQIAPAQ TGVIADYNYK LPDDFTGCVI     120
AWNTNSLDSS NEFFYRRFRH GKIKPYGRDL SNVLFNPSGG TCSAEGLNCY KPLASYGFTQ     180
SSGIGFQPYR VVVLSFELLN APATVCGPKQ STELVKNKCV NFNFNGLTGT GVLTNSTKKF     240
QPFQQFGRDV SDFTDSVRDP KTLEILDIAP CSYGG                                275

SEQ ID NO: 86            moltype = AA   length = 278
FEATURE                  Location/Qualifiers
source                   1..278
                         mol_type = protein
                         organism = SARS-COV-2
SEQUENCE: 86
```

-continued

```
SNFRVAPSKE VVRFPNITNL CPFGEVFNAT TFPSVYAWER KRISNCVADY SVLYNSTSFS  60
TFKCYGVSAT KLNDLCFSNV YADSFVVKGD DVRQIAPGQT GVIADYNYKL PDDFLGCVLA  120
WNTNSKDSST SGNYNYLYRW VRRSKLNPYE RDLSNDIYSP GGQSCSAIGP NCYNPLRPYG  180
FFTTAGVGHQ PYRVVVLSFE LLNAPATVCG PKLSTDLIKN QCVNFNFNGL TGTGVLTSSS  240
KRFQPFQQFG RDVSDFTDSV RDPKTSEILD ISPCSFGG                         278

SEQ ID NO: 87            moltype = AA  length = 278
FEATURE                  Location/Qualifiers
source                   1..278
                         mol_type = protein
                         organism = SARS-COV-2
SEQUENCE: 87
SNFRVAPSKE VVRFPNITNL CPFGEVFNAT TFPSVYAWER KRISNCVADY SVLYNSTSFS  60
TFKCYGVSAT KLNDLCFSNV YADSFVVKGD DVRQIAPGQT GVIADYNYKL PDDFLGCVLA  120
WNTNSKDSST SGNYNYLYRW VRRSKLNPYE RDLSNDIYSP GGQSCSAVGP NCYNPLRPYG  180
FFTTAGVGHQ PYRVVVLSFE LLNAPATVCG PKLSTDLIKN QCVNFNFNGL TGTGVLTPSS  240
KRFQPFQQFG RDVSDFTDSV RDPKTSEILD ISPCSFGG                         278

SEQ ID NO: 88            moltype = AA  length = 278
FEATURE                  Location/Qualifiers
source                   1..278
                         mol_type = protein
                         organism = SARS-COV-2
SEQUENCE: 88
SNFRVAPSKE VVRFPNITNL CPFGEVFNAT TFPSVYAWER KRISNCVADY SILYNSTSFS  60
TFKCYGVSAT KLNDLCFSNV YADSFVVKGD DVRQIAPGQT GVIADYNYKL PDDFLGCVLA  120
WNTNSKDSST SGNYNYLYRW VRRSKLNPYE RDLSNDIYSP GGQSCSAVGP NCYNPLRPYG  180
FFTTAGVGHQ PYRVVVLSFE LLNAPATVCG PKLSTDLIKN QCVNFNFNGL TGTGVLTPSS  240
KRFQPFQQFG RDVSDFTDSV RDPKTSEILD ISPCSFGG                         278

SEQ ID NO: 89            moltype = AA  length = 278
FEATURE                  Location/Qualifiers
source                   1..278
                         mol_type = protein
                         organism = SARS-COV-2
SEQUENCE: 89
SNFRVAPSKE VVRFPNITNL CPFGEVFNAT TFPSVYAWER KRISNCVADY SVLYNSTSFS  60
TFKCYGVSAT KLNDLCFSNV YADSFVVKGD DVRQIAPGQT GVIADYNYKL PDDFTGCVLA  120
WNTRNIDATQ TGNYNYKYRS LRHGKLRPFE RDISNVPFSP DGKPCTPPAF NCYWPLNDYG  180
FYITNGIGYQ PYRVVVLSFE LLNAPATVCG PKLSTDLIKN QCVNFNFNGL TGTGVLTPSS  240
KRFQPFQQFG RDVSDFTDSV RDPKTSEILD ISPCSFGG                         278

SEQ ID NO: 90            moltype = AA  length = 278
FEATURE                  Location/Qualifiers
source                   1..278
                         mol_type = protein
                         organism = SARS-COV-2
SEQUENCE: 90
SNFRVAPSKE VVRFPNITNL CPFGEVFNAT TFPSVYAWER KRISNCVADY SVLYNSTSFS  60
TFKCYGVSAT KLNDLCFSNV YADSFVVKGD DVRQIAPGQT GVIADYNYKL PDDFTGCVLA  120
WNTRNIDATQ TGNYNYKYRS LRHGKLRPFE RDISNVPFSP DGKPCTPPAF NCYWPLNDYG  180
FYITNGIGYQ PYRVVVLSFE LLNAPATVCG PKLSTDLIKN QCVNFNFNGL TGTGVLTPSS  240
KRFQPFQQFG RDVSDFTDSV RDPKTSEILD ISPCSFGG                         278

SEQ ID NO: 91            moltype = AA  length = 278
FEATURE                  Location/Qualifiers
source                   1..278
                         mol_type = protein
                         organism = SARS-COV-2
SEQUENCE: 91
SNFRVAPSKE VVRFPNITNL CPFGEVFNAT TFPSVYAWER KRISNCVADY SVLYNSTSFS  60
TFKCYGVSAT KLNDLCFSNV YADSFVVKGD DVRQIAPGQT GVIADYNYKL PDDFTGCVLA  120
WNTRNIDATQ TGNYNYKYRS LRHGKLRPFE RDISNVPFSP DGKPCTPPAF NCYWPLNDYG  180
FYITNGIGYQ PYRVVVLSFE LLNAPATVCG PKLSTDLIKN QCVNFNFNGL TGTGVLTPSS  240
KRFQPFQQFG RDVSDFTDSV RDPKTSEILD ISPCSFGG                         278

SEQ ID NO: 92            moltype = AA  length = 278
FEATURE                  Location/Qualifiers
source                   1..278
                         mol_type = protein
                         organism = SARS-COV-2
SEQUENCE: 92
SNFRVSPSKE VVRFPNITNL CPFGEVFNAT TFPSVYAWER KRISNCVADY SVLYNSTSFS  60
TFKCYGVSAI KLNDLCFSNV YADSFVVKGD DVRQIAPGQT GVIADYNYKL PDDFMGCVLA  120
WNTRNIDATS SGNFNYKYRS LRHGKLRPFE RDISNVPFSP DGKPCTPPAF NCYWPLNDYG  180
FYTTNGIGYQ PYRVVVLSFE LLNAPATVCG PKLSTDLITN QCVNFNFNGL TGTGVLTPSL  240
KRFQPFQQFG RDFSDFTDSV RDPKTLEVLD ISPCSFGG                         278

SEQ ID NO: 93            moltype = AA  length = 278
```

```
FEATURE                 Location/Qualifiers
source                  1..278
                        mol_type = protein
                        organism = SARS-COV-2
SEQUENCE: 93
SNFRVSPSRE VVRFPNITNL CPFGEVFNAT TFPSVYAWER KRISNCVADY SVLYNSTSFS   60
TFKCYGVSAI KLNDLCFSNV YADSFVVKGD DVRQIAPGQT GVIADYNYKL PDDFMGCVLA  120
WNTRNIDATS SGNFHYKYRS LRHGKLRPFE RDISNVPFSP DGKPCTPPAF NCYWPLNDYG  180
FYTTNGIGYQ PYRVVVLSFE LLNAPATVCG PKLSTDLIITN QCVNFNFNGL TGTGVLTPSS  240
KRFQPFQQFG RDVSDFTDSV RDPKTLEVLD ISPCSFGG                          278

SEQ ID NO: 94          moltype = AA   length = 278
FEATURE                Location/Qualifiers
source                 1..278
                       mol_type = protein
                       organism = SARS-COV-2
SEQUENCE: 94
SNFRVAPSKE VVRFPNITNL CPFGEVFNAT TFPSVYAWER KRISNCVADY SVLYNSTSFS   60
TFKCYGVSAT KLNDLCFSNV YADSFVVKGD DVRQIAPGQT GVIADYNYKL PDDFMGCVLA  120
WNTRNIDATS TGNYNYKYRS LRHGKLRPFE RDISNVPFSP DGKPCTPPAF NCYWPLNDYG  180
FFTTNGIGYQ PYRVVVLSFE LLNAPATVCG PKLSTDLIKN QCVNFNFNGL TGTGVLTSSS  240
KRFQPFQQFG RDVSDFTDSV RDPKTSEILD ISPCSFGG                          278

SEQ ID NO: 95          moltype = AA   length = 278
FEATURE                Location/Qualifiers
source                 1..278
                       mol_type = protein
                       organism = SARS-COV-2
SEQUENCE: 95
SNFRVVPSRD VVRFPNITNL CPFGEVFNAT KFPSVYAWER KRISNCVADY SVLYNSTFFS   60
TFKCYGVSAT KLNDLCFSNV YADSFVVKGD DVRQIAPGQT GVIADYNYKL PDDFMGCVLA  120
WNTRNIDATS TGNYNYKYRY LRHGKLRPFE RDISNVPFSP DGKPCTPPAL NCYWPLNDYG  180
FYTTTGIGYQ PYRVVVLSFE LLNAPATVCG PKLSTDLIKN QCVNFNFNGL TGTGVLTPSS  240
KRFQPFQQFG RDVSDFTDSV RDPKTSEILD ISPCSFGG                          278

SEQ ID NO: 96          moltype = AA   length = 278
FEATURE                Location/Qualifiers
source                 1..278
                       mol_type = protein
                       organism = SARS-COV-2
SEQUENCE: 96
SNFRVVPSGD VVRFPNITNL CPFGEVFNAT KFPSVYAWER KKISNCVADY SVLYNSTFFS   60
TFKCYGVSAT KLNDLCFSNV YADSFVVKGD DVRQIAPGQT GVIADYNYKL PDDFMGCVLA  120
WNTRNIDATS TGNYNYKYRC LRHGKLRPFE RDISNVPFSP DGKPCTPPAF NCYWPLNDYG  180
FYTTTGIGYQ PYRVVVLSFE LLNAPATVCG PKLSTDLIKN QCVNFNFNGL TGTGVLTPSS  240
KRFQPFQQFG RDVSDFTDSV RDPKTSEILD ISPCSFGG                          278

SEQ ID NO: 97          moltype = AA   length = 278
FEATURE                Location/Qualifiers
source                 1..278
                       mol_type = protein
                       organism = SARS-COV-2
SEQUENCE: 97
SNFRVVPSGD VVRFPNITNL CPFGEVFNAT KFPSVYAWER KKISNCVADY SVLYNSTFFS   60
TFKCYGVSAT KLNDLCFSNV YADSFVVKGD DVRQIAPGQT GVIADYNYKL PDDFMGCVLA  120
WNTRNIDATS TGNYNYKYRY LRHGKLRPFE RDISNVPFSP DGKPCTPPAL NCYWPLNDYG  180
FYTTTGIGYQ PYRVVVLSFE LLNAPATVCG PKLSTDLIKN QCVNFNFNGL TGTGVLTPSS  240
KRFQPFQQFG RDVSDFTDSV RDPKTSEILD ISPCSFGG                          278

SEQ ID NO: 98          moltype = AA   length = 278
FEATURE                Location/Qualifiers
source                 1..278
                       mol_type = protein
                       organism = SARS-COV-2
SEQUENCE: 98
SNFRVVPSGD VVRFPNITNL CPFGEVFNAT KFPSVYAWER KKISNCVADY SVLYNSTFFS   60
TFKCYGVSAT KLNDLCFSNV YADSFVVKGD DVRQIAPGQT GVIADYNYKL PDDFMGCVLA  120
WNTRNIDATS TGNYNYKYRY LKHGKLRPFE RDISNVPFSP DGKPCTPPAL NCYWPLNDYG  180
FYTTTGIGYQ PYRVVVLSFE LLNAPATVCG PKLSTDLIKN QCVNFNFNGL TGTGVLTPSS  240
KRFQPFQQFG RDVSDFTDSV RDPKTSEILD ISPCSFGG                          278

SEQ ID NO: 99          moltype = AA   length = 278
FEATURE                Location/Qualifiers
source                 1..278
                       mol_type = protein
                       organism = SARS-COV-2
SEQUENCE: 99
SNFRVVPSGD VVRFPNITNL CPFGEVFNAT KFPSVYAWER KKISNCVADY SVLYNSTFFS   60
TFKCYGVSAT KLNDLCFSNV YVDSFVVKGD DVRQIAPGQT GVIADYNYKL PDDFMGCVLA  120
```

-continued

```
WNTRNIDATS TGNYNYKYRY LRHGKLRPFE RDISNVPFSP DGKPCTPPAL NCYWPLNDYG    180
FYTTTGIGYQ PYRVVVLSFE LLLNAPATVCG PKLSTDLIKN QCVNFNFNGL TGTGVLTPSS   240
KRFQPFQQFG RDVSDFTDSV RDPKTSEILD ISPCSFGG                            278

SEQ ID NO: 100           moltype = AA   length = 278
FEATURE                  Location/Qualifiers
source                   1..278
                         mol_type = protein
                         organism = SARS-COV-2
SEQUENCE: 100
SNFRVVPSGD VVRFPNITNL CPFGEVFNAT KFPSVYAWER KKISNCVVDY SVLYNSTFFS    60
TFKCYGVSAT KLNDLCFSNV YADSFVVKGD DVRQIAPGQT GVIADYNYKL PDDFMGCVLA    120
WNTRNIDATS TGNYNYKYRY LRHGKLRPFE RDISNVPFSP DGKPCTPPAL NCYWPLNDYG    180
FYTTTGIGYQ PYRVVVLSFE LLLNAPATVCG PKLSTDLIKN QCVNFNFNGL TGTGVLTPSS   240
KRFQPFQQFG RDVSDFTDSV RDPKTSEILD ISPCSFGG                            278

SEQ ID NO: 101           moltype = AA   length = 278
FEATURE                  Location/Qualifiers
source                   1..278
                         mol_type = protein
                         organism = SARS-COV-2
SEQUENCE: 101
SNFRVVPSGD VVRFPNITNL CPFGEVFNAT KFPSVYAWER KKISNCVADY SVLYNSTFFS    60
TFKCYGVSAT KLNDLCFSNV YADSFVVKGD DVRQIAPGQT GVIADYNYKL PDDFMGCVLA    120
WNTRNIDATS TGNHNYKYRY LRHGKLRPFE RDISNVPFSP DGKPCTPPAL NCYWPLNDYG    180
FYTTTGIGYQ PYRVVVLSFE LLLNAPATVCG PKLSTDLIKN QCVNFNFNGL TGTGVLTPSS   240
KRFQPFQQFG RDVSDFTDSV RDPKTSEILD ISPCSFGG                            278

SEQ ID NO: 102           moltype = AA   length = 278
FEATURE                  Location/Qualifiers
source                   1..278
                         mol_type = protein
                         organism = SARS-COV-2
SEQUENCE: 102
SNFRVVPSGD VVRFPNITNL CPFGEVFNAT KFPSVYAWER KKISNCVADY SVLYNSTFFS    60
TFKCYGVSAT KLNDLCFSNV YADSFVVKGD DVRQIAPGQT GVIADYNYKL PDDFMGCVLA    120
WNTRNIDATS TGNYNYKYRY LRHGKLRPFE RDISNVPFSP NGKPCTPPAL NCYWPLNDYG    180
FYTTTGIGYQ PYRVVVLSFE LLLNAPATVCG PKLSTDLIKN QCVNFNFNGL TGTGVLTPSS   240
KRFQPFQQFG RDVSDFTDSV RDPKTSEILD ISPCSFGG                            278

SEQ ID NO: 103           moltype = AA   length = 278
FEATURE                  Location/Qualifiers
source                   1..278
                         mol_type = protein
                         organism = SARS-COV-2
SEQUENCE: 103
SNFRVVPSGD VVRFPNITNL CPFGEVFNAT KFPSVYAWER KKISNCVADY SVLYNSTFFS    60
TFKCYGVSAT KLNDLCFSNV YADSFVVKGD DVRQIAPGQT GVIADYNYKL PDDFMGCVLA    120
WNTRNIDATS TGNYNYKYRY LRHGKLRPFE RDISNVPFSP DGKPCTPPAP NCYWPLNDYG    180
FYTTSGIGYQ PYRVVVLSFE LLLNAPATVCG PKLSTDLIKN QCVNFNFNGL TGTGVLTPSS   240
KRFQPFQQFG RDVSDFTDSV RDPKTSEILD ISPCAFGG                            278

SEQ ID NO: 104           moltype = AA   length = 278
FEATURE                  Location/Qualifiers
source                   1..278
                         mol_type = protein
                         organism = SARS-COV-2
SEQUENCE: 104
SNFRVVPSGD VVRFPNITNL CPFGEVFNAT KFPSVYAWER KKISNCVADY SVLYNSTFFS    60
TFKCYGVSAT KLNDLCFSNV YADSFVVKGD DVRQIAPGQT GVIADYNYKL PDDFMGCVLA    120
WNTRNIDATS TGNYNYKYRY LRHGKLRPFE RDISNVPFSP DGKPCTPPAP NCYWPLNGYG    180
FYTTSGIGYQ PYRVVVLSFE LLLNAPATVCG PKLSTDLIKN QCVNFNFNGL TGTGVLTPSS   240
KRFQPFQQFG RDVSDFTDSV RDPKTSEILD ISPCSFGG                            278

SEQ ID NO: 105           moltype = AA   length = 278
FEATURE                  Location/Qualifiers
source                   1..278
                         mol_type = protein
                         organism = SARS-COV-2
SEQUENCE: 105
SNFRVVPSGD VVRFPNITNL CPFGEVFNAT KFPSVYAWER KRISNCVADY SVLYNSTSFS    60
TFKCYGVSAT KLNDLCFSNV YADSFVVKGD DVRQIAPGQT GVIADYNYKL PDDFMGCVLA    120
WNTRNIDATS TGNYNYKYRY LRHGKLRPFE RDISNVPFSP DGKPCTPPAP NCYWPLNGYG    180
FYTTSGIGYQ PYRVVVLSFE LLLNAPATVCG PKLSTDLIKN QCVNFNFNGL TGTGVLTPSS   240
KRFQPFQQFG RDVSDFTDSV RDPKTSEILD ISPCSFGG                            278

SEQ ID NO: 106           moltype = AA   length = 278
FEATURE                  Location/Qualifiers
source                   1..278
```

-continued

```
                            mol_type = protein
                            organism = SARS-COV-2
SEQUENCE: 106
SNFRVVPSGD VVRFPNITNL CPFGEVFNAT KFPSVYAWER KRISNCVADY SVLYNSTSFS    60
TFKCYGVSAT KLNDLCFSNV YADSFVVKGD DVRQIAPGQT GVIADYNYKL PDDFMGCVLA   120
WNTRNIDATS TGNYNYKYRY LRHGKLRPFE RDISNVPFSP DGKPCTPPAP NCYWPLRGYG   180
FYTTSGIGYQ PYRVVVLSFE LLNAPATVCG PKLSTDLIKN QCVNFNFNGL TGTGVLTPSS   240
KRFQPFQQFG RDVSDFTDSV RDPKTSEILD ISPCSFGG                          278

SEQ ID NO: 107          moltype = AA  length = 278
FEATURE                 Location/Qualifiers
source                  1..278
                        mol_type = protein
                        organism = SARS-COV-2
SEQUENCE: 107
SNFRVVPSGD VVRFPNITNL CPFGEVFNAT KFPSVYAWER KRISNCVADY SVLYNSTSFS    60
TFKCYGVSAT KLNDLCFSNV YADSFVVKGD DVRQIAPGQT GVIADYNYKL PDDFMGCVLA   120
WNTRNIDATS TGNYNYKYRY LRHGKLRPFE RDISNVPFSP DGKPCTPPAP NCYWPLRGYG   180
FYTTSGIGYQ PYRVVVLSFE LLNAPATVCG PKLSTDLIKN QCVNFNFNGL TGTGVLTPSS   240
KRFQPFQQFG RDVSDFTDSV RDPKTSEILD ISPCSFGG                          278

SEQ ID NO: 108          moltype = AA  length = 278
FEATURE                 Location/Qualifiers
source                  1..278
                        mol_type = protein
                        organism = SARS-COV-2
SEQUENCE: 108
SNFRVVPSGD VVRFPNITNL CPFGEVFNAT KFPSVYAWER KRISNCVADY SVLYNSTSFS    60
TFKCYGVSAT KLNDLCFSNV YADSFVVKGD DVRQIAPGQT GVIADYNYKL PDDFMGCVLA   120
WNTRNIDATS TGNYNYKHRY LRHGKLRPFE RDISNVPFSP DGKPCTPPAP NCYWPLRGYG   180
FYTTSGIGYQ PYRVVVLSFE LLNAPATVCG PKLSTDLIKN QCVNFNFNGL TGTGVLTPSS   240
KRFQPFQQFG RDVSDFTDSV RDPKTSEILD ISPCSFGG                          278

SEQ ID NO: 109          moltype = AA  length = 278
FEATURE                 Location/Qualifiers
source                  1..278
                        mol_type = protein
                        organism = SARS-COV-2
SEQUENCE: 109
SNFRVVPSGD VVRFPNITNL CPFGEVFNAT KFPSVYAWER KRISNCVADY SVLYNSTSFS    60
TFKCYGVSAT KLNDLCFSNV YADSFVVKGD DVRQIAPGQT GVIADYNYKL PDDFMGCVLA   120
WNTRNIDATS TGNYNYKYRY LRHGKLRPFE RDISNVPFSS DGKPCTPPAP NCYWPLRGYG   180
FYTTSGIGYQ PYRVVVLSFE LLNAPATVCG PKLSTDLIKN QCVNFNFNGL TGTGVLTPSS   240
KRFQPFQQFG RDVSDFTDSV RDPKTSEILD ISPCSFGG                          278

SEQ ID NO: 110          moltype = AA  length = 278
FEATURE                 Location/Qualifiers
source                  1..278
                        mol_type = protein
                        organism = SARS-COV-2
SEQUENCE: 110
SNFRVVPSGD VVRFPNITNL CPFGEVFNAT KFPSVYAWER KRISNCVADY SVLYNSTSFS    60
TFKCYGVSAT KLNDLCFSNV YADSFVVKGD DVRQIAPGQT GVIADYNYKL PDDFMGCVLA   120
WNTRNIDATS TGNYNYKXRY LRHGKLRPFE RDISNVPFSP XGKPCTPPAP NCYWPLRGYG   180
FYTTSGIGYQ PYRVVVLSFE LLNAPATVCG PKLSTDLIKN QCVNFNFNGL TGTGVLTPSS   240
KRFQPFQQFG RDVSDFTDSV RDPKTSEILD ISPCSFGG                          278
```